United States Patent
Crooke et al.

(10) Patent No.: US 9,885,045 B2
(45) Date of Patent: Feb. 6, 2018

(54) METHODS AND COMPOSITIONS FOR MODULATING APOLIPOPROTEIN (A) EXPRESSION

(71) Applicant: Ionis Pharmaceuticals, Inc., Carlsbad, CA (US)

(72) Inventors: Rosanne M. Crooke, Carlsbad, CA (US); Mark J. Graham, San Clemente, CA (US); Susan M. Freier, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 15/331,297

(22) Filed: Oct. 21, 2016

(65) Prior Publication Data

US 2017/0121710 A1 May 4, 2017

Related U.S. Application Data

(63) Continuation of application No. 14/403,557, filed as application No. PCT/US2013/042532 on May 23, 2013, now abandoned.

(60) Provisional application No. 61/651,539, filed on May 24, 2012.

(51) Int. Cl.
 *C12N 15/113* (2010.01)

(52) U.S. Cl.
 CPC .... *C12N 15/113* (2013.01); *C12Y 304/21007* (2013.01); *C12N 2310/11* (2013.01); *C12N 2310/315* (2013.01); *C12N 2310/32* (2013.01); *C12N 2310/321* (2013.01); *C12N 2310/3231* (2013.01); *C12N 2310/3341* (2013.01); *C12N 2310/34* (2013.01); *C12N 2310/341* (2013.01); *C12N 2310/346* (2013.01)

(58) Field of Classification Search
None
See application file for complete search history.

(56) References Cited

U.S. PATENT DOCUMENTS

2003/0119766 A1* 6/2003 Crooke ............... C12N 15/113
 514/44 A

OTHER PUBLICATIONS

Graham et al., "Antisense inhibition of apolipoprotein(a) in cynomolgus monkeys significantly reduces plasma apolipoprotein(a) levels without affecting plasminogen or other major lipid classes" Powerpoint presentation from American Hearth Association(AHA) 2012 Scientific Sessions, presented Nov. 5, 2012.

* cited by examiner

*Primary Examiner* — Tracy Vivlemore
(74) *Attorney, Agent, or Firm* — Grant IP

(57) ABSTRACT

Disclosed herein are antisense compounds and methods for decreasing apo(a) to treat, prevent, or ameliorate diseases, disorders or conditions related to apo(a) or Lp(a). Certain diseases, disorders or conditions related to apo(a) or Lp(a) include inflammatory, cardiovascular and/or metabolic diseases, disorders or conditions. The antisense compounds disclosed herein can be used to treat such diseases, disorders or conditions in an individual in need thereof.

20 Claims, No Drawings

SEQUENCE LISTING

<160> NUMBER OF SEQ ID NOS: 134

<210> SEQ ID NO 1
<211> LENGTH: 6489
<212> TYPE: DNA
<213> ORGANISM: Homo sapiens

<400> SEQUENCE: 1

```
aggtacctttg ggggctggct ttctcaagga agcccagctc cctgtgattg agaatgaagt    60
gtgcaatcgc tatgactggg attgggacac actttctggg cactgctggc cagtcccaaa   120
atggaacata aggaagtggt tcttctactt cttttatttc tgaaatcagc agcacctgag   180
caaagccatg tggtccagga ttgctaccat ggtgatggac agagttatcg aggcacgtac   240
tccaccactg tcacaggaag gacctgccaa gcttggtcat ctatgacacc acatcaacat   300
aataggacca cagaaaacta cccaaatgct ggcttgatca tgaactactg caggaatcca   360
gatgctgtgg cagctcctta ttgttatacg agggatcccg tgtcaggtg ggagtactgc   420
aacctgacgc aatgctcaga cgcagaaggg actgccgtcg cgcctccgac tgttaccccg   480
gttccaagcc tagaggctcc ttccgaacaa gcaccgactg agcaaaggcc tggggtgcag   540
gagtgctacc atggtaatgg acagagttat cgaggcacat actccaccac tgtcacagga   600
agaacctgcc aagcttggtc atctatgaca ccacactcgc atagtcggac cccagaatac   660
tacccaaatg ctggcttgat catgaactac tgcaggaatc cagatgctgt ggcagctcct   720
tattgttata cgagggatcc cggtgtcagg tgggagtact gcaacctgac gcaatgctca   780
gacgcagaag ggactgccgt cgcgcctccg actgttaccc cggttccaag cctagaggct   840
ccttccgaac aagcaccgac tgagcaaagg cctggggtgc aggagtgcta ccatggtaat   900
ggacagagtt atcgaggcac atactccacc actgtcacag gaagaacctg ccaagcttgg   960
tcatctatga caccacactc gcatagtcgg accccagaat actacccaaa tgctggcttg  1020
atcatgaact actgcaggaa tccagatgct gtggcagctc cttattgtta tacgagggat  1080
cccggtgtca ggtgggagta ctgcaacctg acgcaatgct cagacgcaga agggactgcc  1140
gtcgcgcctc cgactgttac cccggttcca agcctagagg ctccttccga acaagcaccg  1200
actgagcaga ggcctgggt gcaggagtgc taccacggta atggacagag ttatcgaggc  1260
acatactcca ccactgtcac tggaagaacc tgccaagctt ggtcatctat gacaccacac  1320
tcgcatagtc ggaccccaga atactaccca aatgctggct tgatcatgaa ctactgcagg  1380
aatccagatg ctgtggcagc tccttattgt tatacgaggg atcccggtgt caggtgggag  1440
tactgcaacc tgacgcaatg ctcagacgca gaagggactg ccgtcgcgcc tccgactgtt  1500
accccggttc aagcctaga ggctccttcc gaacaagcac cgactgagca aaggcctggg  1560
gtgcaggagt gctaccatgg taatggacag agttatcgag gcacatactc caccactgtc  1620
acaggaagaa cctgccaagc ttggtcatct atgacaccac actcgcatag tcggacccca  1680
gaatactacc caaatgctgg cttgatcatg aactactgca ggaatccaga tgctgtggca  1740
gctccttatt gttatacgag ggatcccggt gtcaggtggg agtactgcaa cctgacgcaa  1800
tgctcagacg cagaagggac tgccgtcgcg cctccgactg ttaccccggt tccaagccta  1860
gaggctcctt ccgaacaagc accgactgag caaaggcctg gggtgcagga gtgctaccat  1920
ggtaatggac agagttatcg aggcacatac tccaccactg tcacaggaag aacctgccaa  1980
gcttggtcat ctatgacacc acactcgcat agtcggaccc cagaatacta cccaaatgct  2040
ggcttgatca tgaactactg caggaatcca gatgctgtgg cagctcctta ttgttatacg  2100
agggatcccg tgtcaggtg ggagtactgc aacctgacgc aatgctcaga cgcagaaggg  2160
actgccgtcg cgcctccgac tgttaccccg gttccaagcc tagaggctcc ttccgaacaa  2220
gcaccgactg agcaaaggcc tggggtgcag gagtgctacc atggtaatgg acagagttat  2280
```

```
cgaggcacat actccaccac tgtcacagga agaacctgcc aagcttggtc atctatgaca    2340
ccacactcgc atagtcggac cccagaatac tacccaaatg ctggcttgat catgaactac    2400
tgcaggaatc cagatgctgt ggcagctcct tattgttata cgagggatcc cggtgtcagg    2460
tgggagtact gcaacctgac gcaatgctca gacgcagaag ggactgccgt cgcgcctccg    2520
actgttaccc cggttccaag cctagaggct ccttccgaac aagcaccgac tgagcagagg    2580
cctggggtgc aggagtgcta ccacggtaat ggacagagtt atcgaggcac atactccacc    2640
actgtcactg aagaacctgc caagcttgg tcatctatga caccacactc gcatagtcgg    2700
accccagaat actacccaaa tgctggcttg atcatgaact actgcaggaa tccagatcct    2760
gtggcagccc cttattgtta tacgagggat cccagtgtca ggtgggagta ctgcaacctg    2820
acacaatgct cagacgcaga agggactgcc gtcgcgcctc caactattac cccgattcca    2880
agcctagagg ctccttctga caagcacca actgagcaaa ggcctggggt gcaggagtgc    2940
taccacggaa atggacagag ttatcaaggc acatacttca ttactgtcac aggaagaacc    3000
tgccaagctt ggtcatctat gacaccacac tcgcatagtc ggaccccagc atactaccca    3060
aatgctggct tgatcaagaa ctactgccga atccagatc ctgtggcagc cccttggtgt    3120
tatacaacag atcccagtgt caggtgggag tactgcaacc tgcacgatg ctcagatgca    3180
gaatggactg ccttcgtccc tccgaatgtt attctggctc caagcctaga ggcttttttt    3240
gaacaagcac tgactgagga accccccggg gtacaggact gctactacca ttatggacag    3300
agttaccgag gcacatactc caccactgtc acaggaagaa cttgccaagc ttggtcatct    3360
atgacaccac accagcatag tcggacccca gaaaactacc caaatgctgg cctgaccagg    3420
aactactgca ggaatccaga tgctgagatt cgcccttggt gttacaccat ggatcccagt    3480
gtcaggtggg agtactgcaa cctgacacaa tgcctggtga cagaatcaag tgtccttgca    3540
actctcacgg tggtcccaga tccaagcaca gaggcttctt ctgaagaagc accaacggag    3600
caaagccccg ggtccagga ttgctaccat ggtgatggac agagttatcg aggctcattc    3660
tctaccactg tcacaggaag gacatgtcag tcttggtcct ctatgacacc acactggcat    3720
cagaggacaa cagaatatta tccaaatggt ggcctgacca ggaactactg caggaatcca    3780
gatgctgaga ttagtccttg tgttatacc atggatccca atgtcagatg ggagtactgc    3840
aacctgacac aatgtccagt gacagaatca agtgtccttg cgacgtccac ggctgtttct    3900
gaacaagcac caacggagca aagccccaca gtccaggact gctaccatgg tgatggacag    3960
agttatcgag gctcattctc caccactgtt acaggaagga catgtcagtc ttggtcctct    4020
atgacaccac actggcatca gagaaccaca gaatactacc caaatggtgg cctgaccagg    4080
aactactgca ggaatccaga tgctgagatt cgcccttggt gttataccat ggatcccagt    4140
gtcagatggg agtactgcaa cctgacgcaa tgtccagtga tggaatcaac tctcctcaca    4200
actcccacgg tggtcccagt tccaagcaca gagcttcctt ctgaagaagc accaactgaa    4260
aacagcactg ggtccagga ctgctaccga ggtgatggac agagttatcg aggcacactc    4320
tccaccacta tcacaggaag aacatgtcag tcttggtcgt ctatgacacc acattggcat    4380
cggaggatcc cattatacta tccaaatgct ggcctgacca ggaactactg caggaatcca    4440
gatgctgaga ttcgcccttg tgttacacc atggatccca gtgtcaggtg ggagtactgc    4500
aacctgacac gatgtccagt gacagaatcg agtgtcctca caactcccac agtggccccg    4560
gttccaagca cagaggctcc ttctgaacaa gcaccacctg agaaaagccc tgtggtccag    4620
gattgctacc atggtgatgg acggagttat cgaggcatat cctccaccac tgtcacagga    4680
```

| | | | | |
|---|---|---|---|---|
| aggacctgtc | aatcttggtc | atctatgata | ccacactggc | atcagaggac | cccagaaaac | 4740 |
| tacccaaatg | ctggcctgac | cgagaactac | tgcaggaatc | cagattctgg | gaaacaaccc | 4800 |
| tggtgttaca | caaccgatcc | gtgtgtgagg | tgggagtact | gcaatctgac | acaatgctca | 4860 |
| gaaacagaat | caggtgtcct | agagactccc | actgttgttc | cagttccaag | catggaggct | 4920 |
| cattctgaag | cagcaccaac | tgagcaaacc | cctgtggtcc | ggcagtgcta | ccatggtaat | 4980 |
| ggccagagtt | atcgaggcac | attctccacc | actgtcacag | gaaggacatg | tcaatcttgg | 5040 |
| tcatccatga | caccacaccg | gcatcagagg | accccagaaa | actacccaaa | tgatggcctg | 5100 |
| acaatgaact | actgcaggaa | tccagatgcc | gatacaggcc | cttggtgttt | taccatggac | 5160 |
| cccagcatca | ggtgggagta | ctgcaacctg | acgcgatgct | cagacacaga | agggactgtg | 5220 |
| gtcgctcctc | cgactgtcat | ccaggttcca | agcctagggc | ctccttctga | caagactgt | 5280 |
| atgtttggga | atgggaaagg | ataccggggc | aagaaggcaa | ccactgttac | tgggacgcca | 5340 |
| tgccaggaat | gggctgccca | ggagcc ccat | agacacagca | cgttcattcc | agggacaaat | 5400 |
| aaatgggcag | gtctggaaaa | aaattactgc | cgtaaccctg | atggtgacat | caatggtccc | 5460 |
| tggtgctaca | caatgaatcc | aagaaaactt | tttgactact | gtgatatccc | tctctgtgca | 5520 |
| tcctcttcat | ttgattgtgg | gaagcctcaa | gtggagccga | agaaatgtcc | tggaagcatt | 5580 |
| gtagggggggt | gtgtggccca | cccacattcc | tggccctggc | aagtcagtct | cagaacaagg | 5640 |
| tttggaaagc | acttctgtgg | aggcacctta | atatcccag | agtgggtgct | gactgctgct | 5700 |
| cactgcttga | agaagtcctc | aaggccttca | tcctacaagg | tcatcctggg | tgcacaccaa | 5760 |
| gaagtgaacc | tcgaatctca | tgttcaggaa | atagaagtgt | ctaggctgtt | cttggagccc | 5820 |
| acacaagcag | atattgcctt | gctaaagcta | agcaggcctg | ccgtcatcac | tgacaaagta | 5880 |
| atgccagctt | gtctgccatc | cccagactac | atggtcaccg | ccaggactga | atgttacatc | 5940 |
| actggctggg | gagaaaccca | aggtaccttt | gggactggcc | ttctcaagga | agcccagctc | 6000 |
| cttgttattg | agaatgaagt | gtgcaatcac | tataagtata | tttgtgctga | gcatttggcc | 6060 |
| agaggcactg | acagttgcca | gggtgacagt | ggagggcctc | tggtttgctt | cgagaaggac | 6120 |
| aaatacattt | tacaaggagt | cacttcttgg | ggtcttggct | gtgcacgccc | caataagcct | 6180 |
| ggtgtctatg | ctcgtgtttc | aaggtttgtt | acttggattg | agggaatgat | gagaaataat | 6240 |
| taattggacg | ggagacagag | tgaagcatca | acctacttag | aagctgaaac | gtgggtaagg | 6300 |
| atttagcatg | ctggaaataa | tagacagcaa | tcaaacgaag | acactgttcc | cagctaccag | 6360 |
| ctatgccaaa | ccttggcatt | tttggtattt | ttgtgtataa | gcttttaagg | tctgactgac | 6420 |
| aaattctgta | ttaaggtgtc | atagctatga | catttgttaa | aaataaactc | tgcacttatt | 6480 |
| ttgatttga | | | | | | 6489 |

<210> SEQ ID NO 2
<211> LENGTH: 150001
<212> TYPE: DNA
<213> ORGANISM: Homo sapiens

<400> SEQUENCE: 2

| | | | | |
|---|---|---|---|---|
| atctttcagc | ctctatatta | ttttattgtg | attttaatt | tccttgaatt | ggattttgcc | 60 |
| attgtgctaa | atcttgatga | tcttcatttg | tatccgtagt | ctgaattata | tttctgtcat | 120 |
| ttgagttagc | tcagtcttgt | taagaaccct | tgttggaaaa | ctggtgcagt | tgtttggagg | 180 |
| acatatgacc | ttctggccat | ttgatttatt | ggagttctta | cgttggttct | ttctcatgtc | 240 |

```
tctgtgtggg tgtttcttta actgcagtgt agattgagta cagccaatag acttcttctt      300
tggaggtttt cacagggcca aggccttgta cagggtcttt atttgtagct gacttcttgt      360
ctttggtttc atagtggggc atgttagcaa atagttttg ctgttgaagt tttggggtgt      420
gatccatttt ttatttaat gattgtgtat ttcctttata cctaaaacaa gcagaaaacc      480
agtaaaggtc tttgagtctc tgaattcata actccagcat tcatattgct tcctcaggta      540 agtgggttt tcacccagcc cttaagggtg ttagattatt ttttatgtga aattagccag      600
attgtatttc taaacatgat gtaaaacaat aatgacaaaa gttataataa actagccttc      660
ttaccaaatc cacatgtcta atgtgtgtgg gagggtgtta ggcaggggac ctgcagctaa      720
gggagaggca gacaggcccc atggcccaa atctaggata gtatttggta ttggttgatg      780
ggtgagagaa agagagggaa catctgtgca ggatgtggta tcagcacctg gactacatct      840
tagggattcc ttcttcattt ttcagtatgc cctgacaata attatatcta tcagacttac      900 cccttgacc actggaacac taagactgtt ttgggatctc tgcctgactt tctcagaggt      960
gctggtgagg acattatgag tctggaacct agaaaagcgt tctgactctg ctgactttct     1020
cagaggtgct ggtgaggaca ttatgagtct ggagccctag aaaagcgttc tgactctgcc     1080
actagccaga cagacctgga ctaggcacgt taactctttg tatgacttga ctccaacccc     1140
tcatttgtaa aaccagcatt ttcaagtggt gttttccaca tcagccttt gcataagctg     1200 tcatttgaag aaaggttttt gttgtttgt ttttgttta acaaaaaggt taaaaaccac     1260
tggtctagat aattgcaaag tttgctttcc ttttctgtg cttttctac tattttaaa     1320 atgtcatcct cctggttc ttgatccccc ttctgcact cctgagtctg gaacactga     1380 ggccaactaa aaggaaactt ggcaaaagag gaaacccttt gggtgtgcca ggctgctccc     1440
agtgttttgc acttataaaa atttaaatgc tgcaaacctc taagacttag atattattgt     1500
tcctatttta caagtgagga acctgaggct cagagaaggt gcaggatggc acaggagac     1560 ctgaattgga accctggttc ccacttactg gctgtcggga cttagaaaag tcatgaactc     1620
tcattgattg ttttcttata tgaaatgggg gctgcagggt tgtcggggga gaaacaataa     1680
gaatgtgcat caagtgtcga gcacgtgcta cgcactccat catggcagct cctactaata     1740
tacagaatag agttgtatct aacatgactc tttcttgcaa gtgacagaaa tccaactta     1800 agatggatta agcaaaaag gggaattctt gttgagctga aaagtcttta ggctcacatg     1860
atggccccag ggcccaggcc ctgtccagcc atgcagtagg catcatcctt gggcacaaag     1920
gtgagattct tgtggtggca gatgctgtgg cagctcttgc tttgccagga aagactgagg     1980
aaggccactg tcccccattaa gtgaacaata gttggccagg tctgagaggt tgaacttggg     2040
tcacaggcct gtccctgaac ccatcactga ttggctccaa cctgcatcag ctattacatg     2100
ctagaggtgg aggcaggacc ccactcatac ccagaagggc aaagggtgga tccctcaaca     2160
ggattatggg atgtagggtg atagactgct gggcagccag aaagcaaaca gatcctctcc     2220
aatacctcaa ctgatgaaag caccaagcta aaatcataag gatctgggtg tgaattctgg     2280
ctctaccatc ttccatgtga cattgggcag ttatttaatc tcttttagcc ttggcttct     2340 tacctgtact aacatataag gtgattgtga tgagcatcat catcgtcaac atcatcatca     2400
ccatccacat tgccaccacc actcccatta tcatcttcat caacatcatc accaccgcca     2460
ccatcaccat tatcattacc accaccgcta tcactattat catcacccct aacatcatca     2520
ccatcatcac tatcatcacc accaccatca tcgttactac cactaccacc accatcatca     2580
ccacagccac caccaccatc accatcatta ctactcagca ccaccatcat cattccacca     2640
```

```
ccatcaccat cattccacca tcaccattat cattaccacc accactgtca ctattatcat    2700
caccctcaac atcatcacca ccaccatcat cattactacc accaccacca ccatcaccat    2760
catcatcatt ctaccaccat caccattatc atcaccatca ccatcaccac cgctatcatc    2820
atgataatca ttatcattac caccaccatt agcattatca ttaccaccac catcactatc    2880
actatcacca tcaccacgac cactaccacc atcaccaaca ccatcattac tacccaccac    2940
caccatcatc atcattccac caccatcaca attattacca ccaccaccat caccaccacc    3000
accaccatca ctatcatcat cagtagacat catataacca gtttgtagct ggcccagagc    3060
ctacttgctg tttcttctgc cccacaacca tccacacatt tctaaccacc atcccccact    3120
aggcttctgc ctcgcctggt ctcacctgca ggtccactga gaaaatgatt ctcagaacac    3180
taactagacc atgaggtgcc acaaaacata actcaggcct gttcatcaat tttctacatg    3240
tcaataatga catcaggtca attggcgttc tcagcctctg agagggaggt caaagttttc    3300
ctgctctccc cttcatgttt ccaggtgttc cctgacttgg atcaaatgca gagtttggag    3360
gtgttgaggc caaggggatt ttccaggtca gtcgtcatcc acaatcaatg gactgatcct    3420
gccgctggac ttaccctgct gccctctccc caaggcccca tcaggaggg cttcaatcct     3480 cttgtcacct gtggcctacc tgccctcaga gatgacatct ctatgtcggc cactggatgg    3540
cagcacctac tcgcagacca catcaacttt cctggcaact gcggtaggt tttcaccatt     3600 atcaggatgt ttgccttgct caaatagcag attctagaga acggtgctcc ctcacacaac    3660
tatgtagtcc aggtgatgca ccctctgccc gatgcttggt agtcagaaac ttccatcatg    3720
cagctctgcc cagattgagc tgagctggcc tctggagtga ggtgctggga caaacatctt    3780
ccatgctgct catgtcaact ccagatgcag tcaggtttct gaaccaaagt caatgatcta    3840
agtgcagtca aaggctctgg gggaagaaag agagagtgcc tcatctcttg cctgtgccat    3900
gctcgcaaag caaggatttt tgcaaaattc taatgaaagc tgggcttgca aaattagaaa    3960
actggattat ttgtgagaac actgaaacat ccctgggtgt gtccatctgg aaaaacagca    4020
tttcctctgg caattttgca accgttctat ttgaatttgg caagaaaat aaagcagttt     4080 ttcacaaaag aataaacaca accaggagaa tcttcactct cccaaattgt caagaagta    4140 taaattagaa aatgaatcag gacaatttca acctgttaga ttagctaata tttaaaaatt    4200
gaacactcat acaagtgtgg tgaagtgatt gttttctagt gacattttac actgtcataa    4260
ccttctagaa aataaattgg cagtgttatt gggagacaga aatatgtcta tataatttat    4320
gggaacttag gctcagaaaa tattaaggaa taagaatgaa ctttatgaac aaagatgtgg    4380
agggttggaa gcaagagggg ggccaacgcg cacgggagg aagcatttgg gcagtgactc     4440
cgcagaccca ggctcaggtt gaactagaca acctccttac acctcagttt ccttaactgt    4500
agagcaggag tgatggaact gcctgtttca taggactgtt gtgaggatga agtgagatac    4560
accacattat aagcttgtgc ctggaaagga taatgcttag taaatgatga ctattctttt    4620
ttattgcaat aaaatgtaca cagcgtaaga gttactattt taaccatttt tgcagggtac    4680
caccaagtgg catttagtac attcacagtg gtgtgcaacc atcatcatat ttccagaata    4740
ttttcctcat ccccaaagga aacctcatgc tcattaatca gtagctctcc tttaaaatat    4800
tagttatgaa gatcatagca ctatacaaaa ctcattatgt aatgttgagt gaaaaaatca    4860
gggtgtgaaa ttttgtgata tgatgtaatt agtgaaagaa gcatacaaaa agtctgaaaa    4920
tataaaaaca atagcaattg catttctcag actctacatt taaacattat tctttatggt    4980
```

```
tttaaaagca aagaaaaagg taaagaaaca acaaccaacc gcaaagcacc atgacaaagc    5040
tcagattgtt aaatccaggt ttttggaaca tagactctta tatgacgttt acactctcca    5100
gggttcagag agtctggcag cattgggagc tgccttgtgt tctacagcct cacggacaga    5160
caggaggtcc atcaccactg ctctgttctt ctggagtttc cttgtgaaca tgttgtggac    5220
gtagttacca tttctttcat cttttttaaac acaggtacct ttggggctgg ctttctcaag    5280
gaagcccagc tccctgtgat tgagaatgaa gtgtgcaatc gctatgagtt tctgaatgga    5340
agagtcaaat ccactgagct ctgtgctggg catttggctg gaggcattga cagttgcaag    5400
gtaagaaaag atcaagagac caaagttagt cttgtgctct cctgtctcag tctcagtccc    5460
ttagacttga gtcccaaagt agcgaattca agtaggattt aatcaatgga agaccccagt    5520
ctaagtgttg ctcagaaact ccctagatct gtcccaaatg tatattcaga tcatccaagg    5580
ggacttcttg gggcttgagt tccagatcag cagcaaggga gccataagtg ccataactac    5640
ctcagaccac tcaccctcct ggggtgtccc ggtggccagg gactaaagtg gtgattttttc    5700 tggtagggaa ggaggtagag ggtacaggac agagactaac tgcacacaat atctgagact    5760
ggagctcaga tattgctgat gatcagagtt ggcgtgtctc cccaattgat ttacaactgg    5820
ggcttggata ctgttttaaa cgggaggagc ctcctaacca tcttgacaca accactgacg    5880
tgactacact agagatagac tctttccact taattctacc actcttgctt tacttcatga    5940
gaacgaaaat gtaagattgc accatgaatt catttgcgga aagattgata ctatgctttt    6000 atttttatttt atttttattttt atttttattttt atttttattttt attgagactc tcaccccggt    6060
tgaagtgcac tgacgtgatt ttggctcact gcaacttcca cctcctgggt tcaagtgaat    6120
actccagcct ccctagtagc tgggattaca ggtgcccacc accacgcctg gctaattttt    6180 gtattttttag tagagatggg gtttcaccac attggcctgg ctggtctcaa actcctgacc    6240
ttgtgatcca cctgtcttgg cctcccaaag tgctgggatt acagagttga gccaccgcac    6300
tcgaccctat gtttttatttt taaaaatatt tatttattta tttaagccac aactactaga    6360
ataggaagga ttgatatttt attaattttta tttggtatttt attatttttt tttctttcct    6420
gagacattct tgctctgtca cccaggctgg agtgcagtgg cacattcttg gctcactgca    6480
acctccatct cctgtgttca agcaattcta gtgcctcagc ctacttagta gctgggatga    6540
ctggcatgtg cctccacacc cagctaattt ttgtattttttt tgtagagaca gggttttggc    6600
atgttgccca ggcttgtctc aaactcctgg cctcaggtga tccatctgcc gtggcctccc    6660
aaaatgctgg gattataggc atgagccacc acccctcct ggaaggattg atatcttata    6720
acataattta taattacaga aaacatgtga gttcactagg aataaataaa ttttgaagat    6780
aataaaagat tttcacttat gttgtcattt cggcacagtt tggtatagga tgtgagatg    6840 ttaacattta tacctagctt gctcgtaaac taagacctga aagggttgtg tctatcagct    6900
gcacccctgg gtagcgacac aacctcggga aggcctcagc cccctcctcg tacagcactg    6960
cctgttggaa agcttgaggg aggctatgga tgtgcagcac ttggcagagg gtctggtcat    7020
ggaagttacc agcaaatatg agctactttt atgatttttat tttatccaaa agaaagagaa    7080
tgaaagaaga ggggaggaaa caagactaat caggaaagat gaaggtctag ggtgaggga    7140 aggagtaagg agacataaag gcaatgtgga gcagctgagg ggggaaatgg ctttcaccac    7200
ttcccagcat ctattgacat tgcactctca aatattttat aagactctat attcaaggta    7260
atgtttgaac cctgctgagc cagtggcatg ggtctctgag agaatcatta acttaatttg    7320
actatctggt ttgtgggtgc gtttactctc atgtaagtca acaatgtcct gggattggga    7380
```

```
cacactttct gggcactgct ggccagtccc aaaatggaac ataaggaagt ggttcttcta    7440
cttcttttat ttctgaaatc aggtaagaca tagttttttt aaattataag aattattttt    7500
tctcccacaa tgtagtaaaa atacatatgc catggcttta tgtgcaattc atttaatttt    7560
tgattcatga aattcccagt tcaaaatctt gtatatgatt gaaaaattct taaaaaaata    7620
agtttaattt ccccgtgaag actgtcacgg tgctggaatg aatgggcaga aaaaataatg    7680
gttgattttt ctaatctaaa agagtgtgcc tacatgatgg ccagtctggc tgaaaaataa    7740
atagccattg tagctaacta tgcaaaggat ggctaagctc ttcgcttggt tctcagtttc    7800
attaatttat atcatctctg ttcaggtgcc atgctcccct cactagcaag ttgaaacaat    7860
gaaataactc tttgaatatg tttggttcct tgacctgttc atggagtggg actcagcatt    7920
tctctctttg ttatggcctg agtaaggctt ccatcggta tacatttgct tcttatccct    7980
ggagaaatta tacacatcca tttgccagat gatatacgca tataatgatt caacaaatac    8040
tcagggtatt tgttgagtgg gttaggtccc cacatttta tacatacata cacacataca    8100
caccgtgtgt gattgtgaat gtaagtgtgt gtcctttaca aatactagct tatttagctc    8160
atggtatagg tagggtagca tagtcatccc cattttataa acaaagaaat ctagacttag    8220
gaaaatcatg ttatttgtct cgtgaccaaa ttcccaaatc aaggaaataa agaaacctgg    8280
atttaagcca gatttccaag aaaaaatcta gggctcttct cactttttca tctttgttcc    8340
aacatttgaa aaaataaatc taaacacatt ccaatgtaac tgaagagcag gttaattgtt    8400
tgccacttgc agaatccaat taagaagaga gaagtctggt ataaagaaag tgatttgctt    8460
ccaaagctag cttaggggaa gaaatgcagc agtcctgccg tactacttca ctttaggagc    8520
agaaagtggc acttttaaaa ggcaacagag gaggcgagca aggattcagg ggtccatgct    8580
agcttgggca ccttatccac caggtagttg agcagttgcc tgctggtgcc tttgtgagca    8640
gggtgttgtc ccttgaggca aatctctgga gggtgagagt tttgtagtgg gcatgctttg    8700
gtttataaat cacctgtgaa ctcaggagtt ccatcttgaa gcacatacat agttagatga    8760
acttgccctg cagggagagt ctgatgaaag ggaggtagat gcttgcaatt taatctataa    8820
attaccagat aaaattttac aagttgactt taaagtcaaa cacatttgaa tttagtggaa    8880
gccattcaag aaaatatcaa agaaaataca gagcaggaga agattaagca aagagttttt    8940
tggggaaatt ggtgtctatg tctgtgtgtg tagggagtgc aggggatatg aatattctat    9000
ttcagcccat ggaaactagg atgtagatca ctgtgaactt attcagcagg ctacacccaa    9060
aggctagaac aaacttctct gccacaggat taacatatgt tttaatcgac ctgggggca    9120
cattctctga taagctcttt tggaaagcca ggctttctgt ggacgtgtta tctttccaat    9180
gtgtgctgga atgcccgggg agaggaaaaa gtttctttta cagccatgct cagtgagaag    9240
cggagaaaca tcttctattc acaaattgct aagtctttta cacatgcaaa tatgcataca    9300
cattcacaca ccacagtgag gaagaaattc tcacaccatt aataaaatac atttacttca    9360
gtagcaatat acatctacat tttgcctata atataaaagt attttttccta ttaaaagatt    9420
tgtttaatgt ttcttcacca acaaataaac cctattaaat ccccattgcc atatgagccc    9480
tggaggtgaa tcagagaaac aaaaggattg tggaaaaatc atcaggttaa aaaagaaaa    9540
attgattctg ttttgggata tttcctagca acatgagctg gggaggggat ctcagcagtg    9600
atgctctatg aagcataata aaatgacaca gttacaggta acttagttaa aggggggaaat    9660
aaatggaagt ttcctctttt tgaatatcaa ttgtagcctg ctctgctaca tttcaaaaac    9720
```

```
actcttcaaa atgtttaact gaactcactg taggaagcac cttattaatt tattgtgtgt    9780
tttgaagtca cactgtgagc tatagaattt acccaagcac aactcttcct ggaaaagaga    9840
gttcaaatga gaaacagtgc ggggtgaaga catggatatg ggcctaaaat atctatttct    9900
caatgatatt ttgatatatc tatcaagtgc ttttttagtgg attaggttca gaatgcatca   9960
gccaatgcct gttcaataat ccagttttcc agcatagagc atattaaatt gaggaaggac   10020
aaagtcacag aggtggggag caggtggact gtggccaagg actttgcatg aaacagtgag   10080
cgtgcatcct cctccttgcc ctgccctcat ggtctgtgta ctctcaggag gtcaggacag   10140
gcctttctga gaatgagaat ctgttcatct gcctttctac tggatacttg tcatcggcat   10200
acaaacacat gttctctgca gtgtgtcatc tttcagaacc tcccctgacc ctgtattccc   10260
tagaagtctc gctgctttca gagccaggct tctctcctgc tgccacccc actgctcttc    10320
tagtcactct ttaacccact ccatctgcat gtggccccca ccacacccct caaagtggtc   10380
aaggttgtcc tgttgcttaa ttccatggaa gcttggctat cttcatttta ttagcctctt   10440
ttggcctctc accctgtgaa atcactaca ttttgtgcca gagatggagc tggcatctcc    10500
aggcttggaa agggctgct gaagctcagc caggtgtcct aaggagcctc aggacagggg    10560
atgctcagta gccttgcaat gggaacacag ctgagcccca cttggccacc ctttgccaca   10620
accaggcaga aagcagcttt tgaacagatt tgttgcctca gatttgatct caaagaaaaa   10680
tcgtgggcag tattggtccc aggttctgct tttttacaat ttcctctgaa atctggatgc   10740
ctatcaacac cttggaaaaa ctgaattctc cccaactaat agtggtgtgt cactgtagta   10800
agcctagtac aaaaatggcc ttctttgtgg aggagcttca tatcctccat ttttttttg   10860
cttaatttt gcccaagatg agaacataat ttagttcact ttttatttat tcccaacatc    10920
atccatgcac caacatttt gtaactaaag gagggaccat tcagaagatg cttatcaact    10980
gtcaaagtga cagtgttaca accaatgcac atattgtaag aaatcaaaca atggcctcca   11040
aggttcattt ctacacaggg attagcagat caacatcaat cttggcaaca cagttgccac   11100
tgatggtgtc ttattttttt tatcatgaca tggcaatcaa gagcaaacat gatttattct   11160
tatttaagat tttatggtta gactaggcag atagctagat atgagcagga ggtggaagcc   11220
cctgagagaa tggaggtctg gagaatctga accccagag attacccaag tcctgcatgc    11280
tagacatgag tggaggaggg ggaatacctca ggtagaaaag aatgcccctt aagatgccca   11340
gcagtcgctc actgtgcagt taacttttca gaatgctgct agatacatgc tgatagggag   11400
ggaagagggc aaaggagaaa ttcctaagag atacacggtt gcagttagta tacatctgag   11460
tgctatacaa ccttctttgg gtggtggcaa gaagcaatgc agccattacg tagaattcat   11520
atcaaacacc tgtatcacag gtgttaaaga aacaagaaac attgtacttc ttgtattctt   11580
aataatgatt tgcaatattg tctttagtat cactgcaaac ctctataaat atgatttta    11640
aaaagtattt ctttaggttg gaattacttc tacgcattga cttatcttcc tgggtttcat   11700
tagccgtacc cgttgtactt tcttccttac cactgtttat ctcaaactct tgagattaaa   11760
gtatgggctc aggagggagc gaggagcttc aggactctca cggacctcca gcacagtgta   11820
gctgccttat ggaaaagtgg ccacactgtt ttctgcactg gtccctgccc ctactattcc   11880
tcactgggca gagcacagcc accctggccc tgcctgaaca ttttagtcag tgttggctct   11940
gtgcttctct ggggaggaaa tccaagagac aacccacagc ccctctgcca tttcagctgc   12000
agcagtacca ccgttaatgc ccttgggctt gagaaagaag ggacctggcc acttccctga   12060
cacctccagc acacagcagg gaaagaattc cagtttctct ttcttgtgag ctttcacctg   12120
```

```
ctactcttca ccaggcaagg ctcctggctt gggcccacag tgcaggcacc tcgaactcag    12180
ttgaacattt ccactggctg cactctgtgt ttttgtgggg tgaagctccc agaggtgact    12240
gaaagtcctt ctgccactaa cactgcagtc atactgccct tgctgtactt ggactaggga    12300
aggaaaaaag atcctgagtg ctttactcac accccagtgt gccccagcca ccctatggaa    12360
aagaggccag tgtgtcatcc ctgcaagcac cctgaggccc ctgcccctgc tgccccaag    12420 ctgtagagcc agaatataaa gctggcagaa aaatgtaaaa aggctagact ggcttagcct    12480
cccagcctac atctttctcc tgtgctggat ccttcctgct cttgaacatc ggactccaag    12540
ttcttcagct gtgggacttg gactgtcttc cttgctcctc agattgcagg tggcctatta    12600
tgggaccttg taatcttgtg agttaatacc acttaataag ctccccttg tgtgagtata     12660 tctatatcta tagatagata taggtatact cactatatat acacatatat acatatactc    12720
tctctctctc tctctcatat atatatatat ataatctcct attagttctg tccctctaga    12780
gaaccccgac taatacagat tttcatacca gaagtggttc ttgaggaaca gaatattaag    12840
gatggaattc tttcattggt tttgggactt ctggtgttgg ctgattaata tgattagacc    12900
aaaaaatgct aaggactcta cttctaatag tatggagaac actgatagta cttggcctga    12960
attgtttaga gagttatgca aaataaatgc atttgacact actgattcat cacttatgag    13020
aggcaaggag tttagtgact ctatacataa tacctttgac tatatgtgga gaaccaagga    13080
acataatgaa gttggttgat tgctcctaag ttctctggag aaagagatga aagaaaatga    13140
tgatctcagg ggatctgtct cccaccttca gaagcagata ctgagccaca aatctgctaa    13200
gattgccctg aatgagagtt ttaactcctg tagagaaaga gttgaaattg tgaaaaaaca    13260
gagacaagct gttatcatgc gagtagctga tctgcaacaa gaggtgcatg cacagccttg    13320
ccaggtgttt actgttaaag tgagggcatt gactggaaaa aaatgggacc ctggaacttg    13380
gagtggggat gtgtgggaga accctgatga agctgaggac actgagtttg tgaactctga    13440
tgaaactttt ttgccagaag aaacagtttc cccatcccca gtagtggtaa catcccctcc    13500
ctgacccgtg ctgccattag cctttccacc tttgtctgag gatgtaaacc ctgcactgct    13560
tgaggcaaca gtgatggcct tccctgaggc agctgccagg caagataatg ttgattctcc    13620
tcaagaggca cccctaatgc ccctgaatgc ttctagacct ataactaggc taaattcctt    13680
gcgggcccca gaggtgaggt tcagagtgtg acccatgagg aggtgcatta tactctaaaa    13740
gaactgctta agctttctaa tttatattgg cagaaatctg gagaacaggc atgggaatgg    13800
atattaaggg taagggataa tggtggaagg gacatagagt tggatcaagc tgaatttatt    13860
ggtttggccc tactaagtag ggattctgca tttaatgttg cagctcgggg acttagaaaa    13920
ggttctgata gggccgggag cagtggctca cgcctgtaat cccagcacct gggaggcgg    13980 gggcgggcag atcacgagat caggagattg agacaattct ggctaaaatg gtgaaacccc    14040
atctctgcta aaaatacaaa aattagctgg gcatggtgat gcgtaactgt aatctcatct    14100
acttgggagg ctgaggcaag agaactgctt gaacctgtga ggcagagatt gcagtgagcc    14160
aagatcgccc cactgcattc cagcctggta acagagcaag actccatttc caaaaaaaaa    14220
aaaaaaaaag ttataaatagt ttatttgctt ggttagctga aatatggatt aaaagatggt    14280
ccaatgttag tgagctggaa atgccttggt ttaatgtaga ggaagtgatc caaaggctta    14340
gggagattag gatggtggag tggattagtc actttagacc tactcatccc agctgggagg    14400
gtccagaaga tacacccttg gccgaagctt tgtgaaatag atttgtgaga gcagcacctg    14460
```

```
tatttttgaa gagcccgtaa ttgctcttct ctgtatgtca gatctaacag taggaaccac    14520
agtcactcaa ctacaaaatt taaatacaat gggaataatt ggatcctgag gtggcagggg    14580
ccaagtgttg gcactgaacc atcaaaggca aggtgggcat aactaccata atagacagca    14640
gaggcaaagc agccatcaga atagtctgac tcatgtagag ctctggcatt ggctaattaa    14700
tcatggtgtt cctagaagtg aaattgatgg gaaacctact gtattcctac ttgatttata    14760
taaacaaaaa actgccaggt agaatggact aaagactaat ctgaattata aaaacagaga    14820
atcatgggcc ctcaatcaat ttccagactc gaacctgtta cagttccaga acccactgaa    14880
tgaaggggag gctggatccc cttgaggaag acaccacta ggctactgac aacttatgct    14940
gttactcttt ctcccatcct tccctaagga gacctctggc cttttaccag ggtaactgtg    15000
tgtactggag aaagggaagt aatgagacat tcagaaagt actggacact ggctctgagc    15060
tgacgttgat tccagggtac ccaaaacgtt attgtggttc cccagttaaa gtaggggctt    15120
atggaggtta ggtaattaat ggagttttag ctcatttctg acttacagtg gttccagtgg    15180
gtccctggac ttatcctctg gtcatttcc cagtgccaaa atgcataatt tgtatagaca    15240
tacttattag ctggcagaaa tgccacattg gctccctgac tggtaggatg agggctatta    15300
tggtgggaaa ggccaaacag aagccattag agctgtctct acctagaaaa ataaaaaaat    15360
caaaaacaat atcccatccc tggagggact gaagtgatta gtgtcaccat caaggacttg    15420
aaagacgcag gggtggtgat tcccaccaca tccctgttca actctcccat ttgacctgtg    15480
cagaggacag atggatcttg gaaaatgatg gtggattatt ttaagcttaa ccaagtggtg    15540
actccaattg cagctgctct accagttgtg gttttgttgc ttgagcaaat taacacatct    15600
cctggtgcct ggtatgcagc cattggcttg gcaagtggct ttttctccat tcctgtccat    15660
aagacccacc agaagcaatt tgccttcagc tgacaaggcc agcattatac ctttaccacc    15720
ctacctcagg ggtgtatcaa ctctccagct ttgtgtcata atcttatttg gagagacctt    15780
gctcgctttt cacttccacg agatataaca ctggtccatt acattcatga cattatgatg    15840
attggataca gtgagcaaga agtagcaaac acactgaact tattggtgag acatttgtat    15900
gccagaggat gggaaataaa tccagctaaa atttagggac tttctacctc ggtaaaattt    15960
ctagggttcc agtggcatga gacctatgga gatattcctt ctaaggtgaa gcataacttg    16020
ctgcgtttgg cccctcttac aaccaagaaa gaggcacaat gcctggtggg cctatttgga    16080
ttttggaggc aacacattcc tcgtttgggt gtgttactct ggcccattta tcgagtgacc    16140
tgaaaggctg ccagatttaa gtgcagtcta gaacaaaaga aggctctgaa acaggtccag    16200
gctgctgtga agctgctct gccatttggg ccacatgacc ccgcagatcc aatggtgctt    16260
gaggtgtcag tggcagatag ggatgctgtt tggagccttt ggcaggcccc cataggtgaa    16320
tcacagtgga gacctctagg atttggagc aaggccctgc cacttctgca gataactact    16380
ctccttttga gagacagcta ttggtctgtt attgggcttt ggtggtaact gaacgtttga    16440
ctgtgggtca taaagtcacc atgctacctg aacctgccta tcatgaactg gttgctttct    16500
gacccatcta gccatgaagt gggtcagcac agcggcattt catcatcaaa ttgaagtggt    16560
gtgtatgtga tcgggcttga gcaggtcctg aaggcacaag taagttacat aaggaagtgg    16620
ctcaaatgcc catgttctcc actcatgcca ccctgccttc cctcccccag cctgcaccaa    16680
tggcctcatg gggagttccc tatgatcagt tgacagagga agggaagact aaggactggt    16740
tcatagatgg ttctgcacga tatgcaggca ccacccgaaa gtggacagct gcagcactat    16800
atccactttc taaatgcatg tgtacacttg tgctaagaaa atatctttat tttatttcct    16860
```

```
ttattttcc tttatcatgt gaccttagat ttatggactt cacatcagca tttaagcatt    16920
taagtgttgt tcatatcagc atttaaatat tgttaaccct atgtaataac ttttggtttg    16980
gggattggtg cgtttctggt tgtatgagga tagttgtatt atattaggca taattatgac    17040
cttattattg tctttatttg aagattatgt atgatttcag gatgtgtgta tgggttcaag    17100
ttgacaagga gttggacttg tgatggttaa tactgtcaac ttgattggat tgaaagatgc    17160
aaagtattaa tctcggttat gtctgtgagg gtgtggcaaa aggagattaa catttgagtc    17220
agtgggctgg gaaggcagac ccaccttaa  tctgggtaca caccatctaa tcaagttcca    17280
gtgtggccag attgtaaagc agggagaaaa atgtgaaaag actagactga attagcttcc    17340
cagcctacat ctttctcctg tgccaaatgc ttcctgctct tgaacatcgg actccaagtt    17400
cttcagcgtt gggagttgga ctggctttct tgctcctcag cttgcagagg gcctgttgtg    17460
gaaccttgtg atccgctgag ttaatactac ttaataagat cccctttata tacatataat    17520
atattatatt atatataata tatataatat atattatata taatatatat aatatattat    17580
atattatata taatatatat tatatattat ataatatata tattatatat aatatatatt    17640
atatattata tattatatat aatatatatt atatataata tatataaaat atatatatat    17700
cctattagtt ctgtccctct agagaaccct gactaataca atttatgtca ttaatctcat    17760
ttattgattt gtacacattg aaccaacctt atatcccagg aataaaacct acttgattgt    17820
ggtggattag cttttgatg  tactcttgga ttcaattgct ggtattttat tgagaattt    17880 tgcatctgtg ttcatcaagg atattggctt gaagttttct tttttgttg  ttccatatca    17940 gaatgatgac gacctcatag aatgagttag tctgtcctct tttatctttt ggaattgttt    18000
caggaggctt gatatcagct cttctttata tgactggtat actttggcta ggaatctctc    18060
tggtccaggg gttttctgg  tgtaggtttt taattactga ttcaacttca gaactcatta    18120
ctcattattg agttctaaaa ctcactttca tgtactcttc aaaagactgt cttcttctgt    18180
tgttgagcgg ggtgttctct caaggtcgtt taggtgaagg tggttgctgg tgttcttctg    18240
tatccttact gcttgtcttt ctctttttt  attgactact gaggattaat ggtgatgtgt    18300
ccaactttaa ctctagatta gtctatttct cttttagatt gtaactctgt tttatatatt    18360
ttgaagctct gttgttaggc atgtgtattt ggattgttag gtcttcttga tgatgacctt    18420
tatcattatg taatgtttct tcttatctct ggaagtattc gttgttctga agtctatttg    18480
tgctgatatg aatacagcct tcacagctct attttcacta gtatttgtat atctttttct    18540
cagcttttaa attgagatgt tcagaccatt tgcattaaag tagttgttaa taggattaaa    18600
tttaaatcta ccattaagtt ggttatttct ctttgtccca tttaaacttt gttccttttt    18660
tcatattttt ctgccttcat ttatattgag tttatctcca cgacttactt attaaattaa    18720
tttttaatgg ttttagtatt ttccacaatg tttataatat atactttgat tttttcacat    18780
tccaccttca aatgacagaa ttatactgga tatatagaaa tcttacatca ttgcacttct    18840
ccttcctccc tctcaaaatg ttgtgctatt gctctttgta atagaggctt acttctatta    18900
tgttatagct ctcataatac attgacacta tttttaccct gaataatcag ttgtttttta    18960
aagtgattat gactacaaat attttgaata atttctttat tttaccattt ctggtgctcc    19020
ttatctttta cagtagatcc caatttccat ctggagtcac attctttctg tgaaaaacaa    19080
cctttagcat ttcttatagc acgggactgc tgttgctgtt gtctttcagc ttttctttgt    19140
ctgaagaagt ctttattttg ccttcagttt ttaaaagtga ttttgctgag tatagatact    19200
```

```
gggttgagag tttcattcct tgtatcattt taacaatgat gttccattat attccgtttt    19260
gaatagtttc tgactagaaa tctgatcttt gtttctttgt attcaatagt tccttttct     19320 ctgactgcct ttaagatatt ctcatctttg tttttcaaca gtttgactat aatttgttta    19380
ttattaactt tttgtattta ttctgcttga ggtttcctga gctccttgga tttgcagatt    19440
gttgattttt attgttttg taaaattcat agccattatc tattctactg ttttgttttt     19500
tttttcactt ctctctctct gtattcttct ttttggactg taagtattca aatgttagat    19560
cattcatatt gcttcataaa ccttatatgc ttcttctgct tttttttttt tgtcaggaac    19620
tctttttttg tatctgtgtt ggtttggata agttctagta gactatgttc aagtttatgg    19680
attattttgt tagttgtgtc taattgactc ctcagtgcat tcagagaatt cttcatctct    19740
gatattataa atctcttcct agcattttca tgttactctt ttctatagtt tccatctctt    19800
tgctgaaatt ctcccctat ccatggatat tgtccacctt taccacaaga ttctttaaca     19860
tattaacata ggtatcatac aaacccaaac tgatagtttc cagatggtgt cttttctgag    19920
tctgtctgtc ttgattgctt tattatttaa cagtgactta tcttccctct tcagcttttg    19980
gtgtgtcttg taattgttta atcaaacact gggtatcata aatggaggaa cagtagagat    20040
tgcagtaaat attatttatg ctttgaaatg ggcacccatc ttctgttgaa aatatgtttt    20100
gtggtcaatt gagtcaacct agtaactggt tgaactgaat ttggcatttg tgcttgttgc    20160
ttttatctta aatgcaccac aggtttaaat tcctccagtg atgggttgct gctatctttt    20220
gcttagagtg gggcctgggg tgtggaagaa ttttctcagt gttcctatct attattagat    20280
tttagcagtc actgcatgcc tgcactacag aggggatatc ttcatacaca taatctaacc    20340
ccattgaaac tgctgtttct tcttaatgaa tgctcaatct ttggtggaaa taaacaaatg    20400
ctgtatctcc tggagccact tcagtcttag tcaggttctg cagggctttg aagggaatgc    20460
attctcagta ttcttgtgcc ttatttggat ggaacttgaa cctgtggtgg gtttggagag    20520
aaagagtagc agacgtctgc tatgttcaa tgcaggatgc tgggcacaag aaaatttcca     20580
gtctctcctc caaggaaata agatttgatc atctacctat ccctgagaag tgaagggctt    20640 tgcctgcgt gctagatgca aaaccatttt tctccccca ttgcccagaa acttaaggct      20700
ttggcttttc tgagcagtgg tctagggaat tgtgcaaggt tttcatattt gaccctgaca    20760
gcccatcacc acctacagct tgcagtgcca aatgtatctc cctctgatct ctcctgtcct    20820
gtggtcctca tgaacattaa aagagattt ctaaaaaga gcttgcacat gagcatagtt       20880
tctggtgaga agaattctga tatgttaact tcctctaaac ttttaaataa aatatttcta    20940
agaattaaat aaagttctag aatgatatga atctattcct ttggtttttt gcacgtctgt    21000
ctgcctgcta atcaagagaa gagaatggtc gtaattctca gagactttt cctgtttgtg     21060 tcataaatga cttcacattt ttttctgttc taagaactat tcagcttgat ttcttctgtt    21120
ttaattttag cagcacctga gcaaagccat gtggtccagg attgctacca tggtgatgga    21180
cagagttatc gaggcacgta ctccaccact gtcacaggaa ggacctgcca agcttggtca    21240
tctatgacac cacatcaaca taataggacc acagaaaact acccaaatgc gtatgtcatt    21300
aatcttacag taagcaaaac aaggtccaag taaaatttgt cttagaaaag gtgtgcgtca    21360
agctaacttc ttatgattaa attttctca cacatagaat gcatggcaaa atgtctgaga     21420
aacattactt tgagcaaaga gtatgataga agagaaatgt taagctggct ctctttcctg    21480
agagtttgat aaaatcagga gaatatctgg cggtggtgag gccacaataa tggaaaatca    21540
gaatgtttag acagagtcag cttcaacaac actcactaaa ggtcaatgtg atctttaccc    21600
```

```
cttgaaattc tataattcta atctccaatt cctgaagtga aggttgtgtt ggccttttct   21660
gtcttggctc acaagtaaat gatatgtgca tatctatgga aaggcgaatc tatcttttc    21720 tatatctatg tctattccaa cgggtagaaa cacctgggt cctgagcacc agtggtctga    21780
aggaatacgg gttgccagga agagagaagc aaaggcagga aggcagatga aagtaagaaa   21840
tgagacagat gctaaacaat aaaaagtgcg ggaagataga cagaagctgg ggtctgacca   21900
caccatggcc agtctttcac acataagtga ctaccaaaga caagaaaaaa tgatttccgc   21960
ttgttggaca atagatggta gaggaccaag ggaattgcga gagagagaac aatgagatca   22020
actcaacaga tgcactggtt ttcttcctgg agacccttcc tgcactgaag ggcaggagat   22080
ggagcccaaa aaaaactgta gccatcttgc tgaacagagg agggacattg gagtttggga   22140
ttattcaggt ggctaggatt ttctaggcct gctaacaatg agaacagatt tgtggaggaa   22200
aggagttcta gaaatatgca tagaaatctc ctcgagtcat tggctaaaca tgaagctgca   22260
tgtacacaga aaatagatcc acaagaaagt agggcaaaga acatctacgg aagagcagca   22320
actacaatgg aacagtgagc tcaataaaca tgacagagct caaatagcac taagggatat   22380 tggagttttgg accacacaga ggagagagac ttcactgaac atcttgggca ttcagtagag   22440
acccaggaaa agccatactt taggagtaga attagtatat tcttagaata aaggcagctc   22500
cacacaaaca atagcaaaac tgaaaaggaa gtctccaagc atcagaatga tgtccaagtc   22560
aatgaactgc ctctgagagg aaaactcaac catctttaga ggtaaacatc aaagtcaagt   22620
ggctcagcta tgcagtatcc acagtgtgag gcctaaatat aaaacttgac tacacataga   22680 aacctttttag tgtgacccac aagcaggagg aaaatcagcc aatacaaaca gacccagaag   22740
agacagaaat gattagaatg gcataaaaat ttgacatatc actatataat aattgagttc   22800
taggatttaa gaaaacatga atatagaatg caacagacac cttatccaga gacagtaaga   22860
gtataaagag ccaaatcgaa gaactactaa gagatatgtc ttaaatgaaa aaattactag   22920
atggcctccc catctagtta gacatttcag aagaaaatac caaatgaaaa ataattgcat   22980
agaacctaca gaaccagata cacacataca aaacacacgc atgcatacac acacactcaa   23040
acatgtataa gcttacaaac acacacacac atccacaaat gctgaaaaat gaaatcaacc   23100
gagccacaca gacataaagg aaaacataaa aagatttcct acatgtggga agcaagtcac   23160
agaaaggggg aaggagattg gaacagaaat atatactgaa agcaaggatg gctgaaaatt   23220
ttccaaatat aaagaagatt aaaaaatcac ggactcaaga agctcaatgg atcagaaaaa   23280
taatttctaa aatgacaatt ataggatgcc actgggtaca tagcagttca actgtcagag   23340
ggcaaagaca taatacacag aaaaatctcg taaggaacgg gaaaaacaaa agctgtgtc    23400 ttgctagagg aacagtgata caagtgacta atgtgttccc atcagaaaca ctgcaacctg   23460
gacacaaaag aataacatta aagtaataaa cgtaagaaag aagagctcaa ctgagaaggc   23520
tacatccagc aataaaatgc cttgaagttc atccatgttg gaggaatgca cattgtgcac   23580
tcccctaaac aaagaaaccg gaaactgtaa gactttggaa tcagcaggct tatgtaacaa   23640
aagaggtgac cctaaggaat taaggagaag aagaatagaa caagaaggga actttctgca   23700
gcctatataa tgaagaacct agcaattggc aaatgtagat gaaaatgcta catgttttct   23760
tgatcaaacg tttatatctt tttaaatgag agttgacgag ttgaagcaaa atgataccaa   23820
tatatttaac tttaccatat gtagaagtaa aaatttgaac atgtagcata aatcatgtag   23880
ggattaattg gaagtgtacc actgtaagtt tcttacctca tgcacgatag tatgtaatac   23940
```

```
taataaaagg ttaatgtgtg ggttcaaagg gatattgcaa atcctagagc aatcacaaag    24000
tttttaactc tgaggtttgt tgtataataa caatatttta tgtattcaaa agagggaagc    24060
caaggaagaa aaaaaagtct ttaaagagct ctggctctta gtacatccag ttgctcattg    24120
aatgagcttc ctggaatgga gggtctggga ctgagactag gccacatgtg tagagccact    24180
agagacacaa tgttggatcc ccatggccca taatacattt cccatttcct caggcagcca    24240
caggtcatga atgtgaggat actgagaggt tggagcaacg ttcttgggag gcataaggaa    24300
gagcgaatgc ttcaagatcc ccgcagccca aactcctcag ctgctttgcc tcctaattca    24360
ttgttttttg ctcctccata gctgtccgac ctcttcagat ctcttagtct tcctgccatc    24420
ttcctttatg ccatgggacc cactgttctt tcaactcatc ccccagttct ggagtggctg    24480
tggacagcag aggatagact gagagcagga gagaaggtcc tgcccaggaa cccattctag    24540
agatactgca ttctgcctgg gagcaagttt tccagggcag ctttgagaag tcttgcagaa    24600
acaaacctac ttgaccgaca tgatatggga atgacagaca gtaatactat ttgcacaatg    24660
cttttccatg ggaaaggtag agccttttca ctaggttttg agtacatgga gtgtgagagt    24720
tgacctggaa aggttatcct ccttgatgcc atgttttctc tgaagaacta catgttcgtt    24780
gcaactccca cattagaata tgaagtccta ccgagagaga tacggagact agacagatac    24840
agatgcattt gcatgtgaat acacaatccc acaatacaga cgtcaaaacc cataccagtt    24900
attccagaga gatggattgg gcagaaggca gaaggagaat actctgatcg tttttcggcc    24960
acgtgtgtgt gttatctcag tgtttctaag aagcgtttgc tactttagat tttttattta    25020
aaaaaaatag taataatcta ttaagtatga gagatgtgca gagaggatta gtgatcgaga    25080
gccatttttg ctggtggcaa tcatatggta cttttaatgg gaatattaga aaggcaccgg    25140
taatgacctt gttgcagcac aaaggagaga gtgtgggggtg cccctgcatg ttgtcccacc    25200
tcttgtgacg tgtatcgttt tggaatttcc agtggcttga tcatgaacta ctgcaggaat    25260
ccagatgctg tggcagctcc ttattgttat acgagggatc ccggtgtcag gtgggagtac    25320
tgcaacctga cgcaatgctc agacgcagaa gggactgccg tcgcgcctcc gactgttacc    25380
ccggttccaa gcctagaggc tccttccgaa caaggtaagg agtctgtggc cagacatcta    25440
cacgcttcga tgctgggatg aaaagccatg gaaattccca ctgatgcagc cgccttcaat    25500
ggtaaacgga tgctcgagtg ttgcctgagt tctaccatgt aggaggaagc ctccgtgcac    25560
tctctggggg agccagcgga gtgatttctg gtgcaacgtg gttgggcttt gtctttagga    25620
tgggcacaaa ccctccaggg ggatcgactt caaaattcac cttgttgtaa acgggctac    25680 ctcagtgtcc cagccaaaat ttttattgta acatgctgtc aggtgtgtca ctctttccaa    25740
gccagtaagc ttttccgggg atttcttcaa gtagccagca ttcagagcaa tcttcagcat    25800
tgcagattct gagaaatgtg gctctggagc ctgtcaccct cgagaaacct aagagggctg    25860
cattgattcc atgtggccct gggtctatgg agcagtacat gagctcccag tgctctaagg    25920
ctcttcagcc ctaggctttg aagggagtga tttctcagta ttcttaaacc tctttctgat    25980
gacacttgta cctgtgaggg gtctagagag aaagagtagt agactcctac tttactacaa    26040
ttcaggatgc agggcatgag aggattccct ctctcctcca agggaagaag cttttggcgt    26100
gcacacatcc ctgagaagca aagtgtcttt gtcttcagtc agatacatag gaccgttttc    26160
tgccccatgg cccggaagcc aaaggccttg gctttcatga tcaacggtct agggaaacat    26220
gcaaaatttc catgtctgtc ccaaactctg cccccgacag ccaattacca cctgcagccc    26280
gcattgccaa atgcggtgcc gtttgcatga agattcagta gagtttccta gaaaggtgct    26340
```

```
acctcgtgag ctcactttcc aatgaggaat ctgatctgtt gtgtttctct aaggtgtcag    26400
gtgaaatatt tccaagaact tactacagtt ctagaatggg aggaatctgt tgctttggtg    26460
tttgtttgtt ggtcggtttt ctcacatcca tctgcctatg gataaggaaa agagaacggt    26520
cgtaattctc atagactcct ttctggttgt gtcacaaatg gcttcacatg tttctctatg    26580
ctcagagata ctcagcttga tttcccgtgt tttcatttca gcaccgactg agcaaaggcc    26640
tggggtgcag gagtgctacc atggtaatgg acagagttat cgaggcacat actccaccac    26700
tgtcacagga agaacctgcc aagcttggtc atctatgaca ccacactcgc atagtcggac    26760
cccagaatac tacccaaatg cgtatgtctt tgttctttac cataagagaa gaaagggcca    26820
agtgaagttt ctgttacaag agatgtgtct caagctgagt tctccgaact caacttgtga    26880
cagatgcaga tggcgtagca aaatgtctca ggatgattgc cttggagcta agggtctgag    26940
agaagggaaa tgttaagctc cctctccttc ctcctagttc tattgagcag aagggaaatc    27000
tggaggtgag gagatcacat tatgaagaaa gtcagaatga caaggacca gacacttaga    27060 ttacccttcc acaacaccaa ctaaacgtca atggagactt tccagttgga attccgttat    27120
tctggcttcc acttcctgaa gggaaggttg cgtttgcctt ttctctctgg gttcaagagg    27180
aaagaatagg tgcttattta tggacaggtg aattgatctg tttctatatc tacgtatatt    27240
ccgattgtca gaaaaacact cgttcctaag taccagtggc ctgaagggat acaggttccc    27300
agcaagagaa gatccaagga aggaaggcag atgagagtca gcacagagag ggatgctgaa    27360
aagtaaaagg gatgggtgga tggagagaag cccgggtctg accacccaat ggccaatatt    27420
ttggccacaa gcgactacca gagacatgga aaaatggttt ctacatgtgg gacaacagat    27480
ggtagaggac ctagagaatt gagagagggg caatgatggg ctccactccg cagatgcctt    27540
ggctttcttc ctggataccc ttcctgcact gaatagcaag gagatggagc ccaagcagac    27600
tgtagccatc ttgctgaatg gaggagaggg attggagttt gggatgactg tggtagctga    27660
aatttttcta ggtctgctag aaataagaac tggtttgtgt ggaggaaaag agctctacaa    27720
atacgcatag aagtctcctc cagtcgttgg cctgacatga cgctgcctgt gcacaggaaa    27780
tggttccacg agaaagtgtg gcaaagaaca tttactgaga aacagcaagt acaagagcac    27840
aggaagctca ataagaaga gagagatcac atagcactct gggatactgg agttcttccc    27900
agctagacca gagagtcctc acggagcaca ttgccaattc agtggagacc ccagaacagc    27960
cgtaatttaa aggtacactt agtatattac tagaataaag tcagctgcag acaacccctt    28020
gcacagctgg aaagcaagtg tccaagcatc aaatcggttt ccaatcaatg aagtgcctgt    28080
gagaggaaat ctcaactctc tttagaagta aacaacaaag tcgattgcct cagctatgcg    28140
gtatccgcag agtgagtcct aaatttaaaa tctgactaca tgtagaaaag cgtttcgtgt    28200
gacccatgac caggaaataa atcgggtaat acaaacaggc tcaggaatga gagaaatgat    28260
tagaattgcg tgaaaatttg acatatcagt atgataactg atttcaaata tttaaaaaaa    28320
caacatgcaa gaaagcagat atcatatcaa gagaaattaa cagtacagaa tagccaaatt    28380
aaattaaaga ggtagtataa aaaagtatg tcttaattga aaaaaattac tgtatggccg    28440
gctgatcaat ttagacgttt cagaggaaaa cattacccaa cacacaattc tagagaacct    28500
acagaatgag ctacacacac acacacacac acacacacac acactgaaaa cacacccata    28560
ctcacacaca cgcagaaact cacaagttct aacacacaca gacacgcgca cccctgaaga    28620
aacagtgaaa tataaaatta agcgagcctc acagacatgt aggaaaatat gaaaagattt    28680
```

```
cctgcatgtg ggaagcaagt cacagtaaag agcaagggag tttataatag aaacaaatac   28740
cagaatcaag gatggctgat aacttttcaa ttacgaagaa cattaaaaaa aatcacagaa   28800
tcgtgaaact caagggatca tataggaat ttcggaaaaa aaacccaacc tgtatgatgt    28860
acttttgtac atcacagttc gaaggtaaca aggcaaagat gtaataagaa gaaacctgtc   28920
acgagaaact ggaggaaaaa gagctgtgtc ttcctacaag tacactgata caaattgcca   28980
atgtgttcac ctcagaaaca ctggaagcca gataccaggg aatattgtta aaatgataat   29040
caggaacaaa aagagatcaa ccgggaatgc tgaatccagc aataaaatgc cttgaaggtc   29100
atccatgtcg gataaatgca tattgtgcac tgccccaaag aaagaaaccg gaaactgtaa   29160
gaattggaaa tcagcaggct tatgtaacaa gagaggtgac ccgaaggaat taggtagaag   29220
aagaattgaa caagaaagga acttctgca gcccacgtaa tgaagaatcc agcaattggc    29280
aaatgtagat agatgtaaat gcaaaatatt ttcttgatca aatttctata tctttgtaaa   29340
tgagagttga ctacttgaaa caaaatgata gcaagatatt taacttcagc atatgtagag   29400
gtaagaattt gaaatggtag cataaatcac gaagggatta attcgaagtg taccgttgta   29460
agtttcttta cctcatgcac gatggtgtgt catattaata aaagggtact gtgcgggttc   29520
gaagggatat tgcaaatcct agagcaatca caaaggtttg aactctgagg tttttggtat   29580
aataagaata gtccatgcat tcaaaagagg gaagccaagg aagaactaga agtctttcaa   29640
gagctcaggc tcttatacat ccagttgctc attgaaccag cttcctggaa tggagggtct   29700
ggggttgaga ctaggccaca agtctagagt ctctagagag acagtgttgg aaccccatgg   29760
cccataatac atttcccatt ttctcaggca gccagaggtc atgaatgtga ggatactggg   29820
aggttggagc aacgttcttg ggaggcataa ggaagagcga atgcttcaag atccccgcag   29880 cccaaaactac tcgcctgctt tgccccctaa tgcattttc tctgctgctc cgtagctgtc    29940
cgacctcttc agatctctta gtccaccctg ccgtcttcct ttatgccatg ggtcccactg   30000
ttctttcaac tcatcccct ttccctcagt cccggagtag ctgcggccag cagagggtag    30060
actgagagca ggagagaagg acctgcctag gaaccccttc tagagatact gcatcctgcc   30120
tgggagcaag ttttccaggg cagctttgag aagtcttgga gaaacaaacc tactaaacct   30180
gacagacagt aatactattt gcacaatgct tttctgtggg aaaggtagag ccttttcact   30240
acgtattgag tacatagagt gtgagggttg acctggaacg gctatcctcc tggatgacgt   30300
gtgttttctg aagaactaca tgttcgttgc aactcccaca ttagaatatg aagtcctacc   30360
gagagagata cggagactag acagatacag atgcatttgc atgtgaatac acaatcccac   30420
aatacagacg tcaaaaccca taccagttat tccagagaga tggattgggc agaaggcaga   30480
aggagaatac tctgatcgtt tttcggccac gtgtgtgtgt tatctcagtg tttctaagaa   30540
gcgtttgcta ctttagattt tttatttaaa aaaatagtaa taatctatta agtatgagag   30600
atgtgcagag aggattagtg atcgagagcc attttttgctg gtggcaatca tatggtactt   30660
ttaatgggaa tattagaaag gcaccggtaa tgaccttgtt gcagcacaaa ggagagagtg   30720
tggggtgccc ctgcatgttg tcccacctct tgtgacgtgt atcgttttgg aatttccagt   30780
ggcttgatca tgaactactg caggaatcca gatgctgtgg cagctcctta ttgttatacg   30840
agggatcccg gtgtcaggtg ggagtactgc aacctgacgc aatgctcaga cgcagaaggg   30900
actgccgtcg cgcctccgac tgttaccccg gttccaagcc tagaggctcc ttccgaacaa   30960
ggtaaggagt ctgtggccag acatctacac gcttcgatgc tgggatgaaa agccatgaa    31020 attcccactg atgcagccgc cttcaatggt aaacggatgc tcgagtgttg cctgagttct   31080
```

```
accatgtagg aggaagcctc cgtgcactct ctgggggagc cagcggagtg atttctggtg   31140
caacgtggtt gggctttgtc tttaggatgg gcacaaaccc tccaggggga tcgacttcaa   31200
aattcacctt gttgtaaaac gggctacctc agtgtcccag ccaaaatttt tattgtaaca   31260
tgctgtcagg tgtgtcactc tttccaagcc agtaagcttt tccggggatt tcttcaagta   31320
gccagcattc agagcaatct tcagcattgc agattctgag aaatgtggct ctggagcctg   31380
tcaccctcga gaaacctaag agggctgcat tgattccatg tggccctggg tctatggagc   31440
agtacatgag ctcccagtgc tctaaggctc ttcagcccta ggctttgaag ggagtgattt   31500
ctcagtattc ttaaacctct ttctgatgac acttgtacct gtgaggggtc tagagagaaa   31560
gagtagtaga ctcctacttt actacaattc aggatgcagg gcatgagagg attccctctc   31620
tcctccaagg gaagaagctt ttggcgtgca cacatccctg agaagcaaag tgtctttgtc   31680
ttcagtcaga tacataggac cgttttctgc cccatggccc ggaagccaaa ggccttggct   31740
ttcatgatca acggtctagg gaaacatgca aaatttccat gtctgtccca aactctgccc   31800
ccgacagcca attccaccct gcagcccgca ttgccaaatg cggtgccgtt tgcatgaaga   31860
ttcagtagag tttcctagaa aggtgctacc tcgtgagctc actttccaat gaggaatctg   31920
atctgttgtg tttctctaag gtgtcaggtg aaatatttcc aagaacttac tacagttcta   31980
gaatgggagg aatctgttgc tttggtgttt gtttgttggt cggttttctc acatccatct   32040
gcctatggat aaggaaaaga gaacggtcgt aattctcata gactcctttc tggttgtgtc   32100
acaaatggct tcacatgttt ctctatgctc agagatactc agcttgattt cccgtgtttt   32160
catttcagca ccgactgagc aaaggcctgg ggtgcaggag tgctaccatg gtaatggaca   32220
gagttatcga ggcacatact ccaccactgt cacaggaaga acctgccaag cttggtcatc   32280
tatgacacca cactcgcata gtcggacccc agaatactac ccaaatgcgt atgtctttgt   32340
tctttaccat aagagaagaa agggccaagt gaagtttctg ttacaagaga tgtgtctcaa   32400
gctgagttct ccgaactcaa cttgtgacag atgcagatgg cgtagcaaaa tgtctcagga   32460
tgattgcctt ggagctaagg gtctgagaga agggaaatgt taagctccct ctccttcctc   32520
ctagttctat tgagcagaag ggaaatctgg aggtgaggag atcacattat gaagaaagtc   32580
agaatgacaa aggaccagac acttagatta cccttccaca acaccaacta aacgtcaatg   32640
gagactttcc agttggaatt ccgttattct ggcttccact tcctgaaggg aaggttgcgt   32700
ttgccttttc tctctgggtt caagaggaaa gaataggtgc ttatttatgg acaggtgaat   32760
tgatctgttt ctatatctac gtatattccg attgtcagaa aaacactcgt tcctaagtac   32820
cagtggcctg aagggataca ggttcccagc aagagaagat ccaaggaagg aaggcagatg   32880
agagtcagca cagagaggga tgctgaaaag taaaagggat gggtgatgg agagaagccc   32940
gggtctgacc acccaatggc caatattttg gccacaagcg actaccagag acatggaaaa   33000
atggtttcta catgtgggac aacagatggt agaggaccta gagaattgag agaggggcaa   33060
tgatgggctc cactccgcag atgccttggc tttcttcctg gatacccttc ctgcactgaa   33120
tagcaaggag atggagccca agcagactgt agccatcttg ctgaatggag gagagggatt   33180
ggagtttggg atgactgtgg tagctgaaat ttttctaggt ctgctagaaa taagaactgg   33240
tttgtggagg aaaagagctc tacaaatacg catagaagtc tcctccagtc gttggcctga   33300
catgacgctg cctgtgcaca ggaaatggtt ccacgagaaa gtgtggcaaa gaacatttac   33360
tgagaaacag caagtacaag agcacaggaa gctcaataaa gaagagagag atcacatagc   33420
```

```
actctgggat actggagttc ttcccagcta gaccagagag tcctcacgga gcacattgcc    33480
aattcagtgg agaccccaga acagccgtaa tttaaaggta cacttagtat attactagaa    33540
taaagtcagc tgcagacaac cccttgcaca gctggaaagc aagtgtccaa gcatcaaatc    33600
ggtttccaat caatgaagtg cctgtgagag gaaatctcaa ctctctttag aagtaaacaa    33660
caaagtcgat tgcctcagct atgcggtatc cgcagagtga gtcctaaatt taaaatctga    33720
ctacatgtag aaaagcgttt cgtgtgaccc atgaccagga aataaatcgg gtaatacaaa    33780
caggctcagg aatgagagaa atgattagaa ttgcgtgaaa atttgacata tcagtatgat    33840
aactgatttc aaatatttaa aaaaacaaca tgcaagaaag cagatatcat atcaagagaa    33900
attaacagta cagaatagcc aaattaaatt aaagagctag tataaaaaaa gtatgtctta    33960
attgaaaaaa attactgtat ggccggctga tcaatttaga cgtttcagag gaaaacatta    34020
cccaacacac aattctagag aacctacaga atgagctaca cacacacaca cacacacaca    34080
cacaaactga aaacacaccc atactcacac acacgcagaa actcacaagt tctaacacac    34140
acagacacgc gcacccctga agaaacagtg aaatataaaa ttaagcgagc ctcacagaca    34200
tgtaggaaaa tatgaaaaga tttcctgcat gtgggaagca agtcacagta aagagcaagg    34260
gagtttggaa tagaaacaaa taccggaatc aaggatggct gataactttt caattacgaa    34320
gaacattaaa aaaaatcaca gaatcgtgaa actcaaggga tcacataggg aatttcggaa    34380
aaaaacccca acctgtatga tgtacttttg tacatcacag ttcgaaggta acaaggcaaa    34440
gatataataa gaagaaacct gtcacgagaa actggaggaa aaagagctgt gtcttcctac    34500
aagtacactg atacaaattg ccaatgtgtt cacctcagaa acactggaag ccagatacca    34560
gggaatattg ttaaaatgat aatcaggaac aaaagagat caaccgggaa tgctgaatcc    34620
agcaataaaa tgccttgaag atcatccatg tcggataaat gcatattgtg cactgcccca    34680
aagaaagaaa ccggaaactg taagaattgg aaatcagcag cttatgtaa caagagaggt    34740 gacccgaagg aattaggtag aagaagaatt gaacaagaaa ggaactttct gcagcccacg    34800
taatgaagaa tccagcaatt ggcaaatgta gatagatgta aatgcaaaat attttcttga    34860
tcaaatttct atatctttgt aaatgagagt tgactacttg aaacaaaatg atagcaagat    34920
atttaacttc agcatatgta gaggtaagaa tttgaaatgg tagcataaat cacgaaggga    34980
ttaattcgaa gtgtaccgtt gtaagttttct ttacctcatg cacgatggtg tgtcatatta    35040 ataaagggt actgtgcggg ttcgaaggga tattgcaaat cctagagcaa tcacaaaggt    35100
ttgaactctg aggttttttgg tataataaga atagtccatg cattcaaaag agggaagcca    35160
aggaagaact agaagtcttt caagagctca ggctcttata catccagttg ctcattgaac    35220
cagcttcctg gaatggaggg tctggggttg agactaggcc acaagtctag agtctctaga    35280
gagacagtgt tggaacccca tggcccataa tacatttccc attttctcag gcagccagag    35340
gtcatgaatg tgaggatact gggaggttgg agcaacgttc ttgggaggca taaggaagag    35400
cgaatgcttc aagatccccg cagcccaaac tactcgcctg ctttgccccc taatgcattt    35460
ttctctgctg ctccgtagct gtccgacctc ttcagatctc ttagtccacc ctgccgtctt    35520
cctttatgcc atgggtccca ctgttctttc aactcatccc cctttccctc agtcccggag    35580
tagctgcggc cagcagaggg tagactgaga gcaggagaga aggacctgcc taggaacccc    35640
ttctagagat actgcatcct gcctgggagc aagttttcca gggcagcttt gagaagtctt    35700
ggagaaacaa acctactaaa cctgacagac agtaatacta tttgcacaat gcttttctgt    35760
gggaaaggta gagcctttc actacgtatt gagtacatag agtgtgaggg ttgacctgga    35820
```

```
acggctatcc tcctggatga cgtgtgtttt ctgaagaact acatgttcgt tgcaactccc   35880
acattagaat atgaagtcct accgagagag atacggagac tagacagata cagatgcatt   35940
tgcatgtgaa tacacaatcc cacaatacag acgtcaaaac ccataccagt tattccagag   36000
agatggattg ggtaggaggc agaaggagaa tactctgatc gtttttcggc cacgtgtgtg   36060
tgttatctca gtgtttctaa gaagcgtttg ctactttaga tttttttattt aaaaaaaata   36120 gtaataatct attaagtatg agagatgtgc agagaggatt agtgatcgag agccattttt   36180
gctggtggca atcatatggt acttttaatg ggaatattag aaaggcaccg gtaatgacct   36240
tgttgcagca caaggagag agtgtggggt gcccctgcat gttgtcccac ctcttgtgac   36300
gtgtatcgtt ttggaatttc cagtggcttg atcatgaact actgcaggaa tccagatgct   36360
gtggcagctc cttattgtta tacgagggat cccggtgtca ggtgggagta ctgcaacctg   36420
acgcaatgct cagacgcaga agggactgcc gtcgcgcctc cgactgttac cccggttcca   36480
agcctagagg ctccttccga acaaggtaag gagtctgtgg ccagacatct acacgcttcg   36540
atgctgggat gaaaagccat ggaaattccc actgatgcag ccgccttcaa tggtaaacgg   36600
atgctcgagt gttgccggag ttctgccatg ttgggggaag cctccgtgta ctctctgggg   36660
gagccagcgg agtgatttct ggtgcaactt gggtgggctt tgtctttaga atgggcacaa   36720
accttccagg gtgatgggct tcacaactca cctccttcta aaatgggcta tctcagtgtc   36780
ttagccaaaa ttttattgt aacgtgctgt caggtgtgtg attctttctg tcgcagtaag   36840
cttttctggg gatttcttca gtagccagc agtcagtgca atcttcagca ttgcagattt   36900
caaaaaatgt ggctctggag cctgtcatcc tcgagaaacc taacagggct gcattaattc   36960
catatggtcc tgggtctatg gagcagtata tgagctccca atgctctaag gctcttcagt   37020
cctaggcttt gaagggagtg atttctcagt gttcttaaac ctctttctga tggcacttgt   37080
acctgtgagg ggtctagaga gaaaggttag tagacttctc ctttactgca attcaggatg   37140
cagggcatga gaagattccc tccctcctcc aagggaagaa ggttttggcg tgcacacatc   37200
cttgagaagc aaagtgtctt tgccttcagt cagatatata ggatcgtttt ctgccccatg   37260
gcctggaagc cagaggcctt ggctttcatg atcaacgatc tagggaaaca tgcaaaattt   37320
ccatgtcttt cccctcctct gccctcgaca gccaattacc acctgcatcc tgcattgcca   37380
aatgcagtgc cctttgtatg aacattcagt agagtttcat agaaaggtgc tacttcgtga   37440
gcgcactttg cagtgagaag gagtctgttc tgttctgttt ttctaaggat ttcaggtgaa   37500
atatttccta gaacttacta cagttctaga ttggtaggaa tctgtaggtt tgctgtatgt   37560
tttttggttg gttttctccc atccatctgc ctacaggtaa gggaaagata acgttcgtaa   37620
ttctcataga ctcctttctg gttgtgtcat aaatggcttc acatatttcg ttattctcag   37680
agatactcag tttatttctt gtgttttcat ttcagcaccg actgagcaga ggcctggggt   37740
gcaggagtgc taccacggta atggacagag ttatcgaggc acatactcca ccactgtcac   37800
tggaagaacc tgccaagctt ggtcatctat gacaccacac tcgcatagtc ggaccccaga   37860
atactaccca aatgcgtatg tctttgttct ttaccataag agaagaaagg gccaagtgaa   37920
gtttctgtta caagagatgt gtctcaagct gagttctccg aactcaactt gtgacagatg   37980
cagatggcgt agcaaaatgt ctcaggatga ttgccttgga gctaagggtc tgagagaagg   38040
gaaatgttaa gctccctctc cttcctccta gttctattga gcagaaggga aatctggagg   38100
tgaggagatc acattatgaa gaaagtcaga atgacaaagg accagacact tagattaccc   38160
```

```
ttccacaaca ccaactaaac gtcaatggag actttccagt tggaattccg ttattctggc   38220
ttccacttcc tgaagggaag gttgcgtttg ccttttctct ctgggttcaa gaggaaagaa   38280
taggtgctta tttatggaca ggtgaattga tctgtttcta tatctacgta tattccgatt   38340
gtcagaaaaa cactcgttcc taagtaccag tggcctgaag ggatacaggt tcccagcaag   38400
agaagatcca aggaaggaag gcagatgaga gccagcacag agagggatgc tgaaaagtaa   38460
aagggatggg tggatggaga gaagcccggg tctgaccacc caatggccaa tattttggcc   38520
acaagcgact accagagaca tggaaaaatg gtttctacat gtgggacaac agatggtaga   38580
ggacctagag aattgagaga ggggcaatga tgggctccac tccgcagatg ccttggcttt   38640
cttcctggat acccttcctg cactgaatag caaggagatg gagcccaagc agactgtagc   38700
catcttgctg aatggaggag agggattgga gtttgggatg actgtggtag ctgaaatttt   38760
tctaggtctg ctagaaataa gaactggttt gtggaggaaa agagctctac aaatacgcat   38820
agaagtctcc tccagtcgtt ggcctgacat gacgctgcct gtgcacagga aatggttcca   38880
cgagaaagtg tggcaaagaa catttactga gaaacagcaa gtacaagagc acaggaagct   38940
caataaagaa gagagagatc acatagcact ctgggatact ggagttcttc ccagctagac   39000
cagagagtcc tcacggagca cattgccaat tcagtggaga ccccagaaca gccgtaattt   39060
aaaggtacac ttagtatatt actagaataa agtcagctgc agacaacccc ttgcacagct   39120
ggaaagcaag tgtccaagca tcaaatcggt ttccaatcaa tgaagtgcct gtgggaggaa   39180
atctcaactc tctttagaag taaacaacaa agtcgattgc ctcagctatg cggtatccgc   39240
agagtgagtc ctaaatttaa aatctgacta catgtagaaa agcgtttcgt gtgacccatg   39300
accaggaaat aaatcgggta atacaaacag gctcaggaat gagagaaatg attagaattg   39360
cgtgaaaatt tgacatatca gtatgataac tgatttcaaa tatttaaaaa aacaacatgc   39420
aagaaagcag atatcatatc aagagaaatt aacagtacag aatagccaaa ttaaattaaa   39480
gagctagtat aaaaaaagta tgtcttaatt gaaaaaaatt actgtatggc cggctgatca   39540
aattagacgt ttcagaggaa acattaccc aacacacaat tctagagaac ctacagaatg   39600
agctacacac acacacacac acacacacac acacactgaa aacacaccca tactcacaca   39660
cacgcagaaa ctcacaagtt ctaacacaca cagacacgcg caccccctgaa gaaacagtga   39720 aatataaaat taagcgagcc tcacagacat gtaggaaaat atgaaaagat ttcctgcatg   39780
tgggaagcaa gtcacagtaa agagcaaggg agtttggaat agaaacaaat accggaatca   39840
aggatggctg ataactttc aattacgaag aacattaaaa aaaatcacag aatcgtgaaa   39900
ctcaagggat catataggga atttcggaaa aaaacccaa cctgtatgat gtacttttgt   39960
acatcacagt tcgaaggtaa caaggcaaag atataataag aagaaacctg tcacgagaaa   40020
ctggaggaaa aagagctgtg tcttcctaca agtacactga tacaaattgc caatgtgttc   40080
acctcagaaa cactggaagc cagataccag ggaatattgt taaatgata atcaggaaca   40140 aaaagagatc aaccgggaat gctgaatcca gcaataaaat gccttgaaga tcatccatgt   40200
cggataaatg catattgtgc actgccccaa agaaagaaac cggaaactgt cagaattgga   40260
aatcagcagg cttatgtaac aagagaggtg acccgaagga attaggtaga agaagaattg   40320
aacaagaaag gaactttctg cagcccacgt aatgaagaat ccagcaattg gcaaatgtag   40380
atagatgtaa atgcaaaata tttttcttga t caaatttcta tatctttgta aatgagagtt   40440
gactacttga aacaaaatga tagcaagata tttaacttca gcatatgtag aggtaagaat   40500
ttgaaatggt agcataaatc acgaagggat taattcgaag tgtaccgttg taagtttctt   40560
```

```
tacctcatgc acgatggtgt gtcatattaa taaaagggta ctgtgcgggt tcgaagggat   40620
attgcaaatc ctagagcaat cacaaaggtt tgaactctga ggttttttggt ataataagaa  40680 tagtccatgc attcaaaaga gggaagccaa ggaagaacta gaagtctttc aagagctcag   40740
gctcttatac atccagttgc tcattgaacc agcttcctgg aatggagggt ctggggttga   40800
gactaggcca caagtctaga gtctctagag agacagtgtt ggaaccccat ggcccataat   40860
acatttccca ttttctcagg cagccagagg tcatgaatgt gaggatactg ggaggttgga   40920
gcaacgttct tgggaggcat aaggaagagc gaatgcttca agatccccgc agcccaaact   40980
actcgcctgc tttgccccct aatgcatttt tctctgctgc tccgtagctg tccgacctct   41040
tcagatctct tagtccaccc tgccgtcttc ctttatgcca tgggtcccat tgttctttca   41100
actcatcccc ctttccctca gtcccggagt agctgcggcc agcagagggt agactgagag   41160
caggagagaa ggacctgcct aggaacccct tctagagata ctgcatcctg cctgggagca   41220
agttttccag ggcagctttg agaagtcttg gagaaacaaa cctactaaac ctgacagaca   41280
gtaatactat ttgcacaatg cttttctgtg ggaaaggtag agccttttca ctacgtattg   41340
agtacataga gtgtgagggt tgacctggaa cggctatcct cctggatgac gtgcgttttc   41400
tgaagaacta catgttcgtt gcaactccca cattagaata tgaagtccta ccgagagaga   41460
tacggagact agacagatac agatgcattt gcatgtgaat acacaatccc acaatacaga   41520
cgtcaaaacc cataccagtt attccagaga gatggattgg gcagaaggca gaaggagaat   41580
actctgatcg ttttttcggcc acgtgtgtgt gttatctcag tgtttctaag aagcgtttgc   41640
tactttagat tttttattta aaaaaaatag taataatcta ttaagtatga gagatgtgca   41700
gagaggatta gtgatcgaga gccatttttg ctggtggcaa tcatatggta cttttaatgg   41760
gaatattaga aaggcaccgg taatgacctt gttgcagcac aaaggagaga gtgtggggtg   41820
cccctgcatg ttgtcccacc tcttgtgacg tgtatcgttt tggaatttcc agtggcttga   41880
tcatgaacta ctgcaggaat ccagatgctg tggcagctcc ttattgttat acgagggatc   41940
ccggtgtcag gtgggagtac tgcaacctga cgcaatgctc agacgcagaa gggactgccg   42000
tcgcgcctcc gactgttacc ccggttccaa gcctagaggc tccttccgaa caaggtaagg   42060
agtctgtggc cagacatcta cacgcttcga tgctgggatg aaaagccatg gaaattccca   42120
ctgatgcagc cgccttcaat ggtaaacgga tgctcgagtt ttgcctgagt ctaccatgt   42180 aggaggaagc ctccgtgcac tctctggggg agccagcgga gtgatttctg gtgcaacgtg   42240
gttgggcttt gtctttagga tgggcacaaa ccctccaggg ggatcgactt caaaattcac   42300
cttgttgtaa aacgggctac ctcagtgtcc cagccaaaat ttttattgta acatgctgtc   42360
aggtgtgtca ctctttccaa gccagtaagc ttttccgggg atttcttcaa gtagccagca   42420
ttcagagcaa tcttcagcat tgcagattct gagaaatgtg gctctggagc ctgtcaccct   42480
cgagaaacct aagagggctg cattgattcc atgtggccct gggtctatgg agcagtacat   42540
gagctcccag tgctctaagg ctcttcagcc ctaggctttg aagggagtga tttctcagta   42600
ttcttaaacc tctttctgat gacacttgta cctgtgaggg gtctagagag aaagagtagt   42660
agactcctac tttactacaa ttcaggatgc agggcatgag aggattccct ctctcctcca   42720
agggaagaag ctttttggcgt gcacacatcc ctgagaagca aagtgtcttt gtcttcagtc   42780
agatacatag gaccgttttc tgccccatgg cccggaagcc aaaggccttg gctttcatga   42840
tcaacggtct agggaaacat gcaaaatttc catgtctgtc ccaaactctg cccccgacag   42900
```

```
ccaattacca cctgcagccc gcattgccaa atgcggtgcc gtttgcatga agattcagta    42960
gagtttccta gaaaggtgct acctcgtgag ctcactttcc aatgaggaat ctgatctgtt    43020
gtgtttctct aaggtgtcag gtgaaatatt tccaagaact tactacagtt ctagaatggg    43080
aggaatctgt tgctttggtg tttgtttgtt ggtcggtttt ctcacatcca tctgcctatg    43140
gataaggaaa agagaacggt cgtaattctc atagactcct ttctggttgt gtcacaaatg    43200
gcttcacatg tttctctatg ctcagagata ctcagcttga tttcccgtgt tttcatttca    43260
gcaccgactg agcaaaggcc tggggtgcag gagtgctacc atggtaatgg acagagttat    43320
cgaggcacat actccaccac tgtcacagga agaacctgcc aagcttggtc atctatgaca    43380
ccacactcgc atagtcggac cccagaatac tacccaaatg cgtatgtctt tgttctttac    43440
cataagagaa gaaagggcca agtgaagttt ctgttacaag agatgtgtct caagctgagt    43500
tctccgaact caacttgtga cagatgcaga tggcgtagca aaatgtctca ggatgattgc    43560
cttggagcta agggtctgag agaagggaaa tgttaagctc cctctccttc ctcctagttc    43620
tattgagcag aagggaaatc tggaggtgag gagatcacat tatgaagaaa gtcagaatga    43680
caaaggacca gacacttaga ttaccctttcc acaacaccaa ctaaacgtca atggagactt    43740
tccagttgga attccgttat tctggcttcc acttcctgaa gggaaggttg cgtttgcctt    43800
ttctctctgg gttcaagagg aaagaatagg tgcttattta tggacaggtg aattgatctg    43860
tttctatatc tacgtatatt ccgattgtca gaaaaacact cgttcctaag taccagtggc    43920
ctgaagggat acaggttccc agcaagagaa gatccaagga aggaaggcag atgagagtca    43980
gcacagagag ggatgctgaa aagtaaaagg gatgggtgga tggagagaag cccgggtctg    44040
accacccaat ggccaatatt ttggccacaa gcgactacca gagacatgga aaaatggttt    44100
ctacatgtgg gacaacagat ggtagaggac ctagagaatt gagagagggg caatgatggg    44160
ctccactccg cagatgcctt ggctttcttc ctggataccc ttcctgcact gaatagcaag    44220
gagatggagc ccaagcagac tgtagccatc ttgctgaatg gaggagaggg attggagttt    44280
gggatgactg tggtagctga aattttctca ggtctgctag aaataagaac tggtttgtgg    44340
aggaaaagag ctctacaaat acgcatgaaa gtctcctcca gtcgttggcc tgacatgacg    44400
ctgcctgtgc acaggaaatg gttccacgag aaagtgtggc aaagaacatt tactgagaaa    44460
cagcaagtac aagagcacag gaagctcaat aaagaagaga gagatcacat agcactctgg    44520
gatactggag ttcttcccag ctagaccaga gagtcctcac ggagcacatt gccaattcag    44580
tggagacccc agaacagccg taatttaaag gtacacttag tatattacta gaataaagtc    44640
agctgcagac aacccttgc acagctggaa agcaagtgtc caagcatcaa atcggtttcc    44700
aatcaatgaa gtgcctgtga gaggaaatct caactctctt tagaagtaaa caacaaagtc    44760
gattgcctca gctatgcggt atccgcagag tgagtcctaa atttaaaatc tgactacatg    44820
tagaaaagcg tttcgtgtga cccatgacca ggaaataaat cgggtaatac aaacaggctc    44880
aggaatgaga gaaatgatta gaattgcgtg aaaatttgaa atatcagtat gataactgat    44940
ttcaaatatt taaaaaaaca acatgcaaga aagcagatat catatcaaga gaaattaaca    45000
gtacagaata gccaaattaa attaaagagc tagtataaaa aaagtatgtc ttaattgaaa    45060
aaaattactg tatggccggc tgatcaattt agacgtttca gaggaaaaca ttacccaaca    45120
cacaattcta gagaacctac agaatgagct acacacacac acacacacac acacacaaac    45180
tgaaaacaca cccatactca cacacacgca gaaactcaca agttctaaca cacacagaca    45240
cgcgcacccc tgaagaaaca gtgaaatata aaattaagcg agcctcacag acatgtagga    45300
```

```
aaatatgaaa agatttcctg catgtgggaa gcaagtcaca gtaaagagca agggagtttg   45360
gaatagaaac aaataccaga atcaaggatg gctgataact tttcaattac gaagaacatt   45420
aaaaaaaatc acagaatcgt gaaactcaag ggatcacata gggaatttcg gaaaaaaaac   45480
ccaacctgta tgatgtactt ttgtacatca cagttcgaag gtaacaaggc aaagatataa   45540
taagaagaaa cctgtcacga gaaactggag gaaaaagagc tgtgtcttcc tacaagtaca   45600
ctgatacaaa ttgccaatgt gttcacctca gaaacactgg aagccagata ccagggaata   45660
ttgttaaaat gataatcagg aacaaaaaga gatcaaccgg gaatgctgaa tccagcaata   45720
aaatgccttg aagatcatcc atgtcggata aatgcatatt gtgcactgcc ccaaagaaag   45780
aaaccggaaa ctgtaagaat tggaaatcag caggcttatg taacaagaga ggtgacccga   45840
aggaattagg tagaagaaga attgaacaag aaaggaactt tctgcagccc acgtaatgaa   45900
gaatccagca attggcaaat gtagatagat gtaaatgcaa aatattttct tgatcaaatt   45960
tctatatctt tgtaaatgag agttgactac ttgaaacaaa atgatagcaa gatatttaac   46020
ttcagcatat gtagaggtaa gaatttgaaa tggtagcata aatcacgaag ggattaattc   46080
gaagtgtacc gttgtaagtt tctttacctc atgcacgatg gtgtgtcata ttaataaaag   46140
ggtactgtgc gggttcgaag ggatattgca atcctagag caatcacaaa ggtttgaact   46200
ctgaggtttt tggtataata agaatagtcc atgcattcaa aagagggaag ccaaggaaga   46260
actagaagtc tttcaagagc tcaggctctt atacatccag ttgctcattg aaccagcttc   46320
ctggaatgga gggtctgggg ttgagactag gccacaagtc tagagtctct agagagacag   46380
tgttggaacc ccatggccca taatacattt cccatttct caggcagcca gaggtcatga   46440
atgtgaggat actgggaggt tggagcaacg ttcttgggag gcataaggaa gagcgaatgc   46500
ttcaagatcc ccgcagccca aactactcgc ctgctttgcc ccctaatgca ttttttctctg   46560 ctgctccgta gctgtccgac ctcttcagat ctcttagtcc accctgccgt cttcctttat   46620
gccatgggtc ccactgttct ttcaactcat cccccttttcc ctcagtcccg gagtagctgc   46680
ggccagcaga gggtagactg agagcaggag agaaggacct gcctaggaac cccttctaga   46740
gatactgcat cctgcctggg agcaagtttt ccagggcagc tttgagaagt cttggagaaa   46800
caaacctact aaacctgaca gacagtaata ctatttgcac aatgcttttc tgtgggaaag   46860
gtagagcctt ttcactacgt attgagtaca tagagtgtga gggttgacct ggaacggcta   46920
tcctcctgga tgacgtgtgt tttctgaaga actacatgtt cgttgcaact cccacattag   46980
aatatgaagt cctaccgaga gagatacgga gactagacag atacagatgc atttgcatgt   47040
gaatacacaa tcccacaata cagacgtcaa aacccatacc agttattcca gagagatgga   47100
ttgggcagaa ggcagaagga gaatactctg atcgtttttc ggccacgtgt gtgtgttatc   47160
tcagtgtttc taagaagcgt ttgctacttt agattttta tttaaaaaaa atagtaataa   47220
tctattaagt atgagagatg tgcagagagg attagtgatc gagagccatt tttgctggtg   47280
gcaatcatat ggtactttta atgggaatat tagaaaggca ccggtaatga ccttgttgca   47340
gcacaaagga gagagtgtgg ggtgcccctg catgttgtcc cacctcttgt gacgtgtatc   47400
gttttggaat ttccagtggc ttgatcatga actactgcag gaatccagat gctgtggcag   47460
ctccttattg ttatacgagg gatcccggtg tcaggtggga gtactgcaac ctgacgcaat   47520
gctcagacgc agaagggact gccgtcgcgc ctccgactgt taccccggtt ccaagcctag   47580
aggctccttc cgaacaaggt aaggagtctg tggccagaca tctacacgct tcgatgctgg   47640
```

```
gatgaaaagc catggaaatt cccactgatg cagccgcctt caatggtaaa cggatgctcg   47700
agtgttgcct gagttctacc atgtaggagg aagcctccgt gcactctctg ggggagccag   47760
cggagtgatt tctggtgcaa cgtggttggg ctttgtcttt aggatgggca caaaccctcc   47820 aggggatcg acttcaaaat tcaccttgtt gtaaaacggg ctacctcagt gtcccagcca   47880 aaattttat tgtaacatgc tgtcaggtgt gtcactcttt ccaagccagt aagcttttcc   47940
ggggatttct tcaagtagcc agcattcaga gcaatcttca gcattgcaga ttctgagaaa   48000
tgtggctctg gagcctgtca ccctcgagaa acctaagagg gctgcattga ttccatgtgg   48060
ccctgggtct atggagcagt acatgagctc ccagtgctct aaggctcttc agccctaggc   48120
tttgaaggga gtgatttctc agtattctta aacctctttc tgatgacact tgtacctgtg   48180
aggggtctag agagaaagag tagtagactc ctactttact acaattcagg atgcagggca   48240
tgagaggatt ccctctctcc tccaagggaa gaagcttttg gcgtgcacac atccctgaga   48300
agcaaagtgt ctttgtcttc agtcagatac ataggaccgt tttctgcccc atggcccgga   48360
agccaaaggc cttggctttc atgatcaacg gtctagggaa acatgcaaaa tttccatgtc   48420
tgtcccaaac tcttcccccg acagccaatt accacctgca gcccgcattg ccaaatgcgg   48480
tgccgtttgc atgaagattc agtagagttt cctagaaagg tgctacctcg tgagctcact   48540
ttccaatgag gaatctgatc tgttgtgttt ctctaaggtg tcaggtgaaa tatttccaag   48600
aacttactac agttctagaa tgggaggaat ctgttgcttt ggtgtttgtt tgttggtcgg   48660
ttttctcaca tccatctgcc tatggataag gaaagagaa cggtcgtaat tctcatagac   48720
tcctttctgg ttgtgtcaca aatggcttca catgtttctc tatgctcaga gatactcagc   48780
ttgatttccc gtgttttcat ttcagcaccg actgagcaaa ggcctggggt gcaggagtgc   48840
taccatggta atggacagag ttatcgaggc acatactcca ccactgtcac aggaagaacc   48900
tgccaagctt ggtcatctat gacaccacac tcgcatagtc ggaccccaga atactaccca   48960
aatgcgtatg tctttgttct ttaccataag agaagaaagg gccaagtgaa gtttctgtta   49020
caagagatgt gtctcaagct gagttctccg aactcaactt gtgacagatg cagatggcgt   49080
agcaaaatgt ctcaggatga ttgccttgga gctaagggtc tgagagaagg gaaatgttaa   49140
gctccctctc cttcctccta gttctattga gcagaaggga aatctggagg tgagaagatc   49200
acattatgaa gaaagtcaga atgacaaagg accagacact tagattaccc ttccacaaca   49260
ccaactaaac gtcaatggag actttccagt tggaattccg ttattctggc ttccacttcc   49320
tgaagggaag gttgcgtttg ccttttctct ctgggttcaa gaggaaagaa taggtgctta   49380
tttatggaca ggtgaattga tctgtttcta tatctacgta tattccgatt gtcagaaaaa   49440
cactcgttcc taagtaccag tggcctgaag ggatacaggt tcccagcaag agaagatcca   49500
aggaaggaag gcagatgaga gtcagcacag agagggatgc tgaaaagtaa aagggatggg   49560
tggatggaga gaagcccggg tctgaccacc caatggccaa tattttggcc acaagcgact   49620
accagagaca tggaaaaatg gtttctacat gtgggacaac agatggtaga ggacctagag   49680
aattgagaga ggggcaatga tgggctccac tccgcagatg ccttggcttt cttcctggat   49740
acccttcctg cactgaatag caaggagatg gagcccaagc agactgtagc catcttgctg   49800
aatggaggag agggattgga gtttgggatg actgtggtag ctgaaatttt tctaggtctg   49860
ctagaaataa gaactggttt gtgtggagga aaagagctct acaaatacgc atagaagtct   49920
cctccagtcg ttggcctgac atgacgctgc ctgtgcacag gaaatggttc cacgagaaag   49980
tgtggcaaag aacatttact gagaaacagc aagtacaaga gcacaggaag ctcaataaag   50040
```

```
aagagagaga tcacatagca ctctgggata ctggagttct tcccagctag accagagagt   50100
cctcacggag cacattgcca attcagtgga gaccccagaa cagccgtaat ttaaaggtac   50160
acttagtata ttactagaat aaagtcagct gcagacaacc ccttgcacag ctggaaagca   50220
agtgtccaag catcaaatcg gtttccaatc aatgaagtgc ctgtgagagg aaatctcaac   50280
tctctttaga agtaaacaac aaagtcgatt gcctcagcta tgcggtatcc gcagagtgag   50340
tcctaaattt aaaatctgac tacatgtaga aaagcgtttc gtgtgaccca tgaccaggaa   50400
ataaatcggg taatacaaac aggctcagga atgagagaaa tgattagaat tgcgtgaaaa   50460
tttgacatat cagtatgata actgatttca aatatttaaa aaaacaacat gcaagaaagc   50520
agatatcata tcaagagaaa ttaacagtac agaatagcca aattaaatta agaggtagt    50580 ataaaaaaag tatgtcttaa ttgaaaaaaa ttactgtatg gccggctgat caatttagac   50640
gtttcagagg aaaacattac ccaacacaca attctagaga acctacagaa tgagctacac   50700
acacacacac acacacacac acaaactgaa aacacaccca tactcacaca cacgcagaaa   50760
ctcacaagtt ctaacacaca cagacacgcg caccctgaa gaaacagtga aatataaaat    50820
taagcgagcc tcacagacat gtaggaaaat atgaaaagat ttcctgcatg tgggaagcaa   50880
gtcacagtaa agagcaaggg agtttggaat agaaacaaat accggaatca aggatggctg   50940
ataacttttc aattacgaag aacattaaaa aaaatcacag aatcgtgaaa ctcaagggat   51000
cacataggga atttcggaaa aaaaacccaa cctgtatgat gtacttttgt acatcacagt   51060
tcgaaggtaa caaggcaaag atataataag aagaaacctg tcacgagaaa ctggaggaaa   51120
aagagctgtg tcttcctaca agtacactga tacaaattgc caatgtgttc acctcagaaa   51180
cactggaagc cagataccag ggaatattgt taaaatgata atcaggaaca aaaagagatc   51240
aaccgggaat gctgaatcca gcaataaaat gccttgaagg tcatccatgt cggataaatg   51300
catattgtgc actgccccaa agaaagaaac cggaaactgt aagaattgga aatcagcagg   51360
cttatgtaac aagagaggtg acccgaagga attaggtaga agaagaattg aacaagaaag   51420
gaactttctg cagcccacgt aatgaagaat ccagcaattg gcaaatgtag atagatgtaa   51480
atgcaaaata ttttcttgat caaatttcta tatctttgta aatgagagtt gactacttga   51540
aacaaaatga tagcaagata tttaacttca gcatatgtag aggtaagaat ttgaaatggt   51600
agcataaatc acgaagggat taattcgaag tgtaccgttg taagtttctt tacctcatgc   51660
acgatggtgt gtcatattaa taaaagggta ctgtgcgggt tcgaagggat attgcaaatc   51720
ctagagcaat cacaaaggtt tgaactctga ggttttggt ataataagaa tagtccatgc    51780
attcaaaaga gggaagccaa ggaagaacta gaagtctttc aagagctcag gctcttatac   51840
atccagttgc tcattgaacc agcttcctgg aatggagggt ctggggttga gactaggcca   51900
caagtctaga gtctctagag agacagtgtt ggaacccat ggcccataat acatttccca    51960
ttttctcagg cagccagagg tcatgaatgt gaggatactg ggaggttgga gcaacgttct   52020
tgggaggcat aaggaagagc gaatgcttca agatcccgc agcccaaact actcgcctgc    52080
tttgccccct aatgcatttt tctctgctgc tccgtagctg tccgacctct tcagatctct   52140
tagtccaccc tgccgtcttc ctttatgcca tgggtcccac tgttctttca actcatcccc   52200 cttttccctca gtcccggagt agctgcggcc agcagagggt agactgagag caggagagaa   52260
ggacctgcct aggaacccct tctagagata ctgcatcctg cctgggagca gttttccag    52320 ggcagctttg agaagtcttg gagaaacaaa cctactaaac ctgacagaca gtaatactat   52380
```

```
ttgcacaatg cttttctgtg ggaaaggtag agccttttca ctacgtattg agtacataga   52440
gtgtgagggt tgacctggaa cggctatcct cctggatgac gtgcgttttc tgaagaacta   52500
catgttcgtt gcaactccca cattagaata tgaagtccta ccgagagaga tacggagact   52560
agacagatac agatgcattt gcatgtgaat acacaatccc acaatacaga cgtcaaaacc   52620
cataccagtt attccagaga gatggattgg gcagaaggca gaaggagaat actctgatcg   52680
tttttcggcc acgtgtgtgt gttatctcag tgtttctaag aagcgtttgc tactttagat   52740
tttttattta aaaaaaatag taataatcta ttaagtatga gagatgtgca gagaggatta   52800
gtgatcgaga gccattttg ctggtggcaa tcatatggta cttttaatgg gaatattaga   52860
aaggcaccgg taatgacctt gttgcagcac aaaggagaga gtgtggggtg cccctgcatg   52920
ttgtcccacc tcttgtgacg tgtatcgttt tggaatttcc agtggcttga tcatgaacta   52980
ctgcaggaat ccagatgctg tggcagctcc ttattgttat acgagggatc ccggtgtcag   53040
gtgggagtac tgcaacctga cgcaatgctc agacgcagaa gggactgccg tcgcgcctcc   53100
gactgttacc ccggttccaa gcctagaggc tccttccgaa caaggtaagg agtctgtggc   53160
cagacatcta cacgcttcga tgctgggatg aaaagccatg gaaattccca ctgatgcagc   53220
cgccttcaat ggtaaacgga tgctcgagtg ttgcctgagt tctaccatgt aggaggaagc   53280
ctccgtgcac tctctggggg agccagcgga gtgatttctg gtgcaacgtg gttgggcttt   53340
gtctttagga tgggcacaaa ccctccaggg ggatcgactt caaaattcac cttgttgtaa   53400
aacgggctac ctcagtgtcc cagccaaaat ttttattgta acatgctgtc aggtgtgtca   53460
ctctttccaa gccagtaagc ttttccgggg atttcttcaa gtagccagca ttcagagcaa   53520
tcttcagcat tgcagattct gagaaatgtg gctctggagc ctgtcaccct cgagaaacct   53580
aagagggctg cattgattcc atgtggccct gggtctatgg agcagtacat gagctcccag   53640
tgctctaagg ctcttcagcc ctaggctttg aagggagtga tttctcagta ttcttaaacc   53700
tctttctgat gacacttgta cctgtgaggg gtctagagag aaagagtagt agactcctac   53760
tttactacaa ttcaggatgc agggcatgag aggattccct ctctcctcca agggaagaag   53820
cttttggcgt gcacacatcc ctgagaagca aagtgtcttt gtcttcagtc agatacatag   53880
gaccgttttc tgccccatgg cccggaagcc aaaggccttg gctttcatga tcaacggtct   53940
agggaaacat gcaaaatttc catgtctgtc ccaaactctg cccccgacag ccaattacca   54000
cctgcagccc gcattgccaa atgcggtgcc gtttgcatga agattcagta gagtttccta   54060
gaaaggtgct acctcgtgag ctcactttcc aatgaggaat ctgatctgtt gtgtttctct   54120
aaggtgtcag gtgaaatatt ccaagaact tactacagtt ctagaatggg aggaatctgt   54180
tgctttggtg tttgtttgtt ggtcggtttt ctcacatcca tctgcctatg gataaggaaa   54240
agagaacggt cgtaattctc atagactcct ttctggttgt gtcacaaatg gcttcacatg   54300
tttctctatg ctcagagata ctcagcttga tttcccgtgt tttcatttca gcaccgactg   54360
agcaaaggcc tgggggtgcag gagtgctacc atggtaatgg acagagttat cgaggcacat   54420
actccaccac tgtcacagga agaacctgcc aagcttggtc atctatgaca ccacactcgc   54480
atagtcggac cccagaatac tacccaaatg cgtatgtctt tgttctttac cataagaaa   54540 gaaagggcca agtgaagttt ctgttacaag agatgtgtct caagctgagt tctccgaact   54600
caacttgtga cagatgcaga tggcgtagca aaatgtctca ggatgattgc cttggagcta   54660
agggtctgag agaagggaaa tgttaagctc cctctccttc ctcctagttc tattgagcag   54720
aagggaaatc tggaggtgag gagatcacat tatgaagaaa gtcagaatga caaaggacca   54780
```

```
gacacttaga ttacccttcc acaacaccaa ctaaacgtca atggagactt tccagttgga   54840
attccgttat tctggcttcc acttcctgaa gggaaggttg cgtttgcctt ttctctctgg   54900
gttcaagagg aaagaatagg tgcttattta tggacaggtg aattgatctg tttctatatc   54960
tacgtatatt ccgattgtca gaaaaacact cgttcctaag taccagtggc ctgaagggat   55020
acaggttccc agcaagagaa gatccaagga aggaaggcag atgagagtca gcacagagag   55080
ggatgctgaa aagtaaaagg gatgggtgga tggagagaag cccgggtctg accacccaat   55140
ggccaatatt ttggccacaa gcgactacca gagacatgga aaaatggttt ctacatgtgg   55200
gacaacagat ggtagaggac ctagagaatt gagagagggg caatgatggg ctccactccg   55260
cagatgcctt ggctttcttc ctggataccc ttcctgcact gaatagcaag gagatggagc   55320
ccaagcagac tgtagccatc ttgctgaatg gaggagaggg attggagttt gggatgactg   55380
tggtagctga aattttttcta ggtctgctag aaataagaac tggtttgtgt ggaggaaaag   55440
agctctacaa atacgcatag aagtctcctc cagtcgttgg cctgacatga cgctgcctgt   55500
gcacaggaaa tggttccacg agaaagtgtg gcaaagaaca tttactgaga aacagcaagt   55560
acaagagcac aggaagctca ataaagaaga gagagatcac atagcactct gggatactgg   55620
agttcttccc agctagacca gagagtcctc acggagcaca ttgccaattc agtggagacc   55680
ccagaacagc cgtaatttaa aggtacactt agaatattac tagaataaag tcagctgcag   55740
acaacccctt gcacagctgg aaagcaagtg tccaagcatc aaatcggttt ccaatcaatg   55800
aagtgcctgt gagaggaaat ctcaactctc tttagaagta aacaacaaag tcgattgcct   55860
cagctatgcg gtatccgcag agtgagtcct aaatttaaaa tctgactaca tgtagaaaag   55920
cgtttcgtgt gacccatgac caggaaataa atcgggtaat acaaacaggc tcaggaatga   55980
gagaaatgat tagaattgcg tgaaaatttg acatatcagt atgataactg atttcaaata   56040
tttaaaaaaa caacatgcaa gaaagcagat atcatatcaa gagaaattaa cagtacagaa   56100
tagccaaatt aaattaaaga gctagtataa aaaaagtatg tcttaattga aaaaaattac   56160
tgtatggccg gctgatcaaa ttagacgttt cagaggaaaa cattacccaa cacacaattt   56220
tagagaacct acagaatgag ctacacacac acacacacac acacacacac acacaaactg   56280
aaaacacacc catactcaca cacacgcaga aactcacaag ttctaacaca cacagacacg   56340
cgcaccctg aagaaacagt gaaatataaa attaagcgag cctcacagac atgtaggaaa   56400
atatgaaaag atttcctgca tgtgggaagc aagtcacagt aaagagcaag ggagtttata   56460
atagaaacaa ataccagaat caaggatggc tgataacttt tcaattacga agaacattaa   56520
aaaaaatcac agaatcgtga aactcaaggg atcatatagg gaatttcgga aaaaaaaccc   56580
aacctgtatg atgtacttt gtacatcaca gttcgaaggt aacaaggcaa agatgtaata   56640
agaagaaacc tgtcacgaga aactggagga aaaagagctg tgtcttccta caagtacact   56700
gatacaaatt gccaatgtgt tcacctcaga aacactggaa gccagatacc agggaatatt   56760
gttaaaatga taatcaggaa caaaaagaga tcaaccggga atgctgaatc cagcaataaa   56820
atgccttgaa ggtcatccat gtcggataaa tgcatattgt gcactgcccc aaagaaagaa   56880
accggaaact gtaagaattg gaaatcagca ggcttatgta acaagagagg tgacccgaag   56940
gaattaggta gaagaagaat tgaacaagaa aggaactttc tgcagcccac gtaatgaaga   57000
atccagcaat tggcaaatgt agatagatgt aaatgcaaaa tattttcttg atcaaatttc   57060
tatatctttg taaatgagag ttgactactt gaaacaaaat gatagcaaga tatttaactt   57120
```

```
cagcatatgt agaggtaaga atttgaaatg gtagcataaa tcacgaaggg attaattcga   57180
agtgtaccgt tgtaagtttc tttacctcat gcacgatggt gtgtcatatt aataaaaggg   57240
tactgtgcgg gttcgaaggg atattgcaaa tcctagagca atcacaaagg tttgaactct   57300 gaggttttg gtataataag aatagtccat gcattcaaaa gagggaagcc aaggaagaac    57360
tagaagtctt tcaagagctc aggctcttat acatccagtt gctcattgaa ccagcttcct   57420
ggaatggagg gtctggggtt gagactaggc cacaagtcta gagtctctag agagacagtg   57480
ttggaacccc atggcccata atacatttcc cattttctca ggcagccaga ggtcatgaat   57540
gtgaggatac tggaggttg gagcaacgtt cttgggaggc ataaggaaga gcgaatgctt    57600
caagatcccc gcagcccaaa ctactcgcct gctttgcccc ctaatgcatt tttctctgct   57660
gctccgtagc tgtccgacct cttcagatct cttagtccac cctgccgtct tcctttatgc   57720
catgggtccc actgttcttt caactcatcc cccttcccct cagtcccgga gtagctgcgg   57780
ccagcagagg gtagactgag agcaggagag aaggacctgc ctaggaaccc cttctagaga   57840
tactgcatcc tgcctgggag caagttttcc agggcagctt tgagaagtct tggagaaaca   57900
aacctactaa acctgacaga cagtaatact atttgcacaa tgcttttctg tgggaaaggt   57960
agagcctttt cactacgtat tgagtacata gagtgtgagg gttgacctgg aacggctatc   58020
ctcctggatg acgtgcgttt tctgaagaac tacatgttcg ttgcaactcc cacattagaa   58080
tatgaagtcc taccgagaga gatacggaga ctagacagat acagatgcat ttgcatgtga   58140
atacacaatc ccacaataca gacgtcaaaa cccataccag ttattccaga gagatggatt   58200
gggcagaagg cagaaggaga atactctgat cgttttttcgg ccacgtgtgt gtgttatctc   58260
agtgtttcta agaagcgttt gctactttag atttttttatt taaaaaaaat agtaataatc   58320
tattaagtat gagagatgtg cagagacgat tagtgatcga gagccatttt tgctggtggc   58380
aatcatatgg tacttttaat gggaatatta gaaaggcacc ggtaatgacc ttgttgcagc   58440
acaaaggaga gagtgtgggg tgcccctgca tgttgtccca cctcttgtga cgtgtatcgt   58500
tttggaattt ccagtggctt gatcatgaac tactgcagga atccagatgc tgtggcagct   58560
ccttattgtt atacgaggga tcccggtgtc aggtgggagt actgcaacct gacgcaatgc   58620
tcagacgcag aagggactgc cgtcgcgcct ccgactgtta ccccggttcc aagcctagag   58680
gctccttccg aacaaggtaa ggagtctgtg gccagacatc tacacgcttc gatgctggga   58740
tgaaaagcca tggaaattcc cactgatgca gccgccttca atggtaaacg gatgctcgag   58800
tgttgcctga gttctaccat gtaggaggaa gcctccgtgc actctctggg ggagccagcg   58860
gagtgatttc tggtgcaacg tggttgggct ttgtctttag gatgggcaca aaccctccag   58920
ggggatcgac ttcaaaattc accttgttgt aaaacgggct acctcagtgt cccagccaaa   58980 attttattg taacatgctg tcaggtgtgt cactctttcc aagccagtaa gcttttccgg   59040
ggatttcttc aagtagccag cattcagagc aatcttcagc attgcagatt ctgagaaatg   59100
tggctctgga gcctgtcatc ctcgagaaac ctaacagggc tgcattaatt ccatatggtc   59160
ctgggtctat ggagcagtat atgagctccc aatgctctaa ggctcttcag tcctaggctt   59220
tgaagggagt gatttctcag tgttcttaaa cctcttcctg atggcacttg tacctgtgag   59280
gggtctagag agaaaggtta gtagacttct cctttactgc aattcaggat gcagggcatg   59340
agaagattcc ctccctcctc caagggaaga aggttttggc gtgcacacat ccttgagaag   59400
caaagtgtct ttgccttcag tcagatatat aggatcgttt tctgccccat ggcctggaag   59460
ccagaggcct tggctttcat gatcaacgat ctagggaaac atgcaaaatt tccatgtctt   59520
```

```
tcccctcctc tgccctcgac agccaattac cacctgcatc ctgcattgcc aaatgcagtg   59580 cccttttgtat gaacattcag tagagtttca tagaaaggtg ctacttcgtg agcgcacttt   59640
gcagtgagaa ggagtctgtt ctgttctgtt tttctaagga tttcaggtga aatatttcct   59700
agaacttact acagttctag attggtagga atctgtaggt ttgctgtatg ttttttggtt   59760
ggttttctcc catccatctg cctacaggta agggaaagat aacgttcata attctcatag   59820
actcctttct ggttgtgtca taaatggctt cacatatttc gttattctca gagatactca   59880
gtttatttct tgtgttttca tttcagcacc gactgagcag aggcctgggg tgcaggagtg   59940
ctaccacggt aatggacaga gttatcgagg cacatactcc accactgtca ctggaagaac   60000
ctgccaagct tggtcatcta tgacaccaca ctcgcatagt cggaccccag aatactaccc   60060
aaatgcgtat gtctttgttc tttaccataa gagaataaag ggccaactga gtttctgtg    60120 acaagagaca tgcttcaagc tgagttctcc gaactcaact tgtgtcagat tcagatggtg   60180
tagcaaaatg tctcaggatg atttccttgg agctaagggt ctgagagaag agaaatgtta   60240
agctgcctca ccttcctcct agttttgtgg agcagaaggg aaatgaggag gcgaggagat   60300
caccttatga agaaagtcag aatgacgaac caccaaacac ttagattacc cttgcccaac   60360
acccactaag cgtcaatgaa gactttccag ttggaattcc gttattctga cttccaattc   60420
ctgaagggaa gattgtgttt gccttttctg tctgggctca tgaggaaagt ttatgtgctt   60480
acttatggac aggtgaattg atctgtttct atttctacct gtattccaat agggagaaaa   60540
tctcttggtc ctaagtacca gtggcctgaa aggatagagg ttcccagcaa gagaagatcc   60600
aaggaaggaa ggcagatgag agtcagcaca gagagggatg ctgaaaagta aagggatgg    60660 gtagatggat agaagccctg gtctgaccac cccatggcca atcatttggc cataatcaac   60720
aaccaaagac atggaaaaat ggtttctaca tgtgggacaa cagatggtag aggacctaga   60780
gaattgagag agggccaatg atgagctcaa ctccatagat gccttggctt tcttcctgga   60840 taccctcct gcactgaata gcaaggagat ggagctcaag cagcctgtag ccatctagct    60900
gagcagagga gagggattgg agtttgggat gactctggta ttttctaggt ccgctacaaa   60960
taagaactgg tttgtggagg aaaggagctc tacaaatacg catagaagtc tcctccagta   61020
gttggcctca catgcactg catgtgcaca gaaatggtt ctacagaaag tgtggcaaag     61080
aacatttact gagaaacagc aactacaaga gaacagcaag ctcaattaag aagatagaga   61140
tcacatagca ctctgtgtta ttggagttct taccagctag atgagagagt gctcacggaa   61200
cacattgcca attcagtgga gaccccagaa cagccataat ttcaaagtac aattagtata   61260
ttactagaat aaaggcagct gcagacaacc ccttgcacag ctgaaaagca agtgtccaag   61320
catcaaatgg gtttccaatc aatgaagtgc ctgtgagagg aaatctcaac tctcttcaga   61380
agtaaacaac aaagtcaatt gcctcagcta tgcggtatcc ccagagtgag tcctaaatta   61440
aaaatttgac tacgtgtaga aaagaatttc gtgtgatcca tgaccagaaa ataaatcagg   61500
caatacaaac aggctcagaa atgacatcga taattagaat tgcatgaaaa tttgacatat   61560
cagtatgata actgatttca gatatttaaa aaaagtgcaa caaagcaggt atcatatcaa   61620
gacaaattaa tagtatagaa tagccaaatc aaattaaaga actattatac aaaaagtatg   61680
tcttaaatga agaaattact gtatgtccgc ctgaaaaatt tagatgtttc agaagaaaaa   61740
attaaccaaa aacaattctg cagaacctac agaatgagcc acacacacac acattcaaaa   61800
cacacccata cacacacaca tgcaaaaact cacaagttct aacacacaca caaacacaca   61860
```

```
cacacatgca catccctaaa gaaatagggga aatataaaat taaccgaccc tcagagacat    61920
gcaggaaaat ataagaagat ttcctgcatg tgggaagcaa gtcacagtaa agagcaaggg    61980
agtttggagt agatacaaat accggaatca cggatggctg ataacttttc aattatgaag    62040
aacgttagaa aaatcacaga ttcatgaaac taaagggatc aaataggaaa tttcgagaaa    62100
aaaaactaca tgatgcactt ctctacatca cagttcaaag gtaacaaggc aaggatataa    62160
gaagaagaaa catctcacga gaaactggag aaaaaagagc tgtgtcttcc tagagtacag    62220
tgatacaaat tgctaatgcg ttcacctcag aaacactgga agccagatac cagggaatat    62280
tattaaaatg ataatgagga acaagaagag atcaaccgag aatgctgaat ccagcaataa    62340
aatgccttga agatcatcca tgttggataa atgcatattg tgcactgccc aaaacaaaga    62400
aactggaaag tgtaagactt tggaatcagc aggcttatgt agcaacagag gtgacccgaa    62460
agaattaggt ataagaagaa tagaagaatt gcatgaaaat ttgacatatg actaagataa    62520
ctatttcaaa tatttaaaaa aagatgaata tgtaataaaa cagataaaat atcaaaagaa    62580
agtaacagta ttgactagcc aaatcaaatt aaagacttag tgtaaaaagc tatgtcttaa    62640
aagaaaaaat tactggatgg ctgcctgatc aatttagaca tttctgaata ggaaactaac    62700
caaaaatcaa ttctacagaa ccaactacac acatatatac acatcaaaca cacccataca    62760
cacccacgca aaaactcaca agttcacaca cacacacaca cacacacaac cctcaagaaa    62820
tagtgaaata gaaaaccaac cgaacctcac agacatgttg caaaatagga aaagatttcc    62880
tgcatatggg aagcaagtca cagaaaagag aacgggagat tggaaacaga aacaaatacc    62940
ggaatcaagg atggccgaaa acttttcatt gatcaagaat attaacaaaa tcgcaaaaac    63000
acgaaattca atgcatcaaa taggcgtttc gaaaaaaaga aaaatctgg tatgatgcac    63060 ttttgtactt cacattttca cggtaagaag acaaagatat aataacaaga aacttcttat    63120
gagaaactgg ggaaaaacaa gctgtttctt gctagaagaa cagtgataca aattgctaat    63180
gcattctcgt caaaaacact ggaagccaga taccgggaat gttattaatg tggtaaacag    63240
gaacaagaag agatcaacca agaatgctaa atccagcaat aaaatgcctt gaagatcatc    63300
catgctgcat aaatgtatgt tgtgcactgc cccaaacaaa gaaaccggaa actgtaagaa    63360
tttggaatca gcaggctgat gtaacaagag aggtgaccca aaggaattag gtagaagaag    63420
aatagtacaa gaagggaact ttctgcagcc catgtaatga agaacccagc aattggcaaa    63480
tgtagatgta aatgcaaaat atttttcttga ccaaatttct atatatttt aaatgagcgt    63540 tgactactgg aaacaaaatg atagcaatat atttaatttt agcatatgta gaggtaagaa    63600
tttgaacaag tagcgtaaat catgtaggga ataattagaa gtgtaccatt gtaagtttct    63660
tacctcatgc acaatggtat gtaatattaa taaaatgtta ctgtgtgggt tcaaggagat    63720
attgcaaatc ctagagcaat cacaaagttt tgaactctga ggtatattgt ataataagaa    63780
tattccatgt attcaaaaga gagaagccaa ggaagaaaga aatttgtcac gagtttgggc    63840
tcttagtaca tcctgtagct cattgaacca gcttcctgga atggagggtc tgggattgac    63900
actaggccac atgtatagag tctctagaga gacagtgttt catccccatg gcccgtaata    63960
catttcccat tttctcaggc agccacaggt catgaatgtg aggatagaga gaggttggag    64020
caacgttctt gggaggcata aggaagagca aatgcttcaa gatccccgca gcccaaactc    64080
ctacctgctt tgcccctaa tgcagtgttc ctccgtagct gtccgacctc ttcagatctc    64140
ttagtctacc ctgccatctt cctttatgcc atgggtccca ctgttctttc aactcatccc    64200
cctttccctc agtgcagagt agctgcggcc agcagagggt agactgagag caggagagaa    64260
```

```
ggtcctgccc aggaacccat tctagagatg ctgcattctg cctgggagca agttttccag    64320
ggcagctttg agaagtcttg cagaaacaaa cctatttgac ccacatgata tgggaatgac    64380
agaaagtaat acaatttgca cagtgctttt ccatgggaaa agtagagcct tttcgcgagg    64440
ttttgagtac atagagagtg aaggttgacc tggaaaggtt atcctcctgg atcccatgtt    64500
ttttctgaag aactacctgt tagttgcaac ttgcacatta aatatgaag tcctaccgag     64560 agagatacgg agaactagat aaatacagat acttttgtat gtgaataaac gattccacaa    64620
tacacacatc aaaatccata ccagttattc cagagagatg gattgggcag aaggcagaag    64680
gagaatactc tgatcgtttt ttgcccacgt gtatgtatta tctcagtgtt tctaagaagc    64740
gtttgctact ttagatttt ttttataata ataatctttt aagtatgaga aatgtgcaga     64800
caggattagt gattgagagc catttgtgct tgtggcaatc atatggtact tttatgggaa    64860
tattagaaag gcactggtaa tgaccttgtt gcagcacaaa ggagagggtg tggggtgccc    64920
ctgcatattg tcccacctct tgtgacgtgt atcgttttgg aatttccagt ggcttgatca    64980
tgaactactg caggaatcca gatcctgtgg cagcccctta ttgttatacg agggatccca    65040
gtgtcaggtg ggagtactgc aacctgacac aatgctcaga cgcagaaggg actgccgtcg    65100
cgcctccaac tattaccccg attccaagcc tagaggctcc ttctgaacaa ggtaaggagc    65160
ctgtggccag aaacctacac gtttcgatgc tgggatgaaa agccatggaa attcccactg    65220
atgcagcagc ctccaatggt aaacggatgc tcgagtgttg actgagttct gtcatgtagg    65280
aggaagcctc cgtgcactct ctgggggagc cagcggattg atttctggta caacgttggg    65340
tgggctgtgt ctttagaatt ggcacaaacc ctccagggtg atcgacttca caactcacct    65400
cgttgaaaaa tgggctatct cagtgtctta gccaaaattt ttattgtaac atgctgtcag    65460
atgtgtgact ctttccaagc cagtaagctt ttcctgggac ttcttcaatt agccagcatt    65520
cagtgcaatc ttcagcattg cagattcaga gaaatgtggc tctggagcct gtcacccttg    65580
agaaacaggg ctaacagggt tgcattaatt ccaaatcacc ctggttctat ggagcagtac    65640
atgaactccc aatgatctat gtttcaggac ttcctcagtc ataggtgggc tctgcagccc    65700
taggttttta agtgagtgac tgccccgtgt tctggtggca gttgtacctg tgagcggtct    65760
ggatagaaag agtcggagac ttctgtatta ttgcaactca ggatgtgggt catgagagga    65820
tttcatctct cctgcagggg agtaagctgt tcgcctccac ccatccctga taactgaagt    65880
gtctttgtct gcagtcctag acgaaggact gttgtctctc ccatggccca gaagctgaag    65940
accttgcctt ttgttatgaa acgttcattg ttttcatgtc tgtccgtttc tctgccccta    66000
acacccaatc accatgtatg gcctgtaccc ccaaatgcat cgtgctttgc tgtttgctgc    66060
cccatagtcc tcatgaacat tcagtagaaa ttcccataaa tgtgcttgca cgtgagcaca    66120
gtttccattg agaagccctc tcatttgtcc ttttttttcta agcttttatg tgaaatattt    66180
ctaagaactt actacagttc taaagtgtta ggaatttgtt tctttggtgt ttttgtttgt    66240
tggttggttg ttgcttttct caagtccatc tgcctacaaa taaagaaaca agaatgttac    66300
ttgtcatatt ctcctgaggt cataattctc agagacttt ttctggtttg tgccataagt     66360
ggcttcacat gtttgtctct tcttggaaac actcagtttg atttcttttc ttttcatttc    66420
agcaccaact gagcaaaggc ctggggtgca ggagtgctac cacggaaatg gacagagtta    66480
tcaaggcaca tacttcatta ctgtcacagg aagaacctgc caagcttggt catctatgac    66540
accacactcg catagtcgga ccccagcata ctacccaaat gcgtatgtct attttctta     66600
```

```
ccataagtga aggaagggtc agtggaaatt tctgttagta gagtcatgct tcaagctgag    66660
tgttcaggac tcaagttgtc tcagatgaac agtgcatagc aaaatgtctc aggaacattg    66720
tctttgagca aagagtctaa gagaagacaa atgttaatct ggctctcctt cctcctagtt    66780
taatggagca gaaaggtatc tggaggcaag gatatcacat taagaaacaa gtcaagatga    66840
caaatgatga aactcttaga gtacccttcc acaacaccca ctaaggttca atgcagcctt    66900
ttctccttgg aattctatta aactaaactc caattcctga agtgaaggtt ctgttggggt    66960
tttctgtttt ggcttacaag gaaagtatat atgtatatct atggagaggc aaatctatct    67020
ctttctatat ctacgtctat tccaatatgt agaaacacag tcggttctga ccaccagtgg    67080
tctgaaggga tactggttgt tagagaataa aaatggcagg aaggcagatg agagtcagca    67140
aagagagaga tcctgtaaag taaaagggtg gatagatgga cagaagccca ggtctgacca    67200
gcccatggcc aggctttagg ccataagtga caccaaagac atggaaaaat ggtttctaca    67260
tgttggacaa cagacagtag tggaccaaaa gaatagtgac aggggggaaca atgagatcaa    67320 ctccatagat accttggctt tcttcctgga ggcccttctt gcactgaaga gcaaggtgat    67380
ggagcccaga tggactgtag ccatcttcct gaatgcagga gagagattgg aatttgggac    67440
tactgtggta gctaggattt tataggcctg ctgagaatga gaatggattt gtggatgaaa    67500
ggagctccag gggcacgcat agtagtctcc tcgaatcttt ggctaaacat gacgttgcat    67560
gtgcccagaa aaaggttcca caagaaagta gagaaaagaa tatatcctga ggaatagcaa    67620
ctgcgattga acagtgagct caataaagag gacagagccc tcatagcatt ctgggatact    67680
ggagttctga ccagctggag gagagacctc actgaacctc ttgggaatac agtagagact    67740
ccagaaaagt catactttag gagtagaatt agtaaatttc tagaaaaaaa ggcagctcta    67800
gacaaaccct ggcaaaactg aaaagcaagt ctccaagcat taaaatcatt tccaagtcaa    67860
ttaactgcct gggagaggaa aaccctcttt agaggtaaac aacaaagtca agtggctcag    67920
ctatgtggtg ttcacagtgt gagttctaaa tttaaaactt gactacacat agagaagctt    67980
ttagtatgaa ccatgaccag gtgaaaaatc agtcaataca aatagaccta gaaatgacag    68040
aaatgattag aatggcaaaa aatttgacat atcaatatgt caactgagtt ttaggtttta    68100
agaaaacatg aatacggaat gaagcagata ccatatcaag agacagtaac agtatagaag    68160
agccaaatta aattaaagaa ctagtataag aaggtatgtc ttaaatgaaa aaattactgg    68220
atgtattccc aatggagtga gatgtttcag aagtaaaaac taactgaaaa acaatttat    68280 accacctaca gaaccagcta cacatacaca aatgacacac acatatacac acatactcac    68340
acatgcacag gcttagaaac atgcacgcac acacacacac acacacacac acacctccac    68400
aaatactaaa aaatgaaatc cactgatcct cacagacagg cgggaaaata taaaaagatt    68460
tcctgcatgt gggtaggaag tcacagaagg agaggaagga gagattgcta caggaacaaa    68520
tactggaagc aaggatagct aaaaactttt caaataagaa gaatattaaa aaccacagat    68580
tcaagaagct gaatgaatca gacagggaat ttccaaaaaa aaaaaaaaaa aaactgtatg    68640
attcactttt gtacatcacc gttcaacagt cagaaggcaa agatataata acaagaaaca    68700
tctcatgaga aactggagga aaaagagctg tgtcttgcta aagaacagt gatacaaatt    68760 gctaatgcat tctcatcaga aacactggaa cccagttaac aggggatatc attaaaatga    68820
taaactagaa aaaaagaga tcaaatgaga atgctacatc cagcaataaa atgccttgaa    68880
gatcatccat gttggataaa tgcatattgt gcactgcccc aaataaataa accaaaaact    68940
aataatttgg aatcagcagg cttgtgtaac aagagatgtt gcccaaagaa aattagctag    69000
```

```
aagaagaata gttcaagagg agaactttct gcagcccacg taatgaagaa cccagcaaat   69060
ggcaaatgta gatgtaaatg caaaatattt tcttgatcaa atttctatat cttttttaaat   69120 gagagttgac tacttgaagc aaaatgatag caatatattt aactttagca tatgtagagg   69180
taaaaatttg aacatataga ctaaatcatg tggggaataa ttggaagtgt accattgtaa   69240
gtttcttacc ttatccacga tggtatgtaa tattaatgaa aggttgaatt tgtgggtcca   69300
aagggatatt gtaaatccta aagcaatcat aaaattttga attctgaggg atattatata   69360
ataagaattt tccatgtatc caaagagggg aagccaagga agaaaaagaa gtctttcaag   69420
tactcaagct ctgagcacat ccagttgctc attgaaccag cttcctggaa tggagggtct   69480
gggcttgaga ctaggtcaca tgtgtagagt ctctagagag acagtgttgg atccccatgg   69540
cccataatac atttcccgtt ttcccaggca gccacaggtc acgaatggga ggattctgag   69600
aggttggagc aatgttctta ggaggcataa ggaggagtga atgctctgag atttccccag   69660
cctgaggtcc tccatagctg cccgacctct tcagacctca tagtctgccc agctgtctcc   69720
ctttatgcca tgagtgccac tgttctttca actcatcccc cattccctca gtcccggaat   69780
tgctgtggcc agcagaggat ggactgagag caggagagga agtcctgacc aggaacccat   69840
cctagagata ctgcatcctg cctgaaagct aggtttccag ggcagctttg agaagtcttg   69900
cagaaagaaa cccacttgac ccacctgata cggtatcgac agacaggaat acttttgtg   69960 caatggtttt acatgctgaa catagagcct tttggctaca ttttgagtac attgaatgag   70020
actgctggcc tgggaaggat atcatgctgg atgccatttt tttctctgga gaactatgtg   70080
ttagttccaa ctcgcacatt actatatgaa gtcctacaca gagagatacg gagagctaga   70140
cagatagaga tacttttgta tgtgcataac caattccaca atacacacgt caaaatccat   70200
accagttatt ccagagagat ggattgggca gaaggcagaa ggaggatatt ctgatccctt   70260
tttggccaca tgtatgtata atctcagtgt ttctaggaag tgtgtgctgc attagatttt   70320 ttttcttttaa aaaaagtgat aatatattaa gtatgagaaa tgtgcagaga ggattagaga   70380
ttgagagcca tttgtcattg tggcaattgt atggtatctc ttttgggaat atttcaaagg   70440
caccagtaat gaccttgttg tagcaaaata tacagtgttc ctgcatatgt acccattttt   70500
tgtgatgtgt attcttttgg aatttccagt ggcttgatca agaactactg ccgaaatcca   70560
gatcctgtgg cagccccttg tgttataca acagatccca gtcaggtg ggagtactgc   70620 aacctgacac gatgctcaga tgcagaatgg actgccttcg tccctccgaa tgttattctg   70680
gctccaagcc tagaggcttt ttttgaacaa ggtaagaagt tgtgccagac atttacctgc   70740
ttggatgctg ggatgaaaag ccatggatac ccccactgac gcacaaccct tcagtgctac   70800
actggttctc gtgtgttggt tctgggtctg ccatgtggga ggaagcctta gcgcactctc   70860
tgggggagcc agaggtgtga tttttggtgc aacctgtgcg agctgtgtct ttaggatggg   70920
cggaaaccat tctgggtgct cgacttcacc actccctca ttgtaaaagg gctatctca   70980 ttgtcctaga caaaattctt attgtaatat gctgtcagat gtgtgtgtct ttccaagcca   71040
gtaaactttt ccagggattt cttcaagtag acagcattca gtgcaatctt cagcattgca   71100
gattccgaga aatgtggctc tagatcctgt tatccttgag aaacctaact gggttgcatt   71160
aattccatat ctccctgggt ctgtggagta gtacatgagc tcccgaagct ctatctctca   71220 ggtcttttc agtccgaggc aggttgtgca gttcttagct ttgaagggag tgattttttc   71280
gtgtgctttt gcctctttct gatggaactt gtacctgcgg ggggtctgga gaaaaagagt   71340
```

| | |
|---|---|
| agtagacttt tgctttattg caatgcatta tgctgggcac gagaggattc cctatcttat | 71400 |
| tgtaggtgat aagcttttgg cctccactca tccctgagaa gtgaagtgtt gttgcctaca | 71460 |
| gttttagctg caggactgtt gtctgcccca tcaccaggag tttaatgctt tctttttga | 71520 |
| gcaatcatct agggacacat gcaaggtttt tatatgtcct tgcctcctcc ccaaaaaacc | 71580 |
| attttaatgc ttggagactt gcttttcagc tttgccaaat gcatcaccct ttcttctatg | 71640 |
| ctgttccatg tcgtcatgaa cactctgtag agattcctag aaatgagctt ccatgttagt | 71700 |
| ggagtttccg atgagaagca atctgatatt tcttttccac taagtttac atgaaatatt | 71760 |
| tctaagaact tactacagtt ctagaatggt aggcatctct tactttcgtg tttgtttgtg | 71820 |
| tgttttctca tgtccatttg cctattaata aagaatagag aatggttgta aatctcagtg | 71880 |
| actctttttt ggtttatgtc ataaatggct tcctgtattt ttctgttcta ggaaataata | 71940 |
| agcttgatgt cttctgtttt aatttcagca ctgactgagg aaaccccgg ggtacaggac | 72000 |
| tgctactacc attatggaca gagttaccga ggcacatact ccaccactgt cacaggaaga | 72060 |
| acttgccaag cttggtcatc tatgacacca caccagcata gtcggacccc agaaaactac | 72120 |
| ccaaatgcgt acgtctttgt tctttaccat aagcgaagga agggccaatg gaagtttctg | 72180 |
| ttagaagagt catgcttcaa ggtgactgct caggactcaa cttggctcag atgcagagga | 72240 |
| acatttcctg tgagcaaaag ttcttagaga agactttgtt tttttgagac agagtcttgc | 72300 |
| tttgttgccc aggctggagt gcagtggcat gatctcggct cactgcaagc tccgcctccc | 72360 |
| gggttcacac cattctcctg cttcagcctc tctagcagct gggactacag gcacccacca | 72420 |
| ccacacccgg ctaattttt gtattttag tagagacagg gtttcactgt tctagccagg | 72480 |
| atggtcttgg tctcctgacc tcgtgatccg cctgcctcag cctcccaaag tgctgggatt | 72540 |
| acaggcgtga gccaccgtgc ctggctgaga agacattttt taagctgct ctccttcctc | 72600 |
| ctagttttat ggaagcagaa ggatatatgg agttgagaag atcttattaa taaaacagcc | 72660 |
| gggatgacaa atgaccaaag agttagagta tccttctaca acatcggctg agggttaata | 72720 |
| caacctttc accttggaat tctatcattc taagctctag tccctgaagt gaatgttgtg | 72780 |
| ttggcctttt gcatcttggg tcacagggaa ttgatacttg cacatctatg gagaggcaaa | 72840 |
| tctttttcta tctacttctt tttcaatggg tacaaacaca cttggtcctg agcaccagtg | 72900 |
| gtctgaagag atacggtctg cccagaggag aagaacaaag gcaggaaagc agatgagagt | 72960 |
| cagcaaaggg gcgatgctga aaagtaaaag gggcgggtag atggacagaa gccatgatct | 73020 |
| ggccattcta tggccagtct ttcggccata agtgactacc aaagacacgg caaaacggtt | 73080 |
| tccacatgtt gaacaacaga tgctagagga ccaagagtat tgcaagaggg agaaaatgag | 73140 |
| atcaacccat caatgccttg gctttcttca aggagaccct tcctgcactg aagagcaagg | 73200 |
| agatggagcc caagctgact gtagccatgt tgctgaacag aggagagtga ttggactttg | 73260 |
| ggattactca ggtagttagg attttctagc catgctaaga gtaagaatgg acttgtggag | 73320 |
| gataggagct ccaggcatag aagtctcctc aagtgttagt ctaaacataa agcagcactt | 73380 |
| gcatagaaga ttttccacaa gaaaatatgg caaaaaaaca ccatatattg aggaacaaca | 73440 |
| actcaagggg aacagtgagc ttaataaagg tgacagagct cacatagtgc tctggaatat | 73500 |
| tggagttttg accagctaga gagaagagac ctcattgaaa atcttgggca ttcagtagag | 73560 |
| acctcagaaa agtcagactt tatgagtaga ctttgtatat tcctagaata aaggcagctc | 73620 |
| cagaaaaaac ctagcaaagc tgaaaagcaa atctccaagc attaaaatgg tgtcctagtc | 73680 |
| aattaactgc cttctagaag aaaactcaac actctttaca ggtgaacaac aaagttaagt | 73740 |

```
tgctgagcta tgcaatatcc acagtgtgag tcctaaattt ataactttac tacacataaa    73800
aaagcattta gtgtgaacca taaccaggaa aataatcagt caataaaaat agaaccagga    73860
atgatagaaa tgatttaaat ggcatgagaa tttgacatat tagtatcata actgcattgc    73920
tggatttaag aaaacataaa catggaacgt aacagatatc atatcaaggg aaagtaaaag    73980
gataaaagag tcaaatcaaa ttaaaggact attaaaggt atatcttaaa tgaaaaattc    74040 actgatggt ctcccaatca ggttagttgt ttccagggaa aaaattaact gaaaataat    74100 tcaatagaat ctacagaaat agctgcacat atatacacac aatggcacac gtgcacacac    74160
ccacacccac acaggtgtga atcctagagc cacacgagca ttgaaacata gagaagtaaa    74220
aattgttcat tgaggaatat gtagcaatgc tcaatgtgtt ttaccctaat aagagctttt    74280
gtgatgtatg attgaaaaac tgacacaact gaagagagaa atagataagc ccacactctg    74340
agttagagat ttccttgatt ctctcactat ggttataaat ctttcccaaa cacaacaggc    74400
tagaacaaat atgcagaaaa ttagacatag tatctttgtt ctcaataaaa acgtcgacct    74460
atttaacatt ataccgaact accgagtaca cattaaagtg tgcatggagc attcactgag    74520
gtgtactcta cacatgacct tccagcaagt ctccatagat ttaaaagaat taagtcata    74580 cagagtgtgt cactttattc tcccagaata aagtgagata tgaataatga aagtttgcc    74640 agcttctcaa atatttggga gtcatacggt gcatttcaaa atactctttg ggacaaagaa    74700
aacatcacta aggaatttag aaaagttttg aactgagtaa aatataaca caatttatcc    74760 aaacttagga gatgcagtga atgtctttag gcttttacat aatttttagat gctcttaggg    74820 aaaaacagaa gcatgtaata atcaagattt caaactgcaa ttctcaaagt gtagtctaga    74880
gaaacctgag gacctttgag taccttcaga gacagtccat gaggttaaag gactttgcta    74940
cgtgaaaagt aagatgctat tggccctttt tactttcatt ttccaacaag agaagagggg    75000
agttttccag cagttacata atatgtaatg gcatcatgtc tctgatggct aagaaaatgg    75060
gcaattgttg actttgtgtg ttaaaaaaat tctcagtgtt ggtttcttat actataaata    75120
ttcatcttgt gttttgaaaa agaaaagctc tttggaatcc cctatgaaca aagactttga    75180
cagttgttga tctaagacca cagcttaaat atctacacaa gaaaaaaaaa aaaagcaaat    75240
aagagccaag gaaagcagat ggaaggaagt agtccaaacc agtgacattc agtgaacaag    75300
aaaagagacc aacaagggag taaactcttg aaacagaaag ttgattcttt gaaaagatcc    75360
atatgattga acacagtctg gctaaacaaa tgacagacca atgagggtgc acaaccatca    75420
ccatctggag taacagagga gaggtgccat tactatagca tcttccagtt ctgaaagctg    75480
aaaagaagat tttgagaaca attgtatgtg aataaattca ggaatgttaa tcatgtgggc    75540
caattcctga ggaagacaac aaatcagcaa accagatgct gaatagttag tgtagtcctg    75600
tagagagaca tacagagagg ctgacagaga aatatttgta tgtgcataaa acaatctaca    75660
agacacactt caaaatcaat ctcagttaat ctggaggaac atatttcaca gaaggtggaa    75720
ggagggtatt ctgatcctct tgtacattgt acaacattgt acaatgtaca gagtataatt    75780
gtacaagtac aattgaagtt gtacaagtac aagtgcaact tgcacaatgt acagagtaaa    75840
cattgatgtt tactctcaat tttcttatgg agcacagatg actttggatg tgttacaata    75900
tgaatgataa tttgtctttg agatgttcgc agttgtttag aagttgagga ccatttgtgc    75960
atattatggg acctttagtg aaaatatttc aaagtctctt tttacacttt gttacagcaa    76020
aatgtagagg gcgctaagtg cccttgaatc ttctcccatc tctggtgacc tgtgttgttt    76080
```

```
tgaaatttgc agtggcctga ccaggaacta ctgcaggaat ccagatgctg agattcgccc    76140
ttggtgttac accatggatc ccagtgtcag gtgggagtac tgcaacctga cacaatgcct    76200
ggtgacagaa tcaagtgtcc ttgcaactct cacggtggtc ccagatccaa gcacagaggc    76260
ttcttctgaa gaaggtagga agtctatggc cagacaacca cacccctagga cgttgggatg    76320 aaaagagttg caaaatctta gtgatataga agccttccat gctcacacaa ttccaagtag    76380
aatgtggact cagggtcagc cactgggaag gaacactcag cgccttctct gggagaacca    76440
gagctgtgat gtttggtacc ctgtgaaagg gtggtatcta taggaagggt gcagaccctc    76500
tagggcactg gacttaccac tcccctggtt attcaaagga tcattttagt gtcttagcca    76560
gaagaatatt ctaacatttt gccaaatttg tgaagattta ccaagctcat gataagcctt    76620
tcatggtatt tcttcaagta gtcagtgttc attgcatctt tggctttgcg gtttcggagg    76680
aatgcggttt ttgagtctgt catccttgag aaacctaata tgacttttct tagttccata    76740
tacttctggg tccaggtagc agtacatagc caacaaatgc tccatcgttc tggcctatct    76800
ccatcttaag ccagtcctgc acaactaggc tttgatggga gggatctctc agtgttcttg    76860
cccctccttc tcatggaaca tatatctgtg ttggtctctg agaagaagag tagtggatat    76920
ctactttgtt gcaatgcaga atcctgggcc aaagatacca gccatccctc caagggaata    76980 aaatttggc cagtagccct ctctgagaga caatttgtct ttgcctacga gtcctagatg    77040
caggaccgct tcctgcccca tcttcaagaa gctgaaggct ttggctttgg aggatcagca    77100
gtctagggaa atgtgtgacg gtttcatgtc tgtccccact gacagtcaat caccacctac    77160
aacctgcaca gcctgatgca tagcagtcta gtttcctgcc ttattctcag gaacacccag    77220
aagatgtcta tattaaagag catgcacatg agtgcaattt tgactgatag gcactctgat    77280 cttctttg gtgcctgtgt tttaaaggaa atctttctaa gaactcgtta aagttctaga    77340
atgctatgaa tctttgggtt ttattattgg tatgtccatc tgcctgctag tacagaacag    77400
agcatggtag tctttctcag agacaatgat cctgtttcag tcacagattt cttctgatgc    77460
ttctgtgttc tagaaattac tcagcttgat ttctcctctt tgaatttcag caccaacgga    77520
gcaaagcccc ggggtccagg attgctacca tggtgatgga cagagttatc gaggctcatt    77580
ctctaccact gtcacaggaa ggacatgtca gtcttggtcc tctatgacac cacactggca    77640
tcagaggaca acagaatatt atccaaatgg gtacaacctt gagttttctt caaagacaga    77700
cagcagcccc cttacatttc tcttggaagg gccatgcttc caactaactt cttatgacaa    77760
atttatctca gatctggaat gttgggtaga atgtctcagg cttctttctt caggcacagt    77820
gtctgaaagg agagaaatgt caggccagct ctcttttctc atagttgaca gaagcaggag    77880
gatatttgaa ggtggtgagt tctcatgaat agaaagctca ggacacatgg ccacgtgctt    77940
agaaatagca ccattccaca atgcccacta aagaccaatg caatagttca accagggatt    78000
tctgtcattc taatctccaa gtcctgaagt gaaggttgta ttagccatgt tcatcttggg    78060
caacaaataa aggatatcta tgttgacatc cagatcttcc aatcactttc tcctctaacc    78120
tgtacctggg ttctgagaac aaggtatctg aagagctatg tgttgccagc acatgagggg    78180
caaaagtagg aaggcagctg agagtcagga agtataaaga ttctgaagag ttacacatgc    78240
aggaagatgg acagaaaccc agttcagacc acgtcagcgt ttctgccatg aaggactatc    78300
aaatacatag gaaagtgtt ttcataggtt ggacaacaga catgacaggc ctgagaaaat    78360
tcagaaaggg aatcaaagga gatcaacctt atcatgtccc tggcatcctt ccttgagacc    78420
cttgaagggc aagcagatgg agcccagctg accacagcag tcttgcttaa ctgaggagag    78480
```

```
agactggagt tgtgatgcc tcaggcatct gacgtattct aggctggcta agaatgagag    78540
gggatttgtg gaggaaagga gctccaagaa tacacaccga agtcttctca aggctttggc    78600
taaatacaaa gctgcgtatg cacaaggaga gttttcacaa agaaagaaca ataaagaaaa    78660
gctactgggg aaagaacaac tgcaagggaa cagtgagctc aatggagatg ctagagctca    78720
catagcactg ggggatattt gagttctgac cactcagagg agagacacct cactgaacat    78780
cttgggcatt cagtagaggt caaagaaagc cataatttgg gagtaggatc ttcggattcc    78840
tagaaataag gtgactccag aaacactcca gcaacccttc ttccaagcca gtctaaaagg    78900
atccaaatga tttccaagta aattaactgc cttccagaaa aaagtaaaact caaccctcct    78960 tagaggtaag gaacgaatac aagtttctca gttatatgac atccccagag tgcaacttgc    79020 attttaaaaat ttactagaca caaaagaagt tttcactgtg atccataact gggagaaaaa    79080
tcactcaaca caaataggcc cagaaataat agaaattatg gcattggcaa gaacatttaa    79140
aatgcacctc tgagaactgt gtttcaggaa aatgtcagca aaagctgacc atgagagaaa    79200
tgaatgcata atatcagaaa agaaaagaat tgaagagcca aatggaaatt taaaaactga    79260
gaaaagttat atctgtaatg aggaattcac tggatggcct tataaccagt ttagatatta    79320
tggtaggaaa aggtgaacga gaaatgatt caattaaagc tagacaaacc acaagacaga    79380
cagacagaca caaatacaca tacacacaat gactgaacca attaatcaac agagcctcaa    79440
ggacatctag gaaaacatcc acacatttaa tatatgtgtt aggcaagtca cagaaagaga    79500
ggaaaaagat aatgtgacag aagttatact tgaagccatg acggctgaca aatttccaaa    79560
catacagaaa atgagaaatt catagtcatg aagctcaatg actcaggtat agattttaa    79620 agagcaaaac tctgatttac tggggtacat catagttaaa ttgtctgatt tcaaagctaa    79680
gaagaaaaaa aggggttcc tatgaacaaa cattttgaca gttgatctaa gaccacagct    79740
taaatatcta ggcaaggaaa agcaaataag acacaaggaa aggggatgga tggaaatagt    79800
ccaaaccaat gacattcagt gaacaagaaa atagaccaac aaaggagtaa atccatgaaa    79860
cagaaagttg gttctttgaa aagattcatg tgattgacca cagtctggct gaacagatga    79920
cagaccaagg agggagtaca accatcacca tttgaagtaa caggggagag gagccattgc    79980
tataccatac tccaggtctg aaagctgaca agaagatatc aagaaaaact gtatgtgaat    80040
aaattcatga atgtagatca tgtggatcaa ttccttaggt aaacaacaaa tcagcaaacc    80100
agatactgaa tagattgggt actcctatag aaagacatac agatagccag acagagaaac    80160
atttgtacgt gcataaaaca atctacaaga ctcacttcaa aatctctcag ttaatccaaa    80220
gtaacatatt tggcagaagg tggaaggagg gtattctgat cctttcttgt acacattgat    80280
gttttctctc ggtttttctta tggagtatag acgagtttgg atgtgttaca ataagaatga    80340
taatctgtct ttgaaatgtt cacagttgtt tagaagttga ggacgatttg tgattgttac    80400
aggaccttta gtgagaatat ttcaaagtca ctttttacca ctttgttaca acaaaatgta    80460
gaggatgtct ggtgcccttg tatcttctcc catctctggt gaactgtatt gttttgtaat    80520
ttgcagtggc ctgaccagga actactgcag gaatccagat gctgagatta gtccttggtg    80580
ttataccatg gatcccaatg tcagatggga gtactgcaac ctgacacaat gtccagtgac    80640
agaatcaagt gtccttgcga cgtccacggc tgtttctgaa caaggtaaga agtctctggc    80700
cagacaacca cacccttgga cgttgggata aaaagagttg caaaatctta gtgatacaga    80760
agccttccat gctgcacggg aatctgaatg tggactcagg gtcagccaat gggaaggaag    80820
```

```
cctcagcgcc ttctctgggg gaaccagggc tgagattttt ggcaccccgt gacagggtgg   80880
tgtctttagg aagcgtgcag accttctagg gcactggatt taccactccc ctggttattc   80940
aatagattat ttcagtgtcc tagtgaaaat ggatattcta acatcctgcc aaatttgtga   81000
tgatttacca agctcatcat gagcctttcc tggtatttct tcaagtagac agtactcatt   81060
gcaaacttca gctttacagt ttcagaggaa tgtggttttt gagtctgtca tccttgagaa   81120
acctgatatg actttactta gttccatatc ctcctgggtc taggtaacag tacatagcca   81180
gcaaatgctc tatctccctg tctaccttaa tcttaggcag gtgctgcaca cctaggcttt   81240
gatggaaggg atttcttagt gttcttgccc ctccttctca tggaacacgt atctgtgttg   81300
ctgtttgtga agaagagtag tggatgtcta ctttgttgca atgcaggatc ctgggcccaa   81360
gatttcccgc cgtccctcca agggaataaa attttggcca gtaccctct ctgagagaca   81420 atgtgtcttt gcctggaagt cctagatgga ggaccacttc ctgccccatc ttccagaaac   81480
ttaaggcttt ggctttggag gatcagtgct ctggagaaat gtgtgacggt ttcatgtctg   81540
cccccactga caaccaccac ctacagcctg caccgcctga tgcatggcac tctggtctcc   81600
tgccttgttc tcaggaacac ccaaaagaga tctttgccaa agaacaggca catgagtgca   81660
attttgactg ataggcactc tgatctgtcc tttggtgccc aggttttaaa gaaaatcttt   81720
ctaaaaactc attgaagttc cagaatgcta tgaatctttg agctttgtta ttggcatgtc   81780
catctgccta ctaatgtaga acagagcatg gtcgtcattt tcagagatga tgtcctgttt   81840
ctatcatgga tttttttct catgcttctg tgttctggaa attactcagt ttgttttctc   81900
ctctttgaat ttcagcacca acggagcaaa gccccacagt ccaggactgc taccatggtg   81960
atggacagag ttatcgaggc tcattctcca ccactgttac aggaaggaca tgtcagtctt   82020
ggtcctctat gacaccacac tggcatcaga gaaccacaga atactaccca aatgggtatg   82080
tctttgagtt ttctcccaag agaaacagcc acccacttaa atttctcctg gaagagccat   82140
gcttccagct aacttcttat gacccaattt ctctcagacc cagaatgttg gacagaatgt   82200
ctcaggcttc ttgctttggg cacagggtct gagaggagag aaatgtcagg ccagctctct   82260
tttctcatag ttgatagaag taggaggata cttggaggtg gtgaggtctc atgaatagaa   82320
agctcagaag aacatatgac catgtgctta gaaatagcac cattccacaa tgcccactaa   82380
agaccagtga aatagttcaa ccagggaatt ctgtcattct aatctccaag ccctggagtg   82440
aaggttgtgt ttgccatgtt tgtcttgggt aacaagtgaa ggatatctat attgacttcg   82500
agatcttccg atcactttct cctctaacct gtataaacac attgggttct gagaacaagg   82560
tgtctgaaaa gctatgtgtt gccagcccat gagggggcaaa aggaggaagg cagctgagag   82620
tcaggaagta tagagatgct gaagagttac acattcagga agatggacag aaacccatgt   82680
ctggctatgc cagcctttct gccatgaagg actatcaaat acatgagaaa acagttttca   82740
caggttggac aacagatatg gtaggcttga gagaactgag aaagggaatc aaaggagatc   82800
aacttcatca ttaacctgtc ttccttcctg gacacagtgt tggattgaag acaagcaga   82860 tggagcccag ctgaccacag cagtcttgct taactgagga gagagactgg agtctgcgat   82920
gcctcaggca gctgatgtgt tctaggctgg ctaagaatga aagggattt gtggaagaaa   82980 ggagctccag gaatacacac agaagtctcc tcaaggcttt ggctaaatac aaagctgcgt   83040
atgcacaggg agagttttca taagaaaga acaacaaaga aaagctactt gggaaagaac   83100
aactgcaggg gaacagtaag ctcaatggag atgccagagc tcacatagca ctggggata   83160 tttgaattct gaccactcag aggagaaaca cctcactaca ttttgggcat tcagtagaga   83220
```

```
ccaaagaaag ctgtattttg ggattgggat catcttattc ctagaatcaa ggtgactcca    83280
gaaaaactcc aacaacccct cttccaagcc agtctaaaag gatccaaatg atctccaagt    83340
aaattaactg cattccacaa gaaaaaaaaa actcaacccc ccttagaggc aagggacaaa    83400
tacaagttgc tcagttatat ggcattccta ttgcgttact tctatttaaa aatttaatag    83460
agacacaaga agctttcact gtgatacata actgggagaa aaaatcactc aacacaaaca    83520
ggcccagaaa ttatagaatt gatgacattg gtgagaacat ttaaaatgca cctctgagaa    83580
ctgtgtttca ggaaaatgtc agcaaaagct gaccatgaga gaaacaaaag cagaatagca    83640
agagaaaaga aagaaccgg  agagccaaat gaaaattaaa gaactgagaa aaggtacatc    83700
tctaatgaag aactcactgg atggccttat catcacttta gacattacgg taggaaaggt    83760
gacctagaaa ataattcaat aggagctaca caaatcacag acagacaga  cagaccaaca    83820 gacagaaaca cacacacaca cacacacaca cacacacaca cacacacaca cacacaaaga    83880
ctgaacctat taatcaacag agcctcaagg gcatctagga aaaatccaca catttaatat    83940
atgtgttagg caagtcacag aaggagaaga aaaagatatc atgacagaca ttatacttga    84000
agcgatgatg gctcgcaaca cgccaaatat acagaaaaca agaaactcat agtcaagaag    84060
ctaaatgact caggtataga attttaaaga gcaaaactct atgatttact gggatatatc    84120
atagttaagt tgcctcaatt caaagctaaa aagaaaaaaa gggggttcct atgaacaaca    84180
gctttgacag ctgttgatct aagaccacag cttaaatatc taggcaagga aaagcaaata    84240
aggcacaagg aaagaggatg gaaggaaata gtccaaacca atgacattca gtggaaaaga    84300
aaatagacca acaaaggagt aaatccatga aacagaaagt taggttcttt gaaaagtcta    84360
tatgattggc caaagtctgg ctaaacagat gacagaccaa ggagggagca tatccatcac    84420
catcatgagt aacaggagag atgccatt  gctatagcat cctccaggtg tgaaagctga    84480
gaagtagata ttgagatcaa ctgtatgtaa ataaattcat gaatgtagat catgtggatg    84540
gattgcttag gtaaataaca aatcagcaaa tcaaacactg aatagatcat gcagttttat    84600
agagacttac agacagcctg acagataaac atttgtatgt acgtgaaaca atctccaaga    84660
cacacttcaa aatccctctc ggttaatcca aaggaatgta tttggcagaa ggtagaagga    84720
gggtattctg atcctttctg gtacacattg atgttttctc tcagttttct tataaagcat    84780
agattacttt gaatgtgtta caataagaat cataagctgt ctttgaaatg ttgacagttg    84840
tttagaagtt gaggaccatt tgtgagtgtt atgggacttt agtgagaata tttcaaattt    84900
gcttgtttac actttgttac aagaaaacat agagggtgcc aggtggtgct gtatcttctc    84960
caatctctgg tgacctgtat tgttttggaa tttgcagtgg cctgaccagg aactactgca    85020
ggaatccaga tgctgagatt cgcccttggt gttataccat ggatcccagt gtcagatggg    85080
agtactgcaa cctgacgcaa tgtccagtga tggaatcaac tctcctcaca actcccacgg    85140
tggtcccagt tccaagcaca gagcttcctt ctgaagaagg taagaagcct gcagtcagac    85200
aaccataccc tcggacattg ggataaaaag atttgcaaaa tctttgtgat gcagaaaact    85260
tccatgctgc acaggaagtc gaaggtgaag tcatggacag ccaatgggaa ggaagcttca    85320
gtgccttctc tgggggacc  agagctggga tgttgagtgc cttgtgaggg atggtgtctt    85380
taaaaggggc acagaccctc taggacactg gatttatcac ttccctgtta tcaaacgaat    85440
catattagtg tcctagccaa gatggatatt ctaacatcct gccaaacttg tgaagatata    85500
ccaagctcct aagcctgtcc agccctttct tcaagtaggc agtgtttatt gcagtcttca    85560
```

```
gctttaccat tttgaaggaa tgccattttt gaggctgttg ttcttgagaa acctaacatg    85620
tcttcattag atccgtattg tcctgagact ttgaagcagt acatagccac caaattgttt    85680
atctccccag cctaccttca tcttgggcat gccttccaca cctaggattt gagggaaggg    85740
atttctcagt gttctcatcc ctgcttctca tggaacattt atctccgttg ttttttgaga    85800
agaagagtag tggatgtcag ctttcttgta atgagggatc ctgggcccaa gattccctgt    85860
ctcccctcct aggctataaa attttggcct gtactccttc tccctgagag caatgtgtc     85920 tttacctaca agtcctagat gcaagatcct tttctgcccc acaccccaga atctgaaggc    85980
ttttgctttg gaggagcagt ggtctagtgt gcaagggttt catgtatacc ccccactaac    86040
agccaatcac cacctatagc ctgaacagct tgatgcatgg caccctggtc tcctgccttg    86100
ttctcatgaa cacccagaag aggtgtaagc aaaagaccat tcacatgagt gtaattttga    86160
agtataggca ctctgatctg ttttttgttt gtttctttgt ttgtttgttt tccagggttg    86220
aattaaaata tttatgacta cttattaaat ttctagaatc ctataagtct atttgtattt    86280
ttattctaca tttcaatttg catgctaata tagaagagtg taaattgtta atcctcagat    86340
tattccactt tgtgtgtcat aatttttttc acatttccct tttctaggca atactgagct    86400
tgattttctc ttttaatttc agcaccaact gaaaacagca ctggggtcca ggactgctac    86460
cgaggtgatg gacagagtta tcgaggcaca ctctccacca ctatcacagg aagaacatgt    86520
cagtcttggt cgtctatgac accacattgg catcggagga tcccattata ctatccaaat    86580
gcgtatgtct atcatgttag ccataaaagg aacaatagtc aactaaaatt tctcttagct    86640
ggcccatgct acaagctcac ttcctaggtc caaatttctc atagactcag agtttgtagc    86700
aaaatgtctc aggaaactta cttttgagca aaaggtctga atgaagagaa gttttaggat    86760
tgctatcttt cataacaatt tgatggaagc agcaggatat atggaggtgg tgaagtctca    86820
ttaatgtaaa gctaaggaga tcaaatgacc aaatgctgag acaaagtatc attccacaat    86880
gcccactaaa ggtccatgca gtctttcaac catgcaattc tatcattcta tcctccattc    86940
cctgaagtga aatttgtgtt tgccattttt gacacgaatc agaagtaaca aattcaggct    87000
gggtgcagtg gctcaggcct gtgatcccaa cactttggga ggacaagacg ggcagatcac    87060
cagaggtcag gagttcaaga ccagcctggc taacatggca aaacccccatc tctacgaaaa    87120 attaaaaaat tagccggtca tggtggtggg tacctgtaat tccaactact tgggaggctg    87180
aggcaggaga aacacttgag cctgggattc agagtttgct gtgagccgag aacatgccac    87240
tgcactccag cctgggtgac agagcaagac tcaatctcaa aaaaaaaaaa aagaagaag     87300 aagaagaaaa gaagaagagg aagaagaaga agaggaagaa gaagaagaag aagaaggga    87360 agaggaagag gaggaggagg aggaggagga agaagaagaa gaagaagaag aagaagaaga    87420
agaagaagaa gaagaagaag aagaagaaga agaagaaaat agaaatgagt gcatatattt    87480
atatatgagt actagcctgt atgaacacac tgggttctaa gcaccagttt tctgaaggga    87540
tatgggttgt caggcagagt aaaagcagga atgcagatga gagtcaggaa gtaaacagat    87600
gtggtgatta aaatgggcag gtacatggac aaaaaatgc atgtctgaca aaaactggcc    87660
tcttgccata agtgagtatg aataaatatgg aaaaactgtt tgcacatgtt gaacagcaga    87720
cagtacaacc tgagatagtt tagaaaggga acaaataag atcaaccccca taattaccct    87780 tcctagactt aagggcaaag agttttaacc aaagcattcc acagcagtct tgctaaactg    87840
gggagagaga ctggagtttt gtttactaat aaaaccgaga ttttctaggt taggtaataa    87900
tgagaaagta tttgtggaga aaaggagctc caggaataca cacagaagtc tcttcaagtc    87960
```

```
tctggctgaa cagaaagctg tgtatgcaca gaaagagttt ccagagagaa aggagaacaa   88020
agaacagcta ctggggaaag aacaactgct ggggaacagt gagctcaatg aagatgccag   88080
agctcacata gcactgggag gtatttgagc tctgaccagc ctgaggagag acacttcatt   88140
gaacatcttg ggcattcagc aaagacccca aaaaaccata cttcaggagt agaattaatg   88200
cattcctaga ataaagtcta ctccagaaac accctagaaa agcttagaaa ccaagtctaa   88260
aaagatccaa atgatctcca agtaaattaa ttgcctgtca gaagaaaaca acctcttcag   88320
aggtaaacaa caaaattaaa ttgctcaatt atatagtatg cacaatgtgt ggcatacatt   88380
taaaaatttg ctaaacatac aaaaagcatt tagtgtgacc cataaccagg agaaaaatca   88440
gtcaatacaa atagacccaa aaatgataaa aataacagaa ttggcaagga gatttaaaat   88500
gtatgtatca taattgtgtt caaggattta agaaagcgt ggacaagaaa taaataaatg   88560
gataatatca acagaaagaa aaattgtaaa aggaccaaat ggagagtcaa gaactgaaaa   88620
aaaagacatc tctttaatga gaaaatcact acatggcctt ataatcatat tagatagtac   88680
agatgataaa gctaactaga aaatattagg gtggtgcaaa ccatagcacg cttatacaaa   88740
gcctgagaag ataaacagag cctcaaggac atctatgaaa atatcaaaat atttaatatt   88800
tgtttaaagc aagtcacaga ggaagggaaa gagatattgg aacagaaaaa atacttgaag   88860
cagtgatggc tgatgacttt ctaaatatgg aaaaaatgat aaactcacat agtcaagaag   88920
ctcaatggat cagatatagg attttaaaaa gtaaagctgt atgatttatt tggacacatc   88980
ataattaaat tgtccataat caagataga aagtaaaatc ttatttgaag cccaagggaa   89040
aaaacatacc tttacataga gtaacagtga cacaaatgac tgatgccttc tcatcagaaa   89100
caacacaaat cagaaacaat agaataacac ctttagagtg gtaagaagaa aaaaagatca   89160
aatcagaaac aacaaaataa cacgtttaga gtggtaagga ggaaaacaag atcaaatcag   89220
aaacaatgga ataacacctt tagagtgtaa gaaagaaaaa aagatcaaat caggaacaac   89280
agaataacgc cttcagagtg gtaagaagga aacaagata aaatcagaaa caatgaaata   89340
acacctttag agtagtaaga agaagaaaag atcaggtcag aaaaaatgga ataatatgct   89400
aagaagaaaa aaaaagatca agtcagaaac aatggaataa cacctttaga gtgaaaagaa   89460
ggaaaaaaac ccagcaagct taaacgctat gcacagcaaa caattccact gaaaatgaat   89520
gttacgtaag tacatattct gtcctcctaa aaacaaagaa caaataaaag aatgtttcat   89580
cagcaggatt atgtaataaa agatgtgaaa gaatgctatg taagtagaag aaaaataata   89640
ccatatggga attggcatca aaaccacaaa atactatcaa aacaaaaaaa ctttattgat   89700
aaatttaaca caatatgcaa aagaactata ccatgtatac tacataacat tggtgagaag   89760
aaaattagaa gatctaaata aagacacatc atgcttatag attaaaaaat ccaatgtcac   89820
ttttcacaaa actgatcttt agtttcaacc cacacccaag cagaattcct gcagtctttt   89880
cttgaaaacc taacgaatg tatatgctag aatcaccaag acaatcttta aaagaataa    89940 aaaacttgga ataaaatcac aagtttgtgg gatagatgca tatggtaata tggaaattct   90000
cataaagaca cagtaatcaa gacatgtggt attggctggg acgcttggct gtaatcctaa   90060
cactttggga ggccaagatg agaggattgc ctgagatgag gagttgcaga caagcctggg   90120
caacatagca agaccctcat ctctacaaat atttaaaaaa attagccagg tttggtgcca   90180
tgtgcctgta gtcccagcta ttcaggaagc tgaggtggga ggatcactgg agcccatgag   90240
gtggaggctg aaatgagcca tgattgtgct actgaacttt agcctgggag acagattaaa   90300
```

```
accttccctc tctctctcaa acaaacaaac aaaaaatmaca tagtattggg caaaacatat    90360
gcaaacaaaa acagaaaagg gtcagcataa atttacatat atggtcaatt tattttcaat    90420
acaggtagca aagcaattta atgaggaaat ttttttccaa aattggtctg aaacaactgg    90480
atagccatag aaaaaaacta taacaaatgt gacgcttgaa tcctactgta tgactcaaat    90540
taaattaatt tgagatagct cttagacctc aatgtaacag ctaattctga ggctgaaata    90600
taagactgct atgaaaaagt atagtatctt ataaccttgg agaaggaaaa attttttgag    90660
ggaagaacca gaaaacacta actgtaaaag aaaacaaatg ataatgtgga cattcattga    90720
ataaaaactt atgctcacca aatatgactg ttaagaaaat aaataagtaa gtaacacact    90780
ggaagaaaaa cactctcatc catatatctg acaaatggcc tgtatccaga gtatagaaac    90840
atttctccca ctcactaatc agaggacaaa caacctaatc aaaatgggca acaggcttga    90900
atagtcattt cttaggagaa gatgcacaca gagccaacaa tcacctgaaa aagtgcacaa    90960
catcttagcc atcaaaaatc aagagttata accctcataa gatgacactg aacatccagt    91020
gtacatggat atcattaaga agacacaata ataagtggtg tcaccgattt ggagctagaa    91080
tgtgccactc tctcatatgc tggtggaagt tcaaaatcat acaacaaatt aaaaaatcag    91140
tctgatgctt tcttataaag ttcgataaat atgcatctat cctacaaacc tgtaattcta    91200
ttcttgaata tttaccccccc aaaatgaaaa cataagtcca caaaaatcta tataaatatt    91260
catagcagct ttatgtttta taaactcaaa ataaaaacta tttcaatgtt ttcatcaaaa    91320
gaaaatgaaa actatttaaa tggtttcatc aaaagaaaat gaaaaagaa tttccagtat    91380 atttatacaa aggaatacta ttcatcaaca aggaacaagt tactgatagt ctcagaagca    91440
tgaacaaacc tcaaaaatat attaaggaaa gaagccagac gtcaaagtgt atagtctgta    91500
tgagtccatt catgtgagtt tatagaaaac acaatttatg gtgaaagaaa ccaatagcat    91560
ttgacactgg ccgtgggaag agggtagcag agattgattg agcagccaca caagggagtt    91620
tctggggtgg tgaaaatgtt ctgcattgtg agggcagtgt gggctacaca agtatatgta    91680
tttatcaaat ctcatccagc tacatttaag atctgtgcat ctcactctat gtgaaaatat    91740
actcaactga aaaacagagc aggtatctgt ttcaggtgct acatcacttg atacgtccag    91800
ttgtgttaaa aaccactgcc taacatcctc aaatggggga tctgggcttg agactaggtc    91860
acatgtgtag agtctctaca gagaccgtgt tggattccca tgctccataa tacgttccaa    91920
gttttctcag acagccacag gtcatgaatg tgaggattct gagaggttgg agcaacgttc    91980
ttgggaggca taatggggaa ggcattctcc aagattcctc cagcctgggg tcttcacctg    92040
ctgtgcctct tactgcattg ttttctgact catccatagc cacttgaccc cttcagatcc    92100
catagtctac ctagccgtct ccctttatgc cttgggtccc gctgttcttt caactcatca    92160
cccattcctt cagtcccaga gtggctgcag ccagcagagg atggactgag agcaggagag    92220
gaggtcgtgc ccatgaaccc atcctagaga agcagcatcc tgcctgggag ctagttttcc    92280
agggaagctt ttataagtcc tgtagaccca aacccacttg ctctaccaga tacagtattt    92340
atagtaatac tattttcatg attattttat attgcaaatg tagagcattt atgctacact    92400
atgagtaaat agagtaaggg ggctggcatg ggaattatat aatcttggat gccacttctt    92460
ccttggggaa atgtatttga gttccaactt acatattact atatagtctt atagagagag    92520
agacaaagag ctagacagac agagatatct ttgtatgtgc attaaaaaat ctaagataca    92580
tatttcaaaa tctgtgtcat ttattctgga ggaaagtatt tggcagaagg tgaaggaag    92640 atattctgat cctttcttgt acagacatgt attatctcag ttttcataga gagcatatac    92700
```

```
tactttgat gttttaaaac aaaaattata atctgtgatg tgtccacagt tgtttaaaag    92760
ttgaagctga agaccatttg tgcttgtggc aatattattg tggtataatg ggaatatttc   92820
aaaggcactt gttaacactt tgttacagca aaatgtagag ggcgctaagt gcccttgaat   92880
attctcccat ctctggtgac ctgtgttgtt ttgaaatttg cagtggcctg accaggaact   92940
actgcaggaa tccagatgct gagattcgcc cttggtgtta caccatggat cccagtgtca   93000
ggtgggagta ctgcaacctg acacgatgtc cagtgacaga atcgagtgtc ctcacaactc   93060
ccacagtggc cccggttcca agcacagagg ctccttctga acaaggtaag aaatttgtgg   93120
ttagacatct atatactggg atgaaaaacc atggaaaatc ttactgatgc agaagccttc   93180
agtggtacac tggagggttg gttgagggtc tgcaatgtgg aggaaagcct cagcgccctc   93240
tctgggggat ccagaactgt gattttggc acgctgtgag gaggcagtgt ctttaggaag    93300
ggcacggtgt ctttaggaag ggcacagacc cgccagggca ctggacttac cactcccctg   93360
gttattaaat gggtcatttc agtgtcctag ccaaaatgga tattctaaca gcctgccaaa   93420
tatgtgaaga tttccaagcc aataagcctt tccagtgatt taaagtagac ttttttcatt   93480
gcaatctaca gtttgcagtt tcttaagaac atggcctttg agtatgatat cctagagaaa   93540
cctaaggaga ctgcattatt tttctattgt cctggggctg catagcagga ggtaaccaac   93600
gaatgctgtc tctccctggc ctatctcagt cttttcacag ctctgttcac ctcagctttg   93660
aagttagaaa tttctaggtg ttcttgcctc ttcttctcat gaaacctgca ttggcagtga   93720
gtctacagaa gaagaggaag agaattctgc tttgttacaa ttcaggactc tgggcactag   93780
aagattccct atctctcctc caagggaata agttgtttgt ctctaaccct ccttgagaaa   93840
caatgagtct ttgcctgcac tcctaaatgt aggatgattt cctgcccaaa ttttcaaaag   93900
attaagcctt ttgccttggt atgagcaatg gtctaggaa atgcgcaagg gtcttgtgtc    93960
ggcccctgac tgaccaccag tcacctccta cagcctgcac caaggaatgc attgcattct   94020
ggtcttctgc cctgtggttc tcatgaaaac cagcagagat tcatatgatg gagctgcaca   94080
tgaatgtaat ttccaatgtc cagcattctc ctctgttctt tatctttaga tttaaaaata   94140
atgtttctat gaacttatta aaattctaga atactatgaa tctactgggt cttttcacat   94200 cctttttgcta ctagtagaaa aaagaatagt aataatttc agaggctact gtccagtatg    94260
tgacataaat tgtctcccat gttttctctgc tcatgcaatt actgagtatg atttatttta  94320
ttttaatttc agcaccacct gagaaaagcc ctgtggtcca ggattgctac catggtgatg   94380 gacgagtta tcgaggcata tcctccacca ctgtcacagg aaggacctgt caatcttggt    94440
catctatgat accacactgg catcagagga ccccagaaaa ctacccaaat gcgtatgtat   94500
ttgattaaaa ccataagagg agcaacagcc aactcaaata ttggttagaa gacccatgct   94560
ttaagctcac ttcctaggga caaatttctc ttagactcac attttggcaa aatgtctcag   94620
gacctttgct tttgagcaaa gagtctaaga gaagagaaat tttaggcctg ctattttcc    94680 taatagtttt atggaaggag tagaatatac ggaagtggcg aagtcatatt aatgtaaagc   94740
tcagaagata aatgaccaaa gcttaaacac agcaccattc cacaatgccc actaaaaatc   94800
aatgtcatct ttcactcgtg caattctgtc attctaaatt tcaattcccg aaggtttgtt   94860
tgccattttt gtcatgggta ataagtaaaa aaaaaaaaat taagatgtgt atatatatat   94920
atatatatat atatatacac acacacacac acacacaaac atctgaatat ttatatatat   94980
gtctgaatat ttatatactt gtgtataaaa cttatattta aatttttgca taaatttata   95040
```

```
tatttttaat atttcattaa aaattatatt gtttcactat gtatgtctga gtattttat    95100 atattttaat ataacatttt aaatatttat atataaatat tcaggtatgt aactgaatat    95160
tcatttacac acacaaatat atgtgtgcat gtgtgtatat atatatatac ccatatatat    95220
atatatatat atatatacat atatatatat atatatatat gtatatatat atatatatat    95280
atatatacac acacacacac acacacatac atacaggtat aaacacactg ggcctgaagc    95340
accagtggtc tgaaaggaca tgtgttgcca ggacttgaag agcaaaagca ggaaggcgga    95400
tgagagtcag gaggtacaca aacgctgaaa agtaaaatgg acaagtacat ggacaaaaag    95460
caggtataag cataacagcc ttttggaagt aaatgactat aaaatatatg aaaatactgt    95520
tttcacaagt tgcacaacag atagtagtgt attgagataa tttagaacag aaaacaaatg    95580
tgatcaaccc cataagtgtg ctgtatttca tcatggattg aaggaaaaag agatggagcc    95640
caagaagacc acagcagtct tgatgaactg agagacacca gagtttggga ttacaaaggc    95700
agctgggatt ttctacactt ggtaataatg agaaagaatt tgtggagata aagagctaca    95760
gtcatgtacc tagaagtcac ctcagtgtaa tataaatctg catatgcaca gggagtgatt    95820
ccacaatgaa agtaggacaa agaacagcta ctggggaaag aataactaca agggaacaat    95880
gagttcaatg gagatggcag agctcacaaa gcactggggg atatttgagt tcttaccagc    95940
tagaaaagag acctcattgc aaatcttggg cattcagtag agaccccaga aaagccactc    96000
tttggaaaca gagttgatgt attttaagag caaaatctac tccacaaaaa tcctagcaaa    96060
attgaaaagc aagtcagaaa gaccaaaatc ctctcaacat aaattagttg cccatcagaa    96120
gaaagcttaa cctcttcata ggtaaacaat aaaatcaaat tgctcagtta tctggcatcc    96180
acaatatgtg acataaattt aaaaatttac tagacataca agaagcattt agtgtgatcc    96240
ataaccagga gaaaatcat tcaatacaaa tagacccaga aatgacagaa atgatagaat    96300
tagcaaaaac atttaaaata tacatatgat catttgatct tgtgatcaga tatcacaaga    96360 gaagaaaagag atacttgaac agaaaaaatg cctgaagcaa tgatggctga aaactttcca    96420
aatatgaaga aaaaaagct cacagattca agaaaactaa tcaatcagaa atatgatttt    96480
gaaaagtaaa aatgtatgat ttactttggc aaatcttctt ggttaaattg tctaaaatca    96540
aagaaagcta ggaaaatttt ataagccaga ggaaaaaga ttgtttatat aaaggaacag    96600
ttacacaaat gactgatgcc ttctcatcag aaacaatgaa agtcagaaac aataaagtaa    96660 catcttttaaa gtaatagaag aaaaacccaa gaggtgaggg atcgtggcag acaggaggca    96720
ggactagatt gcagctctgg acagagcagc atgcagaggc tcatattgtg aattttagcc    96780
ccatattgac tgcaagaaca gaccagcaat cctgagagga cccacagacc gtgtgaagga    96840
agcagactgc tcctgcagga taagggagac accccaaata ctgtgagttc cccaactgca    96900
gaagtggaaa agggaggcct tactccctca aacacacccc acaactggag aagctgaaag    96960 tctgttttgca ggagaagttc ccaactttac ctgggcctca gtaaatttag agagctgagc    97020
caagcaaaat atagggtag aggaagcagc agagaagacc tcagagcttg ctggatcccc    97080
aagcagctca ttcctgcctg gcaccacaga gatccatcag aagtgtggcc aaaggaacag    97140
agggtaaaac tccacatgga ggactgctct acctgaactt tctaacaatt tgaacagggg    97200
gagaagcctc ctggccagaa cttggggag ggcatgaatc tggtttgcag acttcacagg    97260
tgggggaagg actaaagccc ttttctttca cagctgggag gtggaaagcc tcaggcaagt    97320
tttcaagcct gactttcccc ccacctggaa acagacttgg agctgttgcg gggttggggg    97380
catggtggga gtaagaccag cccttcagtt tgcatgggtg ctgggtgagg cctgtgactg    97440
```

| | |
|---|---|
| acagcttccc tccacttccc cgacaactca gatgactcag cagaggcagc cataatcctc | 97500 |
| ctaggtacac aactccagtg acctgggaac ttcacccccca caccatacag aagcttcagt | 97560 |
| aagacgtgcc caaggaaagt ctgagctcag acacgcctag tcccacccccc aactgatggt | 97620 |
| ccttccctac ccaccctggt agcagaagac aaagagcata taatctttgg agttctaggg | 97680 |
| cccacccacc tctagtccct ctccacacta gtatagctga tgcaggaggc caaccagcac | 97740 |
| aaaaatagag cattaaacca ccaaagctag gaaccccctat ggagtccatt gcaccctcct | 97800 |
| ccacctccac cagaacaggc actggtatcc acagctgaga gacccataga tggttcacat | 97860 |
| cacaggactc tgtacagaca gtccccagta ccagcccaga gctgggtaga cttgctaggt | 97920 |
| ggcaagaccc agaagacagg caataatcac tgcagttcag ctcacaggaa gccacatcca | 97980 |
| taggaaaaga gggagagtac tacatcaagg gaacaccccca tgggataaaa acatctgaac | 98040 |
| aacagccttc agccctacct tccctctgac acagtctacc caaatgagaa ggaaccagaa | 98100 |
| aaccaaccct ggtaatatga caaaacaagg ctcatcacac tcccagttca ccagcaatgg | 98160 |
| atccaaacca agaagaaatc cctgatttac ctgaaagaga attcaggagg ttagttatta | 98220 |
| agctaatcag ggagggacca gagaaaggca aagcccaatg caaggaaatc caaaaaaaaa | 98280 |
| aaggtataag aagtaaaagg tgaaatattc aacaaaatag atagcttaat aaaaaaacaa | 98340 |
| taaaaaattc agtagacttt ggacacacct ttggaaatgt gacatgctct ggaaagtctc | 98400 |
| agcaatagaa ctgaacaagt agaaaaaata aattcagagc tcaaagacaa ggacttcaaa | 98460 |
| ttaacccaat ccaacaaaga caaagaataa aggataagaa aatatgaaca aagccttcaa | 98520 |
| gatgtctggg attatgttaa atgaccaaat ataagaataa tcgtggctcc tgaggaaaaa | 98580 |
| gacaatacta aaagcttgga aaacatattt gggggaataa ctgggaaaaa cttacctggc | 98640 |
| cttgctggac acctagacat gcaaatacaa gaaacacaaa gaacatgtaa atacaagcag | 98700 |
| cacaaagaac acctgggaaa ttcatcacaa aaagatctta gcctaggcac attctcatca | 98760 |
| ggttatgcaa agttaagacg aaggcaagaa tcttaagagc tgtgagacag aagcaccagg | 98820 |
| taatgtataa aggaaaccct atcagattaa cagccagttt ttcagcagga actgtacaag | 98880 |
| ctataaagga ttgagccct atcatagcct cctcaaacaa aacaattatc agtcaagaat | 98940 |
| tttgtatcca gcgaaagtaa gcatcatata tgaaggaaag atacagtcgt ttttggacaa | 99000 |
| acaaatgcta agagaattca ccattaccaa gtcaccacta gaagaactgc taaaaggagc | 99060 |
| tctaaatctt gaaacaaatc ctagaaacac atgaaaacag aatctcttta aagcataaat | 99120 |
| cacacaggac ctataaaaca aaagtacaag ttaaaaaaca aaaacaaaaa acaaaaccaa | 99180 |
| agtacggagg caataaagaa tatgatgaat gcagtggcac ctcacatttc aatgctaaaa | 99240 |
| ttgaatctaa atggcctaaa tgctccactt aaaggataca aaaagagttg gtggctggca | 99300 |
| agatggctga ataggaacag ctccagtctg ccgctccccg tgagatcaac acatagggtg | 99360 |
| ggtcatttct gcatttccaa ccaaggtacc cggctcatct cattgggact ggttagacag | 99420 |
| tgggtgcagc ccacagaggg tgacctgaag cagggtgggg tgtcacctca cctgggaagt | 99480 |
| ggaaggggtc agggaactcc ctcccctagc caaaggaagc cgtgagggac tgtgccgtga | 99540 |
| agaccagtgc attctggcac aaatactatg cttttcccac ggtctttgca acctgaagac | 99600 |
| caggagattc ccttgggtgc ctacaccacc agggccctgg atttcaagcc caaaactggg | 99660 |
| ctggcatttg ggcagacact aagctagctg caggagtttt ttttcatacc ccagtggtcc | 99720 |
| ctggaatgcc agcaagacag aaccattcac ccccgtgaag aaagggctga agccagggag | 99780 |

```
ctaagtggtc tttctcagtg gatcccaccc ccatggagcc cagcaagcta agctccactg   99840
gcttgaaatt cttgctgcca gcacagcagt ctgaagttga cctgggacgc tcaagcttgg   99900
tgggaggagg ggtatccaca aatactgggg cttgagtagg aggttttccc ctcacagtgt   99960
aagcaaaacc gctaggaagt ttgaactggg cagggtgcac tgcagcttgg caaagccatt  100020
gtagcaagag tgcctctcta gattcctcct ctctgggcag ggcatctctg aaagaaaggc  100080
agcagcccca gtcagaagct tatagataaa actcccatct ccctgggaca gagcaactgg  100140
aggaaggggt ggctgtgagt gcagctccag cagacttagt ttcctgcctg ccagctctga  100200
aaagagcacc agatccccca acacagcact agagctctga taagggacag actgcctcct  100260
caagtgggtc ctggtttcag aagataataa gaaactcctc tgagctaaag gagcatgttc  100320
taacacaatg caaggaagct aagaaccttg aaaaaggtca gaggaattgc taactacagt  100380
aagcagttta gagaagaaca taaatgacct tagggagctg aaaaacacag cacgagaact  100440
tcatgacaca tacacaagta tcaatagcaa aatcgatcaa gtggaagaaa ggatatcaga  100500
gattgaaaat caacttaatg aagtaaagcg tgaaaacaag attaaggaat aaagaatgaa  100560
aaggaatgaa caaatcctcc aagtatggga ctatgtgaaa agattgaacc tacgtttgat  100620
tggtgtacct gaaagtgatg ggagaatgga accaagttgg aaaacactct tcaggatatt  100680
atccaggaga acttccccaa cctagcaaga caggccaaca ttcaaattaa ggaaatacag  100740
agaataccac attcaaattc aggaaataca gagaacacca caaagatact cctcaagaag  100800
agcaacctga agacacataa tcgtcagatt caccaaggtt gaaatgaagg aaaaaaatgt  100860
tgagggcagc cagagagaaa gtttgggtta cccacaaagg gaaccccatc agactaacag  100920
tggatcttcc tgcagaaact ctacaagcca gaagagagtg ggaggccaat attcaacatt  100980 ctttttact attattatac tttaagttct agggtacatg tgcacaaggt gcaggtttgt  101040
tacatatgta tacatgtgcc atgttggtgt gctgcaccca ttaactcttc atttacatta  101100
ggtatatctc ctaatactat ccctccccac tccccccatc ccatgacagg ccccggtgtg  101160
tgatgttccc cactctgtgt ccatgtactc tcattgttca attcccacct atgagtgaga  101220
acattcggtg tttggatttc tgtccttgtg atagtttgct gagaatgatg gtttccagct  101280
tcatccacat ccctacaaag gacatgaagt catccttctt tatggctgca tagtattcca  101340
tggtgtatat gtgccacatt tcttaatcc agtctaccat tgatggacgt ttgtgttggt  101400
tccaagtctt tgctattgtg aatagtgccg caataaacat atgtgtgcat gtgtctttat  101460
agcagcatga tttataatcc tttagatata tatccagtaa ttgtatggct gtgtcaaatg  101520
gtatttctag ttctaaatcc ttgaggaatc accgcactgt cttccacaat ggttgaacta  101580
gtttacagtc ccaccaccag tgtaaaaatg ttcctatttc tccacatcct ctctagcatc  101640
tgttgtttcc tgactttta atgatcacca ttctaactgg tatgagatgg tatctcattg  101700
tggttttgat ttgcatttct ctgatggcca gtgatggtga gcacttttc atgtgtctct  101760 tgactgcata aaagttttct tttgagaatt gtctgttaat atcctttgcc aactttttga  101820
tggggttgtt tgattttttt tcttgtaaat ttgtttatgt tctttgtaga ttctggatat  101880
tagccctttg tcagatgggt agattgtaaa aattttctcc cattctgtag cttgcctgtt  101940
cattctgagg gtagtttctt ttgctgtgca gaagctcttt agtttaatta gatcccattg  102000
gtcaattttg gcttttgttg ctattgcttt tggtgattta gtcatgaagt ccttgcccat  102060
gcctatgtcc tgaatggtat tgcttaggtt ttcttctagg gttatatgg ttttaggtct  102120 aacatttaag tctttaatcc atcttgaatt aattttttata taaggtgtaa ggaagggatc  102180
```

```
cagtttcagc tttctacata tggctaggca gttttcccag caccatgtat taaatagggga 102240
aacctttccc tatttcttgt ttttgtcagg tttgtcatag atcagatggt tgtagatgtg 102300
tggtattatt tctgagggct ctgttctgtt ccattggtct atatctctgt tttggtacca 102360
gtaccatgct gttttggtta ctgtagcctt gtaatgtagt ttgaagtcag gcagagtgat 102420
gcctccagct ttgctttttt ggcttaggat tgtcttggca atgcatgctc ttttttgttc 102480
catatgaact ttaaagtagt tttttccaat tctgtgaaga aagtcattgg tagcttgatg 102540
gggatggcat tgaatctata aattaccttta ggcagtatgg ccattttcac aatattgatt 102600
cttcctatcc atgagcatgg aatgttcttc catttgtttg tgtcctcttt tatttcatta 102660
agcagtggtt tgtagttctc cttgaagagg tccttcccat cccttgtaag ttggattcct 102720
aggtatttta ttctctttga agcaattgtg aatgggagtt catccatgtc cctacaaagg 102780
acatgaagtc atgtatggga atgcttgtga ttttgcaca ttgattttgt atcttgagac 102840
tttgctgaag ttgcttatca gcttaaggag attttggtct gagaagatgg ggttttctaa 102900
atatacaatc atgtcatctg caaacaggga caatttaact tcctcttttc ctaactgaat 102960
accctttatt tccttctcct gcctaattgc cctggccaga acttccaaca ctatgttgaa 103020
taggagtggt gagagagggc atccctgtct tgtgccagtt ttcaaaggga atgcttccag 103080
tttttgccca ttcagtatga tattggctat gggtttgtca taaatagctc ttattatttt 103140
gagatatgtc ccatcaatac atagtttatt gagagttcag catggagagc tgttgaattt 103200
tgtcaaaggc cttttctgca tctattgaga taatcatgtg gttttttgtct ttggttctgt 103260
ttatatgatg gattacattt attgatttgc atatgttgaa ccagccttgc atcccaggga 103320
taaagccaac ttgatcatgg tggataagct ttttgatgtg ctgctggatt cggtttgcca 103380
gtattttatt gaggatttt gcatcaatgt tcatcatgga tgttggtcta aaattctcat 103440
ttttgttgtg tctctgccag gatttggtat caggatgatg ctggcctcat aaaatgagtt 103500
agggaggatt ccctcttttt ctatgattgg aatagtttca gaagaattgg taccagctcc 103560
tctttgtatc tgtggtagaa ttcggctatg aatctctcct ggacttttt tggttggtag 103620
gctcttaatt attgcctcaa tttcagagcc tgttattggt ctattcaagg attcaatttc 103680
tttctggttt agtcttggta gggtgtatgt gtccaggaat ttttccattt cttctagatt 103740
ttctagttta tttgcacaga ggtgtttata atattctctg atggtagttt gtatttctgt 103800
gggattggta gtgatatccc ctttatcatt ttttattgca tctatttgat tcttctctct 103860
tttcttcttt attagtcttg ctagtggtct atcaattttg ttgatctttt caaaaaccaa 103920
gctcctggat tcattgatgt tttgaaggtt tttttgtgtc tctatctcct tcagttctgc 103980
tctggtctta gttatttctt gccttctgct agcttttttaa tgtgtttgct cttgcttctc 104040
tagttctttt aatggtgatg ttagggtgtc aattttagat cttctcctgct ttctcttgtg 104100
ggcatttagt gctgtaaatc tccccctaca cactgcttta aatgtgtccc agagattctg 104160
gtatgttgtg tctttgttgt cattggtttc aaagaatatc tttatttctg ccttcatttc 104220
gttacatacc cagtagtcac tcaggtgcag gttgttcagt ttccatatag ttgagcagtt 104280
tttaatgagt ttcttaatcc tgagtcctag tttgattgca ctgtggtctg agagacagtt 104340
tgttataatt tctgttcttt tacatttgct gaggaatgcc tcacttccaa ctatctggtc 104400
aatttcagaa taagtgcgat gtggtgctga gaagaatgta tattctgttg atttggggtg 104460
gagagttctg tagatgtcta ttaggtctgc ttggtgcaga gctgagttca attcctggat 104520
```

```
atccatgtta actttctgtc tcattgatct gtctaatgtt gacagtgggg tgttaaagtc  104580
tcccattatt attgtgtggg agtctaagtc tctttgtagg tctctaagga cttgctttat  104640
gaatctaggt gctcctgtat tgggtgcata tatatttagg atagttagct cttcttgtta  104700
aattggtccc tttaccatta tgtaatggcc ttctttgtct cttttgatct ttgttagttt  104760
aaagtctgtt ttatcagaga ctaggattgc aaccctgct ttttttgttg ttttccattt  104820
gcttggtaga tcttcctcca tcctttatt ttgagcctat gtgtgtctct gcacgtgaga  104880
tgtgtcttca gaatacagca cactgatgga tcttgactct ttatccaatt ttccagtctg  104940
tgtcttttaa ttggagcatt tagcccattt acatttaagg ttaatatttt tatgtgtgaa  105000
tttgatcctg tcatcatgat gttcgctggt tattttgctc attagttgat gcagtttctt  105060
cctagcatcg atggtttta caatttggca tgtttgtgca gtggctgata ccgattgttt  105120 cttccatgt ttagtgcttc cttcaggagc tcttgtaagg caggcctggt ggtgacaaaa  105180
tctctcagca tttgcttgtc tgtaaaggat tttatttctc cttcacttat gaagcttagt  105240
ttggctggat atgatattct cagttgaaaa ttcttttctt taagaatgtt gaatattggc  105300
tgccactctc ttctggcttg tagagtttct gctgagagat ctgctgttag tctgatgggc  105360
ttccctttgt gggtaacccg acctttctgg tgaatctgac aattatgtgt cttggagtta  105420
ctcttctcga ggagtatttt tgtggcattc tctgtatttc ctgaatttga atgttggcct  105480
gcctttgtag gttggggaag ttctcctgga taatatcctg aagagtgttt ccaacttgg  105540 ttccattctc ctcgtcactt tcaggtacac caagcagatg tagatttggt cttttcacat  105600
agtcccatat ttattggagg ctttgttcat ttcttttac tcctttttt ctctaaactt  105660 ctcttctcgc ttcatttcat tcatttgatc tttaatcact gatacccttt cttccacttg  105720
attgaatcaa ctactgaaac ttgttcatgt gtcacgtagt tctcgtgcca tggttttcag  105780
ctccattaga tcatttaagg tcttctctat gctgtttatt ttagtctgcc attcatctaa  105840 acttttcaa ggttttttagc ttcttttgcaa tgggttcgaa catccttctt tagctcggag  105900
aaatttgtta ttacagatcg tctgaagcct tcttctctca actcatcaaa gtcattctct  105960
gtccagcttt gttctgttgc tcgtgaggag ctgcgttcct tcggaggaga agaggcaccc  106020
tgatttttag aattttcagc tgttctgctc tggtttctcc ccatctttgt ggtttatcta  106080
cctttggttc ttgatgatgg tgatgtacag atggggtttt ggtgtggatg tcttttctgt  106140
ttgttagttt tccttctaac agtcaggacc ctcagctgca ggtctgttgg agtttgctgg  106200
aggtccactc cagtccctgt ttgcctgggt attaccagtg gaggctgcag aacagcaaat  106260
attacagaac agcaaatgtt gctgcctgat tcttcctctg gaagcttcat ctcagagggg  106320
cacccagctg tatgaggtgt cagttggccc ctactgggag gtgtccccca gttaggctac  106380 tcggggtca cggacccact tgaggaggca gtctgtccat tctcagatct caaactctct  106440
gctgggagaa ccactactct cttcaaagct gtcagacagg gatgtttaag tctgcagaag  106500
tttctgctgc cttttgttca gctatgccct gcccccagag gtggagtcta cagaggcagg  106560
caggtctcct tgagctgtgg tgggctccac ccagtttgag cttcctggtc gctttgttta  106620
cctactcaag tctcagcaat ggcagacgcc cctcccccag ctttgctgcc gccttgcagt  106680
tcggtctcag actactgtgc tagcagttca atctcagact gctgtactag cagtgagcaa  106740
ggctctgtgg gcatgggacc ctctgagcca tgtgcaggat ataatctcct ggtgtgccgt  106800
ttgctaagac cattggaaaa gtgcaatatt agggtgggaa tgtcccgatt ttccgggtac  106860
atctgtcatg gcttcccttg gctaggaaag ggaattccct gaccccttac acttcccggg  106920
```

```
tgaggcaata tcccgccttg cttcggctca ctctccgtgg gctgcaccca ctgtctgaca 106980
agccccggtg agatgaaccc agtacctcag ctggaaatgc agaaaccacc catcttctgc 107040
tttgctcatg ctgggaactg tggactggag ctgttcctat tcggccatct tgaaacctcc 107100
cctctctcac gatcacaagg tcccacaata ggccgtctgc aggctgagga gcaagaaaag 107160
ccagtctgaa ttccaaaact gaagaaattg gagtctgatg ttcaagggca ggaaacatcc 107220
agtgccaaag aaagatgtag aatattcaac attcttaaag aaaataattt tcaacctaga 107280
atttcatatc cagccaaact aagctttata caaaggaga agtaaaatcc tttacaaaca 107340
agcaaatgct gaggaatttt gtcaacacca ggcctgcctt acaagaggtc ctgaagaaaa 107400
cactaaatat ggaaaggaaa accagtaac agctactgca aaacatacc aaattgtaaa 107460 caccatcaac actataaaga aactgcatca actaatgggc aaaatagcca gctagcatca 107520
taatgacagg atcaaattca cacataacaa tattaacctt aaatgtaaat gggctaaatg 107580
ccccaattaa aagacacaga ctgggaaatt gaataaagag tcaagaccca ttggtttgct 107640
gtgttcagaa gacccatctc agggtgaaaa gacatacatg ggctcaaaat aaagaaatga 107700
aggaatattt accaagcaaa tggaaagaaa aaaaagcag cggttgcaat cttagtcttt 107760
gatgaaacag actttaaacc atcaaagatc aaaagagaca aggagggca ttacctaatg 107820 gtaaaagtat caatgcaaca agaagatctg actgtcctac ttatatatgc acccaataca 107880
ggagcaccca gattaataaa gcaagttctt agagacctac aaagagactt agacttccac 107940
acaaaaatag tgggagactt taacaccca cagccaatat tagatcgacg tgacagaaaa 108000
ttaacaagga tattcaggac gtgaattcag ctctggacca agctgaccta atagacatct 108060
acagaactcg acaccacaaa tcaacagaat atacattctt ctcagcacca cattgcactt 108120
attctaaaat tgaccacata attggaagta aaacacttct cagcaaatgc cgtagaatgg 108180
aaatcataac aaacagtctc tcagaccaaa gtgcaatcaa actagaactc aggattaata 108240
aactcactca aaaccacaca actatatgga aactgaacaa cctgctcctg aattactact 108300
gggtaaataa caaaattaag gcagaagtag ataagttctt agaaaccaaa gagaacaaag 108360
acacaatgtg ccagaatctc tggtacacag ctaaagccat gtttagaggg aaatttatag 108420
cactaaatgc ccacaggaga aagcgggaaa gatctaaaat caacacccta acatcacaat 108480
tcaaagaacc agagaagcaa gagcaaacaa atacaaaagc tagcagaaga caagaaataa 108540
ctaagatcag agcagaactg aagggggataa agacacgaaa acccttaaa aaattaataa 108600 atccaagagc tggttttttg aaaagattaa caaaatacat agaagcctag ccagactaat 108660
aaagaagaaa atagagaaga atcaaataga cacaataaag aataataaag gggatatcac 108720
caatgatgcc acagaaatac aaactaccat cagagaatac tttaaacacc tctatgcaaa 108780
taaaatagaa aatctaaaag aaatggataa attcctggac acatacaccc tcccaagact 108840
aaaccaggaa gaagtcaaat ccctgaatag accaataaca agttctgaaa tcgaggcagt 108900
aattaatagc ttaccaacca aaaaaagccc agaccagagg gattaacagt caaatcctaa 108960
cagaggtaca aagaagagct agtactattc cttctgaaac tattccacac aatagaaaaa 109020
gagggactcc tgcctaactc attttatgag gccagcatca ttctgatacc aaaacctggc 109080
agagacacaa caagaaaaga aaatttcagg ccaacatccc tgatgaacat caatgtgaaa 109140
atcctcaata aaatactggc aaactgaatc cagcagcaca tcaaaaagct tatccaccat 109200
gatcaagttg gcttcatccc tgggatgcaa ggctggttca acatattcaa atcaataaac 109260
```

```
ataatccatc acataaacag aaccaatgac aaaaaccgta tgattatcgc aatagacgca   109320
gaaaaggcct ttgataaaat tcaataccca atcatgctaa aaactcttaa taaactaggt   109380
attgatggag catgtctcaa aataataaga gctacttatg acaaatgcat agccaatatc   109440
atactgaatg agcagaagct ggaagcattc cctttgaaaa ccagcacaag acaaggatgc   109500
cctctctcac cactcctatt caacatagta ttggaaattc tgtccagggc aatcaggcaa   109560
gagaaagaaa taaaggtatt caagtgggaa gagagggagt caaattattt ctctttgcag   109620
atgacatgat tgtatattta gaaaactcta tcatctcagc ccaaaatctc cttaagctga   109680
taagcaactt cagcaaagtc tcaggataca aaatcaatgt gcaaaaatca caagcattcc   109740
tatacaccaa taagagacac agagccaaat cctgagtgaa ttcccattca caattgctac   109800
aaagagaata aaatatacct aggaatccaa cttacaaggg atgtgaagga cctcttcaag   109860
gagaactaca aaccactgct caaggaaata agataggaca caaacaaatg gaaaacatt    109920 ccatgctaat ggattggaag aatcaatatt gtgaaaattg ccatactgcc caaagtgatt   109980
tatagattca atgttatccc catcaagcta ccattgattt cttcacataa ttagaaaaaa   110040
ctactttcaa tttcatatgg aatagaaaaa gggcctgtat atccaagaca acctaagcaa   110100
aaagaacaaa gctggaggca tcatgctatc tgacttcaaa atatactaca aggctacagt   110160
aacaaaaaca gcatggtatg gtactggtac caaaacagat atatagacca atagaacaga   110220
acagaggcct cagaaataac accacacatc tacaactatt ggatctttga caaactggac   110280
aaaaataagc aatggggaaa ggattcccta tttaataaat ggtgttggga aaactggcta   110340
gccatatgca gaaaactgaa actggatccc ttccttacac cttatacaca aattaactca   110400
agatagatta aagaattaaa tgtaagacct aaaaccataa aaaccctaga agacactttg   110460
ggaggccgag gtggatggat cacgaggtca ggagatcgag accatcttgg ctaacacagt   110520
gaaagcccat ctctactaaa aatacaaaaa attagctggg tgtggtcgtg gcacctgta    110580 gtcccagcta cttgggaggc tgaggcagga gaatggcatg agctgaggag gttgagcttg   110640
cagcaagcca agattgtgcc actgcactcc agcctgggca acagagtgag actccatcaa   110700
aaaaacaaaa acaaaaacaa aaaatcaaac cctagaagaa aacataggca ataccattca   110760
ggacataggc atgggagaag acttcatgac taaaacagca aaaccaatgg caacaaaagc   110820
caaaatttac aaatcagatc taattaaaat aaagagcttc tgcacagcaa aaaactctca   110880
tcagagtgaa aaagcaacct atggagaaaa attctgtggt ctagccatct gacaaagggc   110940
taatgtttag aatgtacaag caacttaaac aaatgtacaa gaaaaaaaaa acaaccccat   111000
caaaaagtgg gcaaaggata tgaacagaca cttctgacag gaagaccttt atgtggctga   111060
caaacatgaa aaaagctcat catcactgtt aattagagaa atgcaaatcg aaaccacaat   111120
gagataccat ctcatgcccg ttagaatggc gatcattaaa aagtcaggaa acaacagatg   111180
ctgaagagga tgtgtggaga agaggaaca catttacact gttggtggga gtgtaaatta    111240
gttcaaccat tgtggaagac agtgcggtga ttcctcaagg atctagaacc agaagtacca   111300
tttgacccag caatcccatt actgggtata tacccaaagg attataaatc attctacaat   111360
aaagacacat gcacacgtat gtttattgta gcactattca caatagcaaa gacttggaac   111420
caactgaaat gcccatcaat gatagactgg ataaagaaaa tgtggcacat atacactgtg   111480
gaatactatg cagccataaa acaggatgag ttcatgtctt ttgcagggac atggatgaag   111540
ctggaaacca tcattctcag caaactaaca caagaacaga aaccaaaca ccatatgttc     111600 tcactcataa gtgtgagttg aacaatgaga acacatggac acaggaaggg gaacatcaca   111660
```

```
cacaggggcc tgttggggag ttgaggctag gggagggatt ggattaggag aaatacctaa  111720
tgtagatgat gggttgctgg gtgcagcaaa ccaccatgac acgtgtatac ctatgtaaca  111780
aacccacaca ttctacacat gtatctcaga acttaaagta taataataat aagatacaga  111840
actgcagaat gaataagaac tcaccaacca tctgctgcct tcaggagact catttaagac  111900
ataaggactc acataaactt aaagtaaatg ggtggaaata ataataagtg gtgtcactga  111960
tgtggaggta gattataaaa ctcttatcat atgctggtgg aagatcaaaa tgataaaacg  112020
aattaaaaaa tcagtcagat ggtttcttaa aaagttccat caatatgcct ctatcttaca  112080
aacctgcaat tctattcctg aatctttatc ccaaggaaat gaaaaagtaa gtccacaaag  112140
agttctatat gaatatttat aggagcttta tttattataa ttcaaactgt aaaaataatt  112200
tcaatgttca tcaataacaa aatgaaaaaa taatttgcaa cctactggta cacttgaata  112260
ctattcagca ctgagtatct taaatagcat ggatggagct caaaaatata ctcaggaaag  112320
aagccatgta tattctgtat gagttcattt acatgagatc atttacattt cctccaaaag  112380
aggaaaaact aatttctgtt gaaagaaacc aatgtatttg cctctggcag tggtaagggg  112440
gtagcacaga ttaattgggt agggactcaa gagagtttct ggggtcacag aaatgttccg  112500
tgtggtgatg ggagtttggg ctccacaggt ataggtgttg atccaaaatc atcaaaaaaa  112560
caacattgca gatctgtgca tctcactctg tgggaaagta tatctcaact gtaaaaaggg  112620
cagaaattgc ttttaaacgc tcagccttttt agcacatcca gttgcttgga gaaccagctt  112680
actcaaatgg gggtctaggc tggagactag gtcacaggca tagagtctct aaactttccc  112740
atggcacata atacgtttca ggttttctca gagagctgca ggttagtaat ctgaggattc  112800
tgacaagttg ggtcaacgtt cctaggaggc atgaatggga gtgcattctc taagatccct  112860
ccaccccagg gtccttgctt tctgtgcctc ttactccatt gttttctgac tcctctgtag  112920
ccactcgacc tcttcagatc ccattgtcta cccagccatc gcccttttatg acttgggtcc  112980
cactgttctt tcatctcatc ctccattccc tcagtttcgg agtggctgcc gctagcagag  113040
gatggactga gagcaggaga ggtggtcctg cccaggaacc catcctagag aaatggcatc  113100
ctgtctggga gctagttttt tagggcaggt tttataagtc ttgtaaagcc agacacactt  113160
gatctacctg gtatgttatt tacagtaata ctattttcat aattgctttt cactctaaaa  113220
gtagagcctt ttagctacac tgtgagtaaa taaaggggct ggcctgggaa tggtatcatg  113280
ttggatgttg tttcttccct gaagtaatat atatcagtta caatttacat gttactgcag  113340
agtcctagag agagacacag agaatgagac agataccaat acatttttat gtgcattaaa  113400
aaaatctaag gccaggcgca gtggctcaca cctgtaatcc cagcactttg ggaggccgag  113460
gtgggtggat cacgaggtca ggagattgag accatcctgg ctaacacggt gaaaccctgt  113520
ctctactaaa aatacaaaaa attagccagg cgtggtggcg ggcgcctgta gtcccagcta  113580
ctcaggagac tgaggcagga gaatggcttg aacccaggag gcagaccttg cagtgagccg  113640
agattgcgcc actgcactcc agtctgggcg acagagcgag actccgtcac aaaaaaaaaa  113700
aaaaatctaa aatgcactct tcaaaatcta tgtcatttat tctggaggaa tgcagttggc  113760
agaaggagga agatattccg aattttctt gtatacattt atgtatgatc tcagttttt  113820
tatggatcat agaccaattt tgatatttta aaataaaaat tataatctat cttggaaatt  113880
tacatggttc tttagaactt gaggaccgtt tttgcttttc ggaatattat tgtacctaaa  113940
atgggaatat tacaacgtca cttttttaaca ctttgttata acaaagtttta gacagcgctg  114000
```

```
ggtgcccctg aatttttttcc cgcctcttgt gacctgtgtt gttttggaat ttgcagtggc   114060
ctgaccgaga actactgcag gaatccagat tctgggaaac aaccctggtg ttacacaacc   114120
gatccgtgtg tgaggtggga gtactgcaat ctgacacaat gctcagaaac agaatcaggt   114180
gtcctagaga ctcccactgt tgttccagtt ccaagcatgg aggctcattc tgaagcaggt   114240
aagaagtctg tggccagata tctacacatt tgaacattgg gatgaaaaga gatggaaaat   114300
ctgactgatg cagaagcctt ccatgctaca cagaaacttg agggtatggc aggtggaaag   114360
aagcctcagc actctctctg gtggagcaat ttttggcgca acgtgcgtgg gcggtgactt   114420
caggaatggt gcaaacccac ctgggcactt gacttaccac tcactttgtt atgaaagggg   114480
ttatctcggt gttccagaca aaattccaat tctaacatca ggccaaattt gtgccaaatt   114540
tcacactagt gagtgtttcc aggcatttat aaaatggac agtgttcatt gcaatcttca    114600
gcattgcagt tgctgaggta tgtggccgct gagtttgtca tcctggggaa acctaatatg   114660
atgatattta ttccatctaa tcctggggct atttggcagt aaataccaca gaatacacta   114720
tttctctggc ttatttcagt cttaggtagg ctctgcacac ctatgcttgg aaggcaggaa   114780
tttcttggtg ttcttgtgcc ttcttctcat ggaacgtgca tctttggtgt gtgttgagag   114840
gaagggtagt agacttctgc tttgttgcaa tgcaggatgc tggaacaaga ggattccctg   114900
tctctactgt aagggaataa gattttagcc tccatccttc tctaagaagc aatgtgtctt   114960
tgcctccaag tactagatgc aggaccatga actgccccgt ccaccagaag cttaaggctt   115020
tggcttttca ggagcaatca tctagggaac tgtgcagggt tttcatgtct gtcccctact   115080
gacagccaat caccatacag cctgcataac ctaatccatc atcgtctggt ttcctgcctc   115140
attgttttca tgaacaacca gtagagagcc atacgaaaga gcttgcacat gagtctttgt   115200
tccaattgta agagcactga taggtccttt tcccaccagg ttttgaatat aaaatttcta   115260
agaacttatt aaaatattag aatgttatta atctattgtt tttgcttcag catgtccttc   115320
tgcttgtgag tatactaaag agaacagtca taattctgaa actactgtcc tgtttgtgtc   115380
ataaattgct tcacatgttt ctgcatacta gtagttactc agcttgattt tgtctatttt   115440
cagcaccaac tgagcaaacc cctgtggtcc ggcagtgcta ccatggtaat ggccagagtt   115500
atcgaggcac attctccacc actgtcacag gaaggacatg tcaatcttgg tcatccatga   115560
caccacaccg gcatcagagg acccagaaa actacccaaa tgagtatgtc tttgatgtta    115620
cttgtaagag gagcaacagc caacttaagt tcctcctaga agagccttgc ttcaagctaa   115680
cttgttagga caaatttccc ttagacccag aaggtgtgtc aaaatgtcca gacaactttg   115740
cttttgatca aagagtctga gagaataggt attttaggct tgctatcttt tctaatagtc   115800
tgatggaagc agaaggctac atggagctga tgaggtcttt ttaatataaa gctcaagaga   115860
tcaaatgatc aaatacttag agtgccattc tacaaggctc ataaaagatc aatgcactct   115920
ttcacccatg caattctatc attctaacct cccttctctg aaatgaaggc ttttgccat    115980 ttttgtcatg ggtcacaagt aaataattca catgtatatg agtatatata taaccaggtg   116040
tgtttattca gactagtatg tatatatata catatatatg ttcataaag ttagtattca    116100 tatatatgtt catatatata tgttcataca gactagtatt catatatata tacatatata   116160
tatacacaca catatatata tatatatata tgttctaggg aaacatgcaa ggtttttatg   116220
tctgtccctg actgatgacc aaatacccta tagcctgcac agctgcaagc tgtatagcca   116280
tacaatttgc aggacacaca cacatacaca cacacacaca cacacacaca cactaacata   116340
taatataata taatataata taatataata taatataata taatataatt aatatatata   116400
```

```
aacctgtgtg aacacactgg gttctaagct ccagttttct gaagggatat gggttgccag   116460
gagaggaaga gcaaaagcaa gaatgtagat gagaattagg aagtaaacag atatggagat   116520
taaaatgggc aggtacatgg acaaaaaacc aggtctgaca aaaactggct ttctgccata   116580
aatgactata aaagatatta aaaaacactt tccacatgtt ggacaagaga cagtacagga   116640
ctgagataat ttagaaaagg aaatgaatga gcgcaactcc gtaactatta tgactttctt   116700
cctggagaac cttcctggac tgaagggcaa ggaattggag ccaaagccaa ccacagcagt   116760
cttgctgaac tgaggaaaga gactggagtt tgggatagct aagaaaatgt gtattttcta   116820
tgctaggtaa taatgagaaa gaatttgtgg tgaaaaggag ctgaaggaat atgcatggaa   116880
gtctaatata aactgcatat gcacagggag aaattctaca aagtgggaca gagaaccact   116940
actggggaaa ggacaaattc agggaaacag tgagctcaat ggtgacgcca gagctcacgt   117000
agcactgggg gataccgggg ttctgatcag cccgaggaga gacacctcat tgaacatctc   117060
gggcattcag tagagacccc agaaaagtca tactttagga gtaggattta tgccttctta   117120
gaataaagac taccccagaa acaccctagt aaagcttaaa aaccaagtct aaaaggaccc   117180
aaatgatctc caagtaaatt aactgcctga cagaagaaaa ctcaaccatc actggaggta   117240
aataacatga ttacagtgct ctgtaatgtt gcattcacaa ggagtgacat catttaaaaa   117300
tttatgaggc aggaaaaagc aattagtgtg atccataact aggagaaaaa ccagtcaata   117360
caaatagacc aagaaatagt agaaacgatg gaattgacaa agaaattaaa actgtatata   117420
tgataattgt gttcaaagat ttaaagaaaa catgaacatg agggaaacaa atgcagaata   117480
taaaaaaaag caaatgcgta aaacaaccaa atggaaatta aagaactaca aaaaagtata   117540
accttaataa aatactcact ggatggcctt aatattagtt tatacattac agaagaaaaa   117600
gtgaaccaga agataactca atgaaagcca tacaatctgt aagacacaca cacacgcaca   117660
cgcgcgcgcg cgcacacaca cacacacaca gagagagaga gagagagaaa gagagagaga   117720
gaaaggctga aaaaaataaa tagaaccttca aggatatcag tgaaaatagc aaaagattta   117780
atatatgggt aaagcaagtc acagaaggac gggaaggaga tattgggaca gaaaaaaata   117840
ctcaaagcaa tgatggctga agactttaca cgtatgaaga aaatgataaa ctcacagtca   117900
agaagctcaa tgaatcagaa atagtatttt taaaagcaaa actctatgat ttacttgggt   117960
acattataga taaatcgtcc aacatcaaag ataacaagga taatcttata agccagagga   118020
aaacaatatc atttacatag agggacagta atgaaagtga ccgatgcctt ctccttggaa   118080
acaatggcat aacatcttta aagtgataaa gagaaataaa aacagatcaa cctaggacga   118140
catgtccagc caaacaaac aaataaacaa aaaaaccctt taaaataaac gtgatgtaaa   118200
tacgtattct gccacctcca gaggaaacaa gcaaaaaaac aaaagaatgt ttccaaggca   118260
ggcttctgta ttaaaagatt ttaaggaaag ttattcaggt agaagaaaaa taataccaga   118320
tgggaacttt aatccatact aagtaatgaa gagccctgga aatggcaaat ggcaatgtca   118380
atataaaata ctcttatttaa tctaattttt aaatgtattt aaaggacaat ttgtgatatt   118440
aattaaaata ataggaatat attgttgttt caacgtatgt agtagtaaaa ttcataaaaa   118500
cagtagcaca aatatgcag atgataactg gaagtatact gttaatgagt tttttgcatt   118560
atccatgaag ttatataata ttaatagatg gttgaatgtg atagtttaag gtgggatatt   118620
ataaatccta ggcaaccaa aaaaatttaa actgagagga atggatagta agaggaatag   118680
tccttttatg caaaagaagg aagaaaaaga ggaataaaga atataaaaga tatggtgtaa   118740
```

```
acagaaaata catagcatta ttgtagacac aaactgaact accttatgag tatattaaat    118800
ataaaaggat taagcattac aaataaaagg cagagattgt aaattgaata aaaaccacag    118860
ctaagtgtgt tcttttttaga ataaatactc tttaagtgta aagatctact ttaaacacca   118920
aaatatgaaa aaggatatat accatgaaaa cctgaatcat aaataagctg gagtggtgat    118980
taatggatgc aggcactcct aaagactaat aagtgaatgt ggtcaaattg aagaaacaaa    119040
agtatatacg tgctcaatgt gcaaaaactt tttctgtata catgctatga tcctttggaa    119100
aattaaagtt ttaaagcaat atcactgaca atagtatcaa aaccaaaaaa tatttagtga    119160
taaatttcac acactatgct caaggactat acaccttgca ctagaaaaca atgttgagga    119220
aagaattaaa agatctaaat atacaccatg cttatagatt aaaagactcc atatcagttc    119280
tcgtgaaatt gatctttgga tgaaacccac acccaagcac tattgcaaca gtcctttttt    119340
ggaaaaaaaa attggaggac ttatatacct taatataaag acttataaaa gtacaggaat    119400
caagacatgt ggtattggcc tggccccttg gctcatgcct gttacccaa catttttggga    119460 ggctgagtct ggaggatggc ttgagcccag atgttcaaga ccagccttag caacagagtg    119520
agaccctctc tctacaaaaa ataaacaatt agatcgatgt gatgacttgc acatgtagtt    119580
tcagctactc ggaatgctga ggtgagagga ttgcttgact caggaggtct agccatgagt    119640
gagcattgat catgcctctg cattccagcc tggatgatgg aatgagacac tgtctcaaaa    119700
aaaaaaaaaa aaaaggatat gtgttattgg ccaaaaaagt atgcaaacct aaaaagggat    119760
ggcccaccac cagacccaca tacatatatg gtaaatggat tttccgtata gatggcaaag    119820
caattcaatg gagacaaaaa tgttttacaa aatcattctg aaccatttgg atatccatga    119880
tacaaaacaa aagcagaact tgacttttgc ttttcatctc aaattatttt gatatctctt    119940
ccacctaagt gtcagagcta aaactgaacc tgaaatatga aagttccatg aaaaaatata    120000
aaatcttcac aaccttggag aaggcaaact tttttgaggc aggagtctgt aaacactcac    120060
tataaaataa aacaaattat aatgtgggct ttcatgaaaa ctcatgctta ccaaaagtca    120120
ttgttaagaa aataaatagg caagtaacac atgagaagaa aaatgctctc tgtccatata    120180
tctgacaaat ggcttgtgtc cagaatatag gaacatttct cccactcact aaacagagga    120240
caaacaacta atgggcaaca gattgaatag gcatttcttg gggatagata gatgtacaca    120300
tagccaataa gcacctgaaa aaatgtccag tatctcagcc atgaaaaata aagagttata    120360
atcatcatga gatgtcacca aacacccaat ggacatggat attattaaga agacaccaca    120420
gtaactgatg tcactgatgt agagcaagga tgtgaaactc tctcatatgc tggtgaaagt    120480
gcaaaatgat acaaccactt ttgaaatcag tctgatagtt tctccaaaag ttcaataaat    120540
gcacttttac cctacaaacc tgcaatcctg tttgtaata tttacccac agaaatggaa      120600 acataagtcc acgaagacat ctccaagaat attcatagca gctttatttt ttataacccc    120660
aaactgtaga caatttcaat gtcaatcaat aagaaaatga ataaataatt tgtgaactag    120720
tcatacaatg gcatactgtt cagcaataaa agggagcatg tttttgatac tctcaaatag    120780
tatggaagat gctcaaaaat attacattaa agaaagatgc cagataacaa aaatgaacat    120840
tatgtatgag tctattgatg taaggttcca gaaaggtaaa actaatttct ggtgaaagaa    120900
accaatatca tttgcctctg gccatgggaa gagagtagca gagattgatt gagcagtaaa    120960
acgaagtttt tttctggggt gatgtaaatg tcctgtattg tgattgaagt gtgagttaca    121020
caagtgtaca tgttcatcag aagtcatcaa actcactcta gatctgtgc atttgactat     121080 acatgaaaat atacctcagt tgaaaataga tcaataacct ccctcatata ctatacttgc    121140
```

```
taacacagcc agctgcttgg agaaccagct tgctggaatg gagaatctgg gcttgagact    121200
gggtcacatg tatagagtct ctacagagac aatgttgcat tcccacggta cataatacat    121260
ttcaaggttt ctcagacagc cacatgtcat gaatgtgagg attctgagag gttggagcaa    121320
cattcctggg aggaacgaag gggagcacat tctccaagat cccccaccac cggggtcctc    121380
accggctgtg ctttttttt tttttttctt gacagagtct cgctctgtcg ccaggcagga    121440
gtgtaatggc ccaatctcgg ctgattgcag cctccaactc cagggttcaa gagattctcc    121500
tgcctcagct tcatgagtag ctgggactac agatgtgcgc cactgcgccc agctaatttt    121560
tgtattttta gtagacagg ggttttgcca tgttggccaa gatggtctcg ctctgttgac    121620
ctcgtgatcc acccgccttg gcttcccaaa gtgctgggat tacaggcgtg agccaaagca    121680
cccagcctgt gcctctcact tactcaattg ttttctgaa ccctccatag ctggtggacc    121740
ttttcagatc ccatagtcta gccagccctc tcactttatg ccttgggtcc cactgttcct    121800
tcatctcatc ccccttctgt cagtcccgca gtggctgtgg ccagtagagg atggactgag    121860
agtaggagag gaggttctgc ccaggaaccc atcctagaga aacagcatcc tgcctgggac    121920
ctagtcttcc aggtcagctt ttataagtct tttagactca aactcacttg acccacctga    121980
agtggtattg acaataatgc tattttcatg gttgttttc actgtaaatg cagagccttt    122040
tagctacacg actagtacag agagtaaggg aggctggcct gggaatgata tcatcttgga    122100
tggcatttcc tccttggaga aatatatgtt agttccaact cacatgttac tatacagtcc    122160
tgtagaaaga gatacagaga gttagacagg tatagacgca tttgtatatg cataacaatc    122220
tataagacac acatcaaaat ccgtataccg gttcctctag gggtatgtgc ttggcagaag    122280
gtagaaggag ggtattctgg ttcctttctt ttgcacattt atgtatgatc tcagttttta    122340
tatggagcat tgatagggtt tggctatgtc cccacccaaa atctcatctt gacttgtaat    122400
ctctataatc ctgataatcc ccatgtgtca agggcaggac caggtggagg taactggatc    122460
atgggggcag tttctcccag gctgttctca tgacagtgag agagtctcct gagatctgat    122520
ggttttgtaa gtgtctggca tttcccctac ttgcacttac tctgtcctgc cgcctgtgaa    122580
gaaggtgcct gtttctccct tgccttctgc catgactgta aatttccaga ggcctcccca    122640
gcaatgtgga actgtgagtc aattaaaact cttttctttg taacttaccc agtctgtctc    122700
gggtatttcc tcatagcaat gtgagaacgg gctaatacaa gcatatacta cttttgatat    122760
tttaaaataa aaattatcat ctatctttga aaggcatgca caaatgggaa gttgaggaac    122820
atttgtgttg tggcaattgt atgatacctt taatgggaat atttcaaaga cacttgttaa    122880
gactttgtta gaacaaaatg tagagggtgc tggatgtccc tgaatattct tccgcctcct    122940
gtaacttgta ttgctttgga atttccagtg gcctgacaat gaactactgc aggaatccag    123000
atgccgatac aggcccttgg tgttttacca tggaccccag catcaggtgg gagtactgca    123060
acctgacgcg atgctcagac acagaaggga ctgtggtcgc cctccgact gtcatccagg    123120
ttccaagcct agggcctcct tctgaacaag gtaagaagtc tgtgtcttac cttgtctagc    123180
acatacctct ctatgtgctt ggacaacggg atgaaaagac atgaaaaacc acactgatgc    123240
agaagccttt agtgctacac gggagctcga gtgttggttg aggttctgcc atgaccaagg    123300
aagtctcagt gccgtccctg ggaaagccag agctgtgatt tttggcacaa cttgtgggag    123360
tagtgacttt aggactggcg caaaacctcc agggtgctca acttaaccac tcaccttatt    123420
ctaaaatggg ttatttcagt gtcccagtca aattcctatt ctaacatgct gtcaactgtg    123480
```

```
tgattatttc caagccaata agcatttcca gtaatttctt aaaatagtgt tcattgcagt 123540
cttcagcgtt gtggctcctg agggatgtgg cccctgattc tgtcgtccta gagaagcctg 123600
acatgactgc attgattctg tatcgtcctg ggtctatgtg gctgcctggc tgtctgtaat 123660
catctgtttt attttattt ttttctacag actgtatgtt tgggaatggg aaaggatacc 123720
ggggcaagaa ggcaaccact gttactggga cgccatgcca ggaatgggct gcccaggagc 123780
cccatagaca cagcacgttc attccaggga caaataaatg ggcaggtctg gaaaaaaatg 123840
taagccactt tgatttggac tcttttcccc tttgctgaca aatcttttca aacagaagag 123900
gggcagagga aaatactgga aagacttcag gaggctaagc gtaattagcc ttagcatgga 123960
aagtgcaagc agcacaggcc agcaaagccc cacgcgtgtg ggggttctca ggcctcttct 124020
cttttgacat ttctttactg tttccattgt tgggtgctgt ttctcgtttc tagtgcttgt 124080
cctctaagcc aggggtcccc actccagtac tggtactggt actggtactg gaactggtaa 124140
ttatctgtgg cctgttagga actgggctgc acagcaggag gtgagcttcg ggggagcaaa 124200
caaagcttca tctgtatttt ctgctgcttc ccatcactct catagctgcc tgagctctgc 124260
cagctgtcag atcagaggca gcattagatt atcatagcac aaaccctatt gtgaactgca 124320
catgtgagga atctagattg catgctcctt atgagaatct aatgcctgat gatctgtcat 124380
gcttccatca cccccagatg ggaccaccta cttgcaggaa aattagctca gggctcccac 124440
tgattttacc ttatggtgag atgcacattt atttcattat atattacaat gtaataataa 124500
ttgaaataaa gtgcacgata aatggaaggt acttgagtca tccttttaacc atcgcccct 124560
cacccccaggt gcacagaaaa attgcctttt atgaaactgg tctctggtgc caaaaaagtt 124620
ggggaaccac actgctctgg gttctagtag tcagagatgc cctctatgag gcttaagtca 124680
gattttcta gaaaagattt ggatgggcca tcaggtcacc atgagacttc ccttagcctc 124740
atgcattctc tgtgatggtt tactttgggg cctatgaata gggaagactg agatataggga 124800
aaaaccaaag tgtctgtgtt cccccactct cacacccatg taacataaca cttctcacac 124860
cagatatggg gggatttctc ctcacacccc aagcgagtct ccagcagata ccagctgggt 124920
gtcctacaat gtaactcggt cctgacactc tatctggaga cagtgtcaga tcccacaagt 124980
taaggctcag tcctacaaga ctgccccact gcagatgcca atcccaagtt gcaggctgtg 125040
acctgtactt ctgcccagct ggataaagat ctgttttct atatgaccct ccatgggttt 125100
gattactttg ctagagtggc tcacagaact cagggaaaca cgttactttt atttacccat 125160
ttattataaa agatattaaa aaggatcctg tgaacagcc aggtggaaga gatgcacagg 125220
gcaaggcacg tgggaagggg ctcagagcct ctatgccctc tccagtgcac cagtccccag 125280
taccctaagt gttcagcaac ccagaagctc tccaagtgca gtcttgttgg gtttttatgg 125340
aggcttcatt acagaggcac agttgattac atcattggcc atcggtgatc ggctcacctt 125400
cggcccctct tccctcctg gaggttggag ggtggggctg aacagttcca accctcaagt 125460
cacatggttg gttcccttgg caaccagccc ctggggctat ccaggaaccc accaagagtt 125520
gcttcattgc agctcccttc acccaggaaa ctccaaggga tttaggagct ctgtgttaag 125580
aactgggggg cagagaccca atatacattt cttattctat cacaatatca caggaagcta 125640
aggatgatac tgcctttgtg tgtcttggct gtggatggtg cataatgcat ggaagtaagc 125700
atttctgaat caacagcaaa caggctttat caggtagaag accctcagc gccccaggga 125760
caaagctcat caatgatgtc ccactgtcct ctgaggctct agctctaaga cctccagtgg 125820
gtcaagctcc tggagaagtg gcacattctc caaagaccct tcagggtcac cacaccctgg 125880
```

```
ttaagggtgt ggcctcataa ctccttttga ctatgactga tggcttacag catagaaaga 125940
ataaactttg tcaaaaaata taataatgat agaaaggaag aaggaacgct cccttttgtc 126000
ttctaagaat agatgtgaaa tgtgtgtgcc ttagaatatc ttctccctct cctgctccac 126060
gtgagctgga gcttacatgc ctgcttgttt tcagtactgc cgtaaccctg atggtgacat 126120
caatggtccc tggtgctaca caatgaatcc aagaaaactt tttgactact gtgatatccc 126180
tctctgtggt aagttgcctt ctgttttggt aaggaaactg cttccttaat atggatttgg 126240
aaaaaaaaaa gcaaaaaaaa cagaaaatgg cttttgagct gagtgcttct ggggaggaga 126300
tggctgccct ctccaccaga gcctgctttt catcatggcc accttgaacc tgccctacta 126360
ttggccccat ttgttaggaa acacccgcc cctcccacca cacacacata aataaaataa 126420
atgtcaaatt cccaaagggc aaacttagag gtgatctaat cagcccggga tagtcccacc 126480
gaacccttct ttgtctagcg tgggatgcat gaaaaacaaa tttagagtca ttatgatgaa 126540
aaactgtcct cttctgcagc tgagaagaaa aaaaaaatac gagcagcagg aaacagctaa 126600
gcatgtaatg cacattgtaa acctcagatg gccatcctag gaaatcaatg aagggtagtg 126660
cagctcttta gccccagatg gccttttctcg taagattact actcatgagt cccattagcg 126720
acattgctta gagactgctt gttaggttcc ttcctcattg ctctgagact cttattggga 126780
gtatgaggct tggatcaggg gaaggggaat tgacattaga tcttaaatga ttggggtaac 126840
aaatccatgg gggaaaaaaa gccacttgta cttgttccct attttcttcc tgctgaccaa 126900
tcaacttgtc tgtccgagtt acagaacacc accctggact tttcttttgt gtaatttggt 126960
tgcttgtggt tgggtctgcc atgtgaaggg accttgagct gggggaagaa ggttggcctc 127020
caagtccact gaagaccagc atcctgagat tgcctgggga ggtggtacag ggcagtgatg 127080
aagatcatgg gagccacact gcccatcgtc acatttgggc cactcctggg gagagcaaga 127140
gggaagaagg agaggttagg gtgataggaa agattctact tggccaatat tattataatg 127200
tggcattgtg gtctctggat ttagtgtgag ttgatagctg acttttttct cgagtgggtg 127260
cttttgttct attttgtcgg tgctattgca gaagcatctt ggtggttcct ctacctcaaa 127320
gtctcttgat ggggtcagtt ccagttctcc gcttctggcc ccatctagta cacgccactg 127380
cctctcactg cctgggctct ctatccttga caggctgcct tgaatttaag cccagtctga 127440
cttacctgcc tcaaacaccc acagtagtgc ctgggactca tgcacctttg actcccatgg 127500
aagggaagtg cagtagcttc ccaggtgcaa ttctgctgtc ctcacccaca ttgaggatgt 127560
atgagaatca ggttcttaga gattggaaa agaaggaaga atgggaacaa gatttcttcc 127620
aatggactgt gaggttcccc accttacttt gatgtaagac aagtgaggtt aaccccaagc 127680
ctggtgagga gggttcccat cagacacttg gaaatcctga ggactgtttc ctgcagaagg 127740
atgtggttgg tgggatattc aggtttgact catgattgag aaagttagag cctctggttg 127800
gagaaagagt ttaataacta tttcatttcc accaacacat tcagtacgaa taataaataa 127860
gtaaaaataa atagaaacat tcagttttat tttgaatagt aggagtaggg tataatttct 127920
gtagttactc ttttagtaca atgatgcatg tttactgtat gtaaggcata ctagcagaaa 127980
ttgagctcag cactagaaaa gatgattgca ttccatgcca tgcttctttt ttacaaaga 128040 cttctataga tagattctca aaacaaccca cagcaaatga aaagttattt ggaaaactca 128100
ggttccagat tcactggagt gtagaatctc tggttggttg gggaggaatt tcctcttgca 128160
gttgttatta ataattatat gaataattat taactatatt aatatttata gttttgaaga 128220
```

```
ccttgaaggg ctggagacaa cagagaagca ttttttgaaca ccctctgtag cccctgcact 128280
gttgtaggca ttgatgggtg gtaccaaaga tgggacactt tccctacctc cagagacctt 128340
gtgggcttgc tgcagagaga aggcagggag gaggaaaaga agaatagagg cacatgtgtg 128400
taaattaccc ccacagcagt cagttagtca tgggaggctc cccagaagaa ctgtcctgaa 128460
gctggctgag agaaggcaac atttcaacat aggacagtta tccttgctac ataaaatcac 128520
atacacacat gcacatatgt ccacacacag agactcacat gcaaaagaat cctttgtgcc 128580
tttcagtaaa ctttacatgg tttagaaaga acttatattt ccttgaaagg agagtgtcct 128640
ttgttgttta ctaccacttt ttaaacttag aagaaaaaat ctaaagagtg tttatgattt 128700
taccatttaa tttcacctttt gagatgtgaa aaactagtgc ttggaattcg tcctgaatta 128760
aacgacacaa ttgctaactt ggactcaaat gcgacttctt ttcccacctt gtgccacagc 128820
atcctcttca tttgattgtg ggaagcctca agtggagccg aagaaatgtc ctggaagcat 128880
tgtagggggg tgtgtggccc acccacattc ctggccctgg caagtcagtc tcagaacaag 128940
gtaagaacag gcccagaaac catctatact gtccttccat gtaagcccca caaacccctt 129000
ctacatttac acagaaccca cacagctgat gcatcaatac ctgcctctct gttttctgaa 129060
ggaggaaaaa atatagaaaa attaaaaaaa gttatattat tataggttct ctacttgaa 129120 aatagccaaa atacaaatct ttttcttgat ctgggcagtt ccatcaaaat ctgtaggcac 129180
agtgatttgc accaagttcc aatacttttg gaaatattg aagatgctct gagggtttct 129240
atggatatcc attgtctcac tgtcagatga aaagaaaggg aagttttag aaatgtgaca 129300 ctttgcagtg agggaggaca agagcaaact tacctacagt ctatcacagg cacagatttt 129360
tttttacact tttgtgaatc attgaattca atgccgaggc tattcatcta ttcacaaaca 129420
catgaacaaa ttatgggttg tgatccccat aaatgaagag taatcagtcc gaacccacag 129480
aacctggaca ttttgggtat cgtttcagtg gaacatgcaa ttcgtaagtt cagtttgctt 129540
gggtgtctct taggaagaac acataggaca cagacccatc tgcctgcatg ttttgcttcc 129600
tcatctcctt tctacaccag ggcacctgtg ctcaattgct gttctcctct aaagagactt 129660
ccttctgtaa gttgtgaaa tgccatcgac aaacctgatc gcatcgcatt tcactctgct 129720
gttgagttga tttttcttta ctttatcgtt tgtaacttct tgctctacag agctttcacc 129780
ttccacatat ttcagattca ttcttttccta aactgtgtgg tggtctatgt cctcactgac 129840
tatcaacata ctgccatcat gcacttccta tctctattcc tcttcgttgc aatctggctc 129900
caagtggctc acaccattat tctgatctat caactgccta cacagtccta gaaagtaagt 129960
gagtcaagaa acatccccca aaagtaaact tttcaggtaa gatcagaaga ccctcatgag 130020
tcactgctgc tcaggatcgt atctggctcc ttgaagagtg accttgcata gatcttgtca 130080
taaaaaatga aagagacctt gggaaggtct tgggctggtc acttttgtca gagtccaggg 130140
ctgtggggtg aaagccacag ctatagagct tcattctgga gtcacttagc tttgctctcc 130200
tggggacagg ctgtgcctat tcttgcctca ggcatcaaaa aaagtggcac agatgggccc 130260
ttctgaaaaa tctcactact ggagcacagc tcgaagtttc tactatcctg acgttgggcg 130320
gtagtccttt gctttgggaa tatgaacatg atcaaaactg agtgaacttg tcttcctggc 130380
tttctgtaca atgaagtaga acaaaccatc caatttgacc aaagccttgg catgttttct 130440
ttctaggttt ggaaagcact tctgtggagg caccttaata tccccagagt gggtgctgac 130500
tgctgctcac tgcttgaaga agtacgttta agggaaaact gacatggggt cttatcttca 130560 agacttttttt cctccctctc ttcctccatc ccttctttct tcccaccctc cccttccttc 130620
```

```
ctccccacct ctcttcctttt tctggaagga acactaggaa ccagggaatg catgcagaat  130680
cctgaggcag aatttccagg gcaattggat gagagaggag ggaagtgttt ctagagggaa  130740
tctgcagagg gaagacccag tgcaagtgat tttttggacc tgtataaacc gcaggacaga  130800
gctgttcact accagaggca tcaatctgta ttgcattgct ctagagcaat atctgaggct  130860
gaataattta taaagaaaag agtttaattg gcacatgttt ctgcaggctt tacaggaagc  130920
aggatgctgt catctcctct gcttctgtgt gggcctaagg aagattacaa tcatggtgga  130980
gggcaaagtg ggagcaggca tgtcacatgg ccagagcagg agcaagagac agagagagat  131040
ggggtggggg tgctgcacaa taccaaatga ccagactttg caagaactaa gagtgagagc  131100
tcactgatca ccatgaagat gtggcccaag ccattcaaga gggatgcacc tctatgatcc  131160 aaacccttt cacaggccat agctccatca ctggggacta cagttgaaca cgagatttag  131220
gtggggacaa atatacaaac tatatcacag tctctgatga acagattga gaacagacct  131280 taactgtcag tttccagcaa attgtgaatt ttgtttcttg ccactcataa gtcactgatt  131340
ctgggtggcc gagggtgtca gagggacagc gccaagttca tggcacagag gatacctgaa  131400
ggggctggac catattttc tcttgacatc ctcatctttt ctaggtcctc aaggccttca  131460
tcctacaagg tcatcctggg tgcacaccaa gaagtgaacc tcgaatctca tgttcaggaa  131520
atagaagtgt ctaggctgtt cttggagccc acacaagcag atattgcctt gctaaagcta  131580
agcaggtact cgctcacctg tggtcttcac cccacgctgg tgaagatatt tgctttatgt  131640 ctgggttta tgggccatgg ccactgcatg gcagtgggga ggaactgtct atcacatgaa  131700
aggctcaagg gctttgggga cagcatcaat cttcaacccc agccctgcca catgttagtt  131760
gtgctcttta aaaaggcaga aggattcgtt tcctcacgtg gaaaaagaga tacccctgtta  131820 cccgtaaaac ttacttaatg ttcaccagtt catccacatt catgatcagg gaaaggttgt  131880
tattccaggc taactattct cctttcataa taatatgctg gagagaatca atgagattg  131940 catttcaaag cgcttgaaaa accaccatat cgagccatgc ttagtgtggg cgcctctaat  132000
cactgctatt caggaggctg acgaggaaga attgcttgag cccaggactt caaggctgta  132060
ggcagctatg attgtgccac tgcactccag gctgggtgac agatcaagac cctgtctcaa  132120
caaaagaaaa gaaaacaaaa caaatgaaca gaaatattcc acaatgtcaa aaaaaaaaa  132180 aacccacaca acatacaatt tacaaatgca aataataata ttattgttgt cttctttgat  132240 tttctcttc ctggtgaaat tttgttttat taagcctgac aaagtgatac ctttgcttac  132300
atcacttaaa gttagtctat ttggacctag gtgacagtac aatcagctaa gaaacagtat  132360
ttgtaggaga ggcaggtttg ggacaggtga caaggcatgt ggggtgctcg ctgtgctggt  132420
ggctctggaa ggcagggtgt caatgcagac agggatgagc atggcctggt tggaaggca  132480 tgggcaggc aggagcctga gctgctctcc tgggcctggt cacaagccca tggcagcttc  132540
tctgggtctg tgaactgagg ggtgatgtcc tggaatcctc tgacactcta ggaaggagag  132600
aagggccttt ctggctcagc ctttataaac agtagctgat ctccctcttg ctccccaggg  132660
tcctccccac catcccagca aatgtgcaaa tacaagatct ctgctcctca tggtcctcag  132720
agagctgggg tgttctgatg gcttgaacaa gtcacttagg aaatgtgggg ttttggaggc  132780
attctctgat aggctgatac gttttgagtt tagagttccc accgcacatc cccacacccc  132840
tagagtctag ggcatttagt gctccatgag ggaacctgta gagtgaggac atctgcatca  132900
caggctgggc cttctagtgt ccagaagcag aaagtgtgtc tgcttcaaag ttggtgctaa  132960
```

```
tgatgatttt tggtcagaat acggcatttc tcatttccat tcctttatcc ccttgaactt   133020
actaaagtag aatcaggtct aaaaaccaga gttctaatct ttaagagtcc ctgggattct   133080
aaggtatatg aatgtccttg gaaaacaata ccatttagtt catgcaaggt gcttatttcc   133140
catcctcttt catttgatgt ctagcatttt actgcattct taccaccacg gtttagtaac   133200
attcacgagg aggaagtgga ggatccagat ggagcaactt gctctgggca cacaaggcat   133260
ttgcaatttt ataccctctt gatgatgtct cagccagaca ttctgcccag tcatcaatgc   133320
cctcttcaat taatatgaaa ggacacactt ggcatgagat tccaatcgtg cacagaatat   133380
acatgagaag tgtgcctttg tcatccctac tttcaaaggc taaggccacc ctcagtttct   133440
tgcatgcaac tgatgccttt caaatgaaac cttacatctg tgtagtccat aggcaaccac   133500
aggcaaatgt gagggtgaaa cgctgtgttc tacattgttc tgtgtcagtg aagcaaggca   133560
gtgccagctc agagggctct ggggcttcaa ggcagggatg cctggttgta ggtactgcca   133620
cttccagctg ggcagtgaaa cataactgct aatactttcc ttacaggcct gccgtcatca   133680
ctgacaaagt aatgccagct tgtctgccat ccccagacta catggtcacc gccaggactg   133740
aatgttacat cactggctgg ggagaaaccc aaggtgagat caattccatt gcccacgtaa   133800
caaattgttt ttgaccttca gtgcatgtta caaaatgagc attttggaga tagttgtaca   133860
aattcctacc catgaatgtg gtctacccac tcctgacttt gcctggacac ctgtctatgt   133920
ctccataatc agtcttcaag ggacttgggc aaggggagcg gtgccatttc cttgagtctc   133980 tctcttttt gttttcagaa tcttttaatt tttttgtaa tgattgtatg tttcccttac   134040
aacaaaaaca aacaccagta gaggtctttg agtctcttaa tcataatttc agcattcata   134100
ttgcttcccc aggtaagtgg ggttttgacc cagccctcaa gttaagggtg ttagattatt   134160
tttcatgtga aattagacag actgcgtttc taaacatggt gcaaacagt aacgacaaaa   134220 gttgtaatta aactattctt cttcccaaat acccacatgt ctaatgtgtg tgtgagggtg   134280
ttaggcaggg gacctgaagc tgggggagag gcagacagtt cccatggccc caagtctagg   134340
atggcatttg gtattggttg atgggtgaga gcaagagagg gaatattttt gtgcatgatg   134400
tggtatcagc acctgtacta catttttatgg attccttctt ctctttgcgg tatgccctga   134460
caataattat atccgtcagc cttacccccct tggcagtagg aaaactgaaa ctgtcttaaa   134520
gtctcagctc tactttctca gaggtgcagg caagggcact gggagtctgg ggccctgaa   134580 aactgttctg actctgccac ttgccagata gacctgaact agacacgtta cctctttgta   134640
ccacttggct ctaatccctt atctgtaaaa ccagcatttt caaatggtgc tttgcacatc   134700
agccttttgc ataagctttg atttgataaa atgttttttg tgttttaaa aagattaaaa   134760 accacaggtt tagataattt caaagtaggc ttcccttttt ctgtcatttt cctattattt   134820
ttaaaacctc acctccttga ctccttgttc ccttttctg cactgctgag tctgggagca   134880
ctgaggccag gtaaaaggaa acttggcaaa tgaggggcac ctatgggtgt gggaggctgc   134940
tcctggtgtt tgcatatttt aaaatttaaa tgctacaaac cactgtgagt taggtattat   135000
tgttcctatt ttaccattga ggaagctggg gctcagagaa ggtggagggt ggtacagaca   135060
aacctgaatt ggaaccctgg ctcctgccta tgggctgtca ggacttagaa aagtcgtgag   135120
ctctcgctga ttgtttcctc agctgatgtg ggctgcaggg ctgttatggg ggaaataata   135180
agaaagtgca tcaagtgctg agcacatcct aagcactcca tcatggcagc tcctactact   135240
aataaagaat agaattatat ctaacatgat tctttcttgc aagtgacaga aaatccaact   135300
caaattggat taagcaaaac aagggaaatt cttagtgagc tgcaaagttt tcaggctcac   135360
```

```
atgatggccc caaatcccag gtcctcccaa tcatggagta ggcactattt gggggcacaa   135420
aggtgacatt cccatggctg cagatgctgt ggtgctgtgg ctgtaccggg aaagaataag   135480
aaaggccact ctcccaatta tgtgaacaat agtctgccca ctctgagaag tcaaacttgg   135540
gtcacagtcc tgcccctgaa cccatcactg actggctctg acctgcacca attgttccat   135600
gttggaggtg aaggcaagac cccactaata cccataaggg gcaaaagtta gatagatcct   135660
tcaagaggat tatgggaggt agggcaaaaa gctgctgggc agccagaaag caaacagagc   135720
ctctatgata cctcaactga tgaaagcatg aagctaaaat cataaggatc tgggtgtgag   135780
ttctggctct cccatcttcc atgtgacatt gggcagttat ttaatctctt ttagcctccg   135840
ctttctcatc ttacatatga gataattgtg aggattaaga ttacacataa tcatcatcat   135900
caccgtccac cactaccacc atcatcccca tcaacatcat cgccaccact atcatcattc   135960
ttactggcac taccatcacc atcaccacca ttccaccacc atcaccaata tcatcactgt   136020
caacatcatt accaccatca ccatcaccac caccatcatc attactacca ctaccactac   136080
taccaccatc accatcacca ccattccacc accatcacca atatcatcac tctcaacatc   136140
atcaccatca ccatcaccac caccatcatc atcattacta ccactaccac tactaccacc   136200
atcaccatca ccactgtccc actactatca gcatgacatc accatcacca ccaccatcat   136260
cattaccacc gctactacca acatcaccat caccacaatt ctactgccat caccattaac   136320
attaccacca ccatcatcac tatcaccatc accaccatca tcaccactgc cattatcact   136380
gccaccatca tcactatcct ctatatttcc tcatctgtat tatcattact accaccatca   136440
ctatcaccac catcgtcacc atcataatca ccatcaacac catctccaat accaccatca   136500
ctgtaaccat catcaccacc accatgatca ctatcaccat catcacaatg atcactgtaa   136560
ccatcattac tacccaccac catcaccact actccaccac catcaccatt atcattacca   136620
tcaccattat caccaccatc atcatcacca gcaccaccat catcaccagc accaccatca   136680
ccatcaccat cattaacacc atcactatca ccattggttt aatcatcacc accatcatca   136740
taaataaaca tcacataacc agggtgtagc tgggtgttga ccccagagcc cactcactgt   136800
ttcctctctc ccaccccccat ccacacattt ctaaccacca tcctgcactg ggctcccagt   136860
ctcctctggt ctcacccaca tgtccactga gaaaaggatt ttcagaacac caactagacc   136920
aggaggagcc acatacataa ctcaggcctg cttatcaact ttctacatgt taataatgac   136980
atcagatcaa tgggtgttct cagcttctca gaaggaggtc aaaattctcc ccctctcccc   137040
ttcatgtgtc cagaccttcc cggatttgga tgtaccaagt gcagagtggt gttgaggcca   137100
agggggctcat ccatgtaagt ctcatctgca atcactgggc tgatcccgtg ccctgtctc   137160
cagggcgcca tcagagaggg cttcaatcct caggttacct gtggcccacc ctgccctcag   137220
aggtgccatc tctacattgg ccacgagatg gcagcacata ctcatagact gcattaattt   137280
cccagcaact cctggtgggt tttccctctt atcaggatgt ttgccttgct cagagagcaa   137340
atctgagagc agtgacacct aacttaactt tcagcaaaat attttgagaa gggtgcccct   137400
ttacacatct gtgcagtcca ggtgatgcat cccatgccca atgctcggta gtcaggagga   137460
gcttcctcca tgcagctctg cggaagagac tcttccacgc tgctcatgta aactccagat   137520
tcggtgtcag ttttctgaca ccgaagacaa tgatctaagt gcagtcaagg gctttgggga   137580
aagcaggaga gagtgcctca gttctagcct gtgccatgct tgcaaagttt tgcaaaattc   137640
taatgagagc tgggcttgca acattggaaa cttggattat ttgtgagagc actgagaaat   137700
```

```
ccctgggcat gtccatctgg aaaaacagca tttcctctgg cactttagca gaggttctgt   137760
ttcaatttgg cgaaggaaat taagcagttt ttcacaaaag aagaactaca acgaggagaa   137820
ttgtccctag tatttcttct ccctaattgt caaggaagtg taaattagaa aatgaatcag   137880
gacaatttcc acctactatg ttagctaata ttttaaaaat tgaatatcac aagggtgagg   137940
caaagtaatt gttttccagt gacatttttcc actgtcacac ccttttagag aataatttgg   138000
caatgttact gtgagataga aatatgtcta tataattatg ggaactgaga cttcagaaag   138060
taataaggaa taagaatgaa atttatgaac aaacatgtgg aaggttggaa gcaagagtgg   138120
ggccaacacg catggggagg aagcatttgg gcagcgactc cgcagaccca gactcaagct   138180
gagctataca acctccttac gcctcagttt cctcaactga agaacaggaa tgacaagtgc   138240
ctgtttcata ggaccgttgt gaggattaag tgagatatac cacattatga gcttgtgcct   138300
ggaaaggttg attcttagta aatgatgact attcttttt attgcaataa aatttataca   138360
acatagagtt actattttaa ccattttttgc aggtaccact gagtggcatt cagtacattc   138420
acaatggtgt gcaaccgtca ccatatttcc aggacatttt tctcatcccc aaaggaaacc   138480
tcatgcccat taagcagtca ctcctcatta aaatattagt tatgaagact gtagcatttt   138540
tttaaaaact catgatataa cattgattga aaaaatcagt ataggaaatt gtgcattatg   138600
atgtaatagt aaaagaagca tataaaaatc tgaaaaagt atataaaaag aatagcaatt   138660
gtatttctca gactctcttt acattgtaaa aatcattttg atagcttcaa aagaaaagca   138720
aaaagtacac aaacaacaac caaccccaaa gcagcatgac aaagcccaga ttgttgaatc   138780
caggtcttgg gaacataaaa tcttatatga catttgcact ttaatgggtc agagagtcca   138840
gtggcattgg gagctgcctt gtgttctgca gcctcacgga cagacaggag gtccagctcc   138900
actgctctgt tcttctggaa tttcctcgtg aacaagcttt ggcctcagta accatttctt   138960
tcatcttttt aaacacaggt acctttggga ctggccttct caaggaagcc cagctccttg   139020
ttattgagaa tgaagtgtgc aatcactata agtatatttg tgctgagcat ttggccagag   139080
gcactgacag ttgccaggta agaaaagatc aatagatcaa agtcttgtgc tctcccgtct   139140
cagtctcagt cccttagacg tcagtcccaa agtggcaaat tcaggaaggt tttgtcagtg   139200
gaagacccca gtctaagtgt tgctcagaaa ctccccagat ctgtccctga atgcatattc   139260
agatcatcta aggagacgtc ttggggcttg agttccagat ccatagcaag ggagccgtaa   139320
gtgccataac tacctcaggc cactcacctt cctggtgtgt gctggtcacc agtgactgaa   139380
gtggtggctt ttccagtaga gaggaaggta gagggtacag gaccgagaca aattacacac   139440
acttaacaat gatgtccagg ctagcccagt ctaaaggaaa caccaagtta ggaagcaatg   139500
catgcaggat tcacaaggga ttattttttt tcccaggaaa aaactaagtg atgtggtttt   139560
gttgaataga ctttgctaag tacttaagca ctgcagatgc ttgagtaata tgctcataag   139620
ttcctttctg atttgaatta ctgggaaaat gtacatatgg ataagagaag gatggcatcc   139680
catattaaaa ggttggcagc ttaaagctca catgaatttt cccctacctc tgtttagggt   139740
gacagtggag ggcctctggt ttgcttcgag aaggacaaat acattttaca aggagtcact   139800
tcttggggtc ttggctgtgc acgcccaat aagcctggtg tctatgctcg tgtttcaagg   139860
tttgttactt ggattgaggg aatgatgaga aataattaat tggacgggag acagagtgaa   139920
gcatcaacct acttagaagc tgaaacgtgg gtaaggattt agcatgctgg aaataataga   139980
cagcaatcaa acgaagacac tgttcccagc taccagctat gccaaacctt ggcatttttg   140040
gtattttgt gtataagctt ttaaggtctg actgacaaat tctgtattaa ggtgtcatag   140100
```

-continued

```
ctatgacatt tgttaaaaat aaactctgca cttattttga tttgaattaa ttttggtttt 140160
ggtcttcaaa attttcatgc tcttttcatc ccatctattt ttattttat tttttagact 140220
ttacgtcctg gggtacatgt gcagaatgtg caggtttgtt acatagatgt acacgtgcca 140280
tggtagtttg ctgcacccat caacctgtca tctaattcgg tatttctttt agttctatcc 140340
ctcccctagc cctccacccc ttgacaggcc caggtgtgtg atgttgccct ccctgtgtcc 140400
atgtgttctc attgttcaac tcacacttat gagtgagaac atgccgtgtt tgttttctg 140460
ttcttgtgtt agtttgctga gaatgatagt ttccagcttc atccatgtcc ctgcaaagga 140520
catgaactca tcctttttta tggctgcata gaattccatg gtgtatatgt gccacatttt 140580
atccaatcta acattgatgg gcaattgggt tggttccaac tctttgctat tgtgaatagt 140640
gccacaataa acatacgtgt gcatgtgttt tcatagcaga atgatttata atcctctggg 140700
tatatacccca gtaatgggat tgcagggtca aatggtgttt ctggtgctag atctttgagg 140760
aatcaccaca ctgtcttcca caatggttga actaatttat gctcccacca acaatatcaa 140820
ggcattccta tttctccaca tcctctccag catctgttgt ttcctgactt tttaatgatc 140880
gccattctaa ctggcatgag atggtatctc attgtggttt tgatttgcat ttctctaatg 140940
atcagtgatg atgagctttt ctcatatgtt tgttggctgc ataaatgcct tttttggaga 141000
agcatctgtt catatccttt gcccactttt tgatggtgtt gttttttttct ggtaaatttg 141060
tttaagttct ttgtagattc tggatattag ccttttgtca gatggataga tggcaaaaat 141120
tttatcctat tatgtaggtt gcctgttcac tccgatgata gtttcttttg ctgtgcagaa 141180
gctctttggt ttaattagat ctcatttgtc tattttggct tttgttacca ttgcttttag 141240
tgttttagtc atgaagtctt ctcccatgct atgtcctgaa tggtattgcc taagtttttct 141300
tccagggttt ttatggtttt aggttttgca tttaagtctt taatccatct tgagttaatt 141360
tttgtataag taatgccctt cttttgtctct tttgatcttt gttggcttaa agtatatttt 141420
atcagagact agaattgcaa tccctgcttt tttttttctt tttgctttcc ttttgcttgg 141480
taaatattct tccatccctt tatttttgagc ctatgtatgt ctgcacatga gataggtttc 141540
ctgaatacag cacaccaatg ggtcttgact ctttattcaa tttgccagtc tgtgtctttt 141600
aattgggggc atttagtcca tttacatttta aggttaatat tgttatgtgt gaatttgatc 141660
ctgtcattat gatgctagcg ggttattttg cccattagtt gatgcagttt cttcatagtg 141720
tggatggcct ttacaatttg gtagtttttg cagtggctgg taccaattgt tccttttccat 141780
gtttagtgct tcgttcagga gctcttgtga ggcaggcctt gtggtgacaa aatcttttcag 141840
catttgcttg tctgtaaagg atttttatttc tcctttgctt atgaagctta gtttcgctgg 141900
gtatgaaatt ctgggttgaa aattatttttc ttttagaatg ttgaatattg gccccactc 141960
tcttcgggct tgtttgggttt ctgcagagag atccactgtt agtctgattg gcttcccttt 142020
ccgggtaacc caacctttct ctctggctgc ccttagaaat ttttccttca tttcaacctt 142080
ggtgaatctg acgattatgt cttgaggtgg ctcttctcga ggagtatctt tgtggtgttc 142140
tctgtatttc ctgaatttga atgttggtct gtcttgctag gttggggaag ctctccttga 142200
taatatcctg aagagtgttt tccaacttgg ttcattctc cccatcactt tcaggtacat 142260
caatcaaatg tagatttggt cttttcacat agtcccatat ttcttggagc ctttgtttat 142320
tccttttcat tctttatcct ctattcttgt cttcttgctt tatttcatta agttgatctt 142380
caatctctga tatccttttct tttgcttgat cgatttggct attgatactt gtatatgctt 142440
```

```
cacaaagttc ttatgctgtg ttttttcagtc agatcaggtc atttatgttc ttctctaaac   142500
tggttattct acttagcaat tcatgtaacc ttttttcaag gttcttagct tctttgcatt   142560
gggttagaac atgctgcttt agctcggagg attttgttat tatacacctt atataatagc   142620
ctgatataac tataagattt ttttgtaagc accatcgtaa ccacaaagca aaaacctaaa   142680
gtagatatac aaaagataaa aaggaatcaa agcataccac tagagaaaat cacttaatca   142740
caaataaaga tacgaagagt ggaataaagg aacgaagggt ctacaaaaca accagaaagc   142800
aattaacaaa atggtgatag cagatcttac ctataaataa ttatcttgaa tggaaatgga   142860
ttaaattttc caataaaaag acatacagtg gccaaataga ttaaaaaata agatccaact   142920
atatgatgcc tataacacac tcacttcacc tgtaaggact caaacagact gaaagtaaag   142980
ggatggaaaa aatattctat gcaaatggaa acaagaagat agaggggtag ttatacagat   143040
tgagtatcac taatccaaac atctgaaatc tgaaatactc caaaattaaa aatgtttaag   143100
tgccaacatg atgttcaaag gaatgttcct tcggagcatt ttggatttttt gtgtttaggg   143160 atgcaaaaac agtaaatata taatttgtat tagtccattc tcacactgct ataaagaata   143220
ctacaaagag actgagtaat tataaaggaa agatgtttaa ttaactcaga gttccacagg   143280
cttaacagga agcatggcta aggaggccac aggaaactta taatcatggc ggaagatgaa   143340
ggagaagcag gcaccttctt cacaaggtgg caggacggag tgtgagtgtg tgaaggagga   143400
actgtcaaac acttataaaa ccatcagatc ttgtgggaac tcactcactc tcacaagaac   143460 agcatagga aaaccgcccc catgatccaa tcccctccca ctgggctcct cccttgacac   143520
atggggatca tgagggttac aattcacgat gagatttggg tgggacacag ccaaaccata   143580
tcataatgca aacattgcaa aaacaattca aaattcaaaa catttctggt ttcaggcatt   143640
ttggataagg gaaactcaac tcaacatgag gtaaagcaga cttaagtca aaaactgtaa   143700 aaagagacga agaagaatgt aataataagg agatcagttc attacaaata tatagcaatt   143760
ataaatatat attaatatat atacccaaaa ttgtagtacc tacatatagt aactaaaaca   143820
aacattaata gatctcacag gagagctaca ctgtaatata atcatagtag cacacttgaa   143880
tagctccact ttcactaatg gacagatcat ccagacagag aatcaatatg gaaacacgag   143940
acttaaacta cactttagcc aagtagacct aacagaaata tatagaacat tccatccaac   144000
agcagtagaa tacacattat tctcaagtgc acagggaata ttctccagaa tagatcatat   144060
gttaggtcac aaaactagtc aaaaaatgta agaagattga aatcatatca ggttttttt   144120 ttagatcata atcgtatgaa actagaaatc aataatgggg gaatattgga aaatccacaa   144180
atagatagaa attaatcaat atgctcctga acaatcaatg agtcgaagaa gatattaaaa   144240
gaggaaattt taaaaaatca agacatgagt tcatgtcctt tgcagggaca tgaatgaagc   144300
tggaaaccat cattctcagc aaactatcat aaggacagaa atccaaacac cgcatgttct   144360
cactcatagg taggaattga acaatgagaa cacttggcca cagggcgggg aacatcacac   144420
accagggctt gtcagggggt gggaagctgg tgaagggata gcattaggag aaaatatctaa   144480 tgtaaatgac gagttgatgg gtgcagcaaa ccaacacggc acatgtatac ctatgtaaca   144540
aacctgcacg ttgtgcacat gtaccccaga acttaaagta taataataaa aaagaaata   144600 tttgtttttg atttatatgc caatcagaca aaatgtgaaa agccctactg aaattaagta   144660
tcaccatgaa agataaattc tggataattt tttcaagttt taacaatgta gctttaattg   144720
gagaaagcta tcatttggaa tgagttaatc tatcctatac taaataagt cacttgctttt   144780 aaaacataat aaatatgatt ttgaattgaa aacaaaaaca actcaagaca aaggaaaatg   144840
```

```
gacacactaa cataccaata atttatagta tgcagcaaaa gtggttttaa gagggaagct    144900
tttaccaata aacacttcca ttaaaaaaga agatctcaaa taagcaacct aagattacac    144960
ctcaacaaac tagacaaaga actaactaac ccaaaagtta gtagaaggaa agaaataata    145020
aagatcacat cagaaatagt aaagactaaa aaactgatac caaaaagaaa taaaactact    145080
agttggtttt caataaaata acaaaattga ccaactttta gctagattaa gaaaaacaga    145140
gaatactcaa ataaaaccag aaagaggaga cattacaata gatactacag aagtacaaac    145200
gatcataaga gactactatg aataattaca tgccaacaaa ttggataact tagaagaaat    145260
ggatgaattc ctagagcaaa aaacctacaa agactgactc agaaagaaat agaaaatctg    145320
aacagaccaa taatgtgtac atgattgtat cagtaataac aagtctccca tcaatgaaaa    145380
ggccaggacc taatggcttc actgctgaag cataccaaac attacaaaga ctaatatcaa    145440
ccctcctcaa actcttctta aaaactaaaa agaaggaatg ctttcacatt cattttatga    145500
ggatagcatt acactgatac taaacacaga aaaataatac gctaataaaa gaacattaca    145560
ggcaatatcc ctgataaaca tatgtgcaaa aatccgcaac aaaatactag aaaactgaat    145620
ccagtagcac tttaaaaaga tcattcacca tgatcaagtg cgatttgttt cacgaatgca    145680
agaatagttc aacttacaca aataaataaa tgaaaggatg gatgataaaa atgtgtatct    145740
atatatatat gttttataca cacacacaca cacacacaca cacacacaca cagaggaata    145800
ttattcagcc ttaatgaaga agaaaatcct gcctttgcat caacctggag gacattataa    145860
taagtgaaat aagccagaca cagaaaggca aatactgtgt gatctcgctt acatatggaa    145920
tctaagaaag tcaaattcct agaaatagag agtagcttag tgattgccag agccgtggaa    145980
gggggaaatg gagagatgtt gatcaaagga tacaactgta tagctttgca agataaaatag    146040 gttctggaga tctaatgtgc agaatggtga ctagagttaa taatactgta ttgcatactt    146100
gaaatttgct aaaagagttg atcttaagtg tcctcaccat atacacaaaa gtattatgtg    146160
aggtggtgaa tattttaatt agcttatgat aataatttca cagtgtacat ctatattaag    146220
gcattacatt gtacatctta aatatatata atttttattt gtgaagtgta cctcaataaa    146280
actgaaaaaa ataattgaaa agtaatgaaa aaaattaaaa gctattatgt gtcaaatgac    146340
attatcaaga aagtgaaaag caacctactg atgaagcaaa cctattgaca aaggcctggt    146400
gtccagaata tattaagatc tctaggctgg gagcagtggc tcacacctgt aatcccagca    146460
cttgggaggg ccaaggtggg aggatcactt gagcctggga gttcgacact gcagtgagct    146520
atgattgggc cactgcccct caggctgcgt gacagagtga gactgccatc tcttaaccca    146580
cttcttattt agaaaaagaa aatatgtagc ttgctgcctg catagtattc ttggggcaaa    146640
tgggaaatga gttaaaaaaa aaaaaagaa ctcttacaac tcaacaataa aagaaaaac    146700 agaacgtgga atagacattt tttccaaaaa agatatacaa ataggcaata agtacatgaa    146760
atgatggtca acatcattag tcattaagaa aatgccaata aaatcacaat gaaataagac    146820
ttcatatcca ttaaaatgtc tataatttaa aaaatggaaa ataacaagca tttgtgagga    146880
tgtggagaaa ttagaatcct gtatattgct ggtgggaatg tacagggaaa atggtttggc    146940
cactgtggaa aacaatttga cagttcctta aaatgctaaa catagaatta ccatgtgatc    147000
taacaatttt actcttaggt gtatatatac aagaattgaa aacaagtgcc caaacagata    147060
ccttgcatga gaatgttcat agcagcactg ttacaacagc cacacccaaa tgtcaatcaa    147120
tagatgaggg gataaacaaa ttgtggttta tacagctaca aaaaggaatg aagtactggt    147180
```

```
atccgctaca tggctgaaac ttgaaagcaa gggctgggat ggggtcatgg aaagtaccag   147240
cttattgggt actgcattgt gctttggggt catgaaaatg ttttggaact ggatggaggt   147300
ggtggttgcc aatgtgaaca tactaaatac aacgcattgt tcactataag actgctactt   147360
ttcttatgag aatttcactt caattaaaaa ataccttcca tgtatccttt ctaaggatga   147420
tactagaata tttgctttgg caaaatgagg aagtaacttt ttttaaaaag gaagatgtgg   147480
gatccatgaa acgggatcaa atatcagaga ggaaaggggg tcttctggat gacagtccat   147540
ggagatccca caactgcaca gcaggccggc tgtgcaccca ggccacacca gagcagagcc   147600
ggtggttccc gaggagctct ctggaagaaa acgctagat ggcctgattg gtttgggggc    147660
atattgaaaa ggtatataac tgagaatttg gagtggaatt aggaaacaga cataaaagct   147720
tacagaaaag aaaataatga attctaggga gaaatataaa aggatactac aggcctcagt   147780
tacataaaca ctgaatattt acttaaccaa aattacaata taattacata attattttag   147840
gtacatatgg caaaaggatg tgtgggtgta tgtagtatgt acggtgtgtg aagtgtatgt   147900
gtgtggtatg tggacggtat gtgtatgctg tgtatgccaa taaatcaca atgaaataag    147960 acttcatatc cattaaaatg tctataattt aaatgtctat aattttaaaa atggaaaaca   148020
cttctcatat ggcaggagca ggagcaaggg tgggggaggt accacacaca cttaaacaac   148080
cagatctcct gagaactcac tatcaggaga acagcacctg gagaaggtgc taaaccattc   148140
atgagttact gccctatgag ccaatcacct cccatcagac cccgcctcca cactaaggat   148200
tacaatttga cttgaaattt gggcatgaac acagatcgaa accatatcaa taggtaatga   148260
ctaaaactga aaaagaagt accacagtca gaaagttatt tagagagctg aaggtaaatg    148320
ccaataggat cagttgaaag aattggaggt ggccgggtgc ggtggctcag gcctgtaatc   148380
ccagcacttt ggaggcgga ggtgggtgga tcgccctgag gtcaggagtt tgagaccagc    148440
ctggccaaca tggtgaaacc cagtctctac taaaaataca aaaattagcc aggcctggtg   148500
gtggacgccg tagtcccagc tactcaagag gctgaggcag gagaatcgct tgaaccaggg   148560
aggtgaaggt tgcagtgaac cgagatcgtg ccactgcact ccagcctggg tgacagagca   148620
aaactccatc tcaaaaataa atgaaataaa gaattggaag tgtttgcctc tggagagaag   148680
gaaacgcagt aattctgtaa aaacagaact ttttacttt ttctttttt tttttttttt     148740 tgagacagag tctccttctg tcacccaggc tggagtgcag tggtgcagtc ttggctcacc   148800
gcaacctctg cctcttgggt tcaagcaatt cccgtgcctc agcctcccaa gtagctagga   148860
ttacagatat gggctgctat atccagctaa tttttttta ttttattag agatgaagtt     148920 tcaccatgtt ggccaatctg gtctcaagct cctggactca tgatcctcct gcctcggcct   148980
tccaaattgc tatgattaca ggtgtgagcc accatgcctg gacagaactt tttgactctt   149040
taaactatgt gcatatataa agctgattta aaaaaaacca agtaaaataa ttttaaaatg   149100
ttccaaaaca gattggatgg gtacacactt catcatgagt ggttgaggga gactgggtta   149160
gagatgagga aattccaggg actggggaaa agttaaaatg acaaactgtt cacaattgtt   149220
aactgcaggt tgtgggaaag ttggtaagtt gctacagtgt tgttccctc tgtaggtttg    149280 catatattta acatttctta aattagcata taatgaact gtgtaatcag ctgtagagtt    149340
gagggtgtgg agctggcaca ggacagctga gctactggtt taaaataaat gacatttaaa   149400
aaaatggcta tttgtagaat taacagatat aagacaccct gatcaaggga tgataagaaa   149460
ggactccagg gctctgtctc agctgtcttg gcaaacctg gaagacatgg gcctctgcaa    149520
ggtctcatac tttcaggagg tgttgatgaa ggatatggac agatctgaag ctctgggcac   149580
```

| | |
|---|---|
| tgcatggtct gagaagagaa gctccggaaa cgcgggagct gagtgcagat gcagaagggc | 149640 |
| tgtcatccag cagaggggta ggtgacaact ggcctagcga gtgacccta tcatggctac | 149700 |
| atttgttgat cactttcttt gtatgaggca ctgctgtgat tgcattaaat ttccacttac | 149760 |
| ctaaatccaa cgttgtgcac ttgtgaattt ctactcttac aaaaaacaca acggcaacaa | 149820 |
| cctcaaacca gtaatctagt caaaaaagca attcccaagg catgacattc agattcatca | 149880 |
| gcactcacag agactacagt gattgctgat aacgccaact taatacctgg ccaacagcat | 149940 |
| ggatcctgac ctccactttt cttgtgtgtt tacagaacca caaaaaggtg cagtgttttc | 150000 |
| a | 150001 |

<210> SEQ ID NO 3
<211> LENGTH: 138001
<212> TYPE: DNA
<213> ORGANISM: Homo sapiens

<400> SEQUENCE: 3

| | |
|---|---|
| ctctcccaaa ttgtcaaaga agtataaatt agaaaatgaa tcaggacaat ttcaacctgt | 60 |
| tagattagct aatatttaaa aattgaacac tcatacaagt gtggtgaagt gattgttttc | 120 |
| tagtgacatt ttacactgtc ataaccttct agaaaataaa ttggcagtgt tattgggaga | 180 |
| cagaaatatg tctatataat ttatgggaac ttaggctcag aaaatattaa ggaataagaa | 240 |
| tgaactttat gaacaaagat gtggagggtt ggaagcaaga gggggccaa cgcgcacggg | 300 |
| gaggaagcat ttgggcagtg actccgcaga cccaggctca ggttaacta gacaacctcc | 360 |
| ttacacctca gtttccttaa ctgtagagca ggagtgatgg aactgcctgt ttcataggac | 420 |
| tgttgtgagg atgaagtgag atacaccaca ttataagctt gtgcctggaa aggataatgc | 480 |
| ttagtaaatg atgactattc ttttttattg caataaaatg tacacagcgt aagagttact | 540 |
| atttaaccca tttttgcagg gtaccaccaa gtggcattta gtacattcac agtggtgtgc | 600 |
| aaccatcatc atatttccag aatattttcc tcatccccaa aggaaacctc atgctcatta | 660 |
| atcagtagct ctcctttaaa atattagtta tgaagatcat agcactatac aaaactcatt | 720 |
| atgtaatgtt gagtgaaaaa atcagggtgt gaaatttgt gatatgatgt aattagtgaa | 780 |
| agaagcatac aaaaagtctg aaaatataaa aacaatagca attgcatttc tcagactcta | 840 |
| catttaaaca ttattcttta tggttttaaa agcaaagaaa aaggtaaaga aacaacaacc | 900 |
| aaccgcaaag caccatgaca aagctcagat tgttaaatcc aggttttttgg aacatagact | 960 |
| cttatatgac gtttacactc tccagggttc agagagtctg gcagcattgg gagctgcctt | 1020 |
| gtgttctaca gcctcacgga cagacaggag gtccatcacc actgctctgt tcttctggag | 1080 |
| tttccttgtg aacatgttgt ggacgtagtt accatttctt tcatcttttt aaacacaggt | 1140 |
| acctttgggg ctggctttct caaggaagcc cagctccctg tgattgagaa tgaagtgtgc | 1200 |
| aatcgctatg agtttctgaa tggaagagtc aaatccactg agctctgtgc tgggcatttg | 1260 |
| gctggaggca ttgacagttg caaggtaaga aaagatcaag agaccaaagt tagtcttgtg | 1320 |
| ctctcctgtc tcagtctcag tcccttagac ttgagtccca agtagcgaa ttcaagtagg | 1380 |
| atttaatcaa tggaagaccc cagtctaagt gttgctcaga aactccctag atctgtccca | 1440 |
| aatgtatatt cagatcatcc aaggggactt cttggggctt gagttccaga tcagcagcaa | 1500 |
| gggagccata agtgccataa ctacctcaga ccactcaccc tcctgggggtg tcccggtggc | 1560 |
| cagggactaa agtggtgatt tttctggtag ggaaggaggt agagggtaca ggacagagac | 1620 |

```
taactgcaca caatatctga gactggagct cagatattgc tgatgatcag agttggcgtg      1680
tctccccaat tgatttacaa ctggggcttg gatactgttt taaacgggag gagcctccta      1740
accatcttga cacaaccact gacgtgacta cactagagat agactctttc cacttaattc      1800
taccactctt gctttacttc atgagaacga aaatgtaaga ttgcaccatg aattcatttg      1860
cggaaagatt gatactatgc ttttatttta ttttatttta ttttatttta ttttatttta      1920
ttttattgag actctcaccc cggttgaagt gcactgacgt gattttggct cactgcaact      1980
tccacctcct gggttcaagt gaatactcca gcctccctag tagctgggat tacaggtgcc      2040
caccaccacg cctggctaat ttttgtattt ttagtagaga tggggtttca ccacattggc      2100
ctggctggtc tcaaactcct gaccttgtga tccacctgtc ttggcctccc aaagtgctgg      2160
gattacagag ttgagccacc gcactcgacc ctatgtttta ttttaaaaa tatttattta       2220 tttatttaag ccacaactac tagaatagga aggattgata ttttattaat tttatttggt      2280
atttattatt ttttttcttt tcctgagaca ttcttgctct gtcacccagg ctggagtgca      2340
gtggcacatt cttggctcac tgcaacctcc atctcctgtg ttcaagcaat tctagtgcct      2400
cagcctactt agtagctggg atgactggca tgtgcctcca cacccagcta atttttgtat      2460
tttttgtaga gacagggttt tggcatgttg cccaggcttg tctcaaactc ctggcctcag      2520
gtgatccatc tgccgtggcc tcccaaaatg ctgggattat aggcatgagc caccaccccc      2580
tcctggaagg attgatatct tataacataa tttataatta cagaaaacat gtgagttcac      2640
taggaataaa taaattttga agataataaa agattttcac ttatgttgtc atttcggcac      2700
agtttggtat aggatgtgga gatgttaaca tttataccta gcttgctcgt aaactaagac      2760
ctgaaagggt tgtgtctatc agctgcaccc ctgggtagcg acacaacctc gggaaggcct      2820 cagcccccctc ctcgtacagc actgcctgtt ggaaagcttg agggaggcta tggatgtgca      2880
gcacttggca gagggtctgg tcatggaagt taccagcaaa tatgagctac ttttatgatt      2940
ttattttatc caaaagaaag agaatgaaag aagaggggag gaaacaagac taatcaggaa      3000
agatgaaggt ctaggggtga gggaaggagt aaggagacat aaaggcaatg tggagcagct      3060
gaggggggaa atggctttca ccacttccca gcatctattg acattgcact ctcaaatatt      3120
ttataagact ctatattcaa ggtaatgttt gaaccctgct gagccagtgg catgggtctc      3180
tgagagaatc attaacttaa tttgactatc tggtttgtgg gtgcgtttac tctcatgtaa      3240
gtcaacaatg tcctgggatt gggacacact ttctgggcac tgctggccag tcccaaaatg      3300
gaacataagg aagtggttct tctacttctt ttatttctga aatcaggtaa gacatagttt      3360
ttttaaatta taagaattat tttttctccc acaatgtagt aaaaatacat atgccatggc      3420
tttatgtgca attcatttaa ttttttgattc atgaaattcc cagttcaaaa tcttgtatat      3480
gattgaaaaa ttcttaaaaa aataagtttta atttccccgt gaagactgtc acggtgctgg      3540
aatgaatggg cagaaaaaat aatggttgat ttttctaatc taaaagagtg tgcctacatg      3600
atggccagtc tggctgaaaa ataaatagcc attgtagcta actatgcaaa ggatggctaa      3660
gctcttcgct tggttctcag tttcattaat ttatatcatc tctgttcagg tgccatgctc      3720
ccctcactag caagttgaaa caatgaaata actctttgaa tatgtttggt tccttgacct      3780
gttcatggag tgggactcag catttctctc tttgttatgg cctgagtaag gctttccatc      3840
ggtatacatt tgcttcttat ccctggagaa attatacaca tccatttgcc agatgatata      3900
cgcatataat gattcaacaa atactcaggg tatttgttga gtgggttagg tccccacatt      3960
tttatacata catacacaca tacacaccgt gtgtgattgt gaatgtaagt gtgtgtccttt    4020
```

```
tacaaatact agcttattta gctcatggta taggtagggt agcatagtca tccccatttt    4080
ataaacaaag aaatctagac ttaggaaaat catgttattt gtctcgtgac caaattccca    4140
aatcaaggaa ataaagaaac ctggatttaa gccagatttc caagaaaaaa tctagggctc    4200
ttctcacttt ttcatctttg ttccaacatt tgaaaaaata aatctaaaca cattccaatg    4260
taactgaaga gcaggttaat tgtttgccac ttgcagaatc caattaagaa gagagaagtc    4320
tggtataaag aaagtgattt gcttccaaag ctagcttagg ggaagaaatg cagcagtcct    4380
gccgtactac ttcactttag gagcagaaag tggcactttt aaaaggcaac agaggaggcg    4440
agcaaggatt caggggtcca tgctagcttg ggcaccttat ccaccaggta gttgagcagt    4500
tgcctgctgg tgcctttgtg agcagggtgt tgtcccttga ggcaaatctc tggagggtga    4560
gagttttgta gtgggcatgc tttggtttat aaatcacctg tgaactcagg agttccatct    4620
tgaagcacat acatagttag atgaacttgc cctgcaggga gagtctgatg aaagggaggt    4680
agatgcttgc aatttaatct ataaattacc agataaaatt ttacaagttg actttaaagt    4740
caaacacatt tgaatttagt ggaagccatt caagaaaata tcaaagaaaa tacagagcag    4800
gagaagatta agcaaagagt tttttgggga aattggtgtc tatgtctgtg tgtgtaggga    4860
gtgcagggga tatgaatatt ctatttcagc ccatggaaac taggatgtag atcactgtga    4920
acttattcag caggctacac ccaaaggcta gaacaaactt ctctgccaca ggattaacat    4980 atgtttttaat cgacctgggg ggcacattct ctgataagct cttttggaaa gccaggcttt    5040
ctgtggacgt gttatctttc caatgtgtgc tggaatgccc ggggagagga aaaagtttct    5100
tttacagcca tgctcagtga gaagcggaga acatcttct attcacaaat tgctaagtct    5160
tttacacatg caaatatgca tacacattca cacaccacag tgaggaagaa attctcacac    5220
cattaataaa atacatttac ttcagtagca atatacatct acattttgcc tataatataa    5280
aagtattttt cctattaaaa gatttgtttta atgtttcttc accaacaaat aaaccctatt    5340
aaatccccat tgccatatga gccctggagg tgaatcagag aaacaaaagg attgtggaaa    5400
aatcatcagg ttaaaaaaag aaaaattgat tctgttttgg gatatttcct agcaacatga    5460
gctggggagg ggatctcagc agtgatgctc tatgaagcat aataaaatga cacagttaca    5520
ggtaacttag ttaaaggggg aaataaatgg aagtttcctc tttttgaata tcaattgtag    5580
cctgctctgc tacatttcaa aaacactctt caaaatgttt aactgaactc actgtaggaa    5640
gcaccttatt aatttattgt gtgttttgaa gtcacactgt gagctataga atttacccaa    5700
gcacaactct tcctggaaaa gagagttcaa atgagaaaca gtgcggggtg aagacatgga    5760
tatgggccta aaatatctat ttctcaatga tattttgata tatctatcaa gtgcttttta    5820
gtggattagg ttcagaatgc atcagccaat gcctgttcaa taatccagtt ttccagcata    5880
gagcatatta aattgaggaa ggacaaagtc acagaggtgg ggagcaggtg gactgtggcc    5940
aaggactttg catgaaacag tgagcgtgca tcctcctcct tgccctgccc tcatggtctg    6000
tgtactctca ggaggtcagg acaggccttt ctgagaatga gaatctgttc atctgccttt    6060
ctactggata cttgtcatcg gcatacaaac acatgttctc tgcagtgtgt catctttcag    6120
aacctcccct gaccctgtat tccctagaag tctcgctgct tcagagccca ggcttctctc    6180
ctgctgccac ccccactgct cttctagtca ctctttaacc cactccatct gcatgtggcc    6240
cccaccacac ccctcaaagt ggtcaaggtt gtcctgttgc ttaattccat ggaagcttgg    6300
ctatcttcat tttattagcc tcttttggcc tctcaccctg tgaaaatcac tacatttgt     6360
```

```
gccagagatg gagctggcat ctccaggctt ggaagagggc tgctgaagct cagccaggtg   6420
tcctaaggag cctcaggaca ggggatgctc agtagccttg caatgggaac acagctgagc   6480
cccacttggc caccctttgc cacaaccagg cagaaagcag cttttgaaca gatttgttgc   6540
ctcagatttg atctcaaaga aaaatcgtgg gcagtattgg tcccaggttc tgcttttta    6600 caatttcctc tgaaatctgg atgcctatca acaccttgga aaaactgaat tctccccaac   6660
taatagtggt gtgtcactgt agtaagccta gtacaaaaat ggccttcttt gtggaggagc   6720
ttcatatcct ccattttttt tttgcttaat ttttgcccaa gatgagaaca taatttagtt   6780
cactttttat ttattcccaa catcatccat gcaccaacat ttttgtaact aaaggaggga   6840
ccattcagaa gatgcttatc aactgtcaaa gtgacagtgt acaaccaat gcacatattg     6900 taagaaatca acaatggcc tccaaggttc atttctacac agggattagc agatcaacat    6960
caatcttggc aacacagttg ccactgatgg tgtcttattt tttttatcat gacatggcaa   7020
tcaagagcaa acatgattta ttcttattta agatttatg gttagactag cagatagct     7080 agatatgagc aggaggtgga agcccctgag agaatggagg tctggagaat ctgaaacccc    7140
agagattacc caagtcctgc atgctagaca tgagtggagg aggggaata cctaggtaga     7200 aaagaatgcc ccttaagatg cccagcagtc gctcactgtg cagttaactt ttcagaatgc   7260
tgctagatac atgctgatag ggagggaaga gggcaaagga gaaattccta agagatacac   7320
ggttgcagtt agtatacatc tgagtgctat acaaccttct ttgggtggtg gcaagaagca   7380
atgcagccat tacgtagaat tcatatcaaa cacctgtatc acaggtgtta aagaaacaag   7440
aaacattgta cttcttgtat tcttaataat gatttgcaat attgtcttta gtatcactgc   7500
aaacctctat aaatatgatt tttaaaaagt atttctttag gttggaatta cttctacgca   7560
ttgacttatc ttcctgggtt tcattagccg taccgttgt actttcttcc ttaccactgt     7620
ttatctcaaa ctcttgagat taaagtatgg gctcaggagg gagcgaggag cttcaggact   7680
ctcacggacc tccagcacag tgtagctgcc ttatggaaaa gtggccacac tgttttctgc   7740
actggtccct gccctacta ttcctcactg gcagagcac agccacctg gccctgcctg      7800 aacattttag tcagtgttgg ctctgtgctt ctctggggag gaaatccaag agacaaccca    7860
cagcccctct gccatttcag ctgcagcagt accaccgtta atgcccttgg gcttgagaaa   7920
gaagggacct ggccacttcc ctgacacctc cagcacacag cagggaaaga attccagttt   7980
ctctttcttg tgagctttca cctgctactc ttcaccaggc aaggctcctg gcttgggccc   8040
acagtgcagg cacctcgaac tcagttgaac atttccactg gctgcactct gtgttttgt    8100 ggggtgaagc tcccagaggt gactgaaagt ccttctgcca ctaacactgc agtcatactg   8160
cccttgctgt acttggacta gggaaggaaa aaagatcctg agtgctttac tcacaccccca  8220 gtgtgcccca gccaccctat ggaaaagagg ccagtgtgtc atccctgcaa gcaccctgag   8280 gccccttgccc ctgctgcccc caagctgtag agccagaata taaagctggc agaaaaatgt  8340
aaaaaggcta gactggctta gcctcccagc ctacatcttt tcctgtgct ggatccttcc    8400 tgctcttgaa catcggactc caagttcttc agctgtggga cttggactgt cttccttgct   8460
cctcagattg caggtggcct attatgggac cttgtaatct tgtgagttaa taccacttaa   8520
taagctcccc tttgtgtgag tatatctata tctatagata gatataggta tactcactat   8580
atatacacat atatacatat actctctctc tctctctctc atatatatat atatataatc   8640
tcctattagt tctgtccctc tagagaaccc cgactaatac agattttcat accagaagtg   8700
gttcttgagg aacagaatat taaggatgga attctttcat tggttttggg acttctggtg   8760
```

```
ttggctgatt aatatgatta gaccaaaaaa tgctaaggac tctacttcta atagtatgga    8820
gaacactgat agtacttggc ctgaattgtt tagagagtta tgcaaaataa atgcatttga    8880
cactactgat tcatcactta tgagaggcaa ggagtttagt gactctatac ataatacctt    8940
tgactatatg tggagaacca aggaacataa tgaagttggt tgattgctcc taagttctct    9000
ggagaaagag atgaaagaaa atgatgatct caggggatct gtctcccacc ttcagaagca    9060
gatactgagc cacaaatctg ctaagattgc cctgaatgag agttttaact cctgtagaga    9120
aagagttgaa attgtgaaaa aacagagaca agctgttatc atgcgagtag ctgatctgca    9180
acaagaggtg catgcacagc cttgccaggt gtttactgtt aaagtgaggg cattgactgg    9240
aaaaaaatgg gaccctggaa cttggagtgg ggatgtgtgg gagaaccctg atgaagctga    9300
ggacactgag tttgtgaact ctgatgaaac tttttttgcca gaagaaacag tttccccatc    9360
cccagtagtg gtaacatccc ctccctgacc cgtgctgcca ttagcctttc cacctttgtc    9420
tgaggatgta aaccctgcac tgcttgaggc aacagtgatg gccttccctg aggcagctgc    9480
caggcaagat aatgttgatt ctcctcaaga ggcaccccta atgcccctga atgcttctag    9540
acctataact aggctaaatt ccttgcgggc cccagaggtg aggttcagag tgtgacccat    9600
gaggaggtgc attatactct aaaagaactg cttaagcttt ctaatttata ttggcagaaa    9660
tctggagaac aggcatggga atggatatta agggtaaggg ataatggtgg aagggacata    9720
gagttggatc aagctgaatt tattggtttg gccctactaa gtagggattc tgcatttaat    9780
gttgcagctc ggggacttag aaaaggttct gatagggccg ggagcagtgg ctcacgcctg    9840
taatcccagc accttgggag gcggggggcgg gcagatcacg agatcaggag attgagacaa    9900
ttctggctaa aatggtgaaa ccccatctct gctaaaaata caaaaattag ctgggcatgg    9960
tgatgcgtaa ctgtaatctc atctacttgg gaggctgagg caagagaact gcttgaacct   10020
gtgaggcaga gattgcagtg agccaagatc gccccactgc attccagcct ggtaacagag   10080
caagactcca tttccaaaaa aaaaaaaaaa aaagttataa tagtttattt gcttggttag   10140
ctgaaatatg gattaaaaga tggtccaatg ttagtgagct ggaaatgcct tggtttaatg   10200
tagaggaagt gatccaaagg cttagggaga ttaggatggt ggagtggatt agtcactta    10260
gacctactca tcccagctgg gagggtccag aagatacacc cttggccgaa gctttgtgaa   10320
atagatttgt gagagcagca cctgtatttt tgaagagccc gtaattgctc ttctctgtat   10380
gtcagatcta acagtaggaa ccacagtcac tcaactacaa aatttaaata caatgggaat   10440
aattggatcc tgaggtggca ggggccaagt gttggcactg aaccatcaaa ggcaaggtgg   10500
gcataactac cataatagac agcagaggca aagcagccat cagaatagtc tgactcatgt   10560
agagctctgg cattggctaa ttaatcatgg tgttcctaga agtgaaattg atgggaaacc   10620
tactgtattc ctacttgatt tatataaaca aaaaactgcc aggtagaatg gactaaagac   10680
taatctgaat tataaaaaca gagaatcatg ggccctcaat caatttccag actcgaacct   10740
gttacagttc cagaacccac tgaatgaagg ggaggctgga tcccccttgag gaaggacacc   10800
actaggctac tgacaactta tgctgttact cttctcccca tccttcccta aggagacctc   10860
tggcctttta ccagggtaac tgtgtgtact ggagaaaggg aagtaatgag acatttcaga   10920
aagtactgga cactggctct gagctgacgt tgattccagg gtacccaaaa cgttattgtg   10980
gttccccagt taaagtaggg gcttatggag gttaggtaat taatgagtt ttagctcatt   11040
tctgacttac agtggttcca gtgggtccct ggacttatcc tctggtcatt ttcccagtgc   11100
```

```
caaaatgcat aatttgtata gacatactta ttagctggca gaaatgccac attggctccc   11160
tgactggtag gatgagggct attatggtgg gaaaggccaa acagaagcca ttagagctgt   11220
ctctacctag aaaaataaaa aaatcaaaaa caatatccca tccctggagg gactgaagtg   11280
attagtgtca ccatcaagga cttgaaagac gcagggtgg tgattcccac cacatccctg    11340
ttcaactctc ccatttgacc tgtgcagagg acagatggat cttggaaaat gatggtggat   11400
tattttaagc ttaaccaagt ggtgactcca attgcagctg ctctaccagt tgtggttttg   11460
ttgcttgagc aaattaacac atctcctggt gcctggtatg cagccattgg cttggcaagt   11520
ggcttttcct ccattcctgt ccataagacc caccagaagc aatttgcctt cagctgacaa   11580
ggccagcatt ataccttac caccctacct caggggtgta tcaactctcc agctttgtgt    11640
cataatctta tttggagaga ccttgctcgc ttttcacttc cacgagatat aacactggtc   11700
cattacattc atgacattat gatgattgga tacagtgagc aagaagtagc aaacacactg   11760
aacttattgg tgagacattt gtatgccaga ggatgggaaa taaatccagc taaaatttag   11820
ggactttcta cctcggtaaa atttctaggg ttccagtggc atgagaccta tggagatatt   11880
ccttctaagg tgaagcataa cttgctgcgt ttggcccctc ttacaaccaa gaaagaggca   11940
caatgcctgg tgggcctatt tggattttgg aggcaacaca ttcctcgttt gggtgtgtta   12000
ctctggccca tttatcgagt gacctgaaag gctgccagat ttaagtgcag tctagaacaa   12060
aagaaggctc tgaaacaggt ccaggctgct gtgaaagctg ctctgccatt tgggccacat   12120
gaccccgcag atccaatggt gcttgaggtg tcagtggcag atagggatgc tgtttggagc   12180 cttggcagg ccccccatagg tgaatcacag tggagacctc taggattttg gagcaaggcc    12240
ctgccacttc tgcagataac tactctcctt tgagagaca gctattggtc tgttattggg     12300 cttggtggt aactgaacgt ttgactgtgg gtcataaagt caccatgcta cctgaacctg     12360
cctatcatga actggttgct ttctgaccca tctagccatg aagtgggtca gcacagcggc   12420
atttcatcat caaattgaag tggtgtgtat gtgatcgggc ttgagcaggt cctgaaggca   12480
caagtaagtt acataaggaa gtggctcaaa tgcccatgtt ctccactcat gccaccctgc   12540
cttccctccc ccagcctgca ccaatggcct catgggagt tccctatgat cagttgacag     12600
aggaagggaa gactaaggac tggttcatag atggttctgc acgatatgca ggcaccaccc   12660
gaaagtggac agctgcagca ctatatccac tttctaaatg catgtgtaca cttgtgctaa   12720
gaaaatatct ttattttatt ccttttattt ttcctttatc atgtgacctt agatttatgg   12780
acttcacatc agcatttaag catttaagtg ttgttcatat cagcatttaa atattgttaa   12840
ccttatgtaa taacttttgg tttggggatt ggtgcgtttc tggttgtatg aggatagttg   12900
tattatatta ggcataatta tgaccttatt attgtcttta tttgaagatt atgtatgatt   12960
tcaggatgtg tgtatgggtt caagttgaca aggagttgga cttgtgatgg ttaatactgt   13020
caacttgatt ggattgaaag atgcaaagta ttaatctcgg ttatgtctgt gagggtgtgg   13080
caaaaggaga ttaacatttg agtcagtggg ctggaaggc agacccaccc ttaatctggg    13140
tacacaccat ctaatcaagt tccagtgtgg ccagattgta aagcagggag aaaaatgtga   13200
aaagactaga ctgaattagc ttcccagcct acatctttct cctgtgccaa atgcttcctg   13260
ctcttgaaca tcggactcca agttcttcag cgttgggagt tggactggct tcttgctcc    13320 tcagcttgca gagggcctgt tgtggaacct tgtgatccgc tgagttaata ctacttaata   13380
agatcccctt tatatacata taatatatta tattatatat aatatatata atatatatta   13440
tatataatat atataatata ttatatatta tatataatat atattatata ttatatataa   13500
```

```
tatatattat atataatata tattatatat tatatattat atataatata tattatatat   13560
aatatatata aaatatatat atatcctatt agttctgtcc ctctagagaa ccctgactaa   13620
tacaatttat gtcattaatc tcatttattg atttgtatac attgaaccaa ccttatatcc   13680
caggaataaa acctacttga ttgtggtgga ttagcttttt gatgtactct tggattcaat   13740
tgctggtatt ttattgagaa ttttttgcatc tgtgttcatc aaggatattg gcttgaagtt   13800 ttctttttt gttgttccat atcagaatga tgacgacctc atagaatgag ttagtctgtc    13860
ctcttttatc ttttggaatt gtttcaggag gcttgatatc agctcttctt tatatgactg   13920
gtatactttg gctaggaatc tctctggtcc aggggttttt ctggtgtagg tttttaatta   13980
ctgattcaac ttcagaactc attactcatt attgagttct aaaactcact ttcatgtact   14040
cttcaaaaga ctgtcttctt ctgttgttga gcggggtgtt ctctcaaggt cgtttaggtg   14100
aaggtggttg ctggtgttct tctgtatcct tactgcttgt cttctctctt ttttattgac   14160
tactgaggat taatggtgat gtgtccaact ttaactctag attagtctat ttctctttta   14220
gattgtaact ctgttttata tattttgaag ctctgttgtt aggcatgtgt atttggattg   14280
ttaggtcttc ttgatgatga cctttatcat tatgtaatgt ttcttcttat ctctggaagt   14340
attcgttgtt ctgaagtcta tttgtgctga tatgaataca gccttcacag ctctattttc   14400
actagtattt gtatatcttt ttctcagctt ttaaattgag atgttcagac catttgcatt   14460
aaagtagttg ttaataggat taaatttaaa tctaccatta agttggttat ttctctttgt   14520
cccatttaaa ctttgttcct tttttcatat ttttctgcct tcatttatat tgagtttatc   14580
tccacgactt acttattaaa ttaattttta atggttttag tattttccac aatgtttata   14640
atatatactt tgattttttc acattccacc ttcaaatgac agaattatac tggatatata   14700
gaaatcttac atcattgcac ttctccttcc tccctctcaa aatgttgtgc tattgctctt   14760
tgtaatagag gcttacttct attatgttat agctctcata atacattgac actattttta   14820
ccctgaataa tcagttgttt tttaaagtga ttatgactac aaatattttg aataatttct   14880
ttattttacc atttctggtg ctccttatct tttacagtag atcccaattt ccatctggag   14940
tcacattctt tctgtgaaaa acaacctttta gcatttctta tagcacggga ctgctgttgc  15000
tgttgtcttt cagcttttct ttgtctgaag aagtctttat tttgccttca gttttttaaaa 15060 gtgatttgc tgagtataga tactggggttg agagtttcat tccttgtatc attttaacaa   15120
tgatgttcca ttatattccg ttttgaatag tttctgacta gaaatctgat ctttgtttct   15180
ttgtattcaa tagttccttt ttctctgact gcctttaaga tattctcatc tttgtttttc   15240
aacagtttga ctataatttg tttattatta acttttgta tttattctgc ttgaggtttc    15300
ctgagctcct tggatttgca gattgttgat tttattgtt tttgtaaaat tcatagccat    15360
tatctattct actgttttgt tttttttttc acttctctct ctctgtattc ttcttttgg    15420 actgtaagta ttcaaatgtt agatcattca tattgcttca taaaccttat atgcttcttc   15480
tgcttttttt tttttgtcag gaactctttt tttgtatctg tgttggtttg gataagttct   15540
agtagactat gttcaagttt atggattatt ttgttagttg tgtctaattg actcctcagt   15600
gcattcagag aattcttcat ctctgatatt ataaatctct tcctagcatt ttcatgttac   15660
tcttttctat agtttccatc tctttgctga aattctcccc ctatccatgg atattgtcca   15720
cctttaccac aagattcttt aacatattaa cataggtatc atacaaaccc aaactgatag   15780
tttccagatg gtgtctttc tgagtctgtc tgtcttgatt gctttattat ttaacagtga   15840
```

```
cttatcttcc ctcttcagct tttggtgtgt cttgtaattg tttaatcaaa cactgggtat    15900
cataaatgga ggaacagtag agattgcagt aaatattatt tatgctttga aatgggcacc    15960
catcttctgt tgaaaatatg ttttgtggtc aattgagtca acctagtaac tggttgaact    16020
gaatttggca tttgtgcttg ttgcttttat cttaaatgca ccacaggttt aaattcctcc    16080
agtgatgggt tgctgctatc ttttgcttag agtggggcct ggggtgtgga agaattttct    16140
cagtgttcct atctattatt agattttagc agtcactgca tgcctgcact acagagggga    16200
tatcttcata cacataatct aaccccattg aaactgctgt ttcttcttaa tgaatgctca    16260
atctttggtg gaaataaaca aatgctgtat ctcctggagc cacttcagtc ttagtcaggt    16320
tctgcagggc tttgaaggga atgcattctc agtattcttg tgccttattt ggatggaact    16380
tgaacctgtg gtgggtttgg agagaaagag tagcagacgt ctgctatgtt gcaatgcagg    16440
atgctgggca caagaaaatt tccagtctct cctccaagga aataagattt gatcatctac    16500
ctatccctga gaagtgaagg gctttgcctg cggtgctaga tgcaaaacca ttttttctccc    16560 cccattgccc agaaacttaa ggctttgcct tttctgagca gtggtctagg gaattgtgca    16620
aggttttcat atttgaccct gacagcccat caccacctac agcttgcagt gccaaatgta    16680
tctccctctg atctctcctg tcctgtggtc ctcatgaaca ttaagaagag atttctaaaa    16740
aagagcttgc acatgagcat agtttctggt gagaagaatt ctgatatgtt aacttcctct    16800
aaacttttaa ataaaatatt tctaagaatt aaataaagtt ctagaatgat atgaatctat    16860
tcctttggtt ttttgcacgt ctgtctgcct gctaatcaag agaagagaat ggtcgtaatt    16920
ctcagagact ttttcctgtt tgtgtcataa atgacttcac atttttttct gttctaagaa    16980
ctattcagct tgatttcttc tgttttaatt ttagcagcac ctgagcaaag ccatgtggtc    17040
caggattgct accatggtga tggacagagt tatcgaggca cgtactccac cactgtcaca    17100
ggaaggacct gccaagcttg gtcatctatg acaccacatc aacataatag gaccacagaa    17160
aactacccaa atgcgtatgt cattaatctt acagtaagca aaacaaggtc caagtaaaat    17220
ttgtcttaga aaggtgtgc gtcaagctaa cttcttatga ttaaatttttt ctcacacata    17280 gaatgcatgg caaatgtct gagaaacatt actttgagca aagagtatga tagaagagaa    17340
atgttaagct ggctctcttt cctgagagtt tgataaaatc aggagaatat ctggcggtgg    17400
tgaggccaca ataatggaaa atcagaatgt ttagacagag tcagcttcaa caacactcac    17460
taaaggtcaa tgtgatcttt acccccttgaa attctataat tctaatctcc aattcctgaa    17520
gtgaaggttg tgttggcctt ttctgtcttg gctcacaagt aaatgatatg tgcatatcta    17580
tggaaaggcg aatctatctt tttctatatc tatgtctatt ccaacgggta gaaacaccct    17640
gggtcctgag caccagtggt ctgaaggaat acgggttgcc aggaagagag aagcaaaggc    17700
aggaaggcag atgaaagtaa gaaatgagac agatgctaaa caataaaaag tgcgggaaga    17760
tagacagaag ctggggtctg accacaccat ggccagtctt tcacacataa gtgactacca    17820
aagacaagaa aaaatgattt ccgcttgttg gacaatagat ggtagaggac caagggaatt    17880
gcgagagaga gaacaatgag atcaactcaa cagatgcact ggttttcttc ctggagaccc    17940
ttcctgcact gaagggcagg agatggagcc caaaaaaaac tgtagccatc ttgctgaaca    18000
gaggagggac attggagttt gggattattc aggtggctag gattttctag gcctgctaac    18060
aatgagaaca gatttgtgga ggaaaggagt tctagaaata tgcatagaaa tctcctcgag    18120
tcattggcta acatgaagc tgcatgtaca cagaaaatag atccacaaga aagtagggca    18180
aagaacatct acggaagagc agcaactaca atggaacagt gagctcaata aacatgacag    18240
```

```
agctcaaata gcactaaggg atattggagt ttggaccaca cagaggagag agacttcact   18300
gaacatcttg ggcattcagt agagacccag gaaaagccat actttaggag tagaattagt   18360
atattcttag aataaaggca gctccacaca aacaatagca aaactgaaaa ggaagtctcc   18420
aagcatcaga atgatgtcca agtcaatgaa ctgcctctga gaggaaaact caaccatctt   18480
tagaggtaaa catcaaagtc aagtggctca gctatgcagt atccacagtg tgaggcctaa   18540
atataaaact tgactacaca tagaaacctt ttagtgtgac ccacaagcag gaggaaaatc   18600
agccaataca aacagaccca gaagagacag aaatgattag aatggcataa aaatttgaca   18660
tatcactata taataattga gttctaggat ttaagaaaac atgaatatag aatgcaacag   18720
acaccttatc cagagacagt aagagtataa agagccaaat cgaagaacta ctaagagata   18780
tgtcttaaat gaaaaaatta ctagatggcc tccccatcta gttagacatt tcagaagaaa   18840
ataccaaatg aaaaataatt gcatagaacc tacagaacca gatacacaca tacaaaacac   18900
acgcatgcat acacacacac tcaaacatgt ataagcttac aaacacacac acacatccac   18960
aaatgctgaa aaatgaaatc aaccgagcca cacagacata aggaaaaaca taaaaagatt   19020
tcctacatgt gggaagcaag tcacagaaag ggggaaggag attggaacag aaatatatac   19080
tgaaagcaag gatggctgaa aattttccaa atataaagaa gattaaaaaa tcacggactc   19140
aagaagctca atggatcaga aaaataattt ctaaaatgac aatttatagga tgccactggg   19200 tacatagcag ttcaactgtc agagggcaaa gacataatac acagaaaaat ctcgtaagga   19260
acgggaaaaa caaaaagctg tgtcttgcta gaggaacagt gatacaagtg actaatgtgt   19320
tcccatcaga aacactgcaa cctggacaca aagaataac attaaagtaa taaacgtaag   19380
aaagaagagc tcaactgaga aggctacatc cagcaataaa atgccttgaa gttcatccat   19440
gttggaggaa tgcacattgt gcactcccct aaacaaagaa accggaaact gtaagacttt   19500
ggaatcagca ggcttatgta acaaaagagg tgaccctaag gaattaagga gaagaagaat   19560
agaacaagaa gggaactttc tgcagcctat ataatgaaga acctagcaat tggcaaatgt   19620
agatgaaaat gctacatgtt ttcttgatca aacgtttata tctttttaaa tgagagttga   19680
cgagttgaag caaaatgata ccaatatatt taactttacc atatgtagaa gtaaaaattt   19740
gaacatgtag cataaatcat gtagggatta attggaagtg taccactgta agtttcttac   19800
ctcatgcacg atagtatgta atactaataa aaggttaatg tgtgggttca aagggatatt   19860
gcaaatccta gagcaatcac aaagttttta actctgaggt ttgttgtata ataacaatat   19920
tttatgtatt caaagagggg aagccaagga agaaaaaaaa gtctttaaag agctctggct   19980
cttagtacat ccagttgctc attgaatgag cttcctggaa tggagggtct gggactgaga   20040
ctaggccaca tgtgtagagc cactagagac acaatgttgg atccccatgg cccataatac   20100
atttcccatt ttctcaggca gccacaggtc atgaatgtga ggatactgag aggttggagc   20160
aacgttcttg ggaggcataa ggaagagcga atgcttcaag atccccgcag cccaaactcc   20220
tcagctgctt tgcctcctaa ttcattgttt tttgctcctc catagctgtc cgacctcttc   20280
agatctctta gtcttcctgc catcttcctt tatgccatgg gacccactgt tctttcaact   20340
catcccccag ttctggagtg gctgtggaca gcagaggata gactgagagc aggagagaag   20400
gtcctgccca ggaacccatt ctagagatac tgcattctgc ctgggagcaa gttttccagg   20460
gcagctttga gaagtcttgc agaaacaaac ctacttgacc gacatgatat gggaatgaca   20520
gacagtaata ctatttgcac aatgcttttc catgggaaag gtagagcctt ttcactaggt   20580
```

```
tttgagtaca tggagtgtga gagttgacct ggaaaggtta tcctccttga tgccatgttt    20640
tctctgaaga actacatgtt cgttgcaact cccacattag aatatgaagt cctaccgaga    20700
gagatacgga gactagacag atacagatgc atttgcatgt aatacacaa tcccacaata    20760 cagacgtcaa aacccatacc agttattcca gagagatgga ttgggcagaa ggcagaagga    20820
gaatactctg atcgtttttc ggccacgtgt gtgtgttatc tcagtgtttc taagaagcgt    20880
ttgctacttt agattttta tttaaaaaaa atagtaataa tctattaagt atgagagatg    20940
tgcagagagg attagtgatc gagagccatt tttgctggtg gcaatcatat ggtacttta    21000 atgggaatat tagaaaggca ccggtaatga ccttgttgca gcacaaagga gagagtgtgg    21060
ggtgcccctg catgttgtcc cacctcttgt gacgtgtatc gttttggaat tccagtggc    21120 ttgatcatga actactgcag gaatccagat gctgtggcag ctccttattg ttatacgagg    21180
gatcccggtg tcaggtggga gtactgcaac ctgacgcaat gctcagacgc agaagggact    21240
gccgtcgcgc ctccgactgt taccccggtt ccaagcctag aggctccttc cgaacaaggt    21300
aaggagtctg tggccagaca tctacacgct tcgatgctgg gatgaaaagc catggaaatt    21360
cccactgatg cagccgcctt caatggtaaa cggatgctcg agtgttgcct gagttctacc    21420
atgtaggagg aagcctccgt gcactctctg ggggagccag cggagtgatt tctggtgcaa    21480
cgtggttggg ctttgtcttt aggatgggca caaaccctcc aggggatcg acttcaaaat    21540 tcaccttgtt gtaaacggg ctacctcagt gtcccagcca aaattttat tgtaacatgc    21600 tgtcaggtgt gtcactcttt ccaagccagt aagcttttcc ggggatttct tcaagtagcc    21660
agcattcaga gcaatcttca gcattgcaga ttctgagaaa tgtggctctg gagcctgtca    21720
ccctcgagaa acctaagagg gctgcattga ttccatgtgg ccctgggtct atggagcagt    21780
acatgagctc ccagtgctct aaggctcttc agccctaggc tttgaaggga gtgatttctc    21840
agtattctta aacctctttc tgatgacact tgtacctgtg aggggtctag agagaaagag    21900
tagtagactc ctactttact acaattcagg atgcagggca tgagaggatt ccctctctcc    21960
tccaagggaa gaagcttttg gcgtgcacac atccctgaga agcaaagtgt ctttgtcttc    22020
agtcagatac ataggaccgt tttctgcccc atggcccgga agccaaaggc cttggctttc    22080
atgatcaacg gtctagggaa acatgcaaaa tttccatgtc tgtcccaaac tctgccccg    22140 acagccaatt accacctgca gcccgcattg ccaaatgcgg tgccgtttgc atgaagattc    22200
agtagagttt cctagaaagg tgctacctcg tgagctcact ttccaatgag gaatctgatc    22260
tgttgtgttt ctctaaggtg tcaggtgaaa tatttccaag aacttactac agttctagaa    22320
tgggaggaat ctgttgcttt ggtgtttgtt tgttggtcgg ttttctcaca tccatctgcc    22380
tatggataag gaaaagagaa cggtcgtaat tctcatagac tcctttctgg ttgtgtcaca    22440
aatggcttca catgtttctc tatgctcaga gatactcagc ttgatttccc gtgttttcat    22500
ttcagcaccg actgagcaaa ggcctggggt gcaggagtgc taccatggta atggacagag    22560
ttatcgaggc acatactcca ccactgtcac aggaagaacc tgccaagctt ggtcatctat    22620
gacaccacac tcgcatagtc ggaccccaga atactaccca aatgcgtatg tctttgttct    22680
ttaccataag agaagaaagg gccaagtgaa gtttctgtta caagagatgt gtctcaagct    22740
gagttctccg aactcaactt gtgacagatg cagatggcgt agcaaaatgt ctcaggatga    22800
ttgccttgga gctaagggtc tgagagaagg gaaatgttaa gctccctctc cttcctccta    22860
gttctattga gcagaaggga aatctggagg tgaggagatc acattatgaa gaaagtcaga    22920
atgacaaagg accagacact tagattaccc ttccacaaca ccaactaaac gtcaatggag    22980
```

```
actttccagt tggaattccg ttattctggc ttccacttcc tgaagggaag gttgcgtttg   23040
cctttctctc ctgggttcaa gaggaaagaa taggtgctta tttatggaca ggtgaattga   23100 tctgttctcta tatctacgta tattccgatt gtcagaaaaa cactcgttcc taagtaccag   23160
tggcctgaag ggatacaggt tcccagcaag agaagatcca aggaaggaag gcagatgaga   23220
gtcagcacag agagggatgc tgaaaagtaa aagggatggg tggatggaga gaagcccggg   23280
tctgaccacc caatggccaa tattttggcc acaagcgact accagagaca tggaaaaatg   23340
gtttctacat gtgggacaac agatggtaga ggacctagag aattgagaga ggggcaatga   23400
tgggctccac tccgcagatg ccttggcttt cttcctggat acccttcctg cactgaatag   23460
caaggagatg gagcccaagc agactgtagc catcttgctg aatggaggag agggattgga   23520
gtttgggatg actgtggtag ctgaaatttt tctaggtctg ctagaaataa gaactggttt   23580
gtgtggagga aaagagctct acaaatacgc atagaagtct cctccagtcg ttggcctgac   23640
atgacgctgc ctgtgcacag gaaatggttc cacgagaaag tgtggcaaag aacatttact   23700
gagaaacagc aagtacaaga gcacaggaag ctcaataaag aagagagaga tcacatagca   23760
ctctgggata ctggagttct tcccagctag accagagagt cctcacggag cacattgcca   23820
attcagtgga gaccccagaa cagccgtaat ttaaaggtac acttagtata ttactagaat   23880
aaagtcagct gcagacaacc ccttgcacag ctggaaagca agtgtccaag catcaaatcg   23940
gtttccaatc aatgaagtgc ctgtgagagg aaatctcaac tctctttaga agtaaacaac   24000
aaagtcgatt gcctcagcta tgcggtatcc gcagagtgag tcctaaattt aaaatctgac   24060
tacatgtaga aaagcgtttc gtgtgaccca tgaccaggaa ataaatcggg taatacaaac   24120
aggctcagga atgagagaaa tgattagaat tgcgtgaaaa tttgacatat cagtatgata   24180
actgatttca atatttaaa aaaacaacat gcaagaaagc agatatcata tcaagagaaa   24240
ttaacagtac agaatagcca aattaaatta aagaggtagt ataaaaaaag tatgtcttaa   24300
ttgaaaaaaa ttactgtatg gccggctgat caatttagac gtttcagagg aaaacattac   24360
ccaacacaca attctagaga acctacgaaa tgagctacac acacacacac acacacacac   24420
acacacactg aaaacacacc catactcaca cacacgcaga aactcacaag ttctaacaca   24480
cacagacacg cgcaccctg aagaaacagt gaaatataaa attaagcgag cctcacagac   24540
atgtaggaaa atatgaaaag atttcctgca tgtgggaagc aagtcacagt aaagagcaag   24600
ggagtttata atagaaacaa ataccagaat caaggatggc tgataacttt tcaattacga   24660
agaacattaa aaaaatcac agaatcgtga aactcaaggg atcatatagg gaatttcgga   24720 aaaaaaccc aacctgtatg atgtactttt gtacatcaca gttcgaaggt aacaaggcaa   24780
agatgtaata agaagaaacc tgtcacgaga aactggagga aaaagagctg tgtcttccta   24840
caagtacact gatacaaatt gccaatgtgt tcacctcaga aacactggaa gccagatacc   24900
agggaatatt gttaaaatga taatcaggaa caaaaagaga tcaaccggga atgctgaatc   24960
cagcaataaa atgccttgaa ggtcatccat gtcggataaa tgcatattgt gcactgcccc   25020
aaagaaagaa accggaaact gtaagaattg gaaatcagca ggcttatgta acaagagagg   25080
tgacccgaag gaattaggta gaagaagaat tgaacaagaa aggaactttc tgcagcccac   25140
gtaatgaaga atccagcaat tggcaaatgt agatagatgt aaatgcaaaa tattttcttg   25200
atcaaatttc tatatctttg taatgagag ttgactactt gaaacaaaat gatagcaaga   25260
tatttaactt cagcatatgt agaggtaaga atttgaaatg gtagcataaa tcacgaaggg   25320
```

```
attaattcga agtgtaccgt tgtaagtttc tttacctcat gcacgatggt gtgtcatatt    25380
aataaaaggg tactgtgcgg gttcgaaggg atattgcaaa tcctagagca atcacaaagg    25440
tttgaactct gaggtttttg gtataataag aatagtccat gcattcaaaa gagggaagcc    25500
aaggaagaac tagaagtctt tcaagagctc aggctcttat acatccagtt gctcattgaa    25560
ccagcttcct ggaatggagg gtctggggtt gagactaggc cacaagtcta gagtctctag    25620
agagacagtg ttggaacccc atggcccata atacatttcc cattttctca ggcagccaga    25680
ggtcatgaat gtgaggatac tgggaggttg gagcaacgtt cttgggaggc ataaggaaga    25740
gcgaatgctt caagatcccc gcagcccaaa ctactcgcct gctttgcccc ctaatgcatt    25800
tttctctgct gctccgtagc tgtccgacct cttcagatct cttagtccac cctgccgtct    25860
tcctttatgc catgggtccc actgttcttt caactcatcc ccctttccct cagtcccgga    25920
gtagctgcgg ccagcagagg gtagactgag agcaggagag aaggacctgc ctaggaaccc    25980
cttctagaga tactgcatcc tgcctgggag caagttttcc agggcagctt tgagaagtct    26040
tggagaaaca aacctactaa acctgacaga cagtaatact atttgcacaa tgcttttctg    26100
tgggaaaggt agagccttt cactacgtat tgagtacata gagtgtgagg gttgacctgg    26160
aacggctatc ctcctggatg acgtgtgttt tctgaagaac tacatgttcg ttgcaactcc    26220
cacattagaa tatgaagtcc taccgagaga gatacggaga ctagacagat acagatgcat    26280
ttgcatgtga atacacaatc ccacaataca gacgtcaaaa cccataccag ttattccaga    26340
gagatggatt gggcagaagg cagaaggaga atactctgat cgttttcgg ccacgtgtgt    26400 gtgttatctc agtgtttcta agaagcgttt gctactttag atttttatt taaaaaata    26460 gtaataatct attaagtatg agagatgtgc agagaggatt agtgatcgag agccattttt    26520
gctggtggca atcatatggt acttttaatg ggaatattag aaaggcaccg gtaatgacct    26580
tgttgcagca caaaggagag agtgtggggt gcccctgcat gttgtcccac ctcttgtgac    26640
gtgtatcgtt ttggaatttc cagtggcttg atcatgaact actgcaggaa tccagatgct    26700
gtggcagctc cttattgtta tacgagggat cccggtgtca ggtgggagta ctgcaacctg    26760
acgcaatgct cagacgcaga agggactgcc gtcgcgcctc cgactgttac cccggttcca    26820
agcctagagg ctccttccga acaaggtaag gagtctgtgg ccagacatct acacgcttcg    26880
atgctgggat gaaaagccat ggaaattccc actgatgcag ccgccttcaa tggtaaacgg    26940
atgctcgagt gttgcctgag ttctaccatg taggaggaag cctccgtgca ctctctgggg    27000
gagccagcgg agtgatttct ggtgcaacgt ggttgggctt tgtctttagg atgggcacaa    27060
accctccagg gggatcgact tcaaaattca ccttgttgta aaacgggcta cctcagtgtc    27120
ccagccaaaa tttttattgt aacatgctgt caggtgtgtc actctttcca agccagtaag    27180
cttttccggg gatttcttca agtagccagc attcagagca atcttcagca ttgcagattc    27240
tgagaaatgt ggctctggag cctgtcaccc tcgagaaacc taagagggct gcattgattc    27300
catgtggccc tgggtctatg gagcagtaca tgagctccca gtgctctaag gctcttcagc    27360
cctaggcttt gaagggagtg atttctcagt attcttaaac ctctttctga tgacacttgt    27420
acctgtgagg ggtctagaga gaaagagtag tagactccta ctttactaca attcaggatg    27480
cagggcatga gaggattccc tctctcctcc aagggaagaa gcttttggcg tgcacacatc    27540
cctgagaagc aaagtgtctt tgtcttcagt cagatacata ggaccgtttt ctgcccatg    27600 gcccggaagc caaaggcctt ggctttcatg atcaacggtc tagggaaaca tgcaaaattt    27660
ccatgtctgt cccaaactct gcccccgaca gccaattacc acctgcagcc cgcattgcca    27720
```

```
aatgcggtgc cgtttgcatg aagattcagt agagtttcct agaaaggtgc tacctcgtga   27780
gctcactttc caatgaggaa tctgatctgt tgtgtttctc taaggtgtca ggtgaaatat   27840
ttccaagaac ttactacagt tctagaatgg gaggaatctg ttgctttggt gtttgtttgt   27900
tggtcggttt tctcacatcc atctgcctat ggataaggaa aagagaacgg tcgtaattct   27960
catagactcc tttctggttg tgtcacaaat ggcttcacat gtttctctat gctcagagat   28020
actcagcttg atttcccgtg ttttcatttc agcaccgact gagcaaaggc ctggggtgca   28080
ggagtgctac catggtaatg acagagtta tcgaggcaca tactccacca ctgtcacagg    28140
aagaacctgc caagcttggt catctatgac accacactcg catagtcgga ccccagaata   28200
ctacccaaat gcgtatgtct ttgttcttta ccataagaga agaaagggcc aagtgaagtt   28260
tctgttacaa gagatgtgtc tcaagctgag ttctccgaac tcaacttgtg acagatgcag   28320
atggcgtagc aaaatgtctc aggatgattg ccttggagct aagggtctga gagaagggaa   28380
atgttaagct ccctctcctt cctcctagtt ctattgagca aagggaaat ctggaggtga    28440 ggagatcaca ttatgaagaa agtcagaatg acaaaggacc agacacttag attacccttc   28500
cacaacacca actaaacgtc aatggagact ttccagttgg aattccgtta ttctggcttc   28560
cacttcctga agggaaggtt gcgtttgcct tttctctctg ggttcaagag gaaagaatag   28620
gtgcttattt atgacaggt gaattgatct gtttctatat ctacgtatat tccgattgtc     28680
agaaaaacac tcgttcctaa gtaccagtgg cctgaaggga tacaggttcc cagcaagaga   28740
agatccaagg aaggaaggca gatgagagtc agcacagaga gggatgctga aaagtaaaag   28800
ggatgggtgg atggagagaa gcccgggtct gaccacccaa tggccaatat tttggccaca   28860
agcgactacc agagacatgg aaaaatggtt tctacatgtg ggacaacaga tggtagagga   28920
cctagagaat tgagagaggg gcaatgatgg gctccactcc gcagatgcct tggctttctt   28980
cctggatacc cttcctgcac tgaatagcaa ggagatggag cccaagcaga ctgtagccat   29040
cttgctgaat ggaggagagg gattggagtt tgggatgact gtggtagctg aaattttct    29100 aggtctgcta gaaataagaa ctggtttgtg gaggaaaaga gctctacaaa tacgcataga   29160
agtctcctcc agtcgttggc ctgacatgac gctgcctgtg cacaggaaat ggttccacga   29220
gaaagtgtgg caaagaacat ttactgagaa acagcaagta caagagcaca ggaagctcaa   29280
taaagaagag agagatcaca tagcactctg ggatactgga gttcttccca gctagaccag   29340
agagtcctca cggagcacat tgccaattca gtggagaccc cagaacagcc gtaatttaaa   29400
ggtacactta gtatattact agaataaagt cagctgcaga caacccctg cacagctgga    29460 aagcaagtgt ccaagcatca aatcggtttc caatcaatga agtgcctgtg agaggaaatc   29520
tcaactctct ttagaagtaa acaacaaagt cgattgcctc agctatgcgg tatccgcaga   29580
gtgagtccta aatttaaaat ctgactacat gtagaaaagc gtttcgtgtg acccatgacc   29640
aggaaataaa tcgggtaata caaacaggct caggaatgag agaaatgatt agaattgcgt   29700
gaaaatttga catatcagta tgataactga tttcaaatat ttaaaaaaac aacatgcaag   29760
aaagcagata tcatatcaag agaaattaac agtacagaat agccaaatta aattaaagag   29820
ctagtataaa aaagtatgt cttaattgaa aaaaattact gtatggccgg ctgatcaatt     29880
tagacgtttc agaggaaaac attcccaac acacaattct agagaaccta cagaatgagc     29940
tacacacaca cacacacaca cacacacaaa ctgaaaacac acccatactc acacacacgc   30000
agaaactcac aagttctaac acacacagac acgcgcaccc ctgaagaaac agtgaaatat   30060
```

```
aaaattaagc gagcctcaca gacatgtagg aaaatatgaa aagatttcct gcatgtggga    30120
agcaagtcac agtaaagagc aagggagttt ggaatagaaa caaataccgg aatcaaggat    30180
ggctgataac ttttcaatta cgaagaacat taaaaaaaat cacagaatcg tgaaactcaa    30240
gggatcacat agggaatttc ggaaaaaaaa cccaacctgt atgatgtact tttgtacatc    30300
acagttcgaa ggtaacaagg caaagatata ataagaagaa acctgtcacg agaaactgga    30360
ggaaaaagag ctgtgtcttc ctacaagtac actgatacaa attgccaatg tgttcacctc    30420
agaaacactg gaagccagat accagggaat attgttaaaa tgataatcag gaacaaaaag    30480
agatcaaccg ggaatgctga atccagcaat aaaatgcctt gaagatcatc catgtcggat    30540
aaatgcatat tgtgcactgc cccaaagaaa gaaaccggaa actgtaagaa ttggaaatca    30600
gcaggcttat gtaacaagag aggtgacccg aaggaattag gtagaagaag aattgaacaa    30660
gaaaggaact ttctgcagcc cacgtaatga agaatccagc aattggcaaa tgtagataga    30720
tgtaaatgca aaatattttc ttgatcaaat ttctatatct ttgtaaatga gagttgacta    30780
cttgaaacaa aatgatagca agatatttaa cttcagcata tgtagaggta agaatttgaa    30840
atggtagcat aaatcacgaa gggattaatt cgaagtgtac cgttgtaagt ttctttacct    30900
catgcacgat ggtgtgtcat attaataaaa gggtactgtg cgggttcgaa gggatattgc    30960
aaatcctaga gcaatcacaa aggtttgaac tctgaggttt ttggtataat aagaatagtc    31020
catgcattca aaagagggaa gccaaggaag aactagaagt cttcaagag ctcaggctct    31080 tatacatcca gttgctcatt gaaccagctt cctggaatgg agggtctggg gttgagacta    31140
ggccacaagt ctagagtctc tagagagaca gtgttggaac cccatggccc ataatacatt    31200
tcccattttc tcaggcagcc agaggtcatg aatgtgagga tactgggagg ttggagcaac    31260
gttcttggga ggcataagga agagcgaatg cttcaagatc cccgcagccc aaactactcg    31320
cctgctttgc cccctaatgc attttttctct gctgctccgt agctgtccga cctcttcaga    31380
tctcttagtc caccctgccg tcttccttta tgccatgggt cccactgttc tttcaactca    31440 tcccccttc cctcagtccc ggagtagctg cggccagcag agggtagact gagagcagga    31500
gagaaggacc tgcctaggaa cccccttctag agatactgca tcctgcctgg gagcaagttt    31560
tccagggcag ctttgagaag tcttggagaa acaaacctac taaacctgac agacagtaat    31620
actatttgca caatgctttt ctgtgggaaa ggtagagcct tttcactacg tattgagtac    31680
atagagtgtg agggttgacc tggaacggct atcctcctgg atgacgtgtg ttttctgaag    31740
aactacatgt tcgttgcaac tcccacatta gaatatgaag tcctaccgag agagatacgg    31800
agactagaca gatacagatg catttgcatg tgaatacaca atcccacaat acagacgtca    31860
aaacccatac cagttattcc agagagatgg attgggtagg aggcagaagg agaatactct    31920
gatcgttttt cggccacgtg tgtgtgttat ctcagtgttt ctaagaagcg tttgctactt    31980
tagatttttt atttaaaaaa aatagtaata atctattaag tatgagagat gtgcagagag    32040
gattagtgat cgagagccat ttttgctggt ggcaatcata tggtactttt aatgggaata    32100
ttagaaaggc accggtaatg accttgttgc agcacaaagg agagagtgtg gggtgcccct    32160
gcatgttgtc ccacctcttg tgacgtgtat cgttttggaa tttccagtgg cttgatcatg    32220
aactactgca ggaatccaga tgctgtggca gctccttatt gttatacgag ggatcccggt    32280
gtcaggtggg agtactgcaa cctgacgcaa tgctcagacg cagaagggac tgccgtcgcg    32340
cctccgactt ttacccggt tccaagccta gaggctcctt ccgaacaagg taaggagtct    32400
gtggccagac atctacacgc ttcgatgctg ggatgaaaag ccatggaaat tcccactgat    32460
```

```
gcagccgcct tcaatggtaa acggatgctc gagtgttgcc ggagttctgc catgttgggg   32520
gaagcctccg tgtactctct gggggagcca gcggagtgat ttctggtgca acttgggtgg   32580
gctttgtctt tagaatgggc acaaaccttc cagggtgatg ggcttcacaa ctcacctcct   32640
tctaaaatgg gctatctcag tgtcttagcc aaaattttta ttgtaacgtg ctgtcaggtg   32700
tgtgattctt tctgtcgcag taagctttc tggggatttc ttcaagtagc cagcagtcag   32760
tgcaatcttc agcattgcag atttcaaaaa atgtggctct ggagcctgtc atcctcgaga   32820
aacctaacag ggctgcatta attccatatg gtcctgggtc tatggagcag tatatgagct   32880
cccaatgctc taaggctctt cagtcctagg ctttgaaggg agtgatttct cagtgttctt   32940
aaacctcttt ctgatggcac ttgtacctgt gaggggtcta gagagaaagg ttagtagact   33000
tctcctttac tgcaattcag gatgcagggc atgagaagat tccctccctc ctccaaggga   33060
agaaggtttt ggcgtgcaca catccttgag aagcaaagtg tctttgcctt cagtcagata   33120
tataggatcg ttttctgccc catggcctgg aagccagagg ccttggcttt catgatcaac   33180
gatctaggga acatgcaaa atttccatgt cttccctc ctctgccctc gacagccaat   33240
taccacctgc atcctgcatt gccaaatgca gtgccctttg tatgaacatt cagtagagtt   33300
tcatagaaag gtgctacttc gtgagcgcac tttgcagtga aaggagtct gttctgttct   33360 gtttttctaa ggatttcagg tgaaatattt cctagaactt actacagttc tagattggta   33420
ggaatctgta ggtttgctgt atgttttttg gttggttttc tcccatccat ctgcctacag   33480
gtaagggaaa gataacgttc gtaattctca tagactcctt tctggttgtg tcataaatgg   33540
cttcacatat ttcgttattc tcagagatac tcagtttatt tcttgtgttt tcatttcagc   33600
accgactgag cagaggcctg gggtgcagga gtgctaccac ggtaatggac agagttatcg   33660
aggcacatac tccaccactg tcactggaag aacctgccaa gcttggtcat ctatgacacc   33720
acactcgcat agtcggaccc cagaatacta cccaaatgcg tatgtctttg ttctttacca   33780
taagagaaga aagggccaag tgaagtttct gttacaagag atgtgtctca agctgagttc   33840
tccgaactca acttgtgaca gatgcagatg gcgtagcaaa atgtctcagg atgattgcct   33900
tggagctaag ggtctgagag aagggaaatg ttaagctccc tctccttcct cctagttcta   33960
ttgagcagaa gggaaatctg gaggtgagga gatcacatta tgaagaaagt cagaatgaca   34020
aaggaccaga cacttagatt acccttccac aacaccaact aaacgtcaat ggagactttc   34080
cagttggaat tccgttattc tggcttccac ttcctgaagg gaaggttgcg tttgccttt   34140 ctctctgggt tcaagaggaa agaataggtg cttatttatg gacaggtgaa ttgatctgtt   34200
tctatatcta cgtatattcc gattgtcaga aaaacactcg ttcctaagta ccagtggcct   34260
gaagggatac aggttcccag caagagaaga tccaaggaag gaaggcagat gagagccagc   34320
acagagaggg atgctgaaaa gtaaaaggga tgggtggatg gagagaagcc cgggtctgac   34380
cacccaatgg ccaatatttt ggccacaagc gactaccaga gacatggaaa aatgttttct   34440
acatgtggga caacagatgg tagaggacct agagaattga gagaggggca atgatgggct   34500
ccactccgca gatgccttgg cttctcttcct ggatacccct cctgcactga atagcaagga   34560
gatggagccc aagcagactg tagccatctt gctgaatgga ggagaggat tggagtttgg   34620 gatgactgtg gtagctgaaa ttttttctagg tctgctagaa ataagaactg gtttgtggag   34680
gaaaagagct ctacaaatac gcatagaagt ctcctccagt cgttggcctg acatgacgct   34740
gcctgtgcac aggaaatggt tccacgagaa agtgtggcaa agaacattta ctgagaaaca   34800
```

```
gcaagtacaa gagcacagga agctcaataa agaagagaga gatcacatag cactctggga  34860
tactggagtt cttcccagct agaccagaga gtcctcacgg agcacattgc caattcagtg  34920 gagacccag aacagccgta atttaaaggt acacttagta tattactaga ataaagtcag   34980
ctgcagacaa ccccttgcac agctggaaag caagtgtcca agcatcaaat cggtttccaa  35040
tcaatgaagt gcctgtggga ggaaatctca actctcttta gaagtaaaca acaaagtcga  35100
ttgcctcagc tatgcggtat ccgcagagtg agtcctaaat ttaaaatctg actacatgta  35160
gaaaagcgtt tcgtgtgacc catgaccagg aaataaatcg ggtaatacaa acaggctcag  35220
gaatgagaga aatgattaga attgcgtgaa aatttgacat atcagtatga taactgattt  35280
caaatattta aaaaacaac atgcaagaaa gcagatatca tatcaagaga aattaacagt   35340
acagaatagc caaattaaat taagagcta gtataaaaaa agtatgtctt aattgaaaaa   35400
aattactgta tggccggctg atcaaattag acgtttcaga ggaaaacatt acccaacaca  35460
caattctaga gaacctacag aatgagctac acacacacac acacacacac acacacacac  35520
tgaaaacaca cccatactca cacacacgca gaaactcaca agttctaaca cacacagaca  35580
cgcgcacccc tgaagaaaca gtgaaatata aaattaagcg agcctcacag acatgtagga  35640
aaatatgaaa agatttcctg catgtgggaa gcaagtcaca gtaaagagca agggagtttg  35700
gaatagaaac aaataccgga atcaaggatg gctgataact tttcaattac gaagaacatt  35760
aaaaaaaatc acagaatcgt gaaactcaag ggatcatata gggaatttcg gaaaaaaaac  35820
ccaacctgta tgatgtactt ttgtacatca cagttcgaag gtaacaaggc aaagatataa  35880
taagaagaaa cctgtcacga gaaactggag gaaaagagc tgtgtcttcc tacaagtaca  35940
ctgatacaaa ttgccaatgt gttcacctca gaaacactgg aagccagata ccagggaata  36000
ttgttaaaat gataatcagg aacaaaaaga gatcaaccgg gaatgctgaa tccagcaata  36060
aaatgccttg aagatcatcc atgtcggata aatgcatatt gtgcactgcc ccaaagaaag  36120
aaaccggaaa ctgtcagaat tggaaatcag caggcttatg taacaagaga ggtgacccga  36180
aggaattagg tagaagaaga attgaacaag aaaggaactt tctgcagccc acgtaatgaa  36240
gaatccagca attggcaaat gtagatagat gtaaatgcaa aatatttct tgatcaaatt   36300 tctatatctt tgtaaatgag agttgactac ttgaaacaaa atgatagcaa gatatttaac  36360
ttcagcatat gtagaggtaa gaatttgaaa tggtagcata atcacgaagg ggattaattc  36420
gaagtgtacc gttgtaagtt tctttacctc atgcacgatg gtgtgtcata ttaataaaag  36480
ggtactgtgc gggttcgaag ggatattgca aatcctagag caatcacaaa ggtttgaact  36540
ctgaggtttt tggtataata agaatagtcc atgcattcaa aagagggaag ccaaggaaga  36600
actagaagtc tttcaagagc tcaggctctt atacatccag ttgctcattg aaccagcttc  36660
ctggaatgga gggtctgggg ttgagactag gccacaagtc tagagtctct agagagacag  36720
tgttggaacc ccatggccca taatacattt cccatttct caggcagcca gaggtcatga   36780
atgtgaggat actgggaggt tggagcaacg ttcttgggag gcataaggaa gagcgaatgc  36840
ttcaagatcc ccgcagccca aactactcgc ctgctttgcc ccctaatgca ttttctctg   36900 ctgctccgta gctgtccgac ctcttcagat ctcttagtcc accctgccgt cttcctttat  36960
gccatgggtc ccattgttct ttcaactcat ccccctttcc ctcagtcccg gagtagctgc  37020
ggccagcaga gggtagactg agagcaggag agaaggacct gcctaggaac ccttctaga   37080 gatactgcat cctgcctggg agcaagtttt ccagggcagc tttgagaagt cttggagaaa  37140
caaacctact aaacctgaca gacagtaata ctatttgcac aatgcttttc tgtgggaaag  37200
```

```
gtagagcctt ttcactacgt attgagtaca tagagtgtga gggttgacct ggaacggcta   37260
tcctcctgga tgacgtgcgt tttctgaaga actacatgtt cgttgcaact cccacattag   37320
aatatgaagt cctaccgaga gagatacgga gactagacag atacagatgc atttgcatgt   37380
gaatacacaa tcccacaata cagacgtcaa aacccatacc agttattcca gagagatgga   37440
ttgggcagaa ggcagaagga gaatactctg atcgtttttc ggccacgtgt gtgtgttatc   37500
tcagtgtttc taagaagcgt ttgctacttt agattttta tttaaaaaaa atagtaataa   37560
tctattaagt atgagagatg tgcagagagg attagtgatc gagagccatt tttgctggtg   37620
gcaatcatat ggtactttta atgggaatat tagaaaggca ccggtaatga ccttgttgca   37680
gcacaaagga gagagtgtgg ggtgcccctg catgttgtcc cacctcttgt gacgtgtatc   37740
gttttggaat ttccagtggc ttgatcatga actactgcag gaatccagat gctgtggcag   37800
ctccttattg ttatacgagg gatcccggtg tcaggtggga gtactgcaac ctgacgcaat   37860
gctcagacgc agaagggact gccgtcgcgc ctccgactgt taccccggtt ccaagcctag   37920
aggctccttc cgaacaaggt aaggagtctg tggccagaca tctacacgct tcgatgctgg   37980
gatgaaaagc catggaaatt cccactgatg cagccgcctt caatggtaaa cggatgctcg   38040
agtgttgcct gagttctacc atgtaggagg aagcctccgt gcactctctg ggggagccag   38100
cggagtgatt tctggtgcaa cgtggttggg ctttgtcttt aggatgggca caaaccctcc   38160 aggggatcg acttcaaaat tcaccttgtt gtaaaacggg ctacctcagt gtcccagcca   38220
aaatttttat tgtaacatgc tgtcaggtgt gtcactcttt ccaagccagt aagcttttcc   38280
ggggatttct tcaagtagcc agcattcaga gcaatcttca gcattgcaga ttctgagaaa   38340
tgtggctctg gagcctgtca ccctcgagaa acctaagagg gctgcattga ttccatgtgg   38400
ccctgggtct atggagcagt acatgagctc ccagtgctct aaggctcttc agccctaggc   38460
tttgaaggga gtgatttctc agtattctta aacctctttc tgatgacact tgtacctgtg   38520
aggggtctag agagaaagag tagtagactc ctactttact acaattcagg atgcagggca   38580
tgagaggatt ccctctctcc tccaagggaa gaagcttttg gcgtgcacac atccctgaga   38640
agcaaagtgt ctttgtcttc agtcagatac ataggaccgt tttctgcccc atggcccgga   38700
agccaaaggc cttggctttc atgatcaacg gtctagggaa acatgcaaaa tttccatgtc   38760
tgtcccaaac tctgcccccg acagccaatt accacctgca gcccgcattg ccaaatgcgg   38820
tgccgtttgc atgaagattc agtagagttt cctagaaagg tgctacctcg tgagctcact   38880
ttccaatgag gaatctgatc tgttgtgttt ctctaaggtg tcaggtgaaa tatttccaag   38940
aacttactac agttctagaa tgggaggaat ctgttgcttt ggtgtttgtt tgttggtcgg   39000
ttttctcaca tccatctgcc tatggataag gaaaagagaa cggtcgtaat tctcatagac   39060
tcctttctgg ttgtgtcaca aatggcttca catgtttctc tatgctcaga gatactcagc   39120
ttgatttccc gtgttttcat ttcagcaccg actgagcaaa ggcctggggt gcaggagtgc   39180
taccatggta atggacagag ttatcgaggc acatactcca ccactgtcac aggaagaacc   39240
tgccaagctt ggtcatctat gacaccacac tcgcatagtc ggaccccaga atactaccca   39300
aatgcgtatg tctttgttct ttaccataag agaagaaagg gccaagtgaa gtttctgtta   39360
caagagatgt gtctcaagct gagttctccg aactcaactt gtgacagatg cagatggcgt   39420
agcaaaatgt ctcaggatga ttgccttgga gctaagggtc tgagagaagg gaatgttaa   39480 gctccctctc cttcctccta gttctattga gcagaaggga aatctggagg tgaggagatc   39540
```

```
acattatgaa gaaagtcaga atgacaaagg accagacact tagattaccc ttccacaaca    39600
ccaactaaac gtcaatggag actttccagt tggaattccg ttattctggc ttccacttcc    39660
tgaagggaag gttgcgtttg cctttctct ctgggttcaa gaggaaagaa taggtgctta    39720
tttatggaca ggtgaattga tctgttcta tatctacgta tattccgatt gtcagaaaaa    39780
cactcgttcc taagtaccag tggcctgaag ggatacaggt tcccagcaag agaagatcca    39840
aggaaggaag gcagatgaga gtcagcacag agagggatgc tgaaaagtaa aagggatggg    39900
tggatggaga gaagcccggg tctgaccacc caatggccaa tattttggcc acaagcgact    39960
accagagaca tggaaaaatg gtttctacat gtgggacaac agatggtaga ggacctagag    40020
aattgagaga ggggcaatga tgggctccac tccgcagatg ccttggcttt cttcctggat    40080
acccttcctg cactgaatag caaggagatg gagcccaagc agactgtagc catcttgctg    40140
aatggaggag agggattgga gtttgggatg actgtggtag ctgaaatttt tctaggtctg    40200
ctagaaataa gaactggttt gtggaggaaa agagctctac aaatacgcat agaagtctcc    40260
tccagtcgtt ggcctgacat gacgctgcct gtgcacagga aatggttcca cgagaaagtg    40320
tggcaaagaa catttactga gaaacagcaa gtacaagagc acaggaagct caataaagaa    40380
gagagagatc acatagcact ctgggatact ggagttcttc ccagctagac cagagagtcc    40440
tcacggagca cattgccaat tcagtggaga ccccagaaca gccgtaattt aaaggtacac    40500
ttagtatatt actagaataa agtcagctgc agacaacccc ttgcacagct ggaaagcaag    40560
tgtccaagca tcaaatcggt ttccaatcaa tgaagtgcct gtgagaggaa atctcaactc    40620
tctttagaag taaacaacaa agtcgattgc ctcagctatg cggtatccgc agagtgagtc    40680
ctaaatttaa aatctgacta catgtagaaa agcgtttcgt gtgacccatg accaggaaat    40740
aaatcgggta atacaaacag gctcaggaat gagagaaatg attagaattg cgtgaaaatt    40800
tgaaatatca gtatgataac tgatttcaaa tatttaaaaa acaacatgc aagaaagcag    40860 atatcatatc aagagaaatt aacagtacag aatagccaaa ttaaattaaa gagctagtat    40920 aaaaaagta tgtcttaatt gaaaaaaatt actgtatggc cggctgatca atttagacgt    40980
ttcagaggaa aacattaccc aacacacaat tctagagaac ctacagaatg agctacacac    41040
acacacacac acacacacac aaactgaaaa cacacccata ctcacacaca cgcagaaact    41100
cacaagttct aacacacaca gacacgcgca cccctgaaga aacagtgaaa tataaaatta    41160
agcgagcctc acagacatgt aggaaaatat gaaaagattt cctgcatgtg ggaagcaagt    41220
cacagtaaag agcaagggag tttggaatag aaacaaatac cagaatcaag gatggctgat    41280
aacttttcaa ttacgaagaa cattaaaaaa aatcacagaa tcgtgaaact caagggatca    41340
catagggaat ttcggaaaaa aaacccaacc tgtatgatgt acttttgtac atcacagttc    41400
gaaggtaaca aggcaaagat ataataagaa gaaacctgtc acgagaaact ggaggaaaaa    41460
gagctgtgtc ttcctacaag tacactgata caaattgcca atgtgttcac ctcgaaaaca    41520
ctggaagcca gataccaggg aatattgtta aaatgataat caggaacaaa aagagatcaa    41580
ccgggaatgc tgaatccagc aataaaatgc cttgaagatc atccatgtcg gataaatgca    41640
tattgtgcac tgccccaaag aaagaaaccg gaaactgtaa gaattggaaa tcagcaggct    41700
tatgtaacaa gagaggtgac ccgaaggaat taggtagaag aagaattgaa caagaaagga    41760
actttctgca gcccacgtaa tgaagaatcc agcaattggc aaatgtagat agatgtaaat    41820 gcaaatatt ttcttgatca aatttctata tctttgtaaa tgagagttga ctacttgaaa    41880
caaaatgata gcaagatatt taacttcagc atatgtagag gtaagaattt gaaatggtag    41940
```

```
cataaatcac gaagggatta attcgaagtg taccgttgta agtttcttta cctcatgcac   42000
gatggtgtgt catattaata aaagggtact gtgcgggttc gaagggatat tgcaaatcct   42060
agagcaatca caaaggtttg aactctgagg tttttggtat aataagaata gtccatgcat   42120
tcaaaagagg gaagccaagg aagaactaga agtctttcaa gagctcaggc tcttatacat   42180
ccagttgctc attgaaccag cttcctggaa tggagggtct ggggttgaga ctaggccaca   42240
agtctagagt ctctagagag acagtgttgg aaccccatgg cccataatac atttcccatt   42300
ttctcaggca gccagaggtc atgaatgtga ggatactggg aggttggagc aacgttcttg   42360
ggaggcataa ggaagagcga atgcttcaag atccccgcag cccaaactac tcgcctgctt   42420
tgccccctaa tgcattttc tctgctgctc cgtagctgtc cgacctcttc agatctctta   42480
gtccaccctg ccgtcttcct ttatgccatg ggtcccactg ttctttcaac tcatccccct   42540
ttccctcagt cccggagtag ctgcggccag cagagggtag actgagagca ggagagaagg   42600
acctgcctag gaaccccttc tagagatact gcatcctgcc tgggagcaag ttttccaggg   42660
cagctttgag aagtcttgga gaaacaaacc tactaaacct gacagacagt aatactattt   42720
gcacaatgct tttctgtggg aaaggtagag ccttttcact acgtattgag tacatagagt   42780
gtgagggttg acctggaacg gctatcctcc tggatgacgt gtgttttctg aagaactaca   42840
tgttcgttgc aactcccaca ttagaatatg aagtcctacc gagagagata cggagactag   42900
acagatacag atgcatttgc atgtgaatac acaatcccac aatacagacg tcaaaaccca   42960
taccagttat tccagagaga tggattgggc agaaggcaga aggagaatac tctgatcgtt   43020
tttcggccac gtgtgtgtgt tatctcagtg tttctaagaa gcgtttgcta ctttagattt   43080
tttatttaaa aaaatagta ataatctatt aagtatgaga gatgtgcaga gaggattagt   43140
gatcgagagc cattttgct ggtggcaatc atatggtact tttaatggga atattagaaa   43200
ggcaccggta atgaccttgt tgcagcacaa aggagagagt gtggggtgcc cctgcatgtt   43260
gtcccacctc ttgtgacgtg tatcgttttg gaatttccag tggcttgatc atgaactact   43320
gcaggaatcc agatgctgtg gcagctcctt attgttatac gagggatccc ggtgtcaggt   43380
gggagtactg caacctgacg caatgctcag acgcagaagg gactgccgtc gcgcctccga   43440
ctgttacccc ggttccaagc ctagaggctc cttccgaaca aggtaaggag tctgtggcca   43500
gacatctaca cgcttcgatg ctgggatgaa aagccatgga aattcccact gatgcagccg   43560
ccttcaatgg taaacggatg ctcgagtgtt gcctgagttc taccatgtag gaggaagcct   43620
ccgtgcactc tctgggggag ccagcggagt gatttctggt gcaacgtggt tgggctttgt   43680
ctttaggatg ggcacaaacc ctccaggggg atcgacttca aaattcacct tgttgtaaaa   43740
cgggctacct cagtgtccca gccaaaattt ttattgtaac atgctgtcag gtgtgtcact   43800
ctttccaagc cagtaagctt ttccggggat ttcttcaagt agccagcatt cagagcaatc   43860
ttcagcattg cagattctga gaaatgtggc tctggagcct gtcaccctcg agaaacctaa   43920
gagggctgca ttgattccat gtggccctgg gtctatggag cagtacatga gctcccagtg   43980
ctctaaggct cttcagccct aggctttgaa gggagtgatt tctcagtatt cttaaacctc   44040
tttctgatga cacttgtacc tgtgagggg ctagagagaa agagtagtag actcctactt   44100
tactacaatt caggatgcag ggcatgagag gattccctct ctcctccaag ggaagaagct   44160
tttggcgtgc acacatccct gagaagcaaa gtgtctttgt cttcagtcag atacatagga   44220
ccgttttctg ccccatggcc cggaagccaa aggccttggc tttcatgatc aacggtctag   44280
```

```
ggaaacatgc aaaatttcca tgtctgtccc aaactcttcc cccgacagcc aattaccacc    44340
tgcagcccgc attgccaaat gcggtgccgt ttgcatgaag attcagtaga gtttcctaga    44400
aaggtgctac ctcgtgagct cactttccaa tgaggaatct gatctgttgt gtttctctaa    44460
ggtgtcaggt gaaatatttc caagaactta ctacagttct agaatgggag gaatctgttg    44520
ctttggtgtt tgtttgttgg tcggttttct cacatccatc tgcctatgga taaggaaaag    44580
agaacggtcg taattctcat agactccttt ctggttgtgt cacaaatggc ttcacatgtt    44640
tctctatgct cagagatact cagcttgatt tcccgtgttt tcatttcagc accgactgag    44700
caaaggcctg gggtgcagga gtgctaccat ggtaatggac agagttatcg aggcacatac    44760
tccaccactg tcacaggaag aacctgccaa gcttggtcat ctatgacacc acactcgcat    44820
agtcggaccc cagaatacta cccaaatgcg tatgtctttg ttctttacca taagagaaga    44880
aagggccaag tgaagtttct gttacaagag atgtgtctca agctgagttc tccgaactca    44940
acttgtgaca gatgcagatg gcgtagcaaa atgtctcagg atgattgcct tggagctaag    45000
ggtctgagag aagggaaatg ttaagctccc tctccttcct cctagttcta ttgagcagaa    45060
gggaaatctg gaggtgagaa gatcacatta tgaagaaagt cagaatgaca aaggaccaga    45120
cacttagatt acccttccac aacaccaact aaacgtcaat ggagactttc cagttggaat    45180
tccgttattc tggcttccac ttcctgaagg gaaggttgcg tttgcctttt ctctctgggt    45240
tcaagaggaa agaataggtg cttatttatg gacaggtgaa ttgatctgtt tctatatcta    45300
cgtatattcc gattgtcaga aaaacactcg ttcctaagta ccagtggcct gaagggatac    45360
aggttcccag caagagaaga tccaaggaag aaggcagat gagagtcagc acagagaggg    45420
atgctgaaaa gtaaaaggga tgggtggatg gagagaagcc cgggtctgac cacccaatgg    45480
ccaatatttt ggccacaagc gactaccaga gacatgaaaa atggtttct acatgtggga    45540
caacagatgg tagaggacct agagaattga gagaggggca atgatgggct ccactccgca    45600
gatgcccttgg ctttcttcct ggatacccctt cctgcactga atagcaagga gatggagccc    45660
aagcagactg tagccatctt gctgaatgga ggagagggat tggagtttgg gatgactgtg    45720
gtagctgaaa ttttctagg tctgctagaa ataagaactg gtttgtgtgg aggaaaagag    45780
ctctacaaat acgcatagaa gtctcctcca gtcgttggcc tgacatgacg ctgcctgtgc    45840
acaggaaatg gttccacgag aaagtgtggc aaagaacatt tactgagaaa cagcaagtac    45900
aagagcacag gaagctcaat aaagaagaga gagatcacat agcactctgg gatactggag    45960
ttcttcccag ctagaccaga gagtcctcac ggagcacatt gccaattcag tggagacccc    46020
agaacagccg taatttaaag gtacacttag tatattacta gaataaagtc agctgcagac    46080
aacccccttgc acagctggaa agcaagtgtc caagcatcaa atcggttttcc aatcaatgaa    46140
gtgcctgtga gaggaaatct caactctctt tagaagtaaa caacaaagtc gattgcctca    46200
gctatgcggt atccgcagag tgagtcctaa atttaaaatc tgactacatg tagaaaagcg    46260
tttcgtgtga cccatgacca ggaaataaat cgggtaatac aaacaggctc aggaatgaga    46320
gaaatgatta gaattgcgtg aaatttgac atatcagtat gataactgat ttcaaatatt    46380
taaaaaaaca acatgcaaga aagcagatat catatcaaga gaaattaaca gtacagaata    46440
gccaaattaa attaaagagg tagtataaaa aaagtatgtc ttaattgaaa aaaattactg    46500
tatggccggc tgatcaattt agacgtttca gaggaaaaca ttacccaaca cacaattcta    46560
gagaacctac agaatgagct acacacacac acacacacac acacacaaac tgaaaacaca    46620
cccatactca cacacacgca gaaactcaca agttctaaca cacacagaca cgcgcacccc    46680
```

```
tgaagaaaca gtgaaatata aaattaagcg agcctcacag acatgtagga aaatatgaaa   46740
agatttcctg catgtgggaa gcaagtcaca gtaaagagca agggagtttg aatagaaac    46800 aaataccgga atcaaggatg gctgataact tttcaattac gaagaacatt aaaaaaaatc   46860
acagaatcgt gaaactcaag ggatcacata gggaatttcg gaaaaaaaac ccaacctgta   46920
tgatgtactt ttgtacatca cagttcgaag gtaacaaggc aaagatataa taagaagaaa   46980
cctgtcacga gaaactggag gaaaagagc tgtgtcttcc tacaagtaca ctgatacaaa    47040
ttgccaatgt gttcacctca gaaacactgg aagccagata ccagggaata ttgttaaaat   47100
gataatcagg aacaaaaaga gatcaaccgg gaatgctgaa tccagcaata aaatgccttg   47160
aaggtcatcc atgtcggata aatgcatatt gtgcactgcc ccaaagaaag aaaccggaaa   47220
ctgtaagaat tggaaatcag caggcttatg taacaagaga ggtgacccga aggaattagg   47280
tagaagaaga attgaacaag aaaggaactt tctgcagccc acgtaatgaa gaatccagca   47340
attggcaaat gtagatagat gtaaatgcaa aatattttct tgatcaaatt tctatatctt   47400
tgtaaatgag agttgactac ttgaaacaaa atgatagcaa gatatttaac ttcagcatat   47460
gtagaggtaa gaatttgaaa tggtagcata aatcacgaag ggattaattc gaagtgtacc   47520
gttgtaagtt tctttacctc atgcacgatg gtgtgtcata ttaataaaag ggtactgtgc   47580
gggttcgaag ggatattgca aatcctagag caatcacaaa ggtttgaact ctgaggtttt   47640
tggtataata agaatagtcc atgcattcaa aagagggaag ccaaggaaga actagaagtc   47700
tttcaagagc tcaggctctt atacatccag ttgctcattg aaccagcttc ctggaatgga   47760
gggtctgggg ttgagactag gccacaagtc tagagtctct agagagacag tgttggaacc   47820
ccatggccca taatacattt cccattttct caggcagcca gaggtcatga atgtgaggat   47880
actgggaggt tggagcaacg ttcttgggag gcataaggaa gagcgaatgc ttcaagatcc   47940
ccgcagccca aactactcgc ctgctttgcc ccctaatgca tttttctctg ctgctccgta   48000
gctgtccgac ctcttcagat ctcttagtcc accctgccgt cttcctttat gccatgggtc   48060
ccactgttct ttcaactcat ccccctttcc ctcagtcccg gagtagctgc ggccagcaga   48120
gggtagactg agagcaggag agaaggacct gcctaggaac cccttctaga gatactgcat   48180
cctgcctggg agcaagtttt ccagggcagc tttgagaagt cttggagaaa caaacctact   48240
aaacctgaca gacagtaata ctatttgcac aatgcttttc tgtgggaaag gtagagcctt   48300
ttcactacgt attgagtaca tagagtgtga gggttgacct ggaacggcta tcctcctgga   48360
tgacgtgcgt tttctgaaga actacatgtt cgttgcaact cccacattag aatatgaagt   48420
cctaccgaga gagatacgga gactagacag atacagatgc atttgcatgt gaatacacaa   48480
tcccacaata cagacgtcaa aacccatacc agttattcca gagagatgga ttgggcagaa   48540
ggcagaagga gaatactctg atcgtttttc ggccacgtgt gtgtgttatc tcagtgtttc   48600
taagaagcgt ttgctacttt agattttta tttaaaaaaa atagtaataa tctattaagt     48660
atgagagatg tgcagagagg attagtgatc gagagccatt tttgctggtg gcaatcatat   48720
ggtactttta atgggaatat tagaaaggca ccggtaatga ccttgttgca gcacaaagga   48780
gagagtgtgg ggtgcccctg catgttgtcc cacctcttgt gacgtgtatc gttttggaat   48840
ttccagtggc ttgatcatga actactgcag gaatccagat gctgtggcag ctccttattg   48900
ttatacgagg gatcccggtg tcaggtggga gtactgcaac ctgacgcaat gctcagacgc   48960
agaagggact gccgtcgcgc ctccgactgt taccccggtt ccaagcctag aggctccttc   49020
```

```
cgaacaaggt aaggagtctg tggccagaca tctacacgct tcgatgctgg gatgaaaagc    49080
catggaaatt cccactgatg cagccgcctt caatggtaaa cggatgctcg agtgttgcct    49140
gagttctacc atgtaggagg aagcctccgt gcactctctg ggggagccag cggagtgatt    49200
tctggtgcaa cgtggttggg cttttgtcttt aggatgggca caaaccctcc aggggggatcg   49260 acttcaaaat tcaccttgtt gtaaaacggg ctacctcagt gtcccagcca aaattttat    49320 tgtaacatgc tgtcaggtgt gtcactcttt ccaagccagt aagcttttcc ggggatttct    49380
tcaagtagcc agcattcaga gcaatcttca gcattgcaga ttctgagaaa tgtggctctg    49440
gagcctgtca ccctcgagaa acctaagagg gctgcattga ttccatgtgg ccctgggtct    49500
atggagcagt acatgagctc ccagtgctct aaggctcttc agccctaggc tttgaaggga    49560
gtgatttctc agtattctta aacctctttc tgatgacact tgtacctgtg aggggtctag    49620
agagaaagag tagtagactc ctactttact acaattcagg atgcagggca tgagaggatt    49680
ccctctctcc tccaagggaa gaagcttttg gcgtgcacac atccctgaga agcaaagtgt    49740
ctttgtcttc agtcagatac ataggaccgt tttctgcccc atggcccgga agccaaaggc    49800
cttggctttc atgatcaacg gtctagggaa acatgcaaaa tttccatgtc tgtcccaaac    49860
tctgcccccg acagccaatt accacctgca gcccgcattg ccaaatgcgg tgccgtttgc    49920
atgaagattc agtagagttt cctagaaagg tgctacctcg tgagctcact ttccaatgag    49980
gaatctgatc tgttgtgttt ctctaaggtg tcaggtgaaa tatttccaag aacttactac    50040
agttctagaa tgggaggaat ctgttgcttt ggtgtttgtt tgttggtcgg ttttctcaca    50100
tccatctgcc tatggataag gaaaagagaa cggtcgtaat tctcatagac tccttctgg     50160 ttgtgtcaca aatggcttca catgtttctc tatgctcaga gatactcagc ttgatttccc    50220
gtgttttcat ttcagcaccg actgagcaaa ggcctgggt gcaggagtgc taccatggta     50280
atggacagag ttatcgaggc acatactcca ccactgtcac aggaagaacc tgccaagctt    50340
ggtcatctat gacaccacac tcgcatagtc ggacccaga atactaccca aatgcgtatg     50400
tctttgttct ttaccataag agaagaaagg gccaagtgaa gtttctgtta caagagatgt    50460
gtctcaagct gagttctccg aactcaactt gtgacagatg cagatggcgt agcaaaatgt    50520
ctcaggatga ttgccttgga gctaagggtc tgagagaagg gaaatgttaa gctccctctc    50580
cttcctccta gttctattga gcagaaggga aatctggagg tgaggagatc acattatgaa    50640
gaaagtcaga atgacaaagg accagacact tagattaccc ttccacaaca ccaactaaac    50700
gtcaatggag actttccagt tggaattccg ttattctggc ttccacttcc tgaagggaag    50760
gttgcgtttg cctttctctc tgggttcaa gaggaaagaa taggtgctta tttatggaca     50820
ggtgaattga tctgtttcta tatctacgta tattccgatt gtcagaaaaa cactcgttcc    50880
taagtaccag tggcctgaag ggatacaggt tcccagcaag agaagatcca aggaaggaag    50940
gcagatgaga gtcagcacag agagggatgc tgaaaagtaa aagggatggg tggatggaga    51000
gaagcccggg tctgaccacc caatggccaa tattttggcc acaagcgact accagagaca    51060
tggaaaaatg gtttctacat gtgggacaac agatggtaga ggacctagag aattgagaga    51120
ggggcaatga tgggctccac tccgcagatg ccttggcttt cttcctggat acccttcctg    51180
cactgaatag caaggagatg gagcccaagc agactgtagc catcttgctg aatggaggag    51240
agggattgga gtttgggatg actgtggtag ctgaaatttt tctaggtctg ctagaaataa    51300
gaactggttt gtgtggagga aaagagctct acaaatacgc atagaagtct cctccagtcg    51360
ttggcctgac atgacgctgc ctgtgcacag gaaatggttc cacgagaaag tgtggcaaag    51420
```

```
aacatttact gagaaacagc aagtacaaga gcacaggaag ctcaataaag aagagagaga   51480
tcacatagca ctctgggata ctggagttct tcccagctag accagagagt cctcacggag   51540
cacattgcca attcagtgga gaccccagaa cagccgtaat ttaaaggtac acttagaata   51600
ttactagaat aaagtcagct gcagacaacc ccttgcacag ctggaaagca agtgtccaag   51660
catcaaatcg gtttccaatc aatgaagtgc ctgtgagagg aaatctcaac tctctttaga   51720
agtaaacaac aaagtcgatt gcctcagcta tgcggtatcc gcagagtgag tcctaaattt   51780
aaaatctgac tacatgtaga aaagcgtttc gtgtgaccca tgaccaggaa ataaatcggg   51840
taatacaaac aggctcagga atgagagaaa tgattagaat tgcgtgaaaa tttgacatat   51900
cagtatgata actgatttca aatatttaaa aaaacaacat gcaagaaagc agatatcata   51960
tcaagagaaa ttaacagtac agaatagcca aattaaatta aagagctagt ataaaaaaag   52020
tatgtcttaa ttgaaaaaaa ttactgtatg gccggctgat caaattagac gtttcagagg   52080
aaaacattac ccaacacaca attttagaga acctacagaa tgagctacac acacacacac   52140
acacacacac acacacacaa actgaaaaca cacccatact cacacacacg cagaaactca   52200
caagttctaa cacacacaga cacgcgcacc cctgaagaaa cagtgaaaata taaaattaag   52260 cgagcctcac agacatgtag gaaaatatga aaagatttcc tgcatgtggg aagcaagtca   52320
cagtaaagag caagggagtt tataataaga acaaatacca gaatcaagga tggctgataa   52380
cttttcaatt acgaagaaca ttaaaaaaaa tcacagaatc gtgaaactca agggatcata   52440
tagggaattt cggaaaaaaa acccaacctg tatgatgtac ttttgtacat cacagttcga   52500
aggtaacaag gcaaagatgt aataagaaga aacctgtcac gagaaactgg aggaaaaga    52560 gctgtgtctt cctacaagta cactgataca aattgccaat gtgttcacct cagaaacact   52620
ggaagccaga taccagggaa tattgttaaa atgataatca ggaacaaaaa gagatcaacc   52680
gggaatgctg aatccagcaa taaaatgcct tgaaggtcat ccatgtcgga taatgcata    52740 ttgtgcactg ccccaaagaa agaaaccgga aactgtaaga attggaaatc agcaggctta   52800
tgtaacaaga gaggtgaccc gaaggaatta ggtagaagaa gaattgaaca agaaaggaac   52860
tttctgcagc ccacgtaatg aagaatccag caattggcaa atgtagatag atgtaaatgc   52920
aaaatatttt cttgatcaaa tttctatatc tttgtaaatg agagttgact acttgaaaca   52980
aaatgatagc aagatattta acttcagcat atgtagaggt aagaatttga aatggtagca   53040
taaatcacga agggattaat tcgaagtgta ccgttgtaag tttctttacc tcatgcacga   53100
tggtgtgtca tattaataaa agggtactgt gcgggttcga agggatattg caaatcctag   53160
agcaatcaca aaggtttgaa ctctgaggtt tttggtataa taagaatagt ccatgcattc   53220
aaaagaggga agccaaggaa gaactagaag tcttccaaga gctcaggctc ttatacatcc   53280
agttgctcat tgaaccagct tcctggaatg gagggtctgg ggttgagact aggccacaag   53340
tctagagtct ctagagagac agtgttggaa cccatggcc cataatacat ttcccatttt    53400
ctcaggcagc cagaggtcat gaatgtgagg atactgggag gttggagcaa cgttcttggg   53460
aggcataagg aagagcgaat gcttcaagat ccccgcagcc caaactactc gcctgctttg   53520 cccctaatg cattttctc tgctgctccg tagctgtccg acctcttcag atctcttagt    53580
ccaccctgcc gtcttccttt atgccatggg tcccactgtt cttcaactc atcccccttt    53640 ccctcagtcc cggagtagct gcggccagca gagggtagac tgagagcagg agagaaggac   53700
ctgcctagga acccccttcta gagatactgc atcctgcctg ggagcaagtt ttccagggca   53760
```

```
gctttgagaa gtcttggaga aacaaaccta ctaaacctga cagacagtaa tactatttgc   53820
acaatgcttt tctgtgggaa aggtagagcc ttttcactac gtattgagta catagagtgt   53880
gagggttgac ctggaacggc tatcctcctg gatgacgtgc gttttctgaa gaactacatg   53940
ttcgttgcaa ctcccacatt agaatatgaa gtcctaccga gagagatacg gagactagac   54000
agatacagat gcatttgcat gtgaatacac aatcccacaa tacagacgtc aaaacccata   54060
ccagttattc cagagagatg gattgggcag aaggcagaag gagaatactc tgatcgtttt   54120
tcggccacgt gtgtgtgtta tctcagtgtt tctaagaagc gtttgctact ttagattttt   54180
tatttaaaaa aaatagtaat aatctattaa gtatgagaga tgtgcagaga cgattagtga   54240
tcgagagcca tttttgctgg tggcaatcat atggtacttt taatgggaat attagaaagg   54300
caccggtaat gaccttgttg cagcacaaag gagagagtgt ggggtgcccc tgcatgttgt   54360
cccacctctt gtgacgtgta tcgttttgga atttccagtg gcttgatcat gaactactgc   54420
aggaatccag atgctgtggc agctccttat tgttatacga gggatcccgg tgtcaggtgg   54480
gagtactgca acctgacgca atgctcagac gcagaaggga ctgccgtcgc gcctccgact   54540
gttaccccgg ttccaagcct agaggctcct tccgaacaag gtaaggagtc tgtggccaga   54600
catctacacg cttcgatgct gggatgaaaa gccatggaaa tcccactga tgcagccgcc    54660 ttcaatggta aacggatgct cgagtgttgc ctgagttcta ccatgtagga ggaagcctcc   54720
gtgcactctc tggggagcc agcggagtga tttctggtgc aacgtggttg ggctttgtct    54780
ttaggatggg cacaaaccct ccaggggat cgacttcaaa attcaccttg ttgtaaaacg    54840
ggctacctca gtgtcccagc caaaatttt attgtaacat gctgtcaggt gtgtcactct    54900
ttccaagcca gtaagctttt ccggggattt cttcaagtag ccagcattca gagcaatctt   54960
cagcattgca gattctgaga aatgtggctc tggagcctgt catcctcgag aaacctaaca   55020
gggctgcatt aattccatat ggtcctgggt ctatggagca gtatatgagc tcccaatgct   55080
ctaaggctct tcagtcctag gctttgaagg gagtgatttc tcagtgttct taaacctctt   55140
tctgatggca cttgtacctg tgaggggtct agagagaaag gttagtagac ttctcctta    55200 ctgcaattca ggatgcaggg catgagaaga ttccctccct cctccaaggg aagaaggttt   55260
tggcgtgcac acatccttga gaagcaaagt gtctttgcct tcagtcagat atataggatc   55320
gttttctgcc ccatggcctg gaagccagag gccttggctt tcatgatcaa cgatctaggg   55380
aaacatgcaa aatttccatg tctttcccct cctctgccct cgacagccaa ttaccacctg   55440
catcctgcat tgccaaatgc agtgcccttt gtatgaacat tcagtagagt ttcatagaaa   55500
ggtgctactt cgtgagcgca ctttgcagtg agaaggagtc tgttctgttc tgttttcta    55560 aggatttcag gtgaaatatt tcctagaact tactacagtt ctagattggt aggaatctgt   55620
aggtttgctg tatgtttttt ggttggtttt ctcccatcca tctgcctaca ggtaagggaa   55680
agataacgtt cataattctc atagactcct ttctggttgt gtcataaatg gcttcacata   55740
tttcgttatt ctcagagata ctcagtttat ttcttgtgtt ttcatttcag caccgactga   55800
gcagaggcct ggggtgcagg agtgctacca cggtaatgga cagagttatc gaggcacata   55860
ctccaccact gtcactggaa gaacctgcca agcttggtca tctatgacac cacactcgca   55920
tagtcggacc ccagaatact acccaaatgc gtatgtcttt gttctttacc ataagagaat   55980
aaagggccaa ctgaagtttc tgtgacaaga gacatgcttc aagctgagtt ctccgaactc   56040
aacttgtgtc agattcagat ggtgtagcaa aatgtctcag gatgatttcc ttggagctaa   56100
gggtctgaga gaagagaaat gttaagctgc ctcaccttcc tcctagtttt gtggagcaga   56160
```

```
agggaaatga ggaggcgagg agatcacctt atgaagaaag tcagaatgac gaaccaccaa   56220
acacttagat taccccttgcc caacacccac taagcgtcaa tgaagacttt ccagttggaa   56280
ttccgttatt ctgacttcca attcctgaag ggaagattgt gtttgccttt tctgtctggg   56340
ctcatgagga aagtttatgt gcttactat ggacaggtga attgatctgt ttctatttct   56400
acctgtattc caatagggag aaaatctctt ggtcctaagt accagtggcc tgaaaggata   56460
gaggttccca gcaagagaag atccaaggaa ggaaggcaga tgagagtcag cacagagagg   56520
gatgctgaaa agtaaaaggg atgggtagat ggatagaagc cctggtctga ccaccccatg   56580
gccaatcatt tggccataat caacaaccaa agacatggaa aaatggtttc tacatgtggg   56640
acaacagatg gtagaggacc tagagaattg agagagggcc aatgatgagc tcaactccat   56700
agatgccttg gctttcttcc tggatacccct tcctgcactg aatagcaagg agatggagct   56760
caagcagcct gtagccatct agctgagcag aggagaggga ttggagtttg ggatgactct   56820
ggtattttct aggtccgcta caaataagaa ctggtttgtg gaggaaagga gctctacaaa   56880
tacgcataga agtctcctcc agtagttggc ctcacatgac actgcatgtg cacagaaaat   56940
ggttctacag aaagtgtggc aaagaacatt tactgagaaa cagcaactac aagagaacag   57000
caagctcaat taagaagata gagatcacat agcactctgt gttattggag ttcttaccag   57060
ctagatgaga gagtgctcac ggaacacatt gccaattcag tggagacccc agaacagcca   57120
taatttcaaa gtacaattag tatattacta gaataaaggc agctgcagac aacccccttgc   57180 acagctgaaa agcaagtgtc caagcatcaa atgggttttcc aatcaatgaa gtgcctgtga   57240
gaggaaatct caactctctt cagaagtaaa caacaaagtc aattgcctca gctatgcggt   57300
atccccagag tgagtcctaa attaaaaatt tgactacgtg tagaaaagaa tttcgtgtga   57360
tccatgacca gaaaataaat caggcaatac aaacaggctc agaaatgaca tcgataatta   57420
gaattgcatg aaaatttgac atatcagtat gataactgat ttcagatatt taaaaaaagt   57480
gcaacaaagc aggtatcata tcaagacaaa ttaatagtat agaatagcca aatcaaatta   57540
aagaactatt atacaaaaag tatgtcttaa atgaagaaat tactgtatgt ccgcctgaaa   57600
aatttagatg tttcagaaga aaaaattaac caaaacaat tctgcagaac ctacagaatg   57660
agccacacac acacacattc aaaacacacc catacacaca cacatgcaaa aactcacaag   57720
ttctaacaca cacacaaaca cacacacaca tgcacatccc taaagaaata gggaaatata   57780
aaattaaccg accctcagag acatgcagga aaatataaga agatttcctg catgtgggaa   57840
gcaagtcaca gtaaagagca agggagtttg gagtagatac aaataccgga atcacgcgatg   57900 gctgataact tttcaattat gaagaacgtt agaaaaatca cagattcatg aaactaaagg   57960
gatcaaatag gaaatttcga gaaaaaaaac tacatgatgc acttctctac atcacagttc   58020
aaaggtaaca aggcaaggat ataagaagaa gaaacatctc acgagaaact ggagaaaaaa   58080
gagctgtgtc ttcctagagt acagtgatac aaattgctaa tgcgttcacc tcagaaacac   58140
tggaagccag ataccaggga atattattaa aatgataatg aggaacaaga agagatcaac   58200
cgagaatgct gaatccagca ataaaatgcc ttgaagatca tccatgttgg ataaatgcat   58260
attgtgcact gcccaaaaca aagaaactgg aaagtgtaag actttggaat cagcaggctt   58320
atgtagcaac agaggtgacc cgaaagaatt aggtataaga agaatagaag aattgcatga   58380
aaatttgaca tatgactaag ataactattt caaatatttta aaaaagatg aatatgtaat   58440 aaaacagata aaatatcaaa agaaagtaac agtattgact agccaaatca aattaaagac   58500
```

```
ttagtgtaaa aagctatgtc ttaaaagaaa aaattactgg atggctgcct gatcaattta  58560
gacatttctg aataggaaac taaccaaaaa tcaattctac agaaccaact acacacatat  58620
atacacatac aacacaccca tacacaccca cgcaaaaact cacaagttca cacacacaca  58680
cacacacaca caaccctcaa gaaatagtga aatagaaaac caaccgaacc tcacagacat  58740
gttgcaaaat aggaaaagat ttcctgcata tgggaagcaa gtcacagaaa agagaacggg  58800
agattggaaa cagaaacaaa taccggaatc aaggatggcc gaaaacttt cattgatcaa  58860 gaatattaac aaaatcgcaa aaacacgaaa ttcaatgcat caaataggcg tttcgaaaaa  58920
aagaaaaaat ctggtatgat gcacttttgt acttcacatt ttcacggtaa aagacaaag  58980 atataataac aagaaacttc ttatgagaaa ctggggaaaa acaagctgtt tcttgctaga  59040
agaacagtga tacaaattgc taatgcattc tcgtcaaaaa cactggaagc cagataccgg  59100
gaatgttatt aatgtggtaa acaggaacaa gaagagatca accaagaatg ctaaatccag  59160
caataaaatg ccttgaagat catccatgct gcataaatgt atgttgtgca ctgccccaaa  59220
caaagaaacc ggaaactgta agaatttgga atcagcaggc tgatgtaaca agagaggtga  59280
cccaaaggaa ttaggtagaa gaagaatagt acaagaaggg aactttctgc agcccatgta  59340
atgaagaacc cagcaattgg caaatgtaga tgtaaatgca aaatattttc ttgaccaaat  59400
ttctatatat ttttaaatga gcgttgacta ctggaaacaa aatgatagca atatatttaa  59460
ttttagcata tgtagaggta agaatttgaa caagtagcgt aaatcatgta gggaataatt  59520
agaagtgtac cattgtaagt ttcttacctc atgcacaatg gtatgtaata ttaataaaat  59580
gttactgtgt gggttcaagg agatattgca aatcctagag caatcacaaa gttttgaact  59640
ctgaggtata ttgtataata agaatattcc atgtattcaa aagagagaag ccaaggaaga  59700
aagaaatttg tcacgagttt gggctcttag tacatcctgt agctcattga accagcttcc  59760
tggaatggag ggtctgggat tgacactagg ccacatgtat agagtctcta gagagacagt  59820
gtttcatccc catggcccgt aatacatttc ccattttctc aggcagccac aggtcatgaa  59880
tgtgaggata gagagaggtt ggagcaacgt tcttgggagg cataaggaag agcaaatgct  59940
tcaagatccc cgcagcccaa actcctacct gctttgcccc ctaatgcagt gttcctccgt  60000
agctgtccga cctcttcaga tctcttagtc taccctgcca tcttccttta tgccatgggt  60060
cccactgttc tttcaactca tcccccttc cctcagtgca gagtagctgc ggccagcaga  60120
gggtagactg agagcaggag agaaggtcct gcccaggaac ccattctaga gatgctgcat  60180
tctgcctggg agcaagtttt ccagggcagc tttgagaagt cttgcagaaa caaacctatt  60240
tgacccacat gatatgggaa tgacagaaag taatacaatt gcacagtgc ttttccatgg  60300 gaaaagtaga gccttttcgc gaggttttga gtacatagag agtgaaggtt gacctggaaa  60360
ggttatcctc ctggatccca tgtttttct gaagaactac ctgttagttg caacttgcac  60420
attagaatat gaagtcctac cgagagagat acggagaact agataaatac agatactttt  60480
gtatgtgaat aaacgattcc acaatacaca catcaaaatc cataccagtt attccagaga  60540
gatggattgg gcagaaggca gaaggagaat actctgatcg ttttttgccc acgtgtatgt  60600
attatctcag tgtttctaag aagcgttgc tactttagat ttttttttat aataataatc  60660
ttttaagtat gagaaatgtg cagacaggat tagtgattga gagccatttg tgcttgtggc  60720
aatcatatgg tactttttatg ggaatattag aaaggcactg gtaatgacct tgttgcagca  60780
caaaggagag ggtgtggggt gccctgcat attgtcccac ctcttgtgac gtgtatcgtt  60840
ttggaatttc cagtggcttg atcatgaact actgcaggaa tccagatcct gtggcagccc  60900
```

```
cttattgtta tacgagggat cccagtgtca ggtgggagta ctgcaacctg acacaatgct   60960
cagacgcaga agggactgcc gtcgcgcctc caactattac cccgattcca agcctagagg   61020
ctccttctga acaaggtaag gagcctgtgg ccagaaacct acacgtttcg atgctgggat   61080
gaaaagccat ggaaattccc actgatgcag cagcctccaa tggtaaacgg atgctcgagt   61140
gttgactgag ttctgtcatg taggaggaag cctccgtgca ctctctgggg gagccagcgg   61200
attgatttct ggtacaacgt tgggtgggct gtgtctttag aattggcaca aaccctccag   61260
ggtgatcgac ttcacaactc acctcgttga aaaatgggct atctcagtgt cttagccaaa   61320
atttttattg taacatgctg tcagatgtgt gactcttttcc aagccagtaa gcttttcctg   61380
ggacttcttc aattagccag cattcagtgc aatcttcagc attgcagatt cagagaaatg   61440
tggctctgga gcctgtcacc cttgagaaac agggctaaca gggttgcatt aattccaaat   61500
caccctggtt ctatggagca gtacatgaac tcccaatgat ctatgtttca ggacttcctc   61560
agtcataggt gggctctgca gccctaggtt tttaagtgag tgactgcccc gtgttctggt   61620
ggcagttgta cctgtgagcg gtctggatag aaagagtcgg agacttctgt attattgcaa   61680
ctcaggatgt gggtcatgag aggatttcat ctctcctgca ggggagtaag ctgttcgcct   61740
ccacccatcc ctgataactg aagtgtcttt gtctgcagtc ctagacgaag gactgttgtc   61800
tctcccatgg cccagaagct gaagaccttg cctttttgtta tgaaacgttc attgttttca   61860
tgtctgtccg tttctctgcc cctaacaccc aatcaccatg tatggcctgt accccaaat   61920 gcatcgtgct ttgctgtttg ctgccccata gtcctcatga acattcagta gaaattccca   61980
taaatgtgct tgcacgtgag cacagtttcc attgagaagc cctctcattt gtccttttt   62040 tctaagcttt tatgtgaaat atttctaaga acttactaca gttctaaagt gttaggaatt   62100
tgtttctttg gtgttttttgt ttgttggttg gttgttgctt ttctcaagtc catctgccta   62160
caaataaaga aacaagaatg ttacttgtca tattctcctg aggtcataat tctcagagac   62220
ttttttctgg tttgtgccat aagtggcttc acatgtttgt ctcttcttgg aaacactcag   62280
tttgatttct tttcttttca tttcagcacc aactgagcaa aggcctgggg tgcaggagtg   62340
ctaccacgga aatggacaga gttatcaagg cacatacttc attactgtca caggaagaac   62400
ctgccaagct tggtcatcta tgacaccaca ctcgcatagt cggacccag catactaccc   62460 aaatgcgtat gtctattttc tttaccataa gtgaaggaag ggtcagtgga aatttctgtt   62520
agtagagtca tgcttcaagc tgagtgttca ggactcaagt tgtctcagat gaacagtgca   62580
tagcaaaatg tctcaggaac attgtctttg agcaaagagt ctaagagaag acaaatgtta   62640
atctggctct ccttcctcct agtttaatgg agcagaaagg tatctggagg caaggatatc   62700
acattaagaa acaagtcaag atgacaaatg atgaaactct tagagtaccc ttccacaaca   62760
cccactaagg ttcaatgcag ccttttctcc ttggaattct attaaactaa actccaattc   62820
ctgaagtgaa ggttctgttg gggttttctg ttttggctta caaggaaagt atatatgtat   62880
atctatggag aggcaaatct atctctttct atatctacgt ctattccaat atgtagaaac   62940
acagtcggtt ctgaccacca gtggtctgaa gggatactgg ttgttagaga ataaaaatgg   63000
caggaaggca gatgagagtc agcaaagaga gagatcctgt aaagtaaaag ggtggataga   63060
tggacagaag cccaggtctg accagcccat ggccaggctt taggccataa gtgacaccaa   63120
agacatggaa aaatggtttc tacatgttgg acaacagaca gtagtggacc aaaagaatag   63180 tgacagggggg aacaatgaga tcaactccat agataccttg gctttcttcc tggaggccct   63240
```

```
tcttgcactg aagagcaagg tgatggagcc cagatggact gtagccatct tcctgaatgc    63300
aggagagaga ttggaatttg ggactactgt ggtagctagg attttatagg cctgctgaga    63360
atgagaatgg atttgtggat gaaaggagct ccaggggcac gcatagtagt ctcctcgaat    63420
ctttggctaa acatgacgtt gcatgtgccc agaaaaaggt tccacaagaa agtagagaaa    63480
agaatatatc ctgaggaata gcaactgcga ttgaacagtg agctcaataa agaggacaga    63540
gccctcatag cattctggga tactggagtt ctgaccagct ggaggagaga cctcactgaa    63600
cctcttggga atacagtaga gactccagaa aagtcatact ttaggagtag aattagtaaa    63660
tttctagaaa aaaaggcagc tctagacaaa ccctggcaaa actgaaaagc aagtctccaa    63720
gcattaaaat catttccaag tcaattaact gcctgggaga ggaaaccct ctttagaggt     63780 aaacaacaaa gtcaagtggc tcagctatgt ggtgttcaca gtgtgagttc taaatttaaa    63840
acttgactac acatagagaa gcttttagta tgaaccatga ccaggtgaaa aatcagtcaa    63900
tacaaataga cctagaaatg acagaaatga ttagaatggc aaaaaatttg acatatcaat    63960
atgtcaactg agttttaggt tttaagaaaa catgaatacg gaatgaagca gataccatat    64020
caagagacag taacagtata gaagagccaa attaaattaa agaactagta taagaaggta    64080
tgtcttaaat gaaaaaatta ctggatgtat tcccaatgga gtgagatgtt tcagaagtaa    64140
aaactaactg aaaaacaatt ttataccacc tacagaacca gctacacata cacaaatgac    64200
acacacatat acacacatac tcacacatgc acaggcttag aaacatgcac gcacacacac    64260
acacacacac acacacacct ccacaaatac taaaaaatga aatccactga tcctcacaga    64320
caggcgggaa aatataaaaa gatttcctgc atgtgggtag gaagtcacag aaggagagga    64380
aggagagatt gctacaggaa caaatactgg aagcaaggat agctaaaaac ttttcaaata    64440
agaagaatat taaaaaccac agattcaaga agctgaatga atcagacagg gaatttccaa    64500
aaaaaaaaaa aaaaaaactg tatgattcac ttttgtacat caccgttcaa cagtcagaag    64560
gcaaagatat aataacaaga aacatctcat gagaaactgg aggaaaaaga gctgtgtctt    64620
gctagaagaa cagtgataca aattgctaat gcattctcat cagaaacact ggaacccagt    64680
taacagggga tatcattaaa atgataaact agaaaaaaaa gagatcaaat gagaatgcta    64740
catccagcaa taaaatgcct tgaagatcat ccatgttgga taaatgcata ttgtgcactg    64800
ccccaaataa ataaaccaaa aactaataat ttggaatcag caggcttgtg taacaagaga    64860
tgttgcccaa agaaaattag ctagaagaag aatagttcaa gaggagaact ttctgcagcc    64920
cacgtaatga agaacccagc aaatggcaaa tgtagatgta aatgcaaaat attttcttga    64980
tcaaatttct atatcttttt aaatgagagt tgactacttg aagcaaaatg atagcaatat    65040
atttaacttt agcatatgta gaggtaaaaa tttgaacata tagactaaat catgtgggga    65100
ataattggaa gtgtaccatt gtaagtttct taccttatcc acgatggtat gtaatattaa    65160
tgaaaggttg aatttgtggg tccaaaggga tattgtaaat cctaaagcaa tcataaaatt    65220
ttgaattctg agggatatta tataataaga attttccatg tatccaaaag agggaagcca    65280
aggaagaaaa agaagtcttt caagtactca agctctgagc acatccagtt gctcattgaa    65340
ccagcttcct ggaatggagg gtctgggctt gagactaggt cacatgtgta gagtctctag    65400
agagacagtg ttggatcccc atggcccata atacatttcc cgttttccca ggcagccaca    65460
ggtcacgaat gggaggattc tgagaggttg gagcaatgtt cttaggaggc ataaggagga    65520
gtgaatgctc tgagatttcc ccagcctgag gtcctccata gctgcccgac ctcttcgagac   65580 ctcatagtct gcccagctgt ctcccttat gccatgagtg ccactgttct ttcaactcat     65640
```

```
cccccattcc ctcagtcccg gaattgctgt ggccagcaga ggatggactg agagcaggag   65700
aggaagtcct gaccaggaac ccatcctaga gatactgcat cctgcctgaa agctaggttt   65760
ccagggcagc tttgagaagt cttgcagaaa gaaacccact tgacccacct gatacggtat   65820
cgacagacag gaatactttt tgtgcaatgg ttttacatgc tgaacataga gcctttggc   65880 tacattttga gtacattgaa tgagactgct ggcctgggaa ggatatcatg ctggatgcca   65940
tttttttctc tggagaacta tgtgttagtt ccaactcgca cattactata tgaagtccta   66000
cacagagaga tacggagagc tagacagata gagatacttt tgtatgtgca taaccaattc   66060
cacaatacac acgtcaaaat ccataccagt tattccagag agatggattg ggcagaaggc   66120
agaaggagga tattctgatc ccttttttggc cacatgtatg tataatctca gtgtttctag   66180
gaagtgtgtg ctgcattaga tttttttttct ttaaaaaaag tgataatata ttaagtatga   66240
gaaatgtgca gagaggatta gagattgaga gccatttgtc attgtggcaa ttgtatggta   66300
tctcttttgg gaatatttca aaggcaccag taatgacctt gttgtagcaa aatatacagt   66360
gttcctgcat atgtacccat ttttttgtgat gtgtattctt ttggaatttc cagtggcttg   66420
atcaagaact actgccgaaa tccagatcct gtggcagccc cttggtgtta tacaacagat   66480
cccagtgtca ggtgggagta ctgcaacctg acacgatgct cagatgcaga atggactgcc   66540
ttcgtccctc cgaatgttat tctggctcca agcctagagg cttttttttga acaaggtaag   66600 aagttgtgcc agacatttac ctgcttggat gctgggatga aaagccatgg atacccccac   66660
tgacgcacaa cccttcagtg ctacactggt tctcgtgtgt tggttctggg tctgccatgt   66720
gggaggaagc cttagcgcac tctctggggg agccagaggt gtgattttttg gtgcaacctg   66780 tgcgagctgt gtctttagga tgggcggaaa ccattctggg tgctcgactt caccactccc   66840
ctcattgtaa aagggctat ctcattgtcc tagacaaaat tcttattgta atatgctgtc   66900
agatgtgtgt gtcttttccaa gccagtaaac ttttccaggg atttcttcaa gtagacagca   66960
ttcagtgcaa tcttcagcat tgcagattcc gagaaatgtg gctctagatc ctgttatcct   67020
tgagaaacct aactgggttg cattaattcc atatctccct gggtctgtgg agtagtacat   67080
gagctcccga agctctatct ctcaggtctt tttcagtccg aggcaggttg tgcagttctt   67140
agctttgaag gggagtgattt tttcgtgtgc ttttgcctct ttctgatgga acttgtacct   67200 gcgggggggtc tggagaaaaa gagtagtaga cttttgcttt attgcaatgc attatgctgg   67260
gcacgagagg attccctatc ttattgtagg tgataagctt ttggcctcca ctcatccctg   67320
agaagtgaag tgttgttgcc tacagttttta gctgcaggac tgttgtctgc cccatcacca   67380
ggagtttaat gctttctttt ttgagcaatc atctagggac acatgcaagg ttttttatatg   67440 tccttgcctc ctccccaaaa aaccatttta atgcttggag acttgctttt cagctttgcc   67500
aaatgcatca cccttttcttc tatgctgttc catgtcgtca tgaacactct gtagagattc   67560
ctagaaatga gcttccatgt tagtggagtt tccgatgaga agcaatctga tatttctttt   67620
ccactaagtt ttacatgaaa tatttctaag aacttactac agttctagaa tggtaggcat   67680
ctcttacttt cgtgtttgtt tgtgtgtttt ctcatgtcca tttgcctatt aataaagaat   67740
agagaatggt tgtaaatctc agtgactctt ttttggttta tgtcataaat ggcttcctgt   67800 attttttctgt tctaggaaat aataagcttg atgtcttctg ttttaatttc agcactgact   67860
gaggaaaccc ccggggtaca ggactgctac taccattatg gacagagtta ccgaggcaca   67920
tactccacca ctgtcacagg aagaacttgc caagcttggt catctatgac accacaccag   67980
```

```
catagtcgga ccccagaaaa ctacccaaat gcgtacgtct ttgttcttta ccataagcga    68040
aggaagggcc aatggaagtt tctgttagaa gagtcatgct tcaaggtgac tgctcaggac    68100
tcaacttggc tcagatgcag aggaacattt cctgtgagca aaagttctta gagaagactt    68160
tgttttttg agacagagtc ttgctttgtt gcccaggctg gagtgcagtg gcatgatctc    68220
ggctcactgc aagctccgcc tcccgggttc acaccattct cctgcttcag cctctctagc    68280
agctgggact acaggcaccc accaccacac ccggctaatt ttttgtattt ttagtagaga    68340
cagggtttca ctgttctagc caggatggtc ttggtctcct gacctcgtga tccgcctgcc    68400
tcagcctccc aaagtgctgg gattacaggc gtgagccacc gtgcctggct gagaagacat    68460
ttttttaagct ggctctcctt cctcctagtt ttatggaagc agaaggatat atggagttga    68520
gaagatctta ttaataaaac agccgggatg acaaatgacc aaagagttag agtatccttc    68580
tacaacatcg gctgagggtt aatacaacct tttcaccttg gaattctatc attctaagct    68640
ctagtccctg aagtgaatgt tgtgttggcc ttttgcatct tgggtcacag ggaattgata    68700
cttgcacatc tatggagagg caaatctttt tctatctact tcttttttcaa tgggtacaaa    68760
cacacttggt cctgagcacc agtggtctga agagatacgg tctgcccaga ggagaagaac    68820
aaaggcagga aagcagatga gagtcagcaa aggggcgatg ctgaaaagta aaggggcgg    68880
gtagatggac agaagccatg atctggccat tctatggcca gtctttcggc cataagtgac    68940
taccaaagac acggcaaaac ggtttccaca tgttgaacaa cagatgctag aggaccaaga    69000
gtattgcaag agggagaaaa tgagatcaac ccatcaatgc cttggctttc ttcaaggaga    69060
cccttcctgc actgaagagc aaggagatgg agcccaagct gactgtagcc atgttgctga    69120
acagaggaga gtgattggac tttgggatta ctcaggtagt taggattttc tagccatgct    69180
aagagtaaga atggacttgt ggaggatagg agctccaggc atagaagtct cctcaagtgt    69240
tagtctaaac ataaagcagc acttgcatag aagattttcc acaagaaaat atggcaaaaa    69300
aacaccatat attgaggaac aacaactaca agggaacagt gagcttaata aaggtgacag    69360
agctcacata gtgctctgga atattggagt tttgaccagc tagagagaag agacctcatt    69420
gaaaatcttg ggcattcagt agagacctca gaaaagtcag actttatgag tagactttgt    69480
atattcctag aataaaggca gctccagaaa aaacctagca aagctgaaaa gcaaatctcc    69540
aagcattaaa atggtgtcct agtcaattaa ctgccttcta gaagaaaact caacactctt    69600
tacaggtgaa caacaaagtt aagttgctga gctatgcaat atccacagtg tgagtcctaa    69660
atttataact ttactacaca taaaaaagca tttagtgtga accataacca ggaaaataat    69720
cagtcaataa aaatagaacc aggaatgata gaaatgattt aaatggcatg agaatttgac    69780
atattagtat cataactgca ttgctggatt taagaaaaca taaacatgga acgtaacaga    69840
tatcatatca agggaaagta aaaggataaa agagtcaaat caaattaaag gactattaaa    69900
aggtatatct taaatgaaaa attcactgga tggtctccca atcaggttag ttgtttccag    69960
ggaaaaaatt aactgaaaaa taattcaata gaatctacag aaatagctgc acatatatac    70020
acacaatggc acacgtgcac acacccacac ccacacaggt gtgaatccta gagccacacg    70080
agcattgaaa catagagaag taaaaattgt tcattgagga atatgtagca atgctcaatg    70140
tgttttaccc taataagagc ttttgtgatg tatgattgaa aaactgacac aactgaagag    70200
agaaatagat aagcccacac tctgagttag agatttcctt gattctctca ctatggttat    70260
aaatctttcc caaacacaac aggctagaac aaatatgcag aaaattagac atagtatctt    70320
tgttctcaat aaaaacgtcg acctatttaa cattataccg aactaccgag tacacattaa    70380
```

```
agtgtgcatg gagcattcac tgaggtgtac tctacacatg accttccagc aagtctccat   70440
agatttaaaa gaattaaagt catacagagt gtgtcacttt attctcccag aataaagtga   70500
gatatgaata atgagaagtt tgccagcttc tcaaatattt gggagtcata cggtgcattt   70560
caaaatactc tttgggacaa agaaaacatc actaaggaat ttagaaaagt tttgaactga   70620
gtaagaatat aacacaattt atccaaactt aggagatgca gtgaatgtct ttaggctttt   70680
acataatttt agatgctctt agggaaaaac agaagcatgt aataatcaag atttcaaact   70740
gcaattctca aagtgtagtc tagagaaacc tgaggacctt tgagtacctt cagagacagt   70800
ccatgaggtt aaaggacttt gctacgtgaa aagtaagatg ctattggccc tttttacttt   70860
cattttccaa caagagaaga ggggagtttt ccagcagtta cataatatgt aatggcatca   70920
tgtctctgat ggctaagaaa atgggcaatt gttgactttg tgtgttaaaa aaattctcag   70980
tgttggtttc ttatactata aatattcatc ttgtgttttg aaaagaaaa gctctttgga   71040 atcccctatg aacaaagact ttgacagttg ttgatctaag accacagctt aaatatctac   71100
acaagaaaaa aaaaaaagc aaataagagc caaggaaagc agatggaagg aagtagtcca   71160
aaccagtgac attcagtgaa caagaaaaga gaccaacaag ggagtaaact cttgaaacag   71220
aaagttgatt ctttgaaaag atccatatga ttgaacacag tctggctaaa caaatgacag   71280
accaatgagg gtgcacaacc atcaccatct ggagtaacag aggagaggtg ccattactat   71340
agcatcttcc agttctgaaa gctgaaaaga agattttgag aacaattgta tgtgaataaa   71400
ttcaggaatg ttaatcatgt gggccaattc ctgaggaaga caacaaatca gcaaaccaga   71460
tgctgaatag ttagtgtagt cctgtagaga gacatacaga gaggctgaca gagaaatatt   71520
tgtatgtgca taaacaatc tacaagacac acttcaaaat caatctcagt taatctggag   71580
gaacatattt cacagaaggt ggaaggaggg tattctgatc ctcttgtaca ttgtacaaca   71640
ttgtacaatg tacagagtat aattgtacaa gtacaattga agttgtacaa gtacaagtgc   71700
aacttgcaca atgtacagag taaacattga tgtttactct caattttctt atggagcaca   71760
gatgactttg gatgtgttac aatatgaatg ataatttgtc tttgagatgt tcgcagttgt   71820
ttagaagttg aggaccattt gtgcatatta tgggacccttt agtgaaaata tttcaaagtc   71880 tcttttttaca ctttgttaca gcaaaatgta gagggcgcta agtgcccttg aatcttctcc   71940
catctctggt gacctgtgtt gttttgaaat ttgcagtggc ctgaccagga actactgcag   72000
gaatccagat gctgagattc gcccttggtg ttacaccatg gatcccagtg tcaggtggga   72060
gtactgcaac ctgacacaat gcctggtgac agaatcaagt gtccttgcaa ctctcacggt   72120
ggtcccagat ccaagcacag aggcttcttc tgaagaaggt aggaagtcta tggccagaca   72180
accacaccct aggacgttgg gatgaaaaga gttgcaaaat cttagtgata tagaagcctt   72240
ccatgctcac acaattccaa gtagaatgtg gactcagggt cagccactgg gaaggaacac   72300
tcagcgccct ctctgggaga accagagctg tgatgtttgg taccctgtga aagggtggta   72360
tctataggaa gggtgcagac cctctagggc actggactta ccactcccct ggttattcaa   72420
aggatcattt tagtgtctta gccagaagaa tattctaaca ttttgccaaa tttgtgaaga   72480
tttaccaagc tcatgataag cctttcatgg tatttcttca agtagtcagt gttcattgca   72540 tcttttggctt tgcggtttcg gaggaatgcg gtttttgagt ctgtcatcct tgagaaacct   72600
aatatgactt tccttagttc catatacttc tgggtccagg tagcagtaca tagccaacaa   72660
atgctccatc gttctggcct atctccatct taagccagtc ctgcacaact aggctttgat   72720
```

```
gggagggatc tctcagtgtt cttgccctc cttctcatgg aacatatatc tgtgttggtc    72780
tctgagaaga agagtagtgg atatctactt tgttgcaatg cagaatcctg ggccaaagat    72840
accagccatc cctccaaggg aataaaattt tggccagtag ccctctctga gagacaattt    72900
gtctttgcct acgagtccta gatgcaggac cgcttcctgc cccatcttca agaagctgaa    72960
ggctttggct ttgaggatc agcagtctag ggaaatgtgt gacggtttca tgtctgtccc    73020
cactgacagt caataccac ctacaacctg cacagcctga tgcatagcag tctagttttcc    73080 tgccttattc tcaggaacac ccagaagatg tctatattaa agagcatgca catgagtgca    73140
attttgactg ataggcactc tgatctttcc tttggtgcct gtgttttaaa ggaaatcttt    73200
ctaagaactc gttaaagttc tagaatgcta tgaatctttg ggttttatta ttggtatgtc    73260
catctgcctg ctagtacaga acagagcatg gtagtctttc tcagagacaa tgatcctgtt    73320
tcagtcacag atttcttctg atgcttctgt gttctagaaa ttactcagct tgatttctcc    73380
tctttgaatt tcagcaccaa cggagcaaag ccccggggtc caggattgct accatggtga    73440
tggacagagt tatcgaggct cattctctac cactgtcaca ggaaggacat gtcagtcttg    73500
gtcctctatg acaccacact ggcatcagag acaacagaa tattatccaa atgggtacaa    73560
ccttgagttt tcttcaaaga cagacagcag ccccttaca tttctcttgg aagggccatg    73620
cttccaacta acttcttatg acaaatttat ctcagatctg gaatgttggg tagaatgtct    73680
caggcttctt tcttcaggca cagtgtctga aggagagaa atgtcaggcc agctctcttt    73740
tctcatagtt gacagaagca ggaggatatt tgaaggtggt gagttctcat gaatagaaag    73800
ctcaggacac atggccacgt gcttagaaat agcaccattc cacaatgccc actaaagacc    73860
aatgcaatag ttcaaccagg gatttctgtc attctaatct ccaagtcctg aagtgaaggt    73920
tgtattagcc atgttcatct tgggcaacaa ataaaggata tctatgttga catccagatc    73980
ttccaatcac tttctcctct aacctgtacc tgggttctga gaacaaggta tctgaagagc    74040
tatgtgttgc cagcacatga ggggcaaaag taggaaggca gctgagagtc aggaagtata    74100
aagattctga agagttacac atgcaggaag atggacagaa acccagttca gaccacgtca    74160
gcgtttctgc catgaaggac tatcaaatac ataggaaaag tgttttcata ggttggacaa    74220
cagacatgac aggcctgaga aaattcagaa agggaatcaa aggagatcaa ccttatcatg    74280
tccctggcat ccttccttga gacccttgaa gggcaagcag atggagccca gctgaccaca    74340
gcagtcttgc ttaactgagg agagagactg gagtttgtga tgcctcaggc atctgacgta    74400
ttctaggctg gctaagaatg agaggggatt tgtggaggaa aggagctcca agaatacaca    74460
ccgaagtctt ctcaaggctt tggctaaata caaagctgcg tatgcacaag gagagttttc    74520
acaaagaaag aacaataaag aaaagctact ggggaaagaa caactgcaag gaacagtga    74580 gctcaatgga gatgctagag ctcacatagc actgggggat atttgagttc tgaccactca    74640
gaggagagac acctcactga acatcttggg cattcagtag aggtcaaaga aagccataat    74700
ttgggagtag gatcttcgga ttcctagaaa taaggtgact ccagaaacac tccagcaacc    74760
cttcttccaa gccagtctaa aaggatccaa atgatttcca agtaaattaa ctgccttcca    74820
gaaaaaagta aactcaaccc tccttagagg taaggaacga atacaagttt ctcagttata    74880
tgacatcccc agagtgcaac ttgcatttaa aaatttacta gacacaaaag aagttttcac    74940
tgtgatccat aactgggaga aaaatcactc aacacaaata ggcccagaaa taatagaaat    75000
tatggcattg gcaagaacat ttaaaatgca cctctgagaa ctgtgtttca ggaaaatgtc    75060
agcaaaagct gaccatgaga gaaatgaatg cataatatca gaaaagaaaa gaattgaaga    75120
```

```
gccaaatgga aatttaaaaa ctgagaaaag ttatatctgt aatgaggaat tcactggatg   75180
gccttataac cagtttagat attatggtag gaaaaggtga acgagaaaat gattcaatta   75240
aagctagaca aaccacaaga cagacagaca gacacaaata cacatacaca caatgactga   75300
accaattaat caacagagcc tcaaggacat ctaggaaaac atccacacat ttaatatatg   75360
tgttaggcaa gtcacagaaa gagaggaaaa agataatgtg acagaagtta tacttgaagc   75420
catgacggct gacaaatttc caaacataca gaaaatgaga aattcatagt catgaagctc   75480
aatgactcag gtatagattt ttaaagagca aaactctgat ttactggggt acatcatagt   75540
taaattgtct gatttcaaag ctaagaagaa aaaaggggg ttcctatgaa caaacatttt    75600
gacagttgat ctaagaccac agcttaaata tctaggcaag gaaaagcaaa taagacacaa   75660
ggaaagggga tggatggaaa tagtccaaac caatgacatt cagtgaacaa gaaaatagac   75720
caacaaagga gtaaatccat gaaacagaaa gttggttctt tgaaaagatt catgtgattg   75780
accacagtct ggctgaacag atgacagacc aaggagggag tacaaccatc accatttgaa   75840
gtaacagggg agaggagcca ttgctatacc atactccagg tctgaaagct gacaagaaga   75900
tatcaagaaa aactgtatgt gaataaattc atgaatgtag atcatgtgga tcaattcctt   75960
aggtaaacaa caaatcagca aaccagatac tgaatagatt gggtactcct atagaaagac   76020
atacagatag ccagacagag aaacatttgt acgtgcataa aacaatctac aagactcact   76080
tcaaaatctc tcagttaatc caaagtaaca tatttggcag aaggtggaag gagggtattc   76140
tgatcctttc ttgtacacat tgatgttttc tctcggtttt cttatggagt atagacgagt   76200
ttggatgtgt tacaataaga atgataatct gtctttgaaa tgttcacagt tgtttagaag   76260
ttgaggacga tttgtgattg ttacaggacc tttagtgaga atatttcaaa gtcacttttt   76320
accactttgt tacaacaaaa tgtagaggat gtctggtgcc cttgtatctt ctcccatctc   76380
tggtgaactg tattgttttg taatttgcag tggcctgacc aggaactact gcaggaatcc   76440
agatgctgag attagtcctt ggtgttatac catggatccc aatgtcagat gggagtactg   76500
caacctgaca caatgtccag tgacagaatc aagtgtcctt gcgacgtcca cggctgtttc   76560
tgaacaaggt aagaagtctc tggccagaca accacaccct tggacgttgg gataaaaaga   76620
gttgcaaaat cttagtgata cagaagcctt ccatgctgca cgggaatctg aatgtggact   76680
cagggtcagc caatgggaag gaagcctcag cgccttctct gggggaacca gggctgagat   76740 tttggcacc ccgtgacagg gtggtgtctt taggaagcgt gcagaccttc tagggcactg    76800
gatttaccac tcccctggtt attcaataga ttatttcagt gtcctagtga aaatggatat   76860
tctaacatcc tgccaaattt gtgatgattt accaagctca tcatgagcct ttcctggtat   76920
ttcttcaagt agacagtact cattgcaaac ttcagcttta cagtttcaga ggaatgtggt   76980
ttttgagtct gtcatccttg agaaacctga tatgacttta cttagttcca tatcctcctg   77040
ggtctaggta acagtacata gccagcaaat gctctatctc cctgtctacc ttaatcttag   77100
gcaggtgctg cacacctagg ctttgatgga agggatttct tagtgttctt gcccctcctt   77160
ctcatggaac acgtatctgt gttgctgttt gtgaagaaga gtagtggatg tctactttgt   77220
tgcaatgcag gatcctgggc ccaagatttc ccgccgtccc tccaagggaa taaaattttg   77280
gccagtaccc ctctctgaga gacaatgtgt ctttgcctgg aagtcctaga tggaggacca   77340
cttcctgccc catcttccag aaacttaagg ctttggcttt ggaggatcag tgctctggag   77400
aaatgtgtga cggtttcatg tctgccccca ctgacaacca ccacctacag cctgcaccgc   77460
```

```
ctgatgcatg gcactctggt ctcctgcctt gttctcagga acacccaaaa gagatctttg    77520
ccaaagaaca ggcacatgag tgcaattttg actgataggc actctgatct gtcctttggt    77580
gcccaggttt taaagaaaat ctttctaaaa actcattgaa gttccagaat gctatgaatc    77640
tttgagcttt gttattggca tgtccatctg cctactaatg tagaacagag catggtcgtc    77700
attttcagag atgatgtcct gtttctatca tggatttttt ttctcatgct tctgtgttct    77760
ggaaattact cagtttgttt tctcctcttt gaatttcagc accaacggag caaagcccca    77820
cagtccagga ctgctaccat ggtgatggac agagttatcg aggctcattc tccaccactg    77880
ttacaggaag acatgtcag tcttggtcct ctatgacacc acactggcat cagagaacca    77940
cagaatacta cccaaatggg tatgtctttg agttttctcc caagagaaac agccacccac    78000
ttaaatttct cctggaagag ccatgcttcc agctaacttc ttatgaccca atttctctca    78060
gacccagaat gttggacaga atgtctcagg cttcttgctt tgggcacagg gtctgagagg    78120
agagaaatgt caggccagct ctcttttctc atagttgata gaagtaggag gatacttgga    78180
ggtggtgagg tctcatgaat agaaagctca gaagaacata tgaccatgtg cttagaaata    78240
gcaccattcc acaatgccca ctaaagacca gtgaaatagt tcaaccaggg aattctgtca    78300
ttctaatctc caagccctgg agtgaaggtt gtgtttgcca tgtttgtctt gggtaacaag    78360
tgaaggatat ctatattgac ttcgagatct tccgatcact ttctcctcta acctgtataa    78420
acacattggg ttctgagaac aaggtgtctg aaaagctatg tgttgccagc ccatgagggg    78480
caaaaggagg aaggcagctg agagtcagga agtatagaga tgctgaagag ttacacattc    78540
aggaagatgg acagaaaccc atgtctggct atgccagcct ttctgccatg aaggactatc    78600
aaatacatga gaaaacagtt tcacaggtt ggacaacaga tatggtaggc ttgagagaac    78660
tgagaaaggg aatcaaagga gatcaacttc atcattaacc tgtcttcctt cctggacaca    78720
gtgttggatt gaaggacaag cagatggagc ccagctgacc acagcagtct tgcttaactg    78780
aggagagaga ctggagtctg cgatgcctca ggcagctgat gtgttctagg ctggctaaga    78840
atgagaaggg atttgtggaa gaaggagct ccaggaatac acacagaagt ctcctcaagg    78900
ctttggctaa atacaaagct gcgtatgcac agggagagtt tcataaaga aagaacaaca    78960 aagaaaagct acttgggaaa gaacaactgc aggggaacag taagctcaat ggagatgcca    79020
gagctcacat agcactgggg gatatttgaa ttctgaccac tcagaggaga aacacctcac    79080
tacattttgg gcattcagta gagaccaaag aaagctgtat tttgggattg ggatcatctt    79140
attcctagaa tcaaggtgac tccagaaaaa ctccaacaac ccttcttcca agccagtcta    79200
aaaggatcca aatgatctcc aagtaaatta actgcattcc acaagaaaaa aaaaactcaa    79260
ccccccttag aggcaaggga caaatacaag ttgctcagtt atatggcatt cctattgcgt    79320
tacttctatt taaaatttta atagagacac aagaagcttt cactgtgata cataactggg    79380
agaaaaaatc actcaacaca aacaggccca gaaattatag aattgatgac attggtgaga    79440
acatttaaaa tgcacctctg agaactgtgt ttcaggaaaa tgtcagcaaa agctgaccat    79500
gagagaaaca aaagcagaat agcaagagaa aagaaaagaa ccggagagcc aaatgaaaat    79560
taaagaactg agaaaggta catctctaat gaagaactca ctggatggcc ttatcatcac    79620
tttagacatt acggtaggaa aggtgaccta gaaaataatt caataggagc tacacaaatc    79680
acaggacaga cagacagacc aacagacaga aacacacaca cacacacaca cacacacaca    79740
cacacacaca cacacacaca aagactgaac ctattaatca acagagcctc aagggcatct    79800
aggaaaaatc cacacatttta atatatgtgt taggcaagtc acagaaggag aagaaaaaga    79860
```

```
tatcatgaca gacattatac ttgaagcgat gatggctcgc aacacgccaa atatacagaa   79920
aacaagaaac tcatagtcaa gaagctaaat gactcaggta tagaatttta aagagcaaaa   79980
ctctatgatt tactgggata tatcatagtt aagttgcctc aattcaaagc taaaagaaa    80040 aaaaggggt  tcctatgaac aacagctttg acagctgttg atctaagacc acagcttaaa   80100
tatctaggca aggaaaagca aataaggcac aaggaaagag gatggaagga aatagtccaa   80160
accaatgaca ttcagtggaa aagaaaatag accaacaaag gagtaaatcc atgaaacaga   80220
aagttaggtt ctttgaaaag tctatatgat tggccaaagt ctggctaaac agatgacaga   80280
ccaaggaggg agcatatcca tcaccatcat gagtaacagg agagagatgc cattgctata   80340
gcatcctcca ggtgtgaaag ctgagaagta gatattgaga tcaactgtat gtaaataaat   80400
tcatgaatgt agatcatgtg gatggattgc ttaggtaaat aacaaatcag caaatcaaac   80460
actgaataga tcatgcagtt ttatagagac ttacagacag cctgacagat aaacatttgt   80520
atgtacgtga aacaatctcc aagacacact tcaaaatccc tctcggttaa tccaaaggaa   80580
tgtatttggc agaaggtaga aggagggtat tctgatcctt tctggtacac attgatgttt   80640
tctctcagtt ttcttataaa gcatagatta ctttgaatgt gttacaataa gaatcataag   80700
ctgtctttga aatgttgaca gttgtttaga agttgaggac catttgtgag tgttatggga   80760
ctttagtgag aatatttcaa atttgcttgt ttacactttg ttacaagaaa acatagaggg   80820
tgccaggtgg tgctgtatct tctccaatct ctggtgacct gtattgtttt ggaatttgca   80880
gtggcctgac caggaactac tgcaggaatc cagatgctga gattcgccct tggtgttata   80940
ccatggatcc cagtgtcaga tgggagtact gcaacctgac gcaatgtcca gtgatggaat   81000
caactctcct cacaactccc acggtggtcc cagttccaag cacagagctt ccttctgaag   81060
aaggtaagaa gcctgcagtc agacaaccat accctcggac attgggataa aaagatttgc   81120
aaaatctttg tgatgcagaa aacttccatg ctgcacagga agtcgaaggt gaagtcatgg   81180
acagccaatg ggaaggaagc ttcagtgcct tctctggggg gaccagagct gggatgttga   81240
gtgccttgtg agggatggtg tctttaaaag gggcacagac cctctaggac actggattta   81300
tcacttccct gttatcaaac gaatcatatt agtgtcctag ccaagatgga tattctaaca   81360
tcctgccaaa cttgtgaaga tataccaagc tcctaagcct gtccagccct ttcttcaagt   81420
aggcagtgtt tattgcagtc ttcagcttta ccatttgaa ggaatgccat ttttgaggct    81480
gttgttcttg agaaacctaa catgtcttca ttagatccgt attgtcctga ctttgaag     81540 cagtacatag ccaccaaatt gtttatctcc ccagcctacc ttcatcttgg gcatgccttc   81600
cacacctagg atttgaggga agggatttct cagtgttctc atccctgctt ctcatggaac   81660
atttatctcc gttgtttttt gagaagaaga gtagtgatg tcagctttct tgtaatgagg    81720
gatcctgggc ccaagattcc ctgtctcccc tcctaggcta taaaattttg gcctgtactc   81780
cttctccctg agaggcaatg tgtctttacc tacaagtcct agatgcaaga tccttttctg   81840
ccccacaccc cagaatctga aggcttttgc tttggaggag cagtggtcta gtgtgcaagg   81900
gtttcatgta taccccccac taacagccaa tcaccaccta tagcctgaac agcttgatgc   81960
atggcaccct ggtctcctgc cttgttctca tgaacaccca gaagaggtgt aagcaaaaga   82020
ccattcacat gagtgtaatt ttgaagtata ggcactctga tctgtttttt gtttgtttct   82080
ttgtttgttt gttttccagg gttgaattaa aatatttatg actacttatt aaatttctag   82140
aatcctataa gtctatttgt attttttattc tacatttcaa tttgcatgct aatatagaag  82200
```

```
agtgtaaatt gttaatcctc agattattcc actttgtgtg tcataatttt tttcacattt    82260
cccttttcta ggcaatactg agcttgattt tctcttttaa tttcagcacc aactgaaaac    82320
agcactgggg tccaggactg ctaccgaggt gatggacaga gttatcgagg cacactctcc    82380
accactatca caggaagaac atgtcagtct tggtcgtcta tgacaccaca ttggcatcgg    82440
aggatcccat tatactatcc aaatgcgtat gtctatcatg ttagccataa aaggaacaat    82500
agtcaactaa aatttctctt agctggccca tgctacaagc tcacttccta ggtccaaatt    82560
tctcatagac tcagagtttg tagcaaaatg tctcaggaaa cttacttttg agcaaaaggt    82620
ctgaatgaag agaagtttta ggattgctat ctttcataac aatttgatgg aagcagcagg    82680
atatatggag gtggtgaagt ctcattaatg taaagctaag gagatcaaat gaccaaatgc    82740
tgagacaaag tatcattcca caatgcccac taaaggtcca tgcagtcttt caaccatgca    82800
attctatcat tctatcctcc attccctgaa gtgaaatttg tgtttgccat ttttgacacg    82860
aatcagaagt aacaaattca ggctgggtgc agtggctcag gcctgtgatc ccaacacttt    82920
gggaggacaa gacgggcaga tcaccagagg tcaggagttc aagaccagcc tggctaacat    82980
ggcaaaaccc catctctacg aaaaattaaa aaattagccg gtcatggtgg tgggtacctg    83040
taattccaac tacttgggag gctgaggcag gagaaacact tgagcctggg attcagagtt    83100
tgctgtgagc cgagaacatg ccactgcact ccagcctggg tgacagagca agactcaatc    83160
tcaaaaaaaa aaaaaaagaa gaagaagaag aaaagaagaa gaggaagaag aagaagagga    83220
agaagaagaa gaagaagaag aggaagagga gaggaggag gaggaggagg aggaagaaga    83280
agaagaagaa gaagaagaag aagaagaaga agaagaagaa gaagaagaag aagaagaaga    83340
aaatagaaat gagtgcatat atttatatat gagtactagc ctgtatgaac acactgggtt    83400
ctaagcacca gttttctgaa gggatatggg ttgtcaggca gagtaaaagc aggaatgcag    83460
atgagagtca ggaagtaaac agatgtggtg attaaaatgg gcaggtacat ggacaaaaaa    83520
atgcatgtct gacaaaaact ggcctcttgc cataagtgag tatgaataat atggaaaaac    83580
tgtttgcaca tgttgaacag cagacagtac aacctgagat agtttagaaa gggaaacaaa    83640
taagatcaac cccataatta cccttcctag acttaagggc aaagagtttt aaccaaagca    83700
ttccacagca gtcttgctaa actggggaga gagactggag ttttgtttac taataaaacc    83760
gagattttct aggttaggta ataatgagaa agtatttgtg gagaaaagga gctccaggaa    83820
tacacacaga agtctcttca agtctctggc tgaacagaaa gctgtgtatg cacagaaaga    83880
gtttccagag agaaaggaga acaaagaaca gctactgggg aaagaacaac tgctgggaa    83940 cagtgagctc aatgaagatg ccagagctca catagcactg ggaggtattt gagctctgac    84000
cagcctgagg agagacactt cattgaacat cttgggcatt cagcaaagac cccaaaaaac    84060
catacttcag gagtagaatt aatgcattcc tagaataaag tctactccag aaacacccta    84120
gaaaagctta gaaccaagt ctaaaaagat ccaaatgatc tccaagtaaa ttaattgcct    84180
gtcagaagaa aacaacctct tcagaggtaa acaacaaat taaattgctc aattatatag    84240
tatgcacaat gtgtggcata catttaaaaa tttgctaaac atacaaaaag catttagtgt    84300
gacccataac caggagaaaa atcagtcaat acaaatagac ccaaaaatga taaaaataac    84360
agaattggca aggagattta aaatgtatgt atcataattg tgttcaagga tttaaagaaa    84420
gcgtggacaa gaaataaata aatggataat atcaacagaa agaaaaattg taaaggacc    84480 aaatggagag tcaagaactg aaaaaaaaga catctcttta atgagaaaat cactacatgg    84540 cctttataatc atattagata gtacagatga taaagctaac tagaaaatat tagggtggtg    84600
```

```
caaaccatag cacgcttata caaagcctga gaagataaac agagcctcaa ggacatctat    84660
gaaaatatca aaatatttaa tatttgttta aagcaagtca cagaggaagg gaaagagata    84720
ttggaacaga aaaaatactt gaagcagtga tggctgatga ctttctaaat atggaaaaaa    84780
tgataaactc acatagtcaa gaagctcaat ggatcagata taggatttta aaaagtaaag    84840
ctgtatgatt tatttggaca catcataatt aaattgtcca taatcaaaga tagaaagtaa    84900
aatcttattt gaagcccaag ggaaaaaaca tacctttaca tagagtaaca gtgacacaaa    84960
tgactgatgc cttctcatca gaacaacac aaatcagaaa caatagaata acacctttag     85020
agtggtaaga agaaaaaaag atcaaatcag aaacaacaaa ataacacgtt tagagtggta    85080
aggaggaaaa caagatcaaa tcagaaacaa tggaataaca cctttagagt gtaagaaaga    85140
aaaaaagatc aaatcaggaa caacagaata acgccttcag agtggtaaga aggaaaacaa    85200
gataaaatca gaaacaatga aataacacct ttagagtagt aagaagaaga aaagatcagg    85260
tcagaaaaaa tggaataata tgctaagaag aaaaaaaaag atcaagtcag aaacaatgga    85320 ataaccctt tagagtgaaa agaaggaaaa aaacccagca agcttaaacg ctatgcacag     85380
caaacaattc cactgaaaat gaatgttacg taagtacata ttctgtcctc ctaaaaacaa    85440
agaacaaata aaagaatgtt tcatcagcag gattatgtaa taaagatgt gaaagaatgc     85500 tatgtaagta aagaaaaat aataccatat gggaattggc atcaaaacca caaaatacta     85560
tcaaaacaaa aaaactttat tgataaattt aacacaatat gcaaagaac tataccatgt     85620 atactacata acattggtga gaagaaaatt agaagatcta aataaagaca catcatgctt    85680
atagattaaa aaatccaatg tcacttttca caaaactgat ctttagtttc aacccacacc    85740
caagcagaat tcctgcagtc ttttcttgaa aacctaacag aatgtatatg ctagaatcac    85800
caagacaatc tttaaaaaga ataaaaaact tggaataaaa tcacaagttt gtgggataga    85860
tgcatatggt aatatggaaa ttctcataaa gacacagtaa tcaagacatg tggtattggc    85920
tgggacgctt ggctgtaatc ctaacacttt gggaggccaa gatgagagga ttgcctgaga    85980
tgaggagttg cagacaagcc tgggcaacat agcaagaccc tcatctctac aaatatttaa    86040
aaaaattagc caggtttggt gccatgtgcc tgtagtccca gctattcagg aagctgaggt    86100
gggaggatca ctggagccca tgaggtggag gctgaaatga gccatgattg tgctactgaa    86160
ctttagcctg ggagacagat taaaaccttc cctctctctc tcaaacaaac aaacaaaaaa    86220
tacatagtat tgggcaaaac atatgcaaac aaaaacagaa aagggtcagc ataaatttac    86280
atatatggtc aatttatttt caatacaggt agcaaagcaa tttaatgagg aaatttttt    86340 ccaaaattgg tctgaaacaa ctggatagcc atagaaaaaa actataacaa atgtgacgct    86400
tgaatcctac tgtatgactc aaattaaatt aatttgagat agctcttaga cctcaatgta    86460
acagctaatt ctgaggctga aatataagac tgctatgaaa aagtatagta tcttataacc    86520
ttggagaagg aaaaattttt tgagggaaga accagaaaac actaactgta aagaaaaca    86580 aatgataatg tggacattca ttgaataaaa acttatgctc accaaatatg actgttaaga    86640
aaataaataa gtaagtaaca cactggaaga aaaacactct catccatata tctgacaaat    86700
ggcctgtatc cagagtatag aaacatttct cccactcact aatcagagga caaacaacct    86760
aatcaaaatg ggcaacaggc ttgaatagtc atttcttagg agaagatgca cacagagcca    86820
acaatcacct gaaaaagtgc acaacatctt agccatcaaa aatcaagagt tataaccctc    86880
ataagatgac actgaacatc cagtgtacat ggatatcatt aagaagacac aataataagt    86940
```

-continued

```
ggtgtcaccg atttggagct agaatgtgcc actctctcat atgctggtgg aagttcaaaa    87000
tcatacaaca aattaaaaaa tcagtctgat gctttcttat aaagttcgat aaatatgcat    87060
ctatcctaca aacctgtaat tctattcttg aatatttacc ccccaaaatg aaaacataag    87120
tccacaaaaa tctatataaa tattcatagc agctttatgt tttataaact caaaataaaa    87180
actatttcaa tgttttcatc aaaagaaaat gaaaactatt taaatggttt catcaaaaga    87240
aaatgaaaaa agaatttcca gtatatttat acaaaggaat actattcatc aacaaggaac    87300
aagttactga tagtctcaga agcatgaaca aacctcaaaa atatattaag gaaagaagcc    87360
agacgtcaaa gtgtatagtc tgtatgagtc cattcatgtg agtttataga aaacacaatt    87420
tatggtgaaa gaaaccaata gcatttgaca ctggccgtgg aagagggta gcagagattg     87480 attgagcagc cacacaaggg agtttctggg gtggtgaaaa tgttctgcat tgtgagggca    87540
gtgtgggcta cacaagtata tgtatttatc aaatctcatc cagctacatt taagatctgt    87600
gcatctcact ctatgtgaaa atatactcaa ctgaaaaaca gagcaggtat ctgtttcagg    87660
tgctacatca cttgatacgt ccagttgtgt taaaaaccac tgcctaacat cctcaaatgg    87720
gggatctggg cttgagacta ggtcacatgt gtagagtctc tacagagacc gtgttggatt    87780
cccatgctcc ataatacgtt ccaagttttc tcagacagcc acaggtcatg aatgtgagga    87840
ttctgagagg ttggagcaac gttcttggga ggcataatgg ggaaggcatt ctccaagatt    87900
cctccagcct ggggtcttca cctgctgtgc ctcttactgc attgttttct gactcatcca    87960
tagccacttg accccttcag atcccatagt ctacctagcc gtctcccttt atgccttggg    88020
tcccgctgtt ctttcaactc atcacccatt ccttcagtcc cagagtggct gcagccagca    88080
gaggatggac tgagagcagg agaggaggtc gtgcccatga acccatccta gagaagcagc    88140
atcctgcctg ggagctagtt ttccagggaa gcttttataa gtcctgtaga cccaaaccca    88200
cttgctctac cagatacagt atttatagta atactatttt catgattatt ttatattgca    88260
aatgtagagc atttatgcta cactatgagt aaatagagta aggggctgg catgggaatt     88320 atataatctt ggatgccact tcttccttgg ggaaatgtat ttgagttcca acttacatat    88380
tactatatag tcttatagag agagagacaa agagctagac agacagagat atctttgtat    88440
gtgcattaaa aaatctaaga tacatatttc aaaatctgtg tcatttattc tggaggaaag    88500
tatttggcag aaggtgaaag gaagatattc tgatcctttc ttgtacagac atgtattatc    88560
tcagttttca tagagagcat atactacttt tgatgtttta aaacaaaaat tataatctgt    88620
gatgtgtcca cagttgttta aaagttgaag ctgaagacca tttgtgcttg tggcaatatt    88680
attgtggtat aatgggaata tttcaaaggc acttgttaac actttgttac agcaaaatgt    88740
agagggcgct aagtgccctt gaatattctc ccatctctgg tgacctgtgt tgttttgaaa    88800
tttgcagtgg cctgaccagg aactactgca ggaatccaga tgctgagatt cgcccttggt    88860
gttacaccat ggatcccagt gtcaggtggg agtactgcaa cctgacacga tgtccagtga    88920
cagaatcgag tgtcctcaca actcccacag tggccccggt tccaagcaca gaggctcctt    88980
ctgaacaagg taagaaattt gtggttagac atctatatac tgggatgaaa accatggaa    89040 aatcttactg atgcagaagc cttcagtggt acactggagg gttggttgag ggtctgcaat    89100
gtggaggaaa gcctcagcgc cctctctggg ggatccagaa ctgtgatttt tggcacgctg    89160
tgaggaggca gtgtctttag gaagggcacg gtgtctttag gaagggcaca gacccgccag    89220
ggcactggac ttaccactcc cctggttatt aaatgggtca tttcagtgtc ctagccaaaa    89280
tggatattct aacagcctgc caaatatgtg aagatttcca agccaataag cctttccagt    89340
```

```
gatttaaagt agactttttt cattgcaatc tacagtttgc agtttcttaa gaacatggcc   89400
tttgagtatg atatcctaga gaaacctaag gagactgcat tattttttcta ttgtcctggg  89460 gctgcatagc aggaggtaac caacgaatgc tgtctctccc tggcctatct cagtctttca   89520
caggctctgt tcacctcagc tttgaagtta gaaatttcta ggtgttcttg cctcttcttc   89580
tcatgaaacc tgcattggca gtgagtctac agaagaagag gaagagaatt ctgctttgtt   89640
acaattcagg actctgggca ctagaagatt ccctatctct cctccaaggg aataagttgt   89700
ttgtctctaa ccctccttga gaaacaatga gtctttgcct gcactcctaa atgtaggatg   89760
atttcctgcc caaattttca aaagattaag ccttttgcct tggtatgagc aatggtctag   89820
ggaaatgcgc aagggtcttg tgtcggcccc tgactgacca ccagtcacct cctacagcct   89880
gcaccaagga atgcattgca ttctggtctt ctgccctgtg gttctcatga aaaccagcag   89940
agattcatat gatggagctg cacatgaatg taatttccaa tgtccagcat tctcctctgt   90000
tctttatctt tagatttaaa aataatgttt ctatgaactt attaaaattc tagaatacta   90060
tgaatctact gggtcttttc acatcctttt gctactagta gaaaaagaa tagtaataat    90120 tttcagaggc tactgtccag tatgtgacat aaattgtctc ccatgtttct ctgctcatgc   90180
aattactgag tatgatttat tttatttttaa tttcagcacc acctgagaaa agccctgtgg  90240
tccaggattg ctaccatggt gatggacgga gttatcgagg catatcctcc accactgtca   90300
caggaaggac ctgtcaatct tggtcatcta tgataccaca ctggcatcag aggaccccag   90360
aaaactaccc aaatgcgtat gtatttgatt aaaaccataa gaggagcaac agccaactca   90420
aatattggtt agaagaccca tgctttaagc tcacttccta gggacaaatt tctcttagac   90480
tcacattttg gcaaaatgtc tcaggacctt tgcttttgag caaagagtct aagagaagag   90540 aaatttagg cctgctatt ttcctaatag ttttatggaa ggagtagaat atacggaagt     90600
ggcgaagtca tattaatgta aagctcagaa gataaatgac caaagcttaa acacagcacc   90660
attccacaat gcccactaaa aatcaatgtc atctttcact cgtgcaattc tgtcattcta   90720
aatttcaatt cccgaaggtt tgtttgccat ttttgtcatg ggtaataagt aaaaaaaaaa   90780
aaattaagat gtgtatatat atatatatat atatatatat acacacacac acacacacac   90840
aaacatctga atatttatat atatgtctga atatttatat acttgtgtat aaaacttata   90900
tttaaatttt tgcataaatt tatatatttt taatatttca ttaaaaatta tattgtttca   90960
ctatgtatgt ctgagtattt ttatatattt taatataaca ttttaaatat ttatataaa   91020 atattcaggt atgtaactga atattcattt acacacacaa atatatgtgt gcatgtgtgt   91080
atatatatat atacccatat atatatatat atatatatat acatatatat atatatatat   91140
atatgtatat atatatatat atatatatat acacacacac acacacacac atacatacag   91200
gtataaacac actgggcctg aagcaccagt ggtctgaaag gacatgtgtt gccaggactt   91260
gaagagcaaa agcaggaagg cggatgagag tcaggaggta cacaaacgct gaaaagtaaa   91320
atggacaagt acatggacaa aaagcaggta taagcataac agccttttgg aagtaaatga   91380
ctataaaata tatgaaaata ctgttttcac aagttgcaca acagatagta gtgtattgag   91440
ataatttaga acagaaaaca aatgtgatca accccataag tgtgctgtat ttcatcatgg   91500
attgaaggaa aaagagatgg agcccaagaa gaccacagca gtcttgatga actgagagac   91560
accagagttt gggattacaa aggcagctgg gattttctac acttggtaat aatgagaaag   91620
aatttgtgga gataaagagc tacagtcatg tacctagaag tcacctcagt gtaatataaa   91680
```

```
tctgcatatg cacagggagt gattccacaa tgaaagtagg acaaagaaca gctactgggg   91740
aaagaataac tacaagggaa caatgagttc aatggagatg gcagagctca caaagcactg   91800
ggggatattt gagttcttac cagctagaaa agagacctca ttgcaaatct tgggcattca   91860
gtagagaccc cagaaaagcc actctttgga aacagagttg atgtatttta agagcaaaat   91920
ctactccaca aaaatcctag caaaattgaa aagcaagtca gaaagaccaa aatcctctca   91980
acataaatta gttgcccatc agaagaaagc ttaacctctt cataggtaaa caataaaatc   92040
aaattgctca gttatctggc atccacaata tgtgacataa atttaaaaat ttactagaca   92100
tacaagaagc atttagtgtg atccataacc aggagaaaaa tcattcaata caaatagacc   92160
cagaaatgac agaaatgata gaattagcaa aaacatttaa aatatacata tgatcatttg   92220
atcttgtgat cagatatcac aagagaagaa agagatactt gaacagaaaa aatgcctgaa   92280
gcaatgatgg ctgaaaactt tccaaatatg aagaaaaaaa agctcacaga ttcaagaaaa   92340
ctaatcaatc agaaatatga ttttgaaaag taaaaatgta tgatttactt tggcaaatct   92400
tcttggttaa attgtctaaa atcaaagaaa gctaggaaaa ttttataagc cagaggaaaa   92460
aagattgttt atataaagga acagttacac aaatgactga tgccttctca tcagaaacaa   92520
tgaaagtcag aaacaataaa gtaacatctt taaagtaata gaagaaaaac ccaagaggtg   92580
agggatcgtg gcagacagga ggcaggacta gattgcagct ctggacagag cagcatgcag   92640
aggctcatat tgtgaatttt agccccatat tgactgcaag aacagaccag caatcctgag   92700
aggacccaca gaccgtgtga aggaagcaga ctgctcctgc aggataaggg agacacccca   92760
aatactgtga gttccccaac tgcagaagtg gaaagggag gccttactcc ctcaaacaca   92820
ccccacaact ggagaagctg aaagtctgtt tgcaggagaa gttcccaact ttacctgggc   92880
ctcagtaaat ttagagagct gagccaagca aaatataggg gtagaggaag cagcagaaa   92940 gacctcagag cttgctggat ccccaagcag ctcattcctg cctggcacca cagagatcca   93000
tcagaagtgt ggccaaagga acagagggta aaactccaca tggaggactg ctctacctga   93060
actttctaac aatttgaaca gggggagaag cctcctggcc agaacttggg ggagggcatg   93120
aatctggttt gcagacttca caggtggggg aaggactaaa gcccttttct ttcacagctg   93180
ggaggtggaa agcctcaggc aagttttcaa gcctgacttt ccccccacct ggaaacagac   93240
ttggagctgt tgcggggttg ggggcatggt gggagtaaga ccagcccttc agtttgcatg   93300
ggtgctgggt gaggcctgtg actgacagct tccctccact tccccgacaa ctcagatgac   93360
tcagcagagg cagccataat cctcctaggt acacaactcc agtgacctgg gaacttcacc   93420
cccacaccat acagaagctt cagtaagacg tgcccaagga aagtctgagc tcagacacgc   93480
ctagtcccac ccccaactga tggtccttcc ctacccaccc tggtagcaga agacaaagag   93540
catataatct ttggagttct agggcccacc cacctctagt ccctctccac actagtatag   93600
ctgatgcagg aggccaacca gcacaaaaat agagcattaa accaccaaag ctaggaaccc   93660
ctatggagtc cattgcaccc tcctccacct ccaccagaac aggcactggt atccacagct   93720
gagagaccca tagatggttc acatcacagg actctgtaca gacagtcccc agtaccagcc   93780
cagagctggg tagacttgct aggtggcaag acccagaaga caggcaataa tcactgcagt   93840
tcagctcaca ggaagccaca tccataggaa aagagggaga gtactacatc aagggaacac   93900
cccatgggat aaaaacatct gaacaacagc cttcagccct accttccctc tgacacagtc   93960
tacccaaatg agaaggaacc agaaaaccaa ccctggtaat atgacaaaac aaggctcatc   94020
acactcccag ttcaccagca atggatccaa accaagaaga aatccctgat ttacctgaaa   94080
```

```
gagaattcag gaggttagtt attaagctaa tcagggaggg accagagaaa ggcaaagccc    94140
aatgcaagga aatccaaaaa aaaaaaggta taagaagtaa aaggtgaaat attcaacaaa    94200
atagatagct taataaaaaa acaataaaaa attcagtaga ctttggacac acctttggaa    94260
atgtgacatg ctctggaaag tctcagcaat agaactgaac aagtagaaaa aataaattca    94320
gagctcaaag acaaggactt caaattaacc caatccaaca aagacaaaga ataaaggata    94380
agaaaatatg aacaaagcct tcaagatgtc tgggattatg ttaaatgacc aaatataaga    94440
ataatcgtgg ctcctgagga aaaagacaat actaaaagct tggaaaacat atttggggga    94500
ataactgggg aaaacttacc tggccttgct ggacacctag acatgcaaat acagaaaaca    94560 caagaacat gtaaatacaa gcagcacaaa gaacacctgg gaaattcatc acaaaaagat    94620
cttagcctag gcacattctc atcaggttat gcaaagttaa gacgaaggca agaatcttaa    94680
gagctgtgag acagaagcac caggtaatgt ataaggaaa ccctatcaga ttaacagcca    94740
gtttttcagc aggaactgta caagctataa aggattggag ccctatcata gcctcctcaa    94800
acaaaacaat tatcagtcaa gaattttgta tccagcgaaa gtaagcatca tatatgaagg    94860
aaagatacag tcgttttgg acaaacaaat gctaagagaa ttcaccatta ccaagtcacc    94920
actagaagaa ctgctaaaag gagctctaaa tcttgaaaca aatcctagaa acacatgaaa    94980
acagaatctc tttaaagcat aaatcacaca ggacctataa aacaaagta caagttaaaa    95040 aacaaaaaca aaaacaaaa ccaaagtacg gaggcaataa agaatatgat gaatgcagtg    95100
gcacctcaca tttcaatgct aaaattgaat ctaaatggcc taaatgctcc acttaaagga    95160
tacaaaaaga gttggtggct ggcaagatgg ctgaatagga acagctccag tctgccgctc    95220
cccgtgagat caacacatag ggtgggtcat ttctgcattt ccaaccaagg tacccggctc    95280
atctcattgg gactggttag acagtgggtg cagcccacag agggtgacct gaagcagggt    95340
ggggtgtcac ctcacctggg aagtggaagg ggtcagggaa ctccctcccc tagccaaagg    95400
aagccgtgag ggactgtgcc gtgaagacca gtgcattctg gcacaaatac tatgcttttc    95460
ccacggtctt tgcaacctga agaccaggag attcccttgg gtgcctacac caccagggcc    95520
ctggatttca agcccaaaac tgggctggca tttgggcaga cactaagcta gctgcaggag    95580
ttttttttca taccccagtg gtccctggaa tgccagcaag acagaaccat tcaccccgt    95640 gaagaaaggg ctgaagccag ggagctaagt ggtctttctc agtggatccc acccccatgg    95700
agcccagcaa gctaagctcc actggcttga aattcttgct gccagcacag cagtctgaag    95760
ttgacctggg acgctcaagc ttggtgggag gaggggtatc cacaaatact ggggcttgag    95820
taggaggttt tccctcaca gtgtaagcaa aaccgctagg aagtttgaac tgggcagggt    95880
gcactgcagc ttggcaaagc cattgtagca agagtgcctc tctagattcc tcctctctgg    95940
gcagggcatc tctgaaagaa aggcagcagc cccagtcaga agcttataga taaaactccc    96000
atctccctgg gacagagcaa ctggaggaag gggtggctgt gagtgcagct ccagcagact    96060
tagtttcctg cctgccagct ctgaaaagag caccagatcc cccaacacag cactagagct    96120
ctgataaggg acagactgcc tcctcaagtg ggtcctggtt tcagaagata ataagaaact    96180
cctctgagct aaaggagcat gttctaacac aatgcaagga agctaagaac cttgaaaaag    96240
gtcagaggaa ttgctaacta cagtaagcag tttagagaag aacataaatg accttaggga    96300
gctgaaaaac acagcacgag aacttcatga cacatacaca agtatcaata gcaaaatcga    96360
tcaagtggaa gaaaggatat cagagattga aaatcaactc aatgaagtaa agcgtgaaaa    96420
```

| | | | | | |
|---|---|---|---|---|---|
| caagattaag | gaataaagaa | tgaaaggaa | tgaacaaatc | ctccaagtat | gggactatgt | 96480 |
| gaaaagattg | aacctacgtt | tgattggtgt | acctgaaagt | gatgggagaa | tggaaccaag | 96540 |
| ttggaaaaca | ctcttcagga | tattatccag | gagaacttcc | ccaacctagc | aagacaggcc | 96600 |
| aacattcaaa | ttaaggaaat | acagagaata | ccacattcaa | attcaggaaa | tacagagaac | 96660 |
| accacaaaga | tactcctcaa | gaagagcaac | ctgaagacac | ataatcgtca | gattcaccaa | 96720 |
| ggttgaaatg | aaggaaaaaa | atgttgaggg | cagccagaga | gaaagtttgg | gttacccaca | 96780 |
| aagggaaccc | catcagacta | acagtggatc | ttcctgcaga | aactctacaa | gccagaagag | 96840 |
| agtgggaggc | caatattcaa | cattcttttt | tactattatt | atactttaag | ttctagggta | 96900 |
| catgtgcaca | aggtgcaggt | tgttacata | tgtatacatg | tgccatgttg | gtgtgctgca | 96960 |
| cccattaact | cttcatttac | attaggtata | tctcctaata | ctatccctcc | ccactccccc | 97020 |
| catcccatga | caggccccgg | tgtgtgatgt | tccccactct | gtgtccatgt | actctcattg | 97080 |
| ttcaattccc | acctatgagt | gagaacattc | ggtgtttgga | tttctgtcct | tgtgatagtt | 97140 |
| tgctgagaat | gatggtttcc | agcttcatcc | acatccctac | aaaggacatg | aagtcatcct | 97200 |
| tctttatggc | tgcatagtat | tccatggtgt | atatgtgcca | catttcctta | atccagtcta | 97260 |
| ccattgatgg | acgtttgtgt | tggttccaag | tctttgctat | tgtgaatagt | gccgcaataa | 97320 |
| acatatgtgt | gcatgtgtct | ttatagcagc | atgatttata | atcctttaga | tatatatcca | 97380 |
| gtaattgtat | ggctgtgtca | aatggtattt | ctagttctaa | atccttgagg | aatcaccgca | 97440 |
| ctgtcttcca | caatggttga | actagtttac | agtcccacca | ccagtgtaaa | atgttccta | 97500 |
| tttctccaca | tcctctctag | catctgttgt | ttcctgactt | tttaatgatc | accattctaa | 97560 |
| ctggtatgag | atggtatctc | attgtggttt | tgatttgcat | ttctctgatg | gccagtgatg | 97620 |
| gtgagcactt | tttcatgtgt | ctcttgactg | cataaaagtt | ttcttttgag | aattgtctgt | 97680 |
| taatatcctt | tgccaacttt | ttgatggggt | tgtttgattt | tttttcttgt | aaatttgttt | 97740 |
| atgttctttg | tagattctgg | atattagccc | tttgtcagat | gggtagattg | taaaaatttt | 97800 |
| ctcccattct | gtagcttgcc | tgttcattct | gagggtagtt | tcttttgctg | tgcagaagct | 97860 |
| ctttagttta | attagatccc | attggtcaat | tttggctttt | gttgctattg | cttttggtga | 97920 |
| tttagtcatg | aagtccttgc | ccatgcctat | gtcctgaatg | gtattgctta | ggttttcttc | 97980 |
| tagggtttat | atggttttag | gtctaacatt | taagtcttta | atccatcttg | aattaattt | 98040 |
| tatataaggt | gtaaggaagg | gatccagttt | cagcttttcta | catatggcta | ggcagttttc | 98100 |
| ccagcaccat | gtattaaata | gggaaaacctt | tccctatttc | ttgttttttgt | caggtttgtc | 98160 |
| atagatcaga | tggttgtaga | tgtgtggtat | tatttctgag | ggctctgttc | tgttccattg | 98220 |
| gtctatatct | ctgttttggt | accagtacca | tgctgttttg | gttactgtag | ccttgtaatg | 98280 |
| tagtttgaag | tcaggcagag | tgatgcctcc | agctttgctt | ttttggctta | ggattgtctt | 98340 |
| ggcaatgcat | gctctttttt | gttccatatg | aactttaaag | tagttttttc | caattctgtg | 98400 |
| aagaaagtca | ttggtagctt | gatggggatg | gcattgaatc | tataaattac | cttaggcagt | 98460 |
| atggccattt | tcacaatatt | gattcttcct | atccatgagc | atggaatgtt | cttccatttg | 98520 |
| tttgtgtcct | cttttatttc | attaagcagt | ggtttgtagt | tctccttgaa | gaggtccttc | 98580 |
| ccatcccttg | taagttggat | tcctaggtat | tttattctct | ttgaagcaat | tgtgaatggg | 98640 |
| agttcatcca | tgtccctaca | aaggacatga | agtcatgtat | gggaatgctt | gtgattttg | 98700 |
| cacattgatt | ttgtatcttg | agactttgct | gaagttgctt | atcagcttaa | ggagattttg | 98760 |
| gtctgagaag | atgggggtttt | ctaaatatac | aatcatgtca | tctgcaaaca | gggacaattt | 98820 |

```
aacttcctct tttcctaact gaatacccct tatttccttc tcctgcctaa ttgccctggc    98880
cagaacttcc aacactatgt tgaataggag tggtgagaga gggcatccct gtcttgtgcc    98940
agttttcaaa gggaatgctt ccagtttttg cccattcagt atgatattgg ctatgggttt    99000
gtcataaata gctcttatta ttttgagata tgtcccatca atacatagtt tattgagagt    99060
tcagcatgga gagctgttga attttgtcaa aggccttttc tgcatctatt gagataatca    99120
tgtggttttt gtctttggtt ctgtttatat gatggattac atttattgat ttgcatatgt    99180
tgaaccagcc ttgcatccca gggataaagc caacttgatc atggtggata agcttttttga   99240 tgtgctgctg gattcggttt gccagtattt tattgaggat ttttgcatca atgttcatca    99300
tggatgttgg tctaaaattc tcattttgt tgtgtctctg ccaggatttg gtatcaggat     99360
gatgctggcc tcataaaatg agttagggag gattccctct ttttctatga ttggaatagt   99420
ttcagaagaa ttggtaccag ctcctctttg tatctgtggt agaattcggc tatgaatctc    99480
tcctggactt ttttttggttg gtaggctctt aattattgcc tcaatttcag agcctgttat   99540
tggtctattc aaggattcaa tttctttctg gtttagtctt ggtagggtgt atgtgtccag    99600
gaatttttcc atttcttcta gattttctag tttatttgca cagagtgtt tataatattc     99660 tctgatggta gtttgtattt ctgtgggatt ggtagtgata tcccctttat catttttat    99720 tgcatctatt tgattcttct ctctttttctt ctttattagt cttgctagtg gtctatcaat   99780
tttgttgatc ttttcaaaaa accagctcct ggattcattg atgttttgaa ggttttttttg   99840 tgtctctatc tccttcagtt ctgctctggt cttagttatt tcttgccttc tgctagcttt    99900
ttaatgtgtt tgctcttgct tctctagttc ttttaatggt gatgttaggg tgtcaatttt    99960
agatctttcc tgctttctct tgtgggcatt tagtgctgta aatctcccc tacacactgc   100020 tttaaatgtg tcccagagat tctggtatgt tgtgtctttg ttgtcattgg tttcaaagaa   100080 tatcttatt tctgccttca tttcgttaca tacccagtag tcactcaggt gcaggttgtt    100140
cagtttccat atagttgagc agttttttaat gagtttctta atcctgagtc ctagtttgat  100200
tgcactgtgg tctgagagac agtttgttat aatttctgtt cttttacatt tgctgaggaa   100260
tgcctcactt ccaactatct ggtcaatttc agaataagtg cgatgtggtg ctgagaagaa   100320
tgtatattct gttgatttgg ggtggagagt tctgtagatg tctattaggt ctgcttggtg    100380
cagagctgag ttcaattcct ggatatccat gttaactttc tgtctcattg atctgtctaa   100440
tgttgacagt ggggtgttaa agtctcccat tattattgtg tgggagtcta agtctctttg   100500
taggtctcta aggacttgct ttatgaatct aggtgctcct gtattgggtg catatatatt  100560
taggatagtt agctcttctt gttaaattgg tccctttacc attatgtaat ggccttcttt   100620
gtctcttttg atctttgtta gttaaagtc tgttttatca gagactagga ttgcaacccc    100680 tgctttttttt gttgtttttcc atttgcttgg tagatcttcc tccatccctt tatttgagc   100740 ctatgtgtgt ctctgcacgt gagatgtgtc ttcagaatac agcacactga tggatcttga   100800
ctctttatcc aattttccag tctgtgtctt ttaattggag catttagccc atttacattt    100860
aaggttaata ttttatatgtg tgaatttgat cctgtcatca tgatgttcgc tggttatttt  100920
gctcattagt tgatgcagtt tcttcctagc atcgatggtt tttacaattt ggcatgtttg   100980
tgcagtggct gataccgatt gtttctttcc atgtttagtg cttccttcag gagctcttgt  101040
aaggcaggcc tggtggtgac aaaatctctc agcatttgct tgtctgtaaa ggatttatt    101100 tctccttcac ttatgaagct tagtttggct ggatatgata ttctcagttg aaaattcttt   101160
```

-continued

```
tctttaagaa tgttgaatat tggctgccac tctcttctgg cttgtagagt ttctgctgag 101220
agatctgctg ttagtctgat gggcttccct ttgtgggtaa cccgaccttt ctggtgaatc 101280
tgacaattat gtgtcttgga gttactcttc tcgaggagta tttttgtggc attctctgta 101340
tttcctgaat ttgaatgttg gcctgccttt gtaggttggg gaagttctcc tggataatat 101400
cctgaagagt gttttccaac ttggttccat tctcctcgtc actttcaggt acaccaagca 101460
gatgtagatt tggtcttttc acatagtccc atatttattg gaggctttgt tcatttcttt 101520
ttactccttt ttttctctaa acttctcttc tcgcttcatt tcattcattt gatctttaat 101580
cactgatacc ctttcttcca cttgattgaa tcaactactg aaacttgttc atgtgtcacg 101640
tagttctcgt gccatggttt tcagctccat tagatcattt aaggtcttct ctatgctgtt 101700
tattttagtc tgccattcat ctaaactttt tcaaggtttt tagcttcttt gcaatggggt 101760
cgaacatcct tctttagctc ggagaaattt gttattacag atcgtctgaa gccttcttct 101820
ctcaactcat caaagtcatt ctctgtccag ctttgttctg ttgctcgtga ggagctgcgt 101880
tccttcggag gagaagaggc accctgattt ttagaatttt cagctgttct gctctggttt 101940
ctccccatct ttgtggttta tctacctttg gttcttgatg atggtgatgt acagatgggg 102000
ttttggtgtg gatgtctttt ctgtttgtta gttttccttc taacagtcag gaccctcagc 102060
tgcaggtctg ttggagtttg ctggaggtcc actccagtcc ctgtttgcct gggtattacc 102120
agtggaggct gcagaacagc aaatattaca gaacagcaaa tgttgctgcc tgattcttcc 102180
tctggaagct tcatctcaga ggggcaccca gctgtatgag gtgtcagttg cccctactg 102240 ggaggtgtcc cccagttagg ctactcgggg gtcacggacc cacttgagga ggcagtctgt 102300
ccattctcag atctcaaact ctctgctggg agaaccacta ctctcttcaa agctgtcaga 102360
cagggatgtt taagtctgca gaagtttctg ctgcctttg ttcagctatg ccctgccccc 102420
agaggtggag tctacagagg caggcaggtc tccttgagct gtggtgggct ccacccagtt 102480
tgagcttcct ggtcgctttg tttacctact caagtctcag caatggcaga cgcccctccc 102540
ccagctttgc tgccgccttg cagttcggtc tcagactact gtgctagcag ttcaatctca 102600
gactgctgta ctagcagtga gcaaggctct gtgggcatgg gaccctctga gccatgtgca 102660
ggatataatc tcctggtgtg ccgtttgcta agaccattgg aaaagtgcaa tattagggtg 102720
ggagtgtccc gattttccgg gtacatctgt catggcttcc cttggctagg aaagggaatt 102780
ccctgacccc ttacacttcc cgggtgaggc aatatcccgc cttgcttcgg ctcactctcc 102840
gtgggctgca cccactgtct gacaagcccc ggtgagatga acccagtacc tcagctgaaa 102900
atgcagaaac cacccatctt ctgctttgct catgctggga actgtggact ggagctgttc 102960
ctattcggcc atcttgaaac ctcccctctc tcacgatcac aaggtccac aataggccgt 103020 ctgcaggctg aggagcaaga aaagccagtc tgaattccaa aactgaagaa attggagtct 103080
gatgttcaag ggcaggaaac atccagtgcc aaagaaagat gtagaatatt caacattctt 103140
aaagaaaata attttcaacc tagaatttca tatccagcca aactaagctt tataacaaag 103200
gagaagtaaa atcctttaca aacaagcaaa tgctgaggaa ttttgtcaac accaggcctg 103260
ccttacaaga ggtcctgaag aaaacactaa atatggaaag gaaaaccag taacagctac 103320 tgcaaaaaca taccaaattg taaacaccat caacactata agaaactgc atcaactaat 103380 gggcaaaata gccagctagc atcataatga caggatcaaa ttcacacata acaatattaa 103440
ccttaaatgt aaatgggcta aatgcccaa ttaaaagaca cagactggga aattgaataa 103500
agagtcaaga cccattggtt tgctgtgttc agaagaccca tctcagggtg aaaagacata 103560
```

```
catgggctca aaataaagaa atgaaggaat atttaccaag caaatggaaa gaaaaaaaaa  103620
gcagcggttg caatcttagt ctttgatgaa acagacttta aaccatcaaa gatcaaaaga  103680
gacaaaggag ggcattacct aatggtaaaa gtatcaatgc aacaagaaga tctgactgtc  103740
ctacttatat atgcacccaa tacaggagca cccagattaa taaagcaagt tcttagagac  103800
ctacaaagag acttagactt ccacacaaaa atagtgggag actttaacac cccacagcca  103860
atattagatc gacgtgacag aaaattaaca aggatattca ggacgtgaat tcagctctgg  103920
accaagctga cctaatagac atctacagaa ctcgacacca caaatcaaca gaatatacat  103980
tcttctcagc accacattgc acttattcta aaattgacca cataattgga agtaaaacac  104040
ttctcagcaa atgccgtaga atggaaatca taacaaacag tctctcagac caaagtgcaa  104100
tcaaactaga actcaggatt aataaactca ctcaaaacca cacaactata tggaaactga  104160
acaacctgct cctgaattac tactgggtaa ataacaaaat taaggcagaa gtagataagt  104220
tcttagaaac caaagagaac aaagacacaa tgtgccagaa tctctggtac acagctaaag  104280
ccatgtttag agggaaattt atagcactaa atgcccacag gagaaagcgg gaaagatcta  104340
aaatcaacac cctaacatca caattcaaag aaccagagaa gcaagagcaa acaaatacaa  104400
aagctagcag aagacaagaa ataactaaga tcagagcaga actgaagggg ataaagacac  104460
gaaaacccct taaaaaatta ataaatccaa gagctggttt tttgaaaaga ttaacaaaat  104520
acatagaagc ctagccagac taataaagaa gaaaatagag aagaatcaaa tagacacaat  104580
aaagaataat aaaggggata tcaccaatga tgccacagaa atacaaacta ccatcagaga  104640
atactttaaa cacctctatg caaataaaat agaaaatcta aagaaatgg ataaattcct  104700
ggacacatac accctcccaa gactaaacca ggaagaagtc aaatccctga atagaccaat  104760
aacaagttct gaaatcgagg cagtaattaa tagcttacca accaaaaaaa gcccagacca  104820
gagggattaa cagtcaaatc ctaacagagg tacaaagaag agctagtact attccttctg  104880
aaactattcc acacaataga aaagaggga ctcctgccta actcattta tgaggccagc  104940
atcattctga taccaaaacc tggcagagac acaacaagaa aagaaaattt caggccaaca  105000
tccctgatga acatcaatgt gaaaatcctc aataaaatac tggcaaactg aatccagcag  105060
cacatcaaaa agcttatcca ccatgatcaa gttggcttca tccctgggat gcaaggctgg  105120
ttcaacatat tcaaatcaat aaacataatc catcacataa acagaaccaa tgacaaaaac  105180
cgtatgatta tcgcaataga cgcagaaaag gcctttgata aaattcaata cccaatcatg  105240
ctaaaaactc ttaataaact aggtattgat ggagcatgtc tcaaaataat aagagctact  105300
tatgacaaat gcatagccaa tatcatactg aatgagcaga gctggaagc attccctttg  105360
aaaaccagca caagacaagg atgccctctc tcaccactcc tattcaacat agtattggaa  105420
attctgtcca gggcaatcag gcaagagaaa gaaataaagg tattcaagtg ggaagagagg  105480
gagtcaaatt atttctcttt gcagatgaca tgattgtata tttagaaaac tctatcatct  105540
cagcccaaaa tctccttaag ctgataagca acttcagcaa agtctcagga tacaaaatca  105600
atgtgcaaaa atcacaagca ttcctataca ccaataagag acacagagcc aaatcctgag  105660
tgaattccca ttcacaattg ctacaaagag aataaaatat acctaggaat ccaacttaca  105720
agggatgtga aggacctctt caaggagaac tacaaaccac tgctcaagga aataagatag  105780
gacacaaaca aatggaaaaa cattccatgc taatggattg gaagaatcaa tattgtgaaa  105840
attgccatac tgcccaaagt gatttataga ttcaatgtta tccccatcaa gctaccattg  105900
```

```
atttcttcac ataattagaa aaaactactt tcaatttcat atggaataga aaagggcct  105960 gtatatccaa gacaacctaa gcaaaaagaa caaagctgga ggcatcatgc tatctgactt  106020
caaaatatac tacaaggcta cagtaacaaa aacagcatgg tatggtactg gtaccaaaac  106080
agatatatag accaatagaa cagaacagag gcctcagaaa taacaccaca catctacaac  106140
tattggatct ttgacaaact ggacaaaaat aagcaatggg gaaaggattc cctatttaat  106200
aaatggtgtt gggaaaactg gctagccata tgcagaaaac tgaaactgga tcccttcctt  106260
acaccttata cacaaattaa ctcaagatag attaaagaat taaatgtaag acctaaaacc  106320
ataaaaaccc tagaagacac tttgggaggc cgaggtggat ggatcacgag gtcaggagat  106380
cgagaccatc ttggctaaca cagtgaaagc ccatctctac taaaaataca aaaaattagc  106440
tgggtgtggt cgtgggcacc tgtagtccca gctacttggg aggctgaggc aggagaatgg  106500
catgagctga ggaggttgag cttgcagcaa gccaagattg tgccactgca ctccagcctg  106560
ggcaacagag tgagactcca tcaaaaaaac aaaaacaaaa acaaaaaatc aaaccctaga  106620
agaaaacata ggcaatacca ttcaggacat aggcatggga gaagacttca tgactaaaac  106680
agcaaaacca atggcaacaa aagccaaaat ttacaaatca gatctaatta aaataaagag  106740
cttctgcaca gcaaaaaact ctcatcagag tgaaaaagca acctatggag aaaaattctg  106800
tggtctagcc atctgacaaa gggctaatgt ttagaatgta caagcaactt aaacaaatgt  106860
acaagaaaaa aaaacaacc ccatcaaaaa gtgggcaaag gatatgaaca gacacttctg  106920
acaggaagac ctttatgtgg ctgacaaaca tgaaaaagc tcatcatcac tgttaattag  106980
agaaatgcaa atcgaaacca caatgagata ccatctcatg cccgttagaa tggcgatcat  107040
taaaaagtca ggaaacaaca gatgctgaag aggatgtgtg gagaaagagg aacacattta  107100
cactgttggt gggagtgtaa attagttcaa ccattgtgga agacagtgcg gtgattcctc  107160
aaggatctag aaccagaagt accatttgac ccagcaatcc cattactggg tatatatccca  107220 aaggattata aatcattcta caataaagac acatgcacac gtatgtttat tgtagcacta  107280
ttcacaatag caaagacttg gaaccaactg aaatgcccat caatgataga ctggataaag  107340
aaaatgtggc acatatacac tgtggaatac tatgcagcca taaaacagga tgagttcatg  107400
tcttttgcag ggacatggat gaagctggaa accatcattc tcagcaaact aacacaagaa  107460
cagaaaacca acaccatat gttctcactc ataagtgtga gttgaacaat gagaacacat  107520
ggacacagga aggggaacat cacacacagg ggcctgttgg ggagttgagg ctaggggagg  107580
gattggatta ggagaaatac ctaatgtaga tgatgggttg ctgggtgcag caaaccacca  107640
tgacacgtgt atacctatgt aacaaaccca cacattctac acatgtatct cagaacttaa  107700
agtataataa taataagata cagaactgca gaatgaataa gaactcacca accatctgct  107760
gccttcagga gactcatttta agacataagg actcacataa acttaaagta aatgggtgga  107820
aataataata agtggtgtca ctgatgtgga ggtagattat aaaactctta tcatatgctg  107880
gtggaagatc aaaatgataa aacgaattaa aaaatcagtc agatggtttc ttaaaaagtt  107940
ccatcaatat gcctctatct tacaaacctg caattctatt cctgaatctt tatcccaagg  108000
aaatgaaaaa gtaagtccac aaagagttct atatgaatat ttataggagc tttatttatt  108060
ataattcaaa ctgtaaaaat aatttcaatg ttcatcaata acaaaatgaa aaaataattt  108120
gcaacctact ggtacacttg aatactattc agcactgagt atcttaaata gcatggatgg  108180
agctcaaaaa tatactcagg aaagaagcca tgtatattct gtatgagttc atttacatga  108240
gatcatttac atttcctcca aaagaggaaa aactaatttc tgttgaaaga aaccaatgta  108300
```

```
tttgcctctg gcagtggtaa gggggtagca cagattaatt gggtagggac tcaagagagt 108360
ttctggggtc acagaaatgt tccgtgtggt gatgggagtt tgggctccac aggtataggt 108420
gttgatccaa aatcatcaaa aaaacaacat tgcagatctg tgcatctcac tctgtgggaa 108480
agtatatctc aactgtaaaa agggcagaaa ttgcttttaa acgctcagcc ttttagcaca 108540
tccagttgct tggagaacca gcttactcaa atggggtct aggctggaga ctaggtcaca 108600
ggcatagagt ctctaaactt tcccatggca cataatacgt ttcaggtttt ctcagagagc 108660
tgcaggttag taatctgagg attctgacaa gttgggtcaa cgttcctagg aggcatgaat 108720
gggagtgcat tctctaagat ccctccaccc cagggtcctt gctttctgtg cctcttactc 108780
cattgttttc tgactcctct gtagccactc gacctcttca gatcccattg tctacccagc 108840
catcgccctt tatgacttgg gtcccactgt tctttcatct catcctccat tccctcagtt 108900
tcggagtggc tgccgctagc agaggatgga ctgagagcag gagaggtggt cctgcccagg 108960
aacccatcct agagaaatgg catcctgtct gggagctagt tttttagggc aggttttata 109020
agtcttgtaa agccagacac acttgatcta cctggtatgt tatttacagt aatactattt 109080
tcataattgc ttttcactct aaaagtagag ccttttagct acactgtgag taaataaagg 109140
ggctggcctg ggaatggtat catgttggat gttgtttctt ccctgaagta atatatatca 109200
gttacaattt acatgttact gcagagtcct agagagagac acagaaatg agacagatac 109260
caatacattt ttatgtgcat taaaaaaatc taaggccagg cgcagtggct cacacctgta 109320
atcccagcac tttgggaggc cgaggtgggt ggatcacgag gtcaggagat tgagaccatc 109380
ctggctaaca cggtgaaacc ctgtctctac taaaaataca aaaaattagc caggcgtggt 109440
ggcgggcgcc tgtagtccca gctactcagg agactgaggc aggagaatgg cttgaaccca 109500
ggaggcagac cttgcagtga gccgagattg cgccactgca ctccagtctg ggcgacagag 109560
cgagactccg tcacaaaaaa aaaaaaaaat ctaaaatgca ctcttcaaaa tctatgtcat 109620
ttattctgga ggaatgcagt tggcagaagg aggaagatat tccgaatttt tcttgtatac 109680
atttatgtat gatctcagtt tttttatgga tcatagacca atttttgatat tttaaaataa 109740
aaattataat ctatcttgga aatttacatg gttctttaga acttgaggac cgttttttgct 109800
tttcggaata ttattgtacc taaaatggga atattacaac gtcactttt aacactttgt 109860
tataacaaag tttagacagc gctgggtgcc cctgaatttt ttcccgcctc ttgtgacctg 109920
tgttgtttg gaatttgcag tggcctgacc gagaactact gcaggaatcc agattctggg 109980
aaacaaccct ggtgttacac aaccgatccg tgtgtgaggt gggagtactg caatctgaca 110040
caatgctcag aaacagaatc aggtgtccta gagactccca ctgttgttcc agttccaagc 110100
atggaggctc attctgaagc aggtaagaag tctgtggcca gatatctaca catttgaaca 110160
ttgggatgaa aagagatgga aaatctgact gatgcagaag ccttccatgc tacacagaaa 110220
cttgagggta tggcaggtgg aaagaagcct cagcactctc tctggtggag caattttttgg 110280
cgcaacgtgc gtgggcggtg acttcaggaa tggtgcaaac ccacctgggc acttgactta 110340
ccactcactt tgttatgaaa ggggttatct cggtgttcca gacaaaattc caattctaac 110400
atcaggccaa atttgtgcca aatttcacac tagtgagtgt ttccaggcat ttattaaaat 110460
ggacagtgtt cattgcaatc ttcagcattg cagttgctga ggtatgtggc cgctgagttt 110520
gtcatcctgg ggaaacctaa tatgatgata tttattccat ctaatcctgg ggctatttgg 110580
cagtaaatac cacagaatac actatttctc tggcttattt cagtcttagg taggctctgc 110640
```

```
acacctatgc ttggaaggca ggaatttctt ggtgttcttg tgccttcttc tcatggaacg   110700
tgcatctttg gtgtgtgttg agaggaaggg tagtagactt ctgctttgtt gcaatgcagg   110760
atgctggaac aagaggattc cctgtctcta ctgtaaggga ataagatttt agcctccatc   110820
cttctctaag aagcaatgtg tctttgcctc caagtactag atgcaggacc atgaactgcc   110880
ccgtccacca gaagcttaag gctttggctt ttcaggagca atcatctagg gaactgtgca   110940
gggttttcat gtctgtcccc tactgacagc caatcaccat acagcctgca taacctaatc   111000
catcatcgtc tggtttcctg cctcattgtt ttcatgaaca accagtagag agccatacga   111060
aagagcttgc acatgagtct ttgttccaat tgtaagagca ctgataggtc cttttcccac   111120
caggttttga atataaaatt tctaagaact tattaaaata ttagaatgtt attaatctat   111180
tgtttttgct tcagcatgtc cttctgcttg tgagtatact aaagagaaca gtcataattc   111240
tgaaactact gtcctgtttg tgtcataaat tgcttcacat gtttctgcat actagtagtt   111300
actcagcttg attttgtcta ttttcagcac caactgagca aaccectgtg gtccggcagt   111360
gctaccatgg taatggccag agttatcgag gcacattctc caccactgtc acaggaagga   111420
catgtcaatc ttggtcatcc atgacaccac accggcatca gaggacccca gaaaactacc   111480
caaatgagta tgtctttgat gttacttgta agaggagcaa cagccaactt aagttcctcc   111540
tagaagagcc ttgcttcaag ctaacttgtt aggacaaatt tcccttagac ccagaaggtg   111600
tgtcaaaatg tccagacaac tttgcttttg atcaaagagt ctgagagaat aggtatttta   111660
ggcttgctat cttttctaat agtctgatgg aagcagaagg ctacatggag ctgatgaggt   111720
cttttaaata taaagctcaa gagatcaaat gatcaaatac ttagagtgcc attctacaag   111780
gctcataaaa gatcaatgca ctcttcacc catgcaattc tatcattcta acctcccttc   111840
tctgaaatga aggcttttg ccattttgt catgggtcac aagtaaataa ttcacatgta   111900
tatgagtata tatataacca ggtgtgttta ttcagactag tatgtatata tatacatata   111960
tatgttcata taagttagta ttcatatata tgttcatata tatatgttca tacagactag   112020
tattcatata tatatacata tatatataca cacacatata tatatatata tatatgttct   112080
agggaaacat gcaaggtttt tatgtctgtc cctgactgat gaccaaatac cctatagcct   112140
gcacagctgc aagctgtata gccatacaat ttgcaggaca cacacacata cacacacaca   112200
cacacacaca cacacactaa catataatat aatataatat aatataatat aatataatat   112260
aatataatat aattaatata tataaacctg tgtgaacaca ctgggttcta agctccagtt   112320
ttctgaaggg atatggggttg ccaggagagg aagagcaaaa gcaagaatgt agatgagaat   112380
taggaagtaa acagatatgg agattaaaat gggcaggtac atggacaaaa aaccaggtct   112440
gacaaaaact ggctttctgc cataaatgac tataaaagat attaaaaaac actttccaca   112500
tgttggacaa gagacagtac aggactgaga taatttagaa aaggaaatga atgagcgcaa   112560
ctccgtaact attatgactt tcttcctgga gaaccttcct ggactgaagg gcaaggaatt   112620
ggagccaaag ccaaccacag cagtcttgct gaactgagga aagagactgg agtttgggat   112680
agctaagaaa atgtgtattt tctatgctag gtaataatga gaaagaattt gtggtgaaaa   112740
ggagctgaag gaatatgcat ggaagtctaa tataaactgc atatgcacag ggagaaattc   112800
tacaaagtgg gacagagaac cactactggg gaaaggacaa attcagggaa acagtgagct   112860
caatggtgac gccagagctc acgtagcact gggggatacc ggggttctga tcagcccgag   112920
gagagacacc tcattgaaca tctcgggcat tcagtgagaa ccccagaaaa gtcatacttt   112980
aggagtagga tttatgcctt cttagaataa agactacccc agaaacaccc tagtaaagct   113040
```

```
taaaaaccaa gtctaaaagg acccaaatga tctccaagta aattaactgc ctgacagaag   113100
aaaactcaac catcactgga ggtaaataac atgattacag tgctctgtaa tgttgcattc   113160
acaaggagtg acatcattta aaaatttatg aggcaggaaa aagcaattag tgtgatccat   113220
aactaggaga aaaaccagtc aatacaaata gaccaagaaa tagtagaaac gatggaattg   113280
acaaagaaat taaaactgta tatatgataa ttgtgttcaa agatttaaag aaaacatgaa   113340
catgagggaa acaaatgcag aatataaaaa aaagcaaatg cgtaaaacaa ccaaatggaa   113400 attaagaac tacaaaaaag tataaccttaa ataaaatact cactggatgg ccttaatatt    113460
agtttataca ttacagaaga aaaagtgaac cagaagataa ctcaatgaaa gccatacaat   113520
ctgtaagaca cacacacacg cacacgcgcg cgcgcgcaca cacacacaca cacagagaga   113580
gagagagaga gaaagagaga gagagaaagg ctgaaaaaaa taaatagaac cttaaggata   113640
tcagtgaaaa tagcaaaaga tttaatatat gggtaaagca agtcacagaa ggacgggaag   113700
gagatattgg gacagaaaaa aatactcaaa gcaatgatgg ctgaagactt tacacgtatg   113760
aagaaaatga taaactcaca gtcaagaagc tcaatgaatc agaaatagta ttttttaaaag  113820 caaaactcta tgatttactt gggtacatta tagataaatc gtccaacatc aaagataaca   113880
aggataatct tataagccag aggaaaacaa tatcatttac atagagggac agtaatgaaa   113940
gtgaccgatg ccttctcctt ggaaacaatg gcataacatc tttaaagtga taaagagaaa   114000
taaaaacaga tcaacctagg acgacatgtc cagccaaaac aaacaaataa acaaaaaaac   114060
cctttaaaat aaacgtgatg taaatacgta ttctgccacc tccagaggaa acaagcaaaa   114120
aaacaaaaga atgtttccaa ggcaggcttc tgtattaaaa gatttttaagg aaagttattc  114180 aggtagaaga aaaataatac cagatgggaa ctttaatcca tactaagtaa tgaagagccc   114240
tggaaatggc aaatggcaat gtcaatataa aatactctta tttatctaat ttttaaatgt   114300
atttaaagga caatttgtga tattaattaa aataatagga atatattgtt gtttcaacgt   114360
atgtagtagt aaaattcata aaaacagtag cacaaataat gcagatgata actggaagta   114420
tactgttaat gagttttttg cattatccat gaagttatat aatattaata gatggttgaa   114480
tgtgatagtt taaggtggga tattataaat cctaggacaa ccaaaaaaat ttaaactgag   114540
aggaatggat agtaagagga atagtccttt tatgcaaaag aaggaagaaa aagaggaata   114600
aagaatataa aagatatggt gtaaacagaa aatacatagc attattgtag acacaaactg   114660
aactacctta tgagtatatt aaatataaaa ggattaagca ttacaaataa aaggcagaga   114720
ttgtaaattg aataaaaacc acagctaagt gtgttctttt tagaataaat actctttaag   114780
tgtaaagatc tactttaaac accaaaatat gaaaaaggat ataccatg aaaacctgaa     114840 tcataaataa gctggagtgg tgattaatgg atgcaggcac tcctaaagac taataagtga   114900
atgtggtcaa attgaagaaa caaaagtata tacgtgctca atgtgcaaaa acttttttctg  114960 tatacatgct atgatccttt ggaaaattaa agttttaaag caatatcact gacaatagta   115020
tcaaaaccaa aaaatattta gtgataaatt tcacacacta tgctcaagga ctatacacct   115080
tgcactagaa aacaatgttg aggaaagaat taaaagatct aaatatacac catgcttata   115140
gattaaaaga ctccatatca gttctcgtga aattgatctt tggatgaaac ccacacccaa   115200
gcactattgc aacagtcctt ttttggaaaa aaaaattgga ggacttatat accttaatat   115260
aaagacttat aaaagtacag gaatcaagac atgtggtatt ggcctggccc cttggctcat   115320
gcctgttacc ccaacatttt gggaggctga gtctggagga tggcttgagc ccagatgttc   115380
```

```
aagaccagcc ttagcaacag agtgagaccc tctctctaca aaaataaac aattagatcg    115440 atgtgatgac ttgcacatgt agtttcagct actcggaatg ctgaggtgag aggattgctt    115500
gactcaggag gtctagccat gagtgagcat tgatcatgcc tctgcattcc agcctggatg    115560
atggaatgag acactgtctc aaaaaaaaaa aaaaaaaagg atatgtgtta ttggccaaaa    115620
aagtatgcaa acctaaaaag ggatggccca ccaccagacc cacatacata tatggtaaat    115680
ggattttccg tatagatggc aaagcaattc aatggagaca aaaatgtttt acaaaatcat    115740
tctgaaccat ttggatatcc atgatacaaa acaaagcag aacttgactt ttgcttttca     115800
tctcaaatta ttttgatatc tcttccacct aagtgtcaga gctaaaactg aacctgaaat    115860
atgaaagttc catgaaaaaa tataaaatct tcacaacctt ggagaaggca aacttttttg    115920
aggcaggagt ctgtaaacac tcactataaa ataaaacaaa ttataatgtg ggctttcatg    115980
aaaactcatg cttaccaaaa gtcattgtta agaaaataaa taggcaagta acacatgaga    116040
agaaaaatgc tctctgtcca tatatctgac aaatggcttg tgtccagaat ataggaacat    116100
ttctcccact cactaaacag aggacaaaca actaatgggc aacagattga ataggcattt    116160
cttggggata gatagatgta cacatagcca ataagcacct gaaaaaatgt ccagtatctc    116220
agccatgaaa ataaagagt tataatcatc atgagatgtc accaacacc caatggacat       116280 ggatattatt aagaagacac cacagtaact gatgtcactg atgtagagca aggatgtgaa     116340
actctctcat atgctggtga aagtgcaaaa tgatacaacc acttttgaaa tcagtctgat     116400
agtttctcca aaagttcaat aaatgcactt ttaccctaca aacctgcaat cctgtttgtg     116460
aatatttacc ccacagaaat ggaaacataa gtccacgaag acatctccaa gaatattcat    116520
agcagcttta ttttttataa ccccaaactg tagacaattt caatgtcaat caataagaaa    116580
atgaataaat aatttgtgaa ctagtcatac aatggcatac tgttcagcaa taaagggag     116640 catgtttttg atactctcaa atagtatgga agatgctcaa aaatattaca ttaaagaaag   116700
atgccagata acaaaaatga acattatgta tgagtctatt gatgtaaggt tccagaaagg   116760
taaaactaat ttctggtgaa agaaaccaat atcatttgcc tctggccatg ggaagagagt   116820
agcagagatt gattgagcag taaaacgaag ttttttttctg gggtgatgta aatgtcctgt   116880
attgtgattg aagtgtgagt tacacaagtg tacatgttca tcagaagtca tcaaactaca   116940
tctaagatct gtgcatttga ctatacatga aaatatacct cagttgaaaa tagatcaata   117000
acctccctca tatactatac ttgctaacac agccagctgc ttggagaacc agcttgctgg   117060
aatggagaat ctgggcttga gactgggtca catgtataga gtctacag agacaatgtt     117120 gcattccac ggtacataat acatttcaag gtttctcaga cagccacatg tcatgaatgt    117180
gaggattctg agaggttgga gcaacattcc tgggaggaac gaaggggagc acattctcca   117240
agatccccca ccaccggggt cctcaccggc tgtgcttttt ttttttttttt tcttgacaga   117300 gtctcgctct gtcgccaggc aggagtgtaa tgggcaatc tcggctgatt gcagcctcca    117360
actccagggt tcaagagatt ctcctgcctc agcttcatga gtagctggga ctacagatgt    117420
gcgccactgc gcccagctaa ttttttgtatt tttagtagag acggggtttt gccatgttgg    117480
ccaagatggt ctcgctctgt tgacctcgtg atccacccgc cttggcttcc caaagtgctg    117540
ggattacagg cgtgagccaa agcacccagc ctgtgcctct cacttactca attgttttc    117600 tgaaccctcc atagctggtg gacctttta gatcccatag tctagccagc cctctcactt     117660
tatgccttgg gtcccactgt tccttcatct catccccctt ctgtcagtcc cgcagtggct    117720
gtggccagta gaggatggac tgagagtagg agaggaggtt ctgcccagga acccatccta   117780
```

```
gagaaacagc atcctgcctg ggacctagtc ttccaggtca gctttttataa gtcttttaga   117840 ctcaaactca cttgacccac ctgaagtggt attgacaata atgctatttt catggttgtt   117900
tttcactgta aatgcagagc cttttagcta cacgactagt acagagagta agggaggctg   117960
gcctgggaat gatatcatct tggatggcat ttcctccttg gagaaatata tgttagttcc   118020
aactcacatg ttactataca gtcctgtaga aagagataca gagagttaga caggtataga   118080
cgcatttgta tatgcataac aatctataag acacacatca aaatccgtat accggttcct   118140
ctaggggtat gtgcttggca gaaggtagaa ggagggtatt ctggttcctt tcttttgcac   118200
atttatgtat gatctcagtt tttatatgga gcattgatag ggtttggcta tgtccccacc   118260
caaaatctca tcttgacttg taatctctat aatcctgata atccccatgt gtcaagggca   118320
ggaccaggtg gaggtaactg gatcatgggg gcagtttctc ccaggctgtt ctcatgacag   118380
tgagagagtc tcctgagatc tgatggtttt gtaagtgtct ggcatttccc ctacttgcac   118440
ttactctgtc ctgccgcctg tgaagaaggt gcctgtttct cccttgcctt ctgccatgac   118500
tgtaaatttc cagaggcctc cccagcaatg tggaactgtg agtcaattaa aactcttttc   118560
tttgtaactt acccagtctg tctcgggtat ttcctcatag caatgtgaga acgggctaat   118620
acaagcatat actactttg atattttaaa ataaaaatta tcatctatct ttgaaaggca   118680
tgcacaaatg ggaagttgag gaacatttgt gttgtggcaa ttgtatgata cctttaatgg   118740
gaatatttca aagacacttg ttaagacttt gttagaacaa aatgtagagg gtgctggatg   118800
tccctgaata ttcttccgcc tcctgtaact tgtattgctt tggaatttcc agtggcctga   118860
caatgaacta ctgcaggaat ccagatgccg atacaggccc ttggtgtttt accatggacc   118920
ccagcatcag gtgggagtac tgcaacctga cgcgatgctc agacacagaa gggactgtgg   118980
tcgctcctcc gactgtcatc caggttccaa gcctagggcc tccttctgaa caaggtaaga   119040
agtctgtgtc ttaccttgtc tagcacatac ctctctatgt gcttggacaa cgggatgaaa   119100
agacatgaaa aaccacactg atgcagaagc ctttagtgct acacgggagc tcgagtgttg   119160
gttgaggttc tgccatgacc aaggaagtct cagtgccgtc cctgggaaag ccagagctgt   119220
gatttttggc acaacttgtg ggagtagtga ctttaggact ggcgcaaaac ctccaggtgt   119280
ctcaacttaa ccactcacct tattctaaaa tgggttattt cagtgtccca gtcaaattcc   119340
tattctaaca tgctgtcaac tgtgtgatta tttccaagcc aataagcatt tccagtaatt   119400
tcttaaaata gtgttcattg cagtcttcag cgttgtggct cctgagggat gtggcccctg   119460
attctgtcgt cctagagaag cctgacatga ctgcattgat tctgtatcgt cctgggtcta   119520
tgtggctgcc tggctgtctg taatcatctg ttttatttt atttttttct acagactgta   119580
tgtttgggaa tgggaaagga taccggggca agaaggcaac cactgttact gggacgccat   119640
gccaggaatg ggctgcccag gagccccata gacacagcac gttcattcca gggacaaata   119700
aatgggcagg tctggaaaaa aatgtaagcc actttgattt ggactctttt tccctttgct   119760
gacaaatctt ttcaaacaga agagggggcag aggaaaatac tggaaagact tcaggaggct   119820
aagcgtaatt agccttagca tggaaagtgc aagcagcaca ggccagcaaa gccccacgcg   119880
tgtgggggtt ctcaggcctc ttctcttttg acatttcttt actgtttcca ttgttgggtg   119940
ctgtttctcg tttctagtgc ttgtcctcta agccaggggt ccccactcca gtactggtac   120000
tggtactggt actggaactg gtaattatct gtggcctgtt aggaactggg ctgcacagca   120060
ggaggtgagc ttcgggggag caaacaaagc ttcatctgta ttttctgctg cttcccatca   120120
```

```
ctctcatagc tgcctgagct ctgccagctg tcagatcaga ggcagcatta gattatcata   120180
gcacaaaccc tattgtgaac tgcacatgtg aggaatctag attgcatgct ccttatgaga   120240
atctaatgcc tgatgatctg tcatgcttcc atcaccccca gatgggacca cctacttgca   120300
ggaaaattag ctcagggctc ccactgattt taccttatgg tgagatgcac atttatttca   120360
ttatatatta caatgtaata ataattgaaa taaagtgcac gataaatgga aggtacttga   120420
gtcatccttt aaccatcgcc ccctcacccc aggtgcacag aaaaattgcc ttttatgaaa   120480
ctggtctctg gtgccaaaaa agttggggaa ccacactgct ctgggttcta gtagtcagag   120540
atgccctcta tgaggcttaa gtcagatttt tctagaaaag atttggatgg gccatcaggt   120600
caccatgaga cttcccttag cctcatgcat tctctgtgat ggtttacttt ggggcctatg   120660
aatagggaag actgagatat aggaaaaacc aaagtgtctg tgttcccca  ctctcacacc   120720 catgtaacat aacacttctc acaccagata tgggggattt tctcctcaca ccccaagcga   120780
gtctccagca gataccagct gggtgtccta caatgtaact cggtcctgac actctatctg   120840
gagacagtgt cagatcccac aagttaaggc tcagtcctac aagactgccc cactgcagat   120900
gccaatccca agttgcaggc tgtgacctgt acttctgccc agctggataa agatctgttt   120960
ttctatatga ccctccatgg gtttgattac tttgctagag tggctcacag aactcaggga   121020
aacacgttac ttttatttac ccatttatta taaaagatat taaaaaggat cctggtgaac   121080
agccaggtgg aagagatgca cagggcaagg cacgtgggaa ggggctcaga gcctctatgc   121140
cctctccagt gcaccagtcc ccagtaccct aagtgttcag caacccagaa gctctccaag   121200
tgcagtcttg ttgggttttt atggaggctt cattacagag gcacagttga ttacatcatt   121260
ggccatcggt gatcggctca ccttcggccc ctcttccctc cctggaggtt ggagggtggg   121320
gctgaacagt tccaaccctc aagtcacatg gttggttccc ttggcaacca gccctgggg   121380 ctatccagga acccaccaag agttgcttca ttgcagctcc cttcacccag gaaactccaa   121440
gggatttagg agctctgtgt taagaactgg ggggcagaga cccaatatac atttcttatt   121500
ctatcacaat atcacaggaa gctaaggatg atactgcctt tgtgtgtctt ggctgtggat   121560
ggtgcataat gcatggaagt aagcatttct gaatcaacag caaacaggct ttatcaggta   121620
gaagacccct cagcgcccca gggacaaagc tcatcaatga tgtcccactg tcctctgagg   121680
ctctagctct aagacctcca gtgggtcaag ctcctggaga agtggcacat tctccaaaga   121740
cccttcaggg tcaccacacc ctggttaagg gtgtggcctc ataactcctt ttgactatga   121800
ctgatggctt acagcataga aagaaataac tttgtcaaaa aatataataa tgatagaaag   121860
gaagaaggaa cgctccccttt tgtcttctaa gaatagatgt gaaatgtgtg tgccttagaa   121920
tatcttctcc ctctcctgct ccacgtgagc tggagcttac atgcctgctt gttttcagta   121980
ctgccgtaac cctgatggtg acatcaatgg tccctggtgc tacacaatga atccaagaaa   122040 acttttttgac tactgtgata tccctctctg tggtaagttg ccttctgttt tggtaaggaa   122100
actgcttcct taatatggat ttggaaaaaa aaaagcaaaa aaaacagaaa atggcttttg   122160
agctgagtgc ttctggggag gagatggctg ccctctccac cagagcctgc ttttcatcat   122220
ggccaccttg aacctgccct actattggcc ccatttgtta ggaaaacacc cgcccctccc   122280
accacacaca cataaataaa ataaatgtca aattcccaaa gggcaaactt agaggtgatc   122340
taatcagccc gggatagtcc caccgaaccc ttctttgtct agcgtgggat gcatgaaaaa   122400
caaatttaga gtcattatga tgaaaaactg tcctcttctg cagctgagaa gaaaaaaaaa   122460
atacgagcag caggaaacag ctaagcatgt aatgcacatt gtaaacctca gatggccatc   122520
```

```
ctaggaaatc aatgaagggt agtgcagctc tttagcccca gatggccttt ctcgtaagat 122580
tactactcat gagtcccatt agcgacattg cttagagact gcttgttagg ttccttcctc 122640
attgctctga gactcttatt gggagtatga ggcttggatc aggggaaggg gaattgacat 122700
tagatcttaa atgattgggg taacaaatcc atggggggaaa aaaagccact tgtacttgtt 122760
ccctattttc ttcctgctga ccaatcaact tgtctgtccg agttacagaa caccaccctg 122820
gacttttctt ttgtgtaatt tggttgcttg tggttgggtc tgccatgtga agggaccttg 122880
agctggggga agaaggttgg cctccaagtc cactgaagac cagcatcctg agattgcctg 122940
gggaggtggt acagggcagt gatgaagatc atggagccca cactgcccat cgtcacattt 123000
gggccactcc tggggagagc aagagggaag aaggagaggt tagggtgata ggaaagattc 123060
tacttggcca atattattat aatgtggcat tgtggtctct ggatttagtg tgagttgata 123120
gctgactttt ttctcgagtg ggtgcttttg ttctattttg tcggtgctat tgcagaagca 123180
tcttggtggt tcctctacct caaagtctct tgatggggtc agttccagtt ctccgcttct 123240
ggccccatct agtacacgcc actgcctctc actgcctggg ctctctatcc ttgacaggct 123300
gccttgaatt taagcccagt ctgacttacc tgcctcaaac acccacagta gtgcctggga 123360
ctcatgcacc tttgactccc atggaaggga agtgcagtag cttcccaggt gcaattctgc 123420
tgtcctcacc cacattgagg atgtatgaga atcaggttct tagagattgg agaaagaagg 123480
aagaatggga acaagatttc ttccaatgga ctgtgaggtt ccccaccttca ctttgatgta 123540 agacaagtga ggttaacccc aagcctggtg aggagggttc ccatcagaca cttggaaatc 123600
ctgaggactg tttcctgcag aaggatgtgg ttggtgggat attcaggttt gactcatgat 123660
tgagaaagtt agagcctctg gttggagaaa gagtttaata actatttcat ttccaccaac 123720
acattcagta cgaataataa ataagtaaaa ataaatagaa acattcagtt ttattttgaa 123780
tagtaggagt agggtataat ttctgtagtt actcttttag tacaatgatg catgtttact 123840
gtatgtaagg catactagca gaaattgagc tcagcactag aaaagatgat tgcattccat 123900
gccatgcttc ttttttacaa aagacttcta tagatagatt ctcaaaacaa cccacagcaa 123960
atgaaaagtt atttggaaaa ctcaggttcc agattcactg gagtgtagaa tctctggttg 124020 gttgggggagg aatttcctct tgcagttgtt attaataatt atatgaataa ttattaacta 124080
tattaatatt tatagttttg aagaccttga agggctggag acaacagaga agcatttttg 124140
aacaccctct gtagcccctg cactgttgta ggcattgatg ggtggtacca agatgggac 124200 actttcccta cctccagaga ccttgtgggc ttgctgcaga gagaaggcag ggaggaggaa 124260
aagaagaata gaggcacatg tgtgtaaatt accccacag cagtcagtta gtcatgggag 124320
gctccccaga agaactgtcc tgaagctggc tgagagaagg caacatttca acataggaca 124380
gttatccttg ctacataaaa tcacatacac acatgcacat atgtccacac acagagactc 124440
acatgcaaaa gaatcctttg tgcctttcag taaactttac atggtttaga aagaacttat 124500
atttccttga aggagagtg tccttttgttg tttactacca cttttaaac ttagaaagaa 124560 aaatctaaag agtgtttatg atttaccat ttaattcac ctttgagatg tgaaaaacta 124620
gtgcttggaa ttcgtcctga attaaacgac acaattgcta acttggactc aaatgcgact 124680
tcttttccca ccttgtgcca cagcatcctc ttcatttgat tgtgggaagc ctcaagtgga 124740
gccgaagaaa tgtcctggaa gcattgtagg ggggtgtgtg gcccacccac attcctggcc 124800
ctggcaagtc agtctcagaa caaggtaaga acaggcccag aaaccatcta tactgtcctt 124860
```

```
ccatgtaagc cccacaaaac ccttctacat ttacacagaa cccacacagc tgatgcatca   124920
atacctgcct ctctgttttc tgaaggagga aaaatatag  aaaaattaaa aaaagttata   124980
ttattatagg ttctctactt ggaaaatagc caaaatacaa atcttttct  tgatctgggc   125040 agttccatca aaatctgtag gcacagtgat ttgcaccaag ttccaatact tttggaaaat   125100
attgaagatg ctctgagggt ttctatggat atccattgtc tcactgtcag atgaaaagaa   125160
agggaagttt ttagaaatgt gacactttgc agtgagggag gacaagagca aacttaccta   125220
cagtctatca caggcacaga ttttttttta cacttttgtg aatcattgaa ttcaatgccg   125280
aggctattca tctattcaca aacacatgaa caaattatgg gttgtgatcc ccataaatga   125340
agagtaatca gtccgaaccc acagaacctg gacattttgg gtatcgtttc agtggaacat   125400
gcaattcgta agttcagttt gcttgggtgt ctcttaggaa gaacacatag gacacagacc   125460
catctgcctg catgttttgc ttcctcatct cctttctaca ccagggcacc tgtgctcaat   125520
tgctgttctc ctctaaagag acttccttct gtaagtttgt gaaatgccat cgacaaacct   125580
gatcgcatcg catttcactc tgctgttgag ttgattttc tttactttat cgtttgtaac    125640
ttcttgctct acagagcttt caccttccac atatttcaga ttcattcttt cctaaactgt   125700
gtggtggtct atgtcctcac tgactatcaa catactgcca tcatgcactt cctatctcta   125760
ttcctcttcg ttgcaatctg gctccaagtg gctcacacca ttattctgat ctatcaactg   125820
cctacacagt cctagaaagt aagtgagtca agaaacatcc cccaaaagta aactttcag    125880 gtaagatcag aagaccctca tgagtcactg ctgctcagga tcgtatctgg ctccttgaag   125940
agtgaccttg catagatctt gtcataaaaa atgaaagaga ccttgggaag gtcttgggct   126000 ggtcacttt  gtcagagtcc agggctgtgg ggtgaaagcc acagctatag agcttcattc   126060
tggagtcact tagctttgct ctcctgggga caggctgtgc ctattcttgc ctcaggcatc   126120 aaaaaagtg  gcacagatgg gcccttctga aaaatctcac tactggagca cagctcgaag   126180
tttctactat cctgacgttg ggcggtagtc ctttgctttg ggaatatgaa catgatcaaa   126240
actgagtgaa cttgtcttcc tggctttctg tacaatgaag tagaacaaac catccaattt   126300
gaccaaagcc ttggcatgtt ttcttttctag gtttggaaag cacttctgtg gaggcacctt   126360
aatatcccca gagtgggtgc tgactgctgc tcactgcttg aagaagtacg tttaagggaa   126420
aactgacatg gggtcttatc ttcaagactt ttttcctccc tctcttcctc catcccttct   126480
ttcttcccac cctccccttc cttcctcccc acctctcttc cttttctgga aggaacacta   126540
ggaaccaggg aatgcatgca gaatcctgag gcagaatttc cagggcaatt ggatgagaga   126600
ggagggaagt gtttctagag ggaatctgca gagggaagac ccagtgcaag tgatttttg    126660 gacctgtata aaccgcagga cagagctgtt cactaccaga ggcatcaatc tgtattgcat   126720
tgctctagag caatatctga ggctgaataa tttataaaga aaagagttta attggcacat   126780
gtttctgcag gctttacagg aagcaggatg ctgtcatctc ctctgcttct gtgtgggcct   126840
aaggaagatt acaatcatgg tggagggcaa agtgggagca ggcatgtcac atggccagag   126900
caggagcaag agacagagag agatggggtg ggggtgctgc acaataccaa atgaccagac   126960
tttgcaagaa ctaagagtga gagctcactg atcaccatga gatgtggcc  caagccattc   127020 aagagggatg cacctctatg atccaaaccc ctttcacagg ccatagctcc atcactgggg   127080
actacagttg aacacgagat ttaggtgggg acaaatatac aaactatatc acagtctctg   127140
atgaaacaga ttgagaacag accttaactg tcagtttcca gcaaattgtg aattttgttt   127200
cttgccactc ataagtcact gattctgggt ggccgagggt gtcagaggga cagcgccaag   127260
```

```
ttcatggcac agaggatacc tgaaggggct ggaccatatt tttctcttga catcctcatc   127320
ttttctaggt cctcaaggcc ttcatcctac aaggtcatcc tgggtgcaca ccaagaagtg   127380
aacctcgaat ctcatgttca ggaaatagaa gtgtctaggc tgttcttgga gcccacacaa   127440
gcagatattg ccttgctaaa gctaagcagg tactcgctca cctgtggtct tcaccccacg   127500
ctggtgaaga tatttgcttt atgtctgggt tttatgggcc atggccactg catggcagtg   127560
gggaggaact gtctatcaca tgaaaggctc aagggctttg gggacagcat caatcttcaa   127620
ccccagccct gccacatgtt agttgtgctc tttaaaaagg cagaaggatt cgtttcctca   127680
cgtgaaaaaa gagataccct gttacccgta aaacttactt aatgttcacc agttcatcca   127740
cattcatgat cagggaaagg ttgttattcc aggctaacta ttctcctttc ataataatat   127800
gctggagaga atcaaatgag attgcatttc aaagcgcttg aaaaaccacc atatcgagcc   127860
atgcttagtg tgggcgcctc taatcactgc tattcaggag gctgacgagg aagaattgct   127920
tgagcccagg acttcaaggc tgtaggcagc tatgattgtg ccactgcact ccaggctggg   127980
tgacagatca agaccctgtc tcaacaaaag aaaagaaaac aaaacaaatg aacagaaata   128040
ttccacaatg tcaaaaaaaa aaaaaaccca cacaacatac aatttacaaa tgcaaataat   128100
aatattattg ttgtcttctt tgattttctc tttcctggtg aaattttgtt ttattaagcc   128160
tgacaaagtg ataccttgc ttacatcact taaagttagt ctatttggac ctaggtgaca   128220
gtacaatcag ctaagaaaca gtatttgtag gagaggcagg tttgggacag gtgacaaggc   128280
atgtggggtg ctcgctgtgc tggtggctct ggaaggcagg gtgtcaatgc agacagggat   128340
gagcatggcc tggttgggaa ggcatggggc aggcaggagc ctgagctgct ctcctgggcc   128400
tggtcacaag cccatggcag cttctctggg tctgtgaact gaggggtgat gtcctggaat   128460
cctctgacac tctaggaagg agagaagggc cttttctggct cagcctttat aaacagtagc   128520
tgatctccct cttgctcccc agggtcctcc ccaccatccc agcaaatgtg caaatacaag   128580
atctctgctc ctcatggtcc tcagagagct ggggtgttct gatggcttga acaagtcact   128640
taggaaatgt ggggttttgg aggcattctc tgataggctg atacgttttg agtttagagt   128700
tcccaccgca catccccaca cccctagagt ctagggcatt tagtgctcca tgagggaacc   128760
tgtagagtga ggacatctgc atcacaggct gggccttcta gtgtccagaa gcagaaagtg   128820
tgtctgcttc aaagttggtg ctaatgatga tttttggtca gaatacggca tttctcattt   128880
ccattccttt atccccttga acttactaaa gtagaatcag gtctaaaaac cagagttcta   128940
atctttaaga gtccctggga ttctaaggta tatgaatgtc cttggaaaac aataccattt   129000
agttcatgca aggtgcttat ttcccatcct cttctattg atgtctagca ttttactgca   129060
ttcttaccac cacggtttag taacattcac gaggaggaag tggaggatcc agatggagca   129120
acttgctctg ggcacacaag gcatttgcaa ttttataccc tcttgatgat gtctcagcca   129180
gacattctgc ccagtcatca atgccctctt caattaatat gaaggacac acttggcatg   129240
agattccaat cgtgcacaga atatacatga gaagtgtgcc tttgtcatcc ctactttcaa   129300
aggctaaggc caccctcagt ttcttgcatg caactgatgc cttttcaaatg aaaccttaca   129360
tctgtgtagt ccataggcaa ccacaggcaa atgtgagggt gaaacgctgt gttctacatt   129420
gttctgtgtc agtgaagcaa ggcagtgcca gctcagaggg ctctggggct tcaaggcagg   129480
gatgcctggt tgtaggtact gccacttcca gctgggcagt gaaacataac tgctaatact   129540
ttccttacag gcctgccgtc atcactgaca aagtaatgcc agcttgtctg ccatcccag   129600
```

```
actacatggt caccgccagg actgaatgtt acatcactgg ctggggagaa acccaaggtg   129660
agatcaattc cattgcccac gtaacaaatt gttttttgacc ttcagtgcat gttacaaaat  129720
gagcattttg gagatagttg tacaaattcc tacccatgaa tgtggtctac ccactcctga   129780
ctttgcctgg acacctgtct atgtctccat aatcagtctt caaggaactt gggcaagggg   129840
agcggtgcca tttccttgag tctctctctt ttttgttttc agaatctttt aattttttt    129900
gtaatgattg tatgtttccc ttacaacaaa aacaaacacc agtagaggtc tttgagtctc   129960
ttaatcataa tttcagcatt catattgctt ccccaggtaa gtggggtttt gacccagccc   130020
tcaagttaag ggtgttagat tatttttcat gtgaaattag acagactgcg tttctaaaca   130080
tggtgcaaaa cagtaacgac aaaagttgta attaaactat tcttcttccc aaatacccac   130140
atgtctaatg tgtgtgtgag ggtgttaggc aggggacctg aagctggggg agaggcagac   130200
agttcccatg gccccaagtc taggatggca tttggtattg gttgatgggt gagagcaaga   130260
gagggaatat ttttgtgcat gatgtggtat cagcacctgt actacatttt atggattcct   130320
tcttctcttt gcggtatgcc ctgacaataa ttatatccgt cagccttacc cccttggcag   130380
taggaaaact gaaactgtct taaagtctca gctctacttt ctcagaggtg caggcaaggg   130440
cactgggagt ctggggccct ggaaaactgt tctgactctg ccacttgcca gatagacctg   130500
aactagacac gttaccctctt tgtaccactt ggctctaatc ccttatctgt aaaaccagca   130560
ttttcaaatg gtgctttgca catcagcctt tgcataagc tttgatttga taaaatgttt     130620
tttgtgtttt taaaagatt aaaaaccaca ggtttagata atttcaaagt aggcttccct    130680
ttttctgtca ttttcctatt attttaaaa cctcacctcc ttgactcctt gttccctttt    130740
tctgcactgc tgagtctggg agcactgagg ccaggtaaaa ggaaacttgg caaatgaggg   130800
gcacctatgg gtgtgggagg ctgctcctgg tgtttgcata tttaaaatt taaatgctac    130860
aaaccactgt gagttaggta ttattgttcc tattttacca ttgaggaagc tggggctcag   130920
agaaggtgga gggtggtaca gacaaacctg aattggaacc ctggctcctg cctatgggct   130980
gtcaggactt agaaaagtcg tgagctctcg ctgattgttt cctcagctga tgtgggctgc   131040
agggctgtta tggggaaat aataagaaag tgcatcaagt gctgagcaca tcctaagcac    131100
tccatcatgg cagctcctac tactaataaa gaatagaatt atatctaaca tgattctttc   131160
ttgcaagtga cagaaaatcc aactcaaatt ggattaagca aaacaaggga aattcttagt   131220
gagctgcaaa gttttcaggc tcacatgatg gccccaaatc ccaggtcctc ccaatcatgg   131280
agtaggcact atttggggc acaaaggtga cattcccatg gctgcagatg ctgtggtgct    131340
gtggctgtac cgggaaagaa taagaaaggc cactctccca attatgtgaa caatagtctg   131400
cccactctga gaagtcaaac ttgggtcaca gtcctgcccc tgaacccatc actgactggc   131460
tctgacctgc accaattgtt ccatgttgga ggtgaaggca agacccact aatacccata    131520
aggggcaaaa gttagataga tccttcaaga ggattatggg aggtagggca aaaagctgct   131580
gggcagccag aaagcaaaca gagcctctat gatacctcaa ctgatgaaag catgaagcta   131640
aaatcataag gatctgggtg tgagttctgg ctctcccatc ttccatgtga cattgggcag   131700
ttatttaatc tcttttagcc tccgcttcct catcttacat atgagataat tgtgaggatt   131760
aagattacac ataatcatca tcatcaccgt ccaccactac caccatcatc cccatcaaca   131820
tcatcgccac cactatcatc attcttactg gcactaccat caccatcacc accattccac   131880
caccatcacc aatatcatca ctgtcaacat cattaccacc atcaccatca ccaccaccat   131940
catcattact accactacca ctactaccac catcaccatc accaccattc caccaccatc   132000
```

```
accaatatca tcactctcaa catcatcacc atcaccatca ccaccaccat catcatcatt   132060
actaccacta ccactactac caccatcacc atcaccactg tcccactact atcagcatga   132120
catcaccatc accaccacca tcatcattac caccgctact accaacatca ccatcaccac   132180
aattctactg ccatcaccat taacattacc accaccatca tcactatcac catcaccacc   132240
atcatcacca ctgccattat cactgccacc atcatcacta tcctctatat ttcctcatct   132300
gtattatcat tactaccacc atcactatca ccaccatcgt caccatcata atcaccatca   132360
acaccatctc caataccacc atcactgtaa ccatcatcac caccaccatg atcactatca   132420
ccatcatcac aatgatcact gtaaccatca ttactaccca ccaccatcac cactactcca   132480
ccaccatcac cattatcatt accatcacca ttatcaccac catcatcatc accagcacca   132540
ccatcatcac cagcaccacc atcaccatca ccatcattaa caccatcact atcaccattg   132600
gtttaatcat caccaccatc atcataaata aacatcacat aaccagggtg tagctgggtg   132660
ttgaccccag agcccactca ctgtttcctc tctcccaccc ccatccacac atttctaacc   132720
accatcctgc actgggctcc cagtctcctc tggtctcacc cacatgtcca ctgagaaaag   132780
gattttcaga acaccaacta gaccaggagg agccacatac ataactcagg cctgcttatc   132840
aactttctac atgttaataa tgacatcaga tcaatgggtg ttctcagctt ctcagaagga   132900
ggtcaaaatt ctccccctct cccttcatg tgtccagacc ttcccggatt tggatgtacc   132960
aagtgcagag tggtgttgag gccaagggc tcatccatgt aagtctcatc tgcaatcact   133020
gggctgatcc cgtggccctg tctccagggc gccatcagag agggcttcaa tcctcaggtt   133080
acctgtggcc caccctgccc tcagaggtgc catctctaca ttggccacga gatggcagca   133140
catactcata gactgcatta atttcccagc aactcctggt gggttttccc tcttatcagg   133200
atgtttgcct tgctcagaga gcaaatctga gagcagtgac acctaactta actttcagca   133260
aaatattttg agaagggtgc cccttttacac atctgtgcag tccaggtgat gcatcccatg   133320
cccaatgctc ggtagtcagg aggagcttcc tccatgcagc tctgcggaag agactcttcc   133380
acgctgctca tgtaaactcc agattcggtg tcagttttct gacaccgaag acaatgatct   133440
aagtgcagtc aagggctttg gggaaagcag gagagagtgc ctcagttcta gcctgtgcca   133500
tgcttgcaaa gttttgcaaa attctaatga gagctgggct tgcaacattg gaaacttgga   133560
ttatttgtga gagcactgag aaatccctgg gcatgtccat ctggaaaaac agcatttcct   133620
ctggcacttt agcagaggtt ctgtttcaat ttggcgaagg aaattaagca gtttttcaca   133680
aaagaagaac tacaacgagg agaattgtcc ctagtatttc ttctccctaa ttgtcaagga   133740
agtgtaaatt agaaaatgaa tcaggacaat ttccacctac tatgttagct aatattttaa   133800
aaattgaata tcacaagggt gaggcaaagt aattgttttc cagtgacatt ttccactgtc   133860
acacccttt agagaataat ttggcaatgt tactgtgaga tagaaatatg tctatataat   133920
tatgggaact gagacttcag aaagtaataa ggaataagaa tgaaatttat gaacaaacat   133980
gtggaaggtt ggaagcaaga gtggggccaa cacgcatggg gaggaagcat ttgggcagcg   134040
actccgcaga cccagactca agctgagcta tacaacctcc ttacgcctca gtttcctcaa   134100
ctgaagaaca ggaatgacaa gtgcctgttt cataggaccg ttgtgaggat taagtgagat   134160
ataccacatt atgagcttgt gcctggaaag gttgattctt agtaaatgat gactattctt   134220
ttttattgca ataaaattta tacaacatag agttactatt ttaaccattt ttgcaggtac   134280
cactgagtgg cattcagtac attcacaatg gtgtgcaacc gtcaccatat ttccaggaca   134340
```

```
tttttctcat ccccaaagga aacctcatgc ccattaagca gtcactcctc attaaaatat   134400
tagttatgaa gactgtagca ttttttttaaa aactcatgat ataacattga ttgaaaaaat   134460
cagtatagga aattgtgcat tatgatgtaa tagtaaaaga agcatataaa aatctgaaaa   134520
aagtatataa aaagaatagc aattgtattt ctcagactct ctttacattg taaaaatcat   134580
tttgatagct tcaaaagaaa agcaaaaagt acacaaacaa caaccaaccc caaagcagca   134640
tgacaaagcc cagattgttg aatccaggtc ttgggaacat aaaatcttat atgacatttg   134700
cactttaatg ggtcagagag tccagtggca ttgggagctg ccttgtgttc tgcagcctca   134760
cggacagaca ggaggtccag ctccactgct ctgttcttct ggaatttcct cgtgaacaag   134820
ctttggcctc agtaaccatt tctttcatct ttttaaacac aggtaccttt gggactggcc   134880
ttctcaagga agcccagctc cttgttattg agaatgaagt gtgcaatcac tataagtata   134940
tttgtgctga gcatttggcc agaggcactg acagttgcca ggtaagaaaa gatcaataga   135000
tcaaagtctt gtgctctccc gtctcagtct cagtcccttta gacgtcagtc ccaaagtggc   135060
aaattcagga aggttttgtc agtggaagac cccagtctaa gtgttgctca gaaactcccc   135120
agatctgtcc ctgaatgcat attcagatca tctaaggaga cgtcttgggg cttgagttcc   135180
agatccatag caagggagcc gtaagtgcca taactacctc aggccactca ccttcctggt   135240
gtgtgctggt caccagtgac tgaagtggtg gcttttccag tagagaggaa ggtagagggt   135300
acaggaccga gacaaattac acacacttaa caatgatgtc caggctagcc cagtctaaag   135360
gaaacaccaa gttaggaagc aatgcatgca ggattcacaa gggattattt ttttttcccag   135420 gaaaaaacta agtgatgtgg ttttgttgaa tagactttgc taagtactta agcactgcag   135480
atgcttgagt aatatgctca taagttcctt tctgatttga attactggga aaatgtacat   135540
atggataaga gaaggatggc atcccatatt aaaaggttgg cagcttaaag ctcacatgaa   135600
ttttccccta cctctgttta gggtgacagt ggagggcctc tggtttgctt cgagaaggac   135660
aaatacattt tacaaggagt cacttcttgg ggtcttggct gtgcacgccc caataagcct   135720
ggtgtctatg ctcgtgtttc aaggtttgtt acttggattg agggaatgat gagaaataat   135780
taattggacg ggagacagag tgaagcatca acctacttag aagctgaaac gtgggtaagg   135840
atttagcatg ctggaaataa tagacagcaa tcaaacgaag acactgttcc cagctaccag   135900
ctatgccaaa ccttggcatt tttggtattt ttgtgtataa gctttttaagg tctgactgac   135960 aaattctgta ttaaggtgtc atagctatga catttgttaa aaataaactc tgcacttatt   136020
ttgatttgaa ttaattttgg ttttggtctt caaaattttc atgctctttt catcccatct   136080 attttttattt ttatttttta gactttacgt cctggggtac atgtgcagaa tgtgcaggtt   136140
tgttacatag atgtacacgt gccatggtag tttgctgcac ccatcaacct gtcatctaat   136200
tcggtatttc ttttagttct atccctcccc tagccctcca cccccttgaca ggcccaggtg   136260 tgtgatgttg ccctccctgt gtccatgtgt tctcattgtt caactcacac ttatgagtga   136320
gaacatgccg tgtttgtttt tctgttcttg tgttagtttg ctgagaatga tagtttccag   136380
cttcatccat gtccctgcaa aggacatgaa ctcatccttt tttatggctg catagaattc   136440
catggtgtat atgtgccaca tttatccaa tctaacattg atgggcaatt gggttggttc   136500
caactctttg ctattgtgaa tagtgccaca ataaacatac gtgtgcatgt gttttcatag   136560
cagaatgatt tataatcctc tgggtatata cccagtaatg ggattgcagg tcaaatggt   136620 gtttctggtg ctagatcttt gaggaatcac cacactgtct tccacaatgg ttgaactaat   136680
ttatgctccc accaacaata tcaaggcatt cctatttctc cacatcctct ccagcatctg   136740
```

```
ttgtttcctg acttttaat gatcgccatt ctaactggca tgagatggta tctcattgtg    136800
gttttgattt gcatttctct aatgatcagt gatgatgagc ttttctcata tgtttgttgg   136860
ctgcataaat gccttttttg gagaagcatc tgttcatatc ctttgcccac tttttgatgg   136920
tgttgttttt ttctggtaaa tttgtttaag ttctttgtag attctggata ttagcctttt   136980
gtcagatgga tagatggcaa aaattttatc ctattatgta ggttgcctgt tcactccgat   137040
gatagtttct tttgctgtgc agaagctctt tggtttaatt agatctcatt tgtctatttt   137100
ggcttttgtt accattgctt ttagtgtttt agtcatgaag tcttctccca tgctatgtcc   137160
tgaatggtat tgcctaagtt ttcttccagg gtttttatgg ttttaggttt tgcatttaag   137220
tctttaatcc atcttgagtt aattttgta taagtaatgc ccttctttgt ctcttttgat    137280
ctttgttggc ttaaagtata ttttatcaga gactagaatt gcaatccctg cttttttttt   137340
tcttttgct ttcctttgc ttggtaaata ttcttccatc cctttatttt gagcctatgt     137400
atgtctgcac atgagatagg tttcctgaat acagcacacc aatgggtctt gactctttat   137460
tcaatttgcc agtctgtgtc ttttaattgg gggcatttag tccatttaca tttaaggtta   137520
atattgttat gtgtgaattt gatcctgtca ttatgatgct agcgggttat tttgcccatt   137580
agttgatgca gtttcttcat agtgtggatg gcctttacaa tttggtagtt tttgcagtgg   137640
ctggtaccaa ttgttccttt ccatgtttag tgcttcgttc aggagctctt gtgaggcagg   137700
ccttgtggtg acaaaatctt tcagcatttg cttgtctgta aaggatttta tttctccttt   137760
gcttatgaag cttagtttcg ctgggtatga aattctgggt tgaaaattat tttctttag    137820
aatgttgaat attggccccc actctcttcg ggcttgttgg gtttctgcag agagatccac   137880
tgttagtctg attggcttcc ctttccgggt aacccaacct ttctctctgg ctgccctag    137940
aaattttcc ttcatttcaa ccttggtgaa tctgacgatt atgtcttgag gtggctcttc    138000
t                                                                   138001
```

<210> SEQ ID NO 4
<211> LENGTH: 13938
<212> TYPE: DNA
<213> ORGANISM: Homo sapiens

<400> SEQUENCE: 4

```
ctgggattgg gacacacttt ctggacactg ctggccagtc ccaaaatgga acataaggaa      60
gtggttcttc tacttctttt atttctgaaa tcagcagcac ctgagcaaag ccatgtggtc     120
caggattgct accatggtga tggacagagt tatcgaggca cgtactccac cactgtcaca    180
ggaaggacct gccaagcttg gtcatctatg acaccacatc aacataatag gaccacagaa    240
aactacccaa atgctggctt gatcatgaac tactgcagga atccagatgc tgtggcagct    300
ccttattgtt atacgaggga tcccggtgtc aggtgggagt actgcaacct gacgcaatgc    360
tcagacgcag aagggactgc cgtcgcgcct ccgactgtta ccccggttcc aagcctagag    420
gctccttccg aacaagcacc gactgagcaa aggcctgggg tgcaggagtg ctaccatggt    480
aatggacaga gttatcgagg cacatactcc accactgtca caggaagaac ctgccaagct    540
tggtcatcta tgacaccaca ctcgcatagt cggaccccag aatactaccc aaatgctggc    600
ttgatcatga actactgcag gaatccagat gctgtggcag ctccttattg ttatacgagg    660
gatcccggtg tcaggtggga gtactgcaac ctgacgcaat gctcagacgc agaagggact    720
gccgtcgcgc ctccgactgt taccccggtt ccaagcctag aggctccttc cgaacaagca    780
```

-continued

| | |
|---|---|
| ccgactgagc aaaggcctgg ggtgcaggag tgctaccatg gtaatggaca gagttatcga | 840 |
| ggcacatact ccaccactgt cacaggaaga acctgccaag cttggtcatc tatgacacca | 900 |
| cactcgcata gtcggacccc agaatactac ccaaatgctg gcttgatcat gaactactgc | 960 |
| aggaatccag atgctgtggc agctccttat tgttatacga gggatcccgg tgtcaggtgg | 1020 |
| gagtactgca acctgacgca atgctcagac gcagaaggga ctgccgtcgc gcctccgact | 1080 |
| gttaccccgg ttccaagcct agaggctcct tccgaacaag caccgactga gcaaaggcct | 1140 |
| ggggtgcagg agtgctacca tggtaatgga cagagttatc gaggcacata ctccaccact | 1200 |
| gtcacaggaa gaacctgcca agcttggtca tctatgacac cacactcgca tagtcggacc | 1260 |
| ccagaatact acccaaatgc tggcttgatc atgaactact gcaggaatcc agatgctgtg | 1320 |
| gcagctcctt attgttatac gagggatccc ggtgtcaggt gggagtactg caacctgacg | 1380 |
| caatgctcag acgcagaagg gactgccgtc gcgcctccga ctgttacccc ggttccaagc | 1440 |
| ctagaggctc cttccgaaca agcaccgact gagcaaaggc ctggggtgca ggagtgctac | 1500 |
| catggtaatg gacagagtta tcgaggcaca tactccacca ctgtcacagg aagaacctgc | 1560 |
| caagcttggt catctatgac accacactcg catagtcgga ccccagaata ctacccaaat | 1620 |
| gctggcttga tcatgaacta ctgcaggaat ccagatgctg tggcagctcc ttattgttat | 1680 |
| acgagggatc ccggtgtcag gtgggagtac tgcaacctga cgcaatgctc agacgcagaa | 1740 |
| gggactgccg tcgcgcctcc gactgttacc ccggttccaa gcctagaggc tcttccgaa | 1800 |
| caagcaccga ctgagcaaag gcctggggtg caggagtgct accatggtaa tggacagagt | 1860 |
| tatcgaggca catactccac cactgtcaca ggaagaacct gccaagcttg gtcatctatg | 1920 |
| acaccacact cgcatagtcg gaccccagaa tactacccaa atgctggctt gatcatgaac | 1980 |
| tactgcagga atccagatgc tgtggcagct ccttattgtt atacgaggga tcccggtgtc | 2040 |
| aggtgggagt actgcaacct gacgcaatgc tcagacgcag aagggactgc cgtcgcgcct | 2100 |
| ccgactgtta ccccggttcc aagcctagag gctccttccg aacaagcacc gactgagcaa | 2160 |
| aggcctgggg tgcaggagtg ctaccatggt aatggacaga gttatcgagg cacatactcc | 2220 |
| accactgtca caggaagaac ctgccaagct tggtcatcta tgacaccaca ctcgcatagt | 2280 |
| cggaccccag aatactaccc aaatgctggc ttgatcatga actactgcag gaatccagat | 2340 |
| gctgtggcag ctccttattg ttatacgagg gatcccggtg tcaggtggga gtactgcaac | 2400 |
| ctgacgcaat gctcagacgc agaagggact gccgtcgcgc ctccgactgt taccccggtt | 2460 |
| ccaagcctag aggctccttc cgaacaagca ccgactgagc aaaggcctgg ggtgcaggag | 2520 |
| tgctaccatg gtaatggaca gagttatcga ggcacatact ccaccactgt cacaggaaga | 2580 |
| acctgccaag cttggtcatc tatgacacca cactcgcata gtcggacccc agaatactac | 2640 |
| ccaaatgctg gcttgatcat gaactactgc aggaatccag atgctgtggc agctccttat | 2700 |
| tgttatacga gggatcccgg tgtcaggtgg gagtactgca acctgacgca atgctcagac | 2760 |
| gcagaaggga ctgccgtcgc gcctccgact gttaccccgg ttccaagcct agaggctcct | 2820 |
| tccgaacaag caccgactga gcaaaggcct ggggtgcagg agtgctacca tggtaatgga | 2880 |
| cagagttatc gaggcacata ctccaccact gtcacaggaa gaacctgcca agcttggtca | 2940 |
| tctatgacac cacactcgca tagtcggacc ccagaatact acccaaatgc tggcttgatc | 3000 |
| atgaactact gcaggaatcc agatgctgtg gcagctcctt attgttatac gagggatccc | 3060 |
| ggtgtcaggt gggagtactg caacctgacg caatgctcag acgcagaagg gactgccgtc | 3120 |
| gcgcctccga ctgttacccc ggttccaagc ctagaggctc cttccgaaca agcaccgact | 3180 |

```
gagcaaaggc ctggggtgca ggagtgctac catggtaatg gacagagtta tcgaggcaca   3240
tactccacca ctgtcacagg aagaacctgc caagcttggt catctatgac accacactcg   3300
catagtcgga ccccagaata ctacccaaat gctggcttga tcatgaacta ctgcaggaat   3360
ccagatgctg tggcagctcc ttattgttat acgagggatc ccggtgtcag gtgggagtac   3420
tgcaacctga cgcaatgctc agacgcagaa gggactgccg tcgcgcctcc gactgttacc   3480
ccggttccaa gcctagaggc tccttccgaa caagcaccga ctgagcaaag gcctggggtg   3540
caggagtgct accatggtaa tggacagagt tatcgaggca catactccac cactgtcaca   3600
ggaagaacct gccaagcttg gtcatctatg acaccacact cgcatagtcg accccagaa   3660 tactacccaa atgctggctt gatcatgaac tactgcagga atccagatgc tgtggcagct   3720
ccttattgtt atacgaggga tcccggtgtc aggtgggagt actgcaacct gacgcaatgc   3780
tcagacgcag aagggactgc cgtcgcgcct ccgactgtta ccccggttcc aagcctagag   3840
gctccttccg aacaagcacc gactgagcaa aggcctgggg tgcaggagtg ctaccatggt   3900
aatggacaga gttatcgagg cacatactcc accactgtca caggaagaac ctgccaagct   3960
tggtcatcta tgacaccaca ctcgcatagt cggaccccag aatactaccc aaatgctggc   4020
ttgatcatga actactgcag gaatccagat gctgtggcag ctccttattg ttatacgagg   4080
gatcccggtg tcaggtggga gtactgcaac ctgacgcaat gctcagacgc agaagggact   4140
gccgtcgcgc ctccgactgt taccccggtt ccaagcctag aggctccttc gaacaagca   4200 ccgactgagc aaaggcctgg ggtgcaggag tgctaccatg gtaatggaca gagttatcga   4260
ggcacatact ccaccactgt cacaggaaga acctgccaag cttggtcatc tatgacacca   4320
cactcgcata gtcggacccc agaatactac ccaaatgctg gcttgatcat gaactactgc   4380
aggaatccag atgctgtggc agctccttat tgttatacga gggatcccgg tgtcaggtgg   4440
gagtactgca acctgacgca atgctcagac gcagaaggga ctgccgtcgc gcctccgact   4500
gttaccccgg ttccaagcct agaggctcct tccgaacaag caccgactga gcaaaggcct   4560
ggggtgcagg agtgctacca tggtaatgga cagagttatc gaggcacata ctccaccact   4620
gtcacaggaa gaacctgcca agcttggtca tctatgacac cacactcgca tagtcggacc   4680
ccagaatact acccaaatgc tggcttgatc atgaactact gcaggaatcc agatgctgtg   4740
gcagctcctt attgttatac gagggatccc ggtgtcaggt gggagtactg caacctgacg   4800
caatgctcag acgcagaagg gactgccgtc gcgcctccga ctgttacccc ggttccaagc   4860
ctagaggctc cttccgaaca agcaccgact gagcaaaggc ctggggtgca ggagtgctac   4920
catggtaatg gacagagtta tcgaggcaca tactccacca ctgtcacagg aagaacctgc   4980
caagcttggt catctatgac accacactcg catagtcgga ccccagaata ctacccaaat   5040
gctggcttga tcatgaacta ctgcaggaat ccagatgctg tggcagctcc ttattgttat   5100
acgagggatc ccggtgtcag gtgggagtac tgcaacctga cgcaatgctc agacgcagaa   5160
gggactgccg tcgcgcctcc gactgttacc ccggttccaa gcctagaggc tccttccgaa   5220
caagcaccga ctgagcaaag gcctggggtg caggagtgct accatggtaa tggacagagt   5280
tatcgaggca catactccac cactgtcaca ggaagaacct gccaagcttg gtcatctatg   5340
acaccacact cgcatagtcg accccagaa tactacccaa atgctggctt gatcatgaac   5400
tactgcagga atccagatgc tgtggcagct ccttattgtt atacgaggga tcccggtgtc   5460
aggtgggagt actgcaacct gacgcaatgc tcagacgcag aagggactgc cgtcgcgcct   5520
```

```
ccgactgtta ccccggttcc aagcctagag gctccttccg aacaagcacc gactgagcaa    5580
aggcctgggg tgcaggagtg ctaccatggt aatggacaga gttatcgagg cacatactcc    5640
accactgtca caggaagaac ctgccaagct tggtcatcta tgacaccaca ctcgcatagt    5700
cggaccccag aatactaccc aaatgctggc ttgatcatga actactgcag gaatccagat    5760
gctgtggcag ctccttattg ttatacgagg gatcccggtg tcaggtggga gtactgcaac    5820
ctgacgcaat gctcagacgc agaagggact gccgtcgcgc ctccgactgt taccccggtt    5880
ccaagcctag aggctccttc cgaacaagca ccgactgagc aaaggcctgg ggtgcaggag    5940
tgctaccatg gtaatggaca gagttatcga ggcacatact ccaccactgt cacaggaaga    6000
acctgccaag cttggtcatc tatgacacca cactcgcata gtcggacccc agaatactac    6060
ccaaatgctg gcttgatcat gaactactgc aggaatccag atgctgtggc agctccttat    6120
tgttatacga gggatcccgg tgtcaggtgg gagtactgca acctgacgca atgctcagac    6180
gcagaaggga ctgccgtcgc gcctccgact gttaccccgg ttccaagcct agaggctcct    6240
tccgaacaag caccgactga gcaaaggcct ggggtgcagg agtgctacca tggtaatgga    6300
cagagttatc gaggcacata ctccaccact gtcacaggaa gaacctgcca agcttggtca    6360
tctatgacac cacactcgca tagtcggacc ccagaatact acccaaatgc tggcttgatc    6420
atgaactact gcaggaatcc agatgctgtg gcagctcctt attgttatac gagggatccc    6480
ggtgtcaggt gggagtactg caacctgacg caatgctcag acgcagaagg gactgccgtc    6540
gcgcctccga ctgttacccc ggttccaagc ctagaggctc cttccgaaca agcaccgact    6600
gagcaaaggc ctggggtgca ggagtgctac catggtaatg gacagagtta tcgaggcaca    6660
tactccacca ctgtcacagg aagaacctgc caagcttggt catctatgac accacactcg    6720
catagtcgga cccagaata ctacccaaat gctggcttga tcatgaacta ctgcaggaat    6780
ccagatgctg tggcagctcc ttattgttat acgagggatc ccggtgtcag gtgggagtac    6840
tgcaacctga cgcaatgctc agacgcagaa gggactgccg tcgcgcctcc gactgttacc    6900
ccggttccaa gcctagaggc tccttccgaa caagcaccga ctgagcaaag gcctggggtg    6960
caggagtgct accatggtaa tggacagagt tatcgaggca catactccac cactgtcaca    7020
ggaagaacct gccaagcttg gtcatctatg acaccacact cgcatagtcg accccagaa    7080
tactacccaa atgctggctt gatcatgaac tactgcagga atccagatgc tgtggcagct    7140
ccttattgtt atacgaggga tcccggtgtc aggtgggagt actgcaacct gacgcaatgc    7200
tcagacgcag aagggactgc cgtcgcgcct ccgactgtta ccccggttcc aagcctagag    7260
gctccttccg aacaagcacc gactgagcaa aggcctgggg tgcaggagtg ctaccatggt    7320
aatggacaga gttatcgagg cacatactcc accactgtca caggaagaac ctgccaagct    7380
tggtcatcta tgacaccaca ctcgcatagt cggaccccag aatactaccc aaatgctggc    7440
ttgatcatga actactgcag gaatccagat gctgtggcag ctccttattg ttatacgagg    7500
gatcccggtg tcaggtggga gtactgcaac ctgacgcaat gctcagacgc agaagggact    7560
gccgtcgcgc ctccgactgt taccccggtt ccaagcctag aggctccttc cgaacaagca    7620
ccgactgagc aaaggcctgg ggtgcaggag tgctaccatg gtaatggaca gagttatcga    7680
ggcacatact ccaccactgt cacaggaaga acctgccaag cttggtcatc tatgacacca    7740
cactcgcata gtcggacccc agaatactac ccaaatgctg gcttgatcat gaactactgc    7800
aggaatccag atgctgtggc agctccttat tgttatacga gggatcccgg tgtcaggtgg    7860
gagtactgca acctgacgca atgctcagac gcagaaggga ctgccgtcgc gcctccgact    7920
```

```
gttaccccgg ttccaagcct agaggctcct tccgaacaag caccgactga gcagaggcct   7980
ggggtgcagg agtgctacca cggtaatgga cagagttatc gaggcacata ctccaccact   8040
gtcactggaa gaacctgcca agcttggtca tctatgacac cacactcgca tagtcggacc   8100
ccagaatact acccaaatgc tggcttgatc atgaactact gcaggaatcc agatgctgtg   8160
gcagctcctt attgttatac gagggatccc ggtgtcaggt gggagtactg caacctgacg   8220
caatgctcag acgcagaagg gactgccgtc gcgcctccga ctgttacccc ggttccaagc   8280
ctagaggctc cttccgaaca agcaccgact gagcaaaggc tggggtgcag gagtgctac   8340 catggtaatg gacagagtta tcgaggcaca tactccacca ctgtcacagg aagaacctgc   8400
caagcttggt catctatgac accacactcg catagtcgga ccccagaata ctacccaaat   8460
gctggcttga tcatgaacta ctgcaggaat ccagatgctg tggcagctcc ttattgttat   8520
acgagggatc ccggtgtcag gtgggagtac tgcaacctga cgcaatgctc agacgcagaa   8580
gggactgccg tcgcgcctcc gactgttacc cggttccaa gcctagaggc tccttccgaa   8640
caagcaccga ctgagcaaag gctgggtg caggagtgct accatggtaa tggacagagt   8700
tatcgaggca catactccac cactgtcaca ggaagaacct gccaagcttg gtcatctatg   8760
acaccacact cgcatagtcg gaccccagaa tactacccaa atgctggctt gatcatgaac   8820
tactgcagga atccagatgc tgtggcagct ccttattgtt atacgaggga tcccggtgtc   8880
aggtgggagt actgcaacct gacgcaatgc tcagacgcag aagggactgc cgtcgcgcct   8940
ccgactgtta ccccggttcc aagcctagag gctccttccg aacaagcacc gactgagcag   9000
aggcctgggg tgcaggagtg ctaccacggt aatggacaga gttatcgagg cacatactcc   9060
accactgtca ctggaagaac ctgccaagct tggtcatcta tgacaccaca ctcgcatagt   9120
cggaccccag aatactaccc aaatgctggc ttgatcatga actactgcag gaatccagat   9180
gctgtggcag ctccttattg ttatacgagg gatcccggtg tcaggtggga gtactgcaac   9240
ctgacgcaat gctcagacgc agaagggact gccgtcgcgc ctccgactgt taccccggtt   9300
ccaagcctag aggctccttc cgaacaagca ccgactgagc agaggcctgg ggtgcaggag   9360
tgctaccacg gtaatggaca gagttatcga ggcacatact ccaccactgt cactggaaga   9420
acctgccaag cttggtcatc tatgacacca cactcgcata gtcggacccc agaatactac   9480
ccaaatgctg gcttgatcat gaactactgc aggaatccag atgctgtggc agctccttat   9540
tgttatacga gggatcccgg tgtcaggtgg gagtactgca acctgacgca atgctcagac   9600
gcagaaggga ctgccgtcgc gcctccgact gttaccccgg ttccaagcct agaggctcct   9660
tccgaacaag caccgactga gcagaggcct ggggtgcagg agtgctacca cggtaatgga   9720
cagagttatc gaggcacata ctccaccact gtcactggaa gaacctgcca agcttggtca   9780
tctatgacac cacactcgca tagtcggacc ccagaatact acccaaatgc tggcttgatc   9840
atgaactact gcaggaatcc agatgctgtg gcagctcctt attgttatac gagggatccc   9900
ggtgtcaggt gggagtactg caacctgacg caatgctcag acgcagaagg gactgccgtc   9960
gcgcctccga ctgttacccc ggttccaagc ctagaggctc cttccgaaca agcaccgact  10020
gagcagaggc ctggggtgca ggagtgctac cacggtaatg gacagagtta tcgaggcaca  10080
tactccacca ctgtcactgg aagaacctgc caagcttggt catctatgac accacactcg  10140
catagtcgga ccccagaata ctacccaaat gctggcttga tcatgaacta ctgcaggaat  10200
ccagatcctg tggcagcccc ttattgttat acgagggatc ccagtgtcag gtgggagtac  10260
```

-continued

| | |
|---|---|
| tgcaacctga cacaatgctc agacgcagaa gggactgccg tcgcgcctcc aactattacc | 10320 |
| ccgattccaa gcctagaggc tccttctgaa caagcaccaa ctgagcaaag gcctggggtg | 10380 |
| caggagtgct accacggaaa tggacagagt tatcaaggca catacttcat tactgtcaca | 10440 |
| ggaagaacct gccaagcttg gtcatctatg acaccacact cgcatagtcg acccccagca | 10500 |
| tactacccaa atgctggctt gatcaagaac tactgccgaa atccagatcc tgtggcagcc | 10560 |
| ccttggtgtt atacaacaga tcccagtgtc aggtgggagt actgcaacct gacacgatgc | 10620 |
| tcagatgcag aatggactgc cttcgtccct ccgaatgtta ttctggctcc aagcctagag | 10680 |
| gcttttttg aacaagcact gactgaggaa accccgggg tacaggactg ctactaccat | 10740 |
| tatggacaga gttaccgagg cacatactcc accactgtca caggaagaac ttgccaagct | 10800 |
| tggtcatcta tgacaccaca ccagcatagt cggaccccag aaaactaccc aaatgctggc | 10860 |
| ctgaccagga actactgcag gaatccagat gctgagattc gcccttggtg ttacaccatg | 10920 |
| gatcccagtg tcaggtggga gtactgcaac ctgacacaat gcctggtgac agaatcaagt | 10980 |
| gtccttgcaa ctctcacggt ggtcccagat ccaagcacag aggcttcttc tgaagaagca | 11040 |
| ccaacggagc aaagccccgg ggtccaggat tgctaccatg gtgatggaca gagttatcga | 11100 |
| ggctcattct ctaccactgt cacaggaagg acatgtcagt cttggtcctc tatgacacca | 11160 |
| cactggcatc agaggacaac agaatattat ccaaatggtg gcctgaccag gaactactgc | 11220 |
| aggaatccag atgctgagat tagtccttgg tgttatacca tggatcccaa tgtcagatgg | 11280 |
| gagtactgca acctgacaca atgtccagtg acagaatcaa gtgtccttgc gacgtccacg | 11340 |
| gctgtttctg aacaagcacc aacgagcaa agccccacag tccaggactg ctaccatggt | 11400 |
| gatggacaga gttatcgagg ctcattctcc accactgtta caggaaggac atgtcagtct | 11460 |
| tggtcctcta tgacaccaca ctggcatcag agaaccacag aatactaccc aaatggtggc | 11520 |
| ctgaccagga actactgcag gaatccagat gctgagattc gcccttggtg ttataccatg | 11580 |
| gatcccagtg tcagatggga gtactgcaac ctgacgcaat gtccagtgat ggaatcaact | 11640 |
| ctcctcacaa ctcccacggt ggtcccagtt ccaagcacag agcttccttc tgaagaagca | 11700 |
| ccaactgaaa acagcactgg ggtccaggac tgctaccgag gtgatggaca gagttatcga | 11760 |
| ggcacactct ccaccactat cacaggaaga acatgtcagt cttggtcgtc tatgacacca | 11820 |
| cattggcatc ggaggatccc attatactat ccaaatgctg gcctgaccag gaactactgc | 11880 |
| aggaatccag atgctgagat tcgcccttgg tgttacacca tggatcccag tgtcaggtgg | 11940 |
| gagtactgca acctgacacg atgtccagtg acagaatcga gtgtcctcac aactcccaca | 12000 |
| gtggcccgg ttccaagcac agaggctcct tctgaacaag caccacctga gaaaagccct | 12060 |
| gtggtccagg attgctacca tggtgatgga cggagttatc gaggcatatc ctccaccact | 12120 |
| gtcacaggaa ggacctgtca atcttggtca tctatgatac cacactggca tcagaggacc | 12180 |
| ccagaaaact acccaaatgc tggcctgacc gagaactact gcaggaatcc agattctggg | 12240 |
| aaacaaccct ggtgttacac aaccgatccg tgtgtgaggt gggagtactg caatctgaca | 12300 |
| caatgctcag aaacagaatc aggtgtccta gagactccca ctgttgttcc agttccaagc | 12360 |
| atggaggctc attctgaagc agcaccaact gagcaaaccc ctgtggtccg gcagtgctac | 12420 |
| catggtaatg gccagagtta tcgaggcaca ttctccacca ctgtcacagg aaggacatgt | 12480 |
| caatcttggt catccatgac accacaccgg catcagagga ccccagaaaa ctacccaaat | 12540 |
| gatgccctga caatgaacta ctgcaggaat ccagatgccg atacaggccc ttggtgtttt | 12600 |
| accatggacc ccagcatcag gtgggagtac tgcaacctga cgcgatgctc agacacagaa | 12660 |

```
gggactgtgg tcgctcctcc gactgtcatc caggttccaa gcctagggcc tccttctgaa    12720
caagactgta tgtttgggaa tgggaaagga taccggggca agaaggcaac cactgttact    12780
gggacgccat gccaggaatg ggctgcccag gagccccata gacacagcac gttcattcca    12840
gggacaaata aatgggcagg tctgaaaaaa aattactgcc gtaaccctga tggtgacatc    12900
aatggtccct ggtgctacac aatgaatcca agaaaacttt ttgactactg tgatatccct    12960
ctctgtgcat cctcttcatt tgattgtggg aagcctcaag tggagccgaa gaaatgtcct    13020
ggaagcattg tagggggggtg tgtggcccac ccacattcct ggccctggca agtcagtctc    13080
agaacaaggt ttggaaagca cttctgtgga ggcaccttaa tatccccaga gtgggtgctg    13140
actgctgctc actgcttgaa gaagtcctca aggccttcat cctacaaggt catcctgggt    13200
gcacaccaag aagtgaacct cgaatctcat gttcaggaaa tagaagtgtc taggctgttc    13260
ttggagccca cacaagcaga tattgccttg ctaaagctaa gcaggcctgc cgtcatcact    13320
gacaaagtaa tgccagcttg tctgccatcc ccagactaca tggtcaccgc caggactgaa    13380
tgttacatca ctggctgggg agaaacccaa ggtacctttg ggactggcct tctcaaggaa    13440
gcccagctcc ttgttattga gaatgaagtg tgcaatcact ataagtatat ttgtgctgag    13500
catttggcca gaggcactga cagttgccag ggtgacagtg gagggcctct ggtttgcttc    13560
gagaaggaca aatacatttt acaaggagtc acttcttggg gtcttggctg tgcacgcccc    13620
aataagcctg gtgtctatgc tcgtgtttca aggtttgtta cttggattga gggaatgatg    13680
agaaataatt aattggacgg gagacagagt gaagcatcaa cctacttaga agctgaaacg    13740
tgggtaagga tttagcatgc tggaaataat agacagcaat caaacgaaga cactgttccc    13800
agctaccagc tatgccaaac cttggcattt ttggtatttt tgtgtataag ctttttaaggt   13860 ctgactgaca aattctgtat taaggtgtca tagctatgac atttgttaaa aataaactct   13920
gcacttattt tgatttga                                                  13938
```

```
<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
acagcaatca aacgaagaca ctg                                             23

<210> SEQ ID NO 6
<211> LENGTH: 28
<212> TYPE: DNA
<213> ORGANISM: Artificial Sequence
<220> FEATURE:
<223> OTHER INFORMATION: Primer

<400> SEQUENCE: 6
agcttataca caaaaatacc aaaaatgc                                        28

<210> SEQ ID NO 7
<211> LENGTH: 27
<212> TYPE: DNA
<213> ORGANISM: Artificial Sequence
<220> FEATURE:
<223> OTHER INFORMATION: Probe

<400> SEQUENCE: 7
```

-continued tcccagctac cagctatgcc aaaccctt                                    27

<210> SEQ ID NO 8
<211> LENGTH: 16
<212> TYPE: DNA
<213> ORGANISM: Artificial Sequence
<220> FEATURE:
<223> OTHER INFORMATION: Primer

<400> SEQUENCE: 8
ccacagtggc cccggt                                                 16

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
acagggcttt tctcaggtgg t                                           21

<210> SEQ ID NO 10
<211> LENGTH: 28
<212> TYPE: DNA
<213> ORGANISM: Artificial Sequence
<220> FEATURE:
<223> OTHER INFORMATION: Probe

<400> SEQUENCE: 10
ccaagcacag aggctccttc tgaacaag                                    28

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
ggcaggtcct tcctgtgaca                                             20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
cctgtgacag tggtggagta                                             20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
tcctgtgaca gtggtggagt                                             20

<210> SEQ ID NO 14
<211> LENGTH: 20
<212> TYPE: DNA
<213> ORGANISM: Artificial Sequence

```
<220> FEATURE:
<223> OTHER INFORMATION: Synthetic oligonucleotide

<400> SEQUENCE: 14
cttcctgtga cagtggtgga                                                   20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
ccttcctgtg acagtggtgg                                                   20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
tccttcctgt gacagtggtg                                                   20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
gtccttcctg tgacagtggt                                                   20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
ggtccttcct gtgacagtgg                                                   20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
aggtccttcc tgtgacagtg                                                   20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
caggtccttc ctgtgacagt                                                   20
```

```
<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
gcaggtcctt cctgtgacag                                                    20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
tggcaggtcc ttcctgtgac                                                    20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
ttggcaggtc cttcctgtga                                                    20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
cttggcaggt ccttcctgtg                                                    20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
gcttggcagg tccttcctgt                                                    20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
tcttcctgtg acagtggtgg                                                    20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 27
ttcttcctgt gacagtggtg                                                   20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
gttcttcctg tgacagtggt                                                   20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
ggttcttcct gtgacagtgg                                                   20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
aggttcttcc tgtgacagtg                                                   20

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31
caggttcttc ctgtgacagt                                                   20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
tggcaggttc ttcctgtgac                                                   20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
ttggcaggtt cttcctgtga                                                   20

<210> SEQ ID NO 34
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
cttggcaggt tcttcctgtg                                            20

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
agcttggcag gttcttcctg                                            20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
actatgcgag tgtggtgtca                                            20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
gactatgcga gtgtggtgtc                                            20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
cgactatgcg agtgtggtgt                                            20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
ccgactatgc gagtgtggtg                                            20

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
```
tccgactatg cgagtgtggt                                            20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
gtccgactat gcgagtgtgg                                            20

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
ggtccgacta tgcgagtgtg                                            20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
gggtccgact atgcgagtgt                                            20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
ctgctcagtc ggtgcttgtt                                            20

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
cctctgctca gtcggtgctt                                            20

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 46
gcctctgctc agtcggtgct                                            20

<210> SEQ ID NO 47
<211> LENGTH: 20
<212> TYPE: DNA

<213> ORGANISM: Artificial Sequence
<220> FEATURE:
<223> OTHER INFORMATION: Synthetic oligonucleotide

<400> SEQUENCE: 47
cttccagtga cagtggtgga					20

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 48
ttcttccagt gacagtggtg					20

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
gttcttccag tgacagtggt					20

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
ggttcttcca gtgacagtgg					20

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 51
gaccttaaaa gcttatacac					20

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
gtcagacctt aaaagcttat					20

<210> SEQ ID NO 53
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 53
tgtcagtcag accttaaaag					20

```
<210> SEQ ID NO 54
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 54
gaatttgtca gtcagacctt                                               20

<210> SEQ ID NO 55
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 55
agaatttgtc agtcagacct                                               20

<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 56
ccttaataca gaatttgtca                                               20

<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 57
gctccgttgg tgcttgttca                                               20

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 58
tgctccgttg gtgcttgttc                                               20

<210> SEQ ID NO 59
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 59
ttgctccgtt ggtgcttgtt                                               20

<210> SEQ ID NO 60
<211> LENGTH: 20
<212> TYPE: DNA
<213> ORGANISM: Artificial Sequence
<220> FEATURE:
```

-continued

<223> OTHER INFORMATION: Synthetic oligonucleotide

<400> SEQUENCE: 60
tttgctccgt tggtgcttgt					20

<210> SEQ ID NO 61
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 61
ctttgctccg ttggtgcttg					20

<210> SEQ ID NO 62
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 62
tcctgtaaca gtggtggaga					20

<210> SEQ ID NO 63
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 63
ttcctgtaac agtggtggag					20

<210> SEQ ID NO 64
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 64
cttcctgtaa cagtggtgga					20

<210> SEQ ID NO 65
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 65
ccttcctgta acagtggtgg					20

<210> SEQ ID NO 66
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 66
tccttcctgt aacagtggtg					20

```
<210> SEQ ID NO 67
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 67
gtccttcctg taacagtggt                                           20

<210> SEQ ID NO 68
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 68
tgtccttcct gtaacagtgg                                           20

<210> SEQ ID NO 69
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 69
tggagccaga ataacattcg                                           20

<210> SEQ ID NO 70
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 70
cctctaggct tggagccaga                                           20

<210> SEQ ID NO 71
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 71
agttcttcct gtgacagtgg                                           20

<210> SEQ ID NO 72
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 72
gtccgactat gctggtgtgg                                           20

<210> SEQ ID NO 73
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 73
ggtccgacta tgctggtgtg                                              20

<210> SEQ ID NO 74
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 74
gggtccgact atgctggtgt                                              20

<210> SEQ ID NO 75
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 75
cctctaggct tggaatcggg                                              20

<210> SEQ ID NO 76
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 76
gttcagaagg agcctctagg                                              20

<210> SEQ ID NO 77
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 77
tgttcagaag gagcctctag                                              20

<210> SEQ ID NO 78
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 78
gcttgttcag aaggagcctc                                              20

<210> SEQ ID NO 79
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 79
tgcttgttca gaaggagcct                                              20

<210> SEQ ID NO 80
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 80
gtgcttgttc agaaggagcc                                              20

<210> SEQ ID NO 81
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 81
ggtgcttgtt cagaaggagc                                              20

<210> SEQ ID NO 82
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 82
tggtgcttgt tcagaaggag                                              20

<210> SEQ ID NO 83
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 83
gctcagttgg tgcttgttca                                              20

<210> SEQ ID NO 84
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 84
tgctcagttg gtgcttgttc                                              20

<210> SEQ ID NO 85
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 85
gcttggatct gggaccaccg                                              20

<210> SEQ ID NO 86
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 86
```
gcctccatgc ttggaactgg					20

<210> SEQ ID NO 87
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 87
gctcagttgg tgctgcttca					20

<210> SEQ ID NO 88
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 88
cctcgataac tctggccatt					20

<210> SEQ ID NO 89
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 89
tcctgtgaca gtggtggaga					20

<210> SEQ ID NO 90
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 90
gtaggttgat gcttcactct					20

<210> SEQ ID NO 91
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 91
cgtttgattg ctgtctatta					20

<210> SEQ ID NO 92
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 92
ctctgtgctt ggatctggga					20

<210> SEQ ID NO 93
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 93
cctctgtgct tggatctggg                                              20

<210> SEQ ID NO 94
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 94
gcctctgtgc ttggatctgg                                              20

<210> SEQ ID NO 95
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 95
agaagcctct gtgcttggat                                              20

<210> SEQ ID NO 96
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 96
ttcagaagaa gcctctgtgc                                              20

<210> SEQ ID NO 97
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 97
gctccgttgg tgcttcttca                                              20

<210> SEQ ID NO 98
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 98
tttgctccgt tggtgcttct                                              20

<210> SEQ ID NO 99
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 99
gctttgctcc gttggtgctt                                              20

```
<210> SEQ ID NO 100
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 100
ggctttgctc cgttggtgct                                               20

<210> SEQ ID NO 101
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 101
gggctttgct ccgttggtgc                                               20

<210> SEQ ID NO 102
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 102
ccttcctgtg acagtggtag                                               20

<210> SEQ ID NO 103
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 103
tccttcctgt gacagtggta                                               20

<210> SEQ ID NO 104
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 104
tgtccttcct gtgacagtgg                                               20

<210> SEQ ID NO 105
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 105
cctctaggct tggaaccggg                                               20

<210> SEQ ID NO 106
<211> LENGTH: 20
<212> TYPE: DNA
<213> ORGANISM: Artificial Sequence
<220> FEATURE:
<223> OTHER INFORMATION: Synthetic oligonucleotide
```

<400> SEQUENCE: 106
tgcttgttcg gaaggagcct                                          20

<210> SEQ ID NO 107
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 107
gtgcttgttc ggaaggagcc                                          20

<210> SEQ ID NO 108
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 108
gcttggaact gggaccaccg                                          20

<210> SEQ ID NO 109
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 109
ctgtgcttgg aactgggacc                                          20

<210> SEQ ID NO 110
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 110
ctctgtgctt ggaactggga                                          20

<210> SEQ ID NO 111
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 111
cctgtgacag tggtgga                                             17

<210> SEQ ID NO 112
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 112
tcctgtgaca gtggtgg                                             17

<210> SEQ ID NO 113

```
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 113
ttcctgtgac agtggtg                                                 17

<210> SEQ ID NO 114
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 114
cttcctgtga cagtggt                                                 17

<210> SEQ ID NO 115
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 115
ccttcctgtg acagtgg                                                 17

<210> SEQ ID NO 116
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 116
tccttcctgt gacagtg                                                 17

<210> SEQ ID NO 117
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 117
gtccttcctg tgacagt                                                 17

<210> SEQ ID NO 118
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 118
ggtccttcct gtgacag                                                 17

<210> SEQ ID NO 119
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 119
```
ccgactatgc gagtgtg                                              17

<210> SEQ ID NO 120
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 120
gtccgactat gcgagtg                                              17

<210> SEQ ID NO 121
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 121
ggtccgacta tgcgagt                                              17

<210> SEQ ID NO 122
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 122
gtcagacctt aaaagct                                              17

<210> SEQ ID NO 123
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 123
aagcctctgt gcttgga                                              17

<210> SEQ ID NO 124
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 124
agcctctgtg cttggat                                              17

<210> SEQ ID NO 125
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 125
gcctctgtgc ttggatc                                              17

<210> SEQ ID NO 126
<211> LENGTH: 17
<212> TYPE: DNA

```
<213> ORGANISM: Artificial Sequence
<220> FEATURE:
<223> OTHER INFORMATION: Synthetic oligonucleotide

<400> SEQUENCE: 126
gctccgttgg tgcttct                                                     17

<210> SEQ ID NO 127
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 127
ctctgtgctt ggaactg                                                     17

<210> SEQ ID NO 128
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 128
tgcctcgata actctgt                                                     17

<210> SEQ ID NO 129
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 129
tgtgcctcga taactct                                                     17

<210> SEQ ID NO 130
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 130
gctcagttgg tgctgct                                                     17

<210> SEQ ID NO 131
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 131
gcgtttgctc ttcttcttgc gtttttt                                          27

<210> SEQ ID NO 132
<211> LENGTH: 3987
<212> TYPE: DNA
<213> ORGANISM: Macaca mulatta

<400> SEQUENCE: 132
atgtatcgtt ttggaatttc cagtggcttg atcaggaact actgcaggaa tccagatcct      60
gtggcagccc cttattgtta tacgatggat cccaatgtca ggtgggagta ctgcaacctg     120
```

```
acacaatgct cagatgcaga agggactgcc gtcgcacctc cgaatgtcac cctggttcca      180
agcctagagg ctccttccga acaatcaccg actgagcaaa ggcctgggt gcaggagtgc       240 taccacggta atggacagag ttatcgaggc acatacttca ccactgtgac aggaagaacc      300
tgccaagctt ggtcatctat gacaccgcac tctcatagtc gga ccccgga aaactaccca    360 aatggtggct tgatcaggaa ctactgcagg aatccagatc ctgtggcagc cccttattgt     420
tataccatgg atcccaatgt caggtgggag tactgcaacc taacacaatg ctcagacgca     480
gaagggattg ccgtcacacc tctgactgtt accccggttc caagcctaga ggctccttcc    540
aagcaagcac caactgagca aaggcctggt gtccaggagt gctaccatgg taatggacag     600
agttatcgag gcacatactt caccactgtg acaggaagaa cctgccaagc ttggtcatct     660
atgacaccac attctcatag tcgtacccca gaaaactacc caaatggcag tccgacctct    720
tcagatctct tagtctaccc tgccgtcttc cttgatgcca tgggtcccac tgttctttca     780
actcatccgc tttccctcag tcccggagtg gctgcgacca gcagaggata tattgagagc     840
aagagagaag caccgactga gcaaaggcct ggggtgcagg agtgctacca cggtaatgga     900
cagagttatc gaggcacata cttcaccact gtgacaggaa gaacctgcca agcttggtca    960
tctatgacac cgcactctca gtcggacccc ggaaaactac ccaaatgg tggcttgatc     1020 aggaactact gcaggaatcc agatcctgtg cagccccctt attgttatac catggatccc    1080
agtgtcaggt gggagtactg caacctgaca caatgctcag acgcagaagg gactgccgtc    1140
gcacctccga atgtcacccc ggttccaagc ctagaggctc cttctgagca agcaccaact    1200
gagcaaaggc ttggggtgca ggagtgctac cacagtaatg gacagagtta tcgaggcaca    1260
tacttcacca ctgtgacagg aagaacctgc caagcttggt catctatgac accacactct    1320
catagtcgga ccccagaaaa ctacccaaat gctggcttgg tcaagaacta ctgccgaaat    1380
ccagatcctg tggcagcccc ttggtgttat acaacggatc ccagtgtcag gtgggagtac    1440
tgcaacctga cacgatgctc agatgcagaa gggactgctg tcgtgcctcc aaatattatt    1500
ccggttccaa gcctagaggc ttttcttgaa caagaaccga ctgaggaaac ccccggggta    1560
caggagtgct actaccatta tggacagagt tatagaggca catactccac cactgttaca    1620
ggaagaactt gccaagcttg gtcatctatg acaccacacc agcatagtcg dacccccaaaa    1680 aactatccaa atgctggcct gaccaggaac tactgcagga atccagatgc tgagattcgc    1740
ccttggtgtt ataccatgga tcccagtgtc aggtgggagt actgcaacct gacacaatgt    1800
ctggtgacag aatcaagtgt ccttgaaact ctcacagtgg tcccagatcc aagcacacag    1860
gcttcttctg aagaagcacc aacggagcaa agtcccgagg tccaggactg ctaccatggt    1920
gatggacaga gttatcgagg ctcattctcc accactgtca caggaaggac atgtcagtct    1980
tggtcctcta tgacaccaca ctggcatcag aggacaacag aatattatcc agatggtggc    2040
ctgaccagga actactgcag gaatccagat gctgagattc gcccttggtg ttataccatg    2100
gatcccagtg tcaggtggga gtactgcaac ctgacacaat gtccagtgac agaatcaagt    2160
gtcctcgcaa cgtccatggc tgtttctgaa caagcaccaa tggagcaaag ccccggggtc    2220
caggactgct accatggtga tggacagagt tatcgaggtt cattctccac cactgtcaca    2280
ggaaggacat gtcagtcttg gtcctctatg acaccacact ggcatcagag gaccatagaa    2340
tactacccaa atggtggcct gaccaagaac tactgcagga atccagatgc tgagattcgc    2400
ccttggtgtt ataccatgga tcccagagtc agatgggagt actgcaacct gacacaatgt    2460
```

```
gtggtgatgg aatcaagtgt ccttgcaact cccatggtgg tcccagttcc aagcagagag    2520
gttccttctg aagaagcacc aactgaaaac agccctgggg tccaggactg ctaccaaggt    2580
gatggacaga gttatcgagg cacattctcc accactatca caggaagaac atgtcagtct    2640
tggttgtcta tgacaccaca tcggcatcgg aggatcccat tacgctatcc aaatgctggc    2700
ctgaccagga actattgcag aaatccagat gctgagattc gcccttggtg ttacaccatg    2760
gatcccagtg tcaggtggga gtactgcaac ctgacacaat gtccagtgac agaatcaagt    2820
gtcctcacaa ctcccacggt ggtcccggtt ccaagcacag aggctccttc tgaacaagca    2880
ccacctgaga aaagccctgt ggtccaggat tgctaccatg gtgatggaca gagttatcga    2940
ggcacatcct ccaccactgt cacaggaagg aactgtcagt cttggtcatc tatgatacca    3000
cactggcatc agaggacccc agaaaactac ccaaatgctg gcctgaccag gaactactgc    3060
aggaatccag attctgggaa caacccctgg tgttacacga ctgatccatg tgtgaggtgg    3120
gagtactgca acctgacaca atgctcagaa acagaatcag gtgtcctaga gactcccact    3180
gttgttccgg ttccaagcat ggaagctcat tctgaagcag caccaactga gcaaaccccct    3240 gtggtccagc agtgctacca tgtaatgga cagagttatc gaggcacatt ctccaccact    3300
gtcacaggaa ggacatgtca atcttggtca tccatgacac cacaccagca taagaggacc    3360
ccggaaaacc acccaaatga tggcttgaca atgaactact gcaggaatcc agatgctgac    3420 acaggcccctt ggtgttttac catggacccc agcgtcaggc gggagtactg caacctgacg    3480
cgatgctcag acacagaagg gactgtggtc acacctccga ctgttatccc ggttccaagc    3540
ctagaggctc cttctgaaca agtgcttgga attcatcctg aattaaacga cacaattgct    3600
aacttggact caaaggtgaa ttcttttccca ccttgtgcca cagcatcctc ttcatttgat    3660
tgtgggaagc tcaagtgga gccaaagaaa tgtcctggaa gcattgtagg tgggtgtgtg    3720
gcccacccac attcctggcc ctggcaagtc agtcttagaa caaggttggg aaagcacttc    3780
tgtggaggca ccttaatatc cccagagtgg gtgctgactg ctgcttgctg cttggagacg    3840
ttctcaaggc cttccttcta caaggtcatc ctgggtgcac accaagaagt gaatctcgaa    3900
tctcatgttc aagaaataga agtgtctagg ttgttcttgg agcccatagg agcagatatt    3960
gccttgctaa agctaagcag gtactaa                                         3987
```

<210> SEQ ID NO 133
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 133
ggttcttcca gtgacagtgg                                                  20

<210> SEQ ID NO 134
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 134
atgcctcgat aactccgtcc                                                  20

METHODS AND COMPOSITIONS FOR MODULATING APOLIPOPROTEIN (A) EXPRESSION

SEQUENCE LISTING

The present application is being filed along with a Sequence Listing in electronic format. The Sequence Listing is provided as a file entitled BIOL0177USC2SEQ_ST25.txt created Oct. 21, 2016, which is 424 Kb in size. The information in the electronic format of the sequence listing is incorporated herein by reference in its entirety.

FIELD

Embodiments described herein provide methods, compounds, and compositions for reducing expression of apolipoprotein (a) mRNA and protein in an animal. Such methods, compounds, and compositions are useful to treat, prevent, or ameliorate cardiovascular and/or metabolic diseases, disorders or conditions.

BACKGROUND

Lipoproteins are globular, micelle-like particles that consist of a non-polar core of acylglycerols and cholesteryl esters surrounded by an amphiphilic coating of protein, phospholipid and cholesterol. Lipoproteins have been classified into five broad categories on the basis of their functional and physical properties: chylomicrons, very low density lipoproteins (VLDL), intermediate density lipoproteins (IDL), low density lipoproteins (LDL), and high density lipoproteins (HDL). Chylomicrons transport dietary lipids from intestine to tissues. VLDLs, IDLs and LDLs all transport triacylglycerols and cholesterol from the liver to tissues. HDLs transport endogenous cholesterol from tissues to the liver Lipoprotein particles undergo continuous metabolic processing and have variable properties and compositions. Lipoprotein densities increase without increasing particle diameter because the density of their outer coatings is less than that of the inner core. The protein components of lipoproteins are known as apolipoproteins. At least nine apolipoproteins are distributed in significant amounts among the various human lipoproteins.

The lipoprotein(a) [Lp(a)] particle was identified nearly 50 years ago and is comprised of a highly unique LDL particle in which one apolipoprotein B (apoB) protein is linked via a disulfide bond to a single apolipoprotein(a) [apo(a)] protein. The apo(a) protein shares a high degree of homology with plasminogen particularly within the kringle IV type 2 repetitive domain. Levels of circulating Lp(a) are inversely proportional to the number of kringle IV type 2 variable repeats present in the molecule and, as both alleles are co-expressed within individuals, can display heterozygous plasma isoform profiles (Kraft et al., Eur J Hum Genet, 1996; 4(2): 74-87). It is thought that this kringle repeat domain in apo(a) may be responsible for its pro-thrombotic and anti-fibrinolytic properties, potentially enhancing atherosclerotic progression.

Apo(a) is transcriptionally regulated by IL-6 and in studies in rheumatoid arthritis patients treated with an IL-6 inhibitor (tocilizumab), plasma levels were reduced by 30% after 3 month treatment (Schultz et al., PLoS One 2010; 5:e14328).

Apo(a) has been shown to preferentially bind oxidized phospholipids and potentiate vascular inflammation (Bergmark et al., J Lipid Res 2008; 49:2230-2239; Tsimikas et al., Circulation. 2009; 119(13):1711-1719).

Further, studies suggest that the Lp(a) particle may also stimulate endothelial permeability, induce plasminogen activator inhibitor type-1 expression and activate macrophage interleukin-8 secretion (Koschinsky and Marcovina, Curr Opin Lipidol 2004; 15:167-174). Importantly, recent genetic association studies revealed that Lp(a) was an independent risk factor for myocardial infarction, stroke, peripheral vascular disease and abdominal aortic aneurysm (Rifai et al., Clin Chem 2004; 50:1364-71; Erqou et al., JAMA 2009; 302:412-23; Kamstrup et al., Circulation 2008; 117:176-84). Further, in the recent Precocious Coronary Artery Disease (PROCARDIS) study, Clarke et al. (Clarke et al., NEJM (2009) 361; 2518-2528) described robust and independent associations between coronary heart disease and plasma Lp(a) concentrations. Additionally, Solfrizzi et al., suggested that increased serum Lp(a) may be linked to an increased risk for Alzheimer's Disease (AD) (Solfrizzi et al., J Neurol Neurosurg Psychiatry 2002, 72:732-736. Currently, in the clinic setting, examples of indirect apo(a) inhibitors for treating cardiovascular disease include aspirin, Niaspan, Mipomersen, Anacetrapib, Epirotirome and Lomitapide which reduce plasma Lp(a) levels by 18%, 39%, 32%, 36%, 43% and 17%, respectively. Additionally, Lp(a) apheresis has been used in the clinic to reduce apo(a) containing Lp(a) particles.

To date, therapeutic strategies to treat cardiovascular disease by directly targeting apo(a) levels have been limited. Ribozyme oligonucleotides (U.S. Pat. No. 5,877,022) and antisense oligonucleotides (WO 2005/000201; WO 2003/014397; U.S. Pat. No. 8,138,328; Merki et al., J Am Coll Cardiol 2011; 57:1611-1621) have been developed, but none of the compounds directly targeting apo(a) are currently used in the clinic.

Thus, there remains a clear unmet medical need for novel agents which can potently and selectively reduce apo(a) levels in patients at enhanced risk for cardiovascular events due to chronically elevated plasma Lp(a) levels.

SUMMARY

Provided herein are compositions and methods for modulating expression of apo(a) mRNA and protein. In certain embodiments, the apo(a) specific inhibitor decreases expression of apo(a) mRNA and protein.

In certain embodiments, the composition is an apo(a) specific inhibitor. In certain embodiments, the apo(a) specific inhibitor is a nucleic acid, protein, or small molecule. In certain embodiments, the apo(a) specific inhibitor is an antisense oligonucleotide targeting apo(a). In certain embodiments, the apo(a) specific inhibitor is a modified oligonucleotide consisting of 12 to 30 linked nucleosides and comprising a nucleobase sequence comprising a portion of at least 8 contiguous nucleobases complementary to an equal length portion of nucleobases 3901 to 3920 of SEQ ID NO: 1, wherein the nucleobase sequence of the modified oligonucleotide is at least 80% complementary to SEQ ID NO: 1. In certain embodiments, the apo(a) specific inhibitor is a modified oligonucleotide consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of the nucleobase sequence of SEQ ID NO: 1-130, 133, 134. In certain embodiments, the apo(a) specific inhibitor is a modified oligonucleotide consisting of 20 linked nucleosides and having a nucleobase sequence comprising at least 8 contiguous nucleobases of any of SEQ ID NO: 58, wherein the modified oligonucleotide comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein each internucleoside linkage is a phosphorothioate linkage and wherein each cytosine residue is a 5-methylcytosine.

Certain embodiments provide a composition comprising a compound described herein, or a salt thereof, and a pharmaceutically acceptable carrier or diluent.

In certain embodiments, the modulation of apo(a) expression occurs in a cell or tissue. In certain embodiments, the modulations occur in a cell or tissue in an animal. In certain embodiments, the animal is a human. In certain embodiments, the modulation is a reduction in apo(a) mRNA level. In certain embodiments, the modulation is a reduction in apo(a) protein level. In certain embodiments, both apo(a) mRNA and protein levels are reduced. Such reduction may occur in a time-dependent or in a dose-dependent manner.

Certain embodiments provide compositions and methods for use in therapy. Certain embodiments provide compositions and methods for preventing, treating, delaying, slowing the progression and/or ameliorating apo(a) related diseases, disorders, and conditions. Certain embodiments provide compositions and methods for preventing, treating, delaying, slowing the progression and/or ameliorating Lp(a) related diseases, disorders, and conditions. In certain embodiments, such diseases, disorders, and conditions are inflammatory, cardiovascular and/or metabolic diseases, disorders, and conditions. In certain embodiments, the compositions and methods for therapy include administering an apo(a) specific inhibitor to an individual in need thereof. In certain embodiments, the apo(a) specific inhibitor is a nucleic acid. In certain embodiments, the nucleic acid is an antisense compound. In certain embodiments, the antisense compound is a modified oligonucleotide.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or", unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl" (also 2'-MOE, MOE, 2'-O(CH$_2$)$_2$—OCH$_3$ and 2'-O-(2-methoxyethyl)) refers to an O-methoxyethyl modification of the 2' position of a furanosyl ring. A 2'-O-methoxyethyl modified sugar is a modified sugar.

"2'-deoxyribonucleoside" means a nucleoside comprising 2'-H furanosyl sugar moiety, as found in naturally occurring deoxyribonucleosides (DNA).

"2'-MOE nucleoside" (also 2'-O-methoxyethyl nucleoside) means a nucleoside comprising a 2'-MOE modified sugar moiety. "2'-O-methoxyethyl nucleotide" means a nucleotide comprising a 2'-O-methoxyethyl modified sugar moiety.

"3'-fluoro-HNA" (also "F-HNA" or "3'-F-HNA") means the sugar moiety of a nucleoside having the following structure.

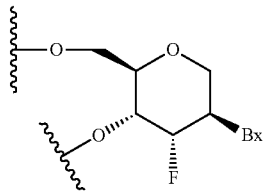

wherein Bx is a nucleobase.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5' position. A 5-methylcytosine is a modified nucleobase.

"About" means within ±10% of a value. For example, if it is stated, "a marker may be increased by about 50%", it is implied that the marker may be increased between 45%-55%.

"Active pharmaceutical agent" means the substance or substances in a pharmaceutical composition that provide a therapeutic benefit when administered to an individual. For example, in certain embodiments an antisense oligonucleotide targeted to apo(a) is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" or "administration" means providing a pharmaceutical agent to an individual, and includes, but is not limited to, administering by a medical professional and self-administering. Administration of a pharmaceutical agent to an individual can be continuous, chronic, short or intermittent. Administration can parenteral or non-parenteral.

"Agent" means an active substance that can provide a therapeutic benefit when administered to an animal. "First Agent" means a therapeutic compound of the invention. For example, a first agent can be an antisense oligonucleotide targeting apo(a). "Second agent" means a second therapeutic compound of the invention (e.g. a second antisense oligonucleotide targeting apo(a)) and/or a non-apo(a) therapeutic compound.

"Amelioration" or "ameliorate" or "ameliorating" refers to a lessening of at least one indicator, sign, or symptom of an associated disease, disorder, or condition. The severity of indicators can be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody can refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, snoRNAs, miRNAs, and satellite repeats. As used herein, the term "antisense compound" encompasses pharmaceutically acceptable derivatives of the compounds described herein.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid. As used herein, the term "antisense oligonucleotide" encompasses pharmaceutically acceptable derivatives of the compounds described herein.

"Apo(a)" means any nucleic acid or protein sequence encoding apo(a). For example, in certain embodiments, apo(a) includes a DNA sequence encoding apo(a), a RNA sequence transcribed from DNA encoding apo(a) (including genomic DNA comprising introns and exons), a mRNA sequence encoding apo(a), or a peptide sequence encoding apo(a).

"Apo(a) nucleic acid" means any nucleic acid encoding apo(a). For example, in certain embodiments, an apo(a) nucleic acid includes a DNA sequence encoding apo(a), a RNA sequence transcribed from DNA encoding apo(a) (including genomic DNA comprising introns and exons), and a mRNA sequence encoding apo(a).

"Apo(a) mRNA" means a mRNA encoding an apo(a) protein.

"Apo(a) protein" means any protein sequence encoding Apo(a).

"Apo(a) specific inhibitor" refers to any agent capable of specifically inhibiting the expression of an apo(a) nucleic acid and/or apo(a) protein. For example, apo(a) specific inhibitors include nucleic acids (including antisense compounds), peptides, antibodies, small molecules, and other agents capable of inhibiting the expression of apo(a) nucleic acid and/or apo(a) protein. In certain embodiments, by specifically modulating apo(a) nucleic acid expression and/or apo(a) protein expression, apo(a) specific inhibitors can affect other components of the lipid transport system including downstream components. Similarly, in certain embodiments, apo(a) specific inhibitors can affect other molecular processes in an animal.

"Atherosclerosis" means a hardening of the arteries affecting large and medium-sized arteries and is characterized by the presence of fatty deposits. The fatty deposits are called "atheromas" or "plaques," which consist mainly of cholesterol and other fats, calcium and scar tissue, and damage the lining of arteries.

"Bicyclic sugar" means a furanosyl ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"Cap structure" or "terminal cap moiety" means chemical modifications, which have been incorporated at either terminus of an antisense compound.

"Cardiovascular disease" or "cardiovascular disorder" refers to a group of conditions related to the heart, blood vessels, or the circulation. Examples of cardiovascular diseases include, but are not limited to, aneurysm, angina, arrhythmia, atherosclerosis, cerebrovascular disease (stroke), coronary heart disease, hypertension, dyslipidemia, hyperlipidemia, hypertriglyceridemia and hypercholesterolemia.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Cholesterol" is a sterol molecule found in the cell membranes of all animal tissues. Cholesterol must be transported in an animal's blood plasma by lipoproteins including very low density lipoprotein (VLDL), intermediate density lipoprotein (IDL), low density lipoprotein (LDL), and high density lipoprotein (HDL). "Plasma cholesterol" refers to the sum of all lipoproteins (VDL, IDL, LDL, HDL) esterified and/or non-esterified cholesterol present in the plasma or serum.

"Cholesterol absorption inhibitor" means an agent that inhibits the absorption of exogenous cholesterol obtained from diet.

"Co-administration" means administration of two or more agents to an individual. The two or more agents can be in a single pharmaceutical composition, or can be in separate pharmaceutical compositions. Each of the two or more agents can be administered through the same or different routes of administration. Co-administration encompasses parallel or sequential administration.

"Complementarity" means the capacity for pairing between nucleobases of a first nucleic acid and a second nucleic acid. In certain embodiments, complementarity between the first and second nucleic acid can be between two DNA strands, between two RNA strands, or between a DNA and an RNA strand. In certain embodiments, some of the nucleobases on one strand are matched to a complementary hydrogen bonding base on the other strand. In certain embodiments, all of the nucleobases on one strand are matched to a complementary hydrogen bonding base on the other strand. In certain embodiments, a first nucleic acid is an antisense compound and a second nucleic acid is a target nucleic acid. In certain such embodiments, an antisense oligonucleotide is a first nucleic acid and a target nucleic acid is a second nucleic acid.

"Constrained ethyl" or "cEt" refers to a bicyclic nucleoside having a furanosyl sugar that comprises a methyl (methyleneoxy) (4'-CH(CH$_3$)—O-2') bridge between the 4' and the 2' carbon atoms.

"Constrained ethyl nucleoside" (also cEt nucleoside) means a nucleoside comprising a bicyclic sugar moiety comprising a 4'-CH(CH$_3$)—O-2' bridge.

"Contiguous nucleobases" means nucleobases immediately adjacent to each other.

"Cross-reactive" means an oligomeric compound targeting one nucleic acid sequence can hybridize to a different nucleic acid sequence. For example, in some instances an antisense oligonucleotide targeting human apo(a) can cross-react with an apo(a) from another species. Whether an oligomeric compound cross-reacts with a nucleic acid sequence other than its designated target depends on the degree of complementarity the compound has with the non-target nucleic acid sequence. The higher the complementarity between the oligomeric compound and the non-target nucleic acid, the more likely the oligomeric compound will cross-react with the nucleic acid.

"Cure" means a method that restores health or a prescribed treatment for an illness.

"Coronary heart disease (CM)" means a narrowing of the small blood vessels that supply blood and oxygen to the heart, which is often a result of atherosclerosis.

"Deoxyribonucleotide" means a nucleotide having a hydrogen at the 2' position of the sugar portion of the nucleotide. Deoxyribonucleotides can be modified with any of a variety of substituents.

"Diabetes mellitus" or "diabetes" is a syndrome characterized by disordered metabolism and abnormally high blood sugar (hyperglycemia) resulting from insufficient levels of insulin or reduced insulin sensitivity. The characteristic symptoms are excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy.

"Diabetic dyslipidemia" or "type 2 diabetes with dyslipidemia" means a condition characterized by Type 2 diabetes, reduced HDL-C, elevated triglycerides (TG), and elevated small, dense LDL particles.

"Diluent" means an ingredient in a composition that lacks pharmacological activity, but is pharmaceutically necessary or desirable. For example, the diluent in an injected composition can be a liquid, e.g. saline solution.

"Dyslipidemia" refers to a disorder of lipid and/or lipoprotein metabolism, including lipid and/or lipoprotein overproduction or deficiency. Dyslipidemias can be manifested by elevation of lipids such as chylomicron, cholesterol and triglycerides as well as lipoproteins such as low-density lipoprotein (LDL) cholesterol.

"Dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide.

"Dose" means a specified quantity of a pharmaceutical agent provided in a single administration, or in a specified time period. In certain embodiments, a dose can be administered in one, two, or more boluses, tablets, or injections. For example, in certain embodiments where subcutaneous administration is desired, the desired dose requires a volume not easily accommodated by a single injection, therefore, two or more injections can be used to achieve the desired dose. In certain embodiments, the pharmaceutical agent is administered by infusion over an extended period of time or continuously. Doses can be stated as the amount of pharmaceutical agent per hour, day, week, or month. Doses can also be stated as mg/kg or g/kg.

"Effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

"Fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a second nucleic acid is a target nucleic acid.

"Furanosyl" means a structure comprising a 5-membered ring comprising four carbon atoms and one oxygen atom.

"Gapmer" means a chimeric antisense compound in which an internal region having a plurality of nucleosides that support RNaseH cleavage is positioned between external regions having one or more nucleosides, wherein the nucleosides comprising the internal region are chemically distinct from the nucleoside or nucleosides comprising external regions. The internal region may be referred to as a "gap" and the external regions may be referred to as the "wings."

"Gap-widened" means a chimeric antisense compound having a gap segment of 12 or more contiguous 2'-deoxyribonucleosides positioned between and immediately adjacent to 5' and 3' wing segments having from one to six nucleosides.

"Glucose" is a monosaccharide used by cells as a source of energy and inflammatory intermediate. "Plasma glucose" refers to glucose present in the plasma.

"High density lipoprotein-C" or "HDL-C" means cholesterol associated with high density lipoprotein particles. Concentration of HDL-C in serum (or plasma) is typically quantified in mg/dL or nmol/L. "Serum HDL-C" and "plasma HDL-C" mean HDL-C in serum and plasma, respectively.

"HMG-CoA reductase inhibitor" means an agent that acts through the inhibition of the enzyme HMG-CoA reductase, such as atorvastatin, rosuvastatin, fluvastatin, lovastatin, pravastatin, and simvastatin.

"Hybridization" means the annealing of complementary nucleic acid molecules. In certain embodiments, complementary nucleic acid molecules include an antisense compound and a target nucleic acid.

"Hypercholesterolemia" means a condition characterized by elevated cholesterol or circulating (plasma) cholesterol, LDL-cholesterol and VLDL-cholesterol, as per the guidelines of the Expert Panel Report of the National Cholesterol Educational Program (NCEP) of Detection, Evaluation of Treatment of high cholesterol in adults (see, Arch. Int. Med. (1988) 148, 36-39).

"Hyperlipidemia" or "hyperlipemia" is a condition characterized by elevated serum lipids or circulating (plasma) lipids. This condition manifests an abnormally high concentration of fats. The lipid fractions in the circulating blood are cholesterol, low density lipoproteins, very low density lipoproteins, chylomicrons and triglycerides. The Fredrickson classification of hyperlipidemias is based on the pattern of TG and cholesterol-rich lipoprotein particles, as measured by electrophoresis or ultracentrifugation and is commonly used to characterize primary causes of hyperlipidemias such as hypertriglyceridemia (Fredrickson and Lee, Circulation, 1965, 31:321-327; Fredrickson et al., New Eng J Med, 1967, 276 (1): 34-42).

"Hypertriglyceridemia" means a condition characterized by elevated triglyceride levels. Its etiology includes primary (i.e. genetic causes) and secondary (other underlying causes such as diabetes, metabolic syndrome/insulin resistance, obesity, physical inactivity, cigarette smoking, excess alcohol and a diet very high in carbohydrates) factors or, most often, a combination of both (Yuan et al. *CMAJ,* 2007, 176:1113-1120).

"Identifying" or "selecting an animal with metabolic or cardiovascular disease" means identifying or selecting a subject prone to or having been diagnosed with a metabolic disease, a cardiovascular disease, or a metabolic syndrome; or, identifying or selecting a subject having any symptom of a metabolic disease, cardiovascular disease, or metabolic syndrome including, but not limited to, hypercholesterolemia, hyperglycemia, hyperlipidemia, hypertriglyceridemia, hypertension increased insulin resistance, decreased insulin sensitivity, above normal body weight, and/or above normal body fat content or any combination thereof. Such identification can be accomplished by any method, including but not limited to, standard clinical tests or assessments, such as measuring serum or circulating (plasma) cholesterol, measuring serum or circulating (plasma) blood-glucose, measuring serum or circulating (plasma) triglycerides, measuring blood-pressure, measuring body fat content, measuring body weight, and the like.

"Improved cardiovascular outcome" means a reduction in the occurrence of adverse cardiovascular events, or the risk thereof. Examples of adverse cardiovascular events include, without limitation, death, reinfarction, stroke, cardiogenic shock, pulmonary edema, cardiac arrest, and atrial dysrhythmia.

"Immediately adjacent" means there are no intervening elements between the immediately adjacent elements, for example, between regions, segments, nucleotides and/or nucleosides.

"Increasing HDL" or "raising HDL" means increasing the level of HDL in an animal after administration of at least one compound of the invention, compared to the HDL level in an animal not administered any compound.

"Individual" or "subject" or "animal" means a human or non-human animal selected for treatment or therapy.

"Individual in need thereof" refers to a human or non-human animal selected for treatment or therapy that is in need of such treatment or therapy.

"Induce", "inhibit", "potentiate", "elevate", "increase", "decrease", "reduce" or the like denote quantitative differences between two states. For example, "an amount effective to inhibit the activity or expression of apo(a)" means that the level of activity or expression of apo(a) in a treated sample will differ from the level of apo(a) activity or expression in an untreated sample. Such terms are applied to, for example, levels of expression, and levels of activity.

"Inflammatory condition" refers to a disease, disease state, syndrome, or other condition resulting in inflammation. For example, rheumatoid arthritis and liver fibrosis are inflammatory conditions. Other examples of inflammatory conditions include sepsis, myocardial ischemia/reperfusion injury, adult respiratory distress syndrome, nephritis, graft rejection, inflammatory bowel disease, multiple sclerosis, arteriosclerosis, atherosclerosis and vasculitis.

"Inhibiting the expression or activity" refers to a reduction or blockade of the expression or activity of a RNA or protein and does not necessarily indicate a total elimination of expression or activity.

"Insulin resistance" is defined as the condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to metabolic syndrome and type 2 diabetes.

"Insulin sensitivity" is a measure of how effectively an individual processes glucose. An individual having high insulin sensitivity effectively processes glucose whereas an individual with low insulin sensitivity does not effectively process glucose.

"Internucleoside linkage" refers to the chemical bond between nucleosides.

"Intravenous administration" means administration into a vein.

"Linked nucleosides" means adjacent nucleosides which are bonded together.

"Lipid-lowering" means a reduction in one or more lipids (e.g., LDL, VLDL) in a subject. "Lipid-raising" means an increase in a lipid (e.g., HDL) in a subject. Lipid-lowering or lipid-raising can occur with one or more doses over time.

"Lipid-lowering therapy" or "lipid lowering agent" means a therapeutic regimen provided to a subject to reduce one or more lipids in a subject. In certain embodiments, a lipid-lowering therapy is provided to reduce one or more of apo(a), CETP, apoB, total cholesterol, LDL-C, VLDL-C, IDL-C, non-HDL-C, triglycerides, small dense LDL particles, and Lp(a) in a subject. Examples of lipid-lowering therapy include, but are not limited to, apoB inhibitors, statins, fibrates and MTP inhibitors.

"Lipoprotein", such as VLDL, LDL and HDL, refers to a group of proteins found in the serum, plasma and lymph and are important for lipid transport. The chemical composition of each lipoprotein differs, for example, in that the HDL has a higher proportion of protein versus lipid, whereas the VLDL has a lower proportion of protein versus lipid.

"Lp(a)" comprises apo(a) and a LDL like particle containing apoB. The apo(a) is linked to the apoB by a disulfide bond.

"Low density lipoprotein-cholesterol (LDL-C)" means cholesterol carried in low density lipoprotein particles. Concentration of LDL-C in serum (or plasma) is typically quantified in mg/dL or nmol/L. "Serum LDL-C" and "plasma LDL-C" mean LDL-C in the serum and plasma, respectively.

"Major risk factors" refers to factors that contribute to a high risk for a particular disease or condition. In certain embodiments, major risk factors for coronary heart disease include, without limitation, cigarette smoking, hypertension, high LDL, low HDL-C, family history of coronary heart disease, age, and other factors disclosed herein.

"Metabolic disorder" or "metabolic disease" refers to a condition characterized by an alteration or disturbance in metabolic function. "Metabolic" and "metabolism" are terms well known in the art and generally include the whole range of biochemical processes that occur within a living organism. Metabolic disorders include, but are not limited to, hyperglycemia, prediabetes, diabetes (type 1 and type 2), obesity, insulin resistance, metabolic syndrome and dyslipidemia due to type 2 diabetes.

"Metabolic syndrome" means a condition characterized by a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Mismatch" or "non-complementary nucleobase" refers to the case when a nucleobase of a first nucleic acid is not capable of pairing with the corresponding nucleobase of a second or target nucleic acid.

"Mixed dyslipidemia" means a condition characterized by elevated cholesterol and elevated triglycerides.

"Modified internucleoside linkage" refers to a substitution or any change from a naturally occurring internucleoside bond (i.e. a phosphodiester internucleoside bond). For example, a phosphorothioate linkage is a modified internucleoside linkage.

"Modified nucleobase" refers to any nucleobase other than adenine, cytosine, guanine, thymidine, or uracil. For example, 5-methylcytosine is a modified nucleobase. An "unmodified nucleobase" means the purine bases adenine (A) and guanine (G), and the pyrimidine bases thymine (T), cytosine (C), and uracil (U).

"Modified nucleoside" means a nucleoside having at least one modified sugar moiety, and/or modified nucleobase.

"Modified nucleotide" means a nucleotide having at least one modified sugar moiety, modified internucleoside linkage and/or modified nucleobase.

"Modified oligonucleotide" means an oligonucleotide comprising at least one modified nucleotide.

"Modified sugar" refers to a substitution or change from a natural sugar. For example, a 2'-O-methoxyethyl modified sugar is a modified sugar.

"MOE nucleoside" means a nucleoside comprising a 2'-substituted sugar moiety comprising MOE at the 2'-position.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids (ssDNA), double-stranded nucleic acids (dsDNA), small interfering ribonucleic acids (siRNA), and microRNAs (miRNA). A nucleic acid may also comprise any combination of these elements in a single molecule.

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the oligonucleotide and the target nucleic acid are considered to be complementary at that nucleobase pair.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base, and not necessarily the linkage at one or more positions of an oligomeric compound; for example nucleoside mimetics having morpholino, cyclohexenyl, cyclohexyl, tetrahydropyranyl, bicyclo or tricyclo sugar mimetics such as non-furanose sugar units.

"Nucleotide" means a nucleoside having a phosphate group covalently linked to the sugar portion of the nucleoside.

"Nucleotide mimetic" includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage).

"Oligomeric compound" or "oligomer" means a polymer of linked monomeric subunits which is capable of hybridizing to a region of a nucleic acid molecule. In certain embodiments, oligomeric compounds are oligonucleosides. In certain embodiments, oligomeric compounds are oligonucleotides. In certain embodiments, oligomeric compounds are antisense compounds. In certain embodiments, oligomeric compounds are antisense oligonucleotides. In certain embodiments, oligomeric compounds are chimeric oligonucleotides.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration. Administration can be continuous, chronic, short or intermittent.

"Peptide" means a molecule formed by linking at least two amino acids by amide bonds. Peptide refers to polypeptides and proteins.

"Pharmaceutical agent" means a substance that provides a therapeutic benefit when administered to an individual. For example, in certain embodiments, an antisense oligonucleotide targeted to apo(a) is a pharmaceutical agent.

"Pharmaceutical composition" or "composition" means a mixture of substances suitable for administering to an individual. For example, a pharmaceutical composition can comprise one or more active agents and a pharmaceutical carrier e.g., a sterile aqueous solution.

"Pharmaceutically acceptable carrier" means a medium or diluent that does not interfere with the structure of the compound. Certain of such carriers enable pharmaceutical compositions to be formulated as, for example, tablets, pills, dragees, capsules, liquids, gels, syrups, slurries, suspension and lozenges for the oral ingestion by a subject. Certain of such carriers enable pharmaceutical compositions to be formulated for injection, infusion or topical administration. For example, a pharmaceutically acceptable carrier can be a sterile aqueous solution.

"Pharmaceutically acceptable derivative" encompasses derivatives of the compounds described herein such as solvates, hydrates, esters, prodrugs, polymorphs, isomers, isotopically labelled variants, pharmaceutically acceptable salts and other derivatives known in the art.

"Pharmaceutically acceptable salts" means physiologically and pharmaceutically acceptable salts of antisense compounds, i.e., salts that retain the desired biological activity of the parent compound and do not impart undesired toxicological effects thereto. The term "pharmaceutically acceptable salt" or "salt" includes a salt prepared from pharmaceutically acceptable non-toxic acids or bases, including inorganic or organic acids and bases. "Pharmaceutically acceptable salts" of the compounds described herein may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002). Sodium salts of antisense oligonucleotides are useful and are well accepted for therapeutic administration to humans. Accordingly, in one embodiment the compounds described herein are in the form of a sodium salt.

"Phosphorothioate linkage" means a linkage between nucleosides where the phosphodiester bond is modified by replacing one of the non-bridging oxygen atoms with a sulfur atom. A phosphorothioate linkage (P=S) is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form (i.e., a drug) within the body or cells thereof by the action of endogenous enzymes or other chemicals or conditions.

"Raise" means to increase in amount. For example, to raise plasma HDL levels means to increase the amount of HDL in the plasma.

"Reduce" means to bring down to a smaller extent, size, amount, or number. For example, to reduce plasma triglyceride levels means to bring down the amount of triglyceride in the plasma.

"Region" or "target region" is defined as a portion of the target nucleic acid having at least one identifiable structure, function, or characteristic. For example, a target region may encompass a 3' UTR, a 5' UTR, an exon, an intron, an exon/intron junction, a coding region, a translation initiation region, translation termination region, or other defined nucleic acid region. The structurally defined regions for apo(a) can be obtained by accession number from sequence databases such as NCBI and such information is incorporated herein by reference. In certain embodiments, a target region may encompass the sequence from a 5' target site of one target segment within the target region to a 3' target site of another target segment within the target region.

"Ribonucleotide" means a nucleotide having a hydroxy at the 2' position of the sugar portion of the nucleotide. Ribonucleotides can be modified with any of a variety of substituents.

"Second agent" or "second therapeutic agent" means an agent that can be used in combination with a "first agent". A second therapeutic agent can include, but is not limited to, antisense oligonucleotides targeting apo(a) or apoB. A second agent can also include anti-apo(a) antibodies, apo(a) peptide inhibitors, cholesterol lowering agents, lipid lowering agents, glucose lowering agents and anti-inflammatory agents.

"Segments" are defined as smaller, sub-portions of regions within a nucleic acid. For example, a "target segment" means the sequence of nucleotides of a target nucleic acid to which one or more antisense compounds is targeted. "5' target site" refers to the 5'-most nucleotide of a target segment. "3' target site" refers to the 3'-most nucleotide of a target segment. Alternatively, a "start site" can refer to the 5'-most nucleotide of a target segment and a "stop site" refers to the 3'-most nucleotide of a target segment. A target segment can also begin at the "start site" of one sequence and end at the "stop site" of another sequence.

"Shortened" or "truncated" versions of antisense oligonucleotides or target nucleic acids taught herein have one, two or more nucleosides deleted.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity to a target nucleic acid to induce a desired effect while exhibiting minimal or no effects on non-target nucleic acids under conditions in which specific binding is desired, i.e. under physiological conditions in the case of in vivo assays and therapeutic treatments.

"Statin" means an agent that inhibits the activity of HMG-CoA reductase.

"Subcutaneous administration" means administration just below the skin.

"Subject" means a human or non-human animal selected for treatment or therapy.

"Sugar moiety" means a naturally occurring sugar moiety or a modified sugar moiety of a nucleoside.

"Symptom of cardiovascular disease or disorder" means a phenomenon that arises from and accompanies the cardiovascular disease or disorder and serves as an indication of it. For example, angina; chest pain; shortness of breath; palpitations; weakness; dizziness; nausea; sweating; tachycardia; bradycardia; arrhythmia; atrial fibrillation; swelling in the lower extremities; cyanosis; fatigue; fainting; numbness of the face; numbness of the limbs; claudication or cramping of muscles; bloating of the abdomen; or fever are symptoms of cardiovascular disease or disorder.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Therapeutically effective amount" means an amount of a pharmaceutical agent that provides a therapeutic benefit to an individual.

"Therapeutic lifestyle change" means dietary and lifestyle changes intended to lower fat/adipose tissue mass and/or cholesterol. Such change can reduce the risk of developing heart disease, and may includes recommendations for dietary intake of total daily calories, total fat, saturated fat, polyunsaturated fat, monounsaturated fat, carbohydrate, protein, cholesterol, insoluble fiber, as well as recommendations for physical activity.

"Treat" or "treating" refers to administering a compound described herein to effect an alteration or improvement of a disease, disorder, or condition.

"Triglyceride" or "TG" means a lipid or neutral fat consisting of glycerol combined with three fatty acid molecules.

"Type 2 diabetes," (also known as "type 2 diabetes mellitus", "diabetes mellitus, type 2", "non-insulin-dependent diabetes", "NIDDM", "obesity related diabetes", or "adult-onset diabetes") is a metabolic disorder that is primarily characterized by insulin resistance, relative insulin deficiency, and hyperglycemia.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Wing segment" means one or a plurality of nucleosides modified to impart to an oligonucleotide properties such as enhanced inhibitory activity, increased binding affinity for a target nucleic acid, or resistance to degradation by in vivo nucleases.

Certain Embodiments

Certain embodiments provide a compounds and methods for decreasing apo(a) mRNA and protein expression. In certain embodiments, the compound is an apo(a) specific inhibitor for treating, preventing, or ameliorating an apo(a) associated disease. In certain embodiments, the compound is an antisense oligonucleotide targeting apo(a).

Certain embodiments provide a compounds and methods for decreasing Lp(a) levels. In certain embodiments, the compound is an apo(a) specific inhibitor for treating, preventing, or ameliorating an Lp(a) associated disease. In certain embodiments, the compound is an antisense oligonucleotide targeting apo(a).

Certain embodiments provide a compound comprising a modified oligonucleotide targeting apo(a) consisting of 12 to 30 linked nucleosides. In certain embodiments, the modified oligonucleotide consists of 15 to 30, 18 to 24, 19 to 22, 13 to 25, 14 to 25, 15 to 25 linked nucleosides. In certain embodiments, the modified oligonucleotide comprises at least 12, at least 13, at least 14, at least 15, at least 16, at least 17, at least 18, at least 19, at least 20, at least 21, at least 22, at least 23, at least 24, at least 25, at least 26, at least 27, at least 28, at least 29 or 30 linked nucleosides. In certain embodiments, the modified oligonucleotide consists of 20 linked nucleosides.

Certain embodiments provide a compound comprising a modified oligonucleotide targeting apo(a) comprising at least 8, at least 9, at least 10, at least 11, at least 12, at least 13, at least 14, at least 15, at least 16, at least 17, at least 18, at least 19, or 20 contiguous nucleobases complementary to an equal length portion of any of SEQ ID NOs: 1-4. Certain embodiments provide a compound comprising a modified oligonucleotide targeting an apo(a) segment comprising at least 8, at least 9, at least 10, at least 11, at least 12, at least 13, at least 14, at least 15, at least 16, at least 17, at least 18, at least 19, or 20 contiguous nucleobases complementary to an equal length portion of any of the target segments shown in Tables 3-13 and 28-30. In the tables, the "Start Site" refers to the 5'-most nucleotide of a target segment and "Stop Site" refers to the 3'-most nucleotide of a target segment. A target segment can range from the start site to the stop site of each sequence listed in the tables. Alternatively, the target segment can range from the start site of one sequence and end at the stop site of another sequence. For example, as shown in Table 5, a target segment can range from 3901-3920, the start site to the stop site of SEQ ID NO: 58. In another example, as shown in Table 5, a target segment can range from 3900-3923, the start site of SEQ ID NO: 57 to the stop site of SEQ ID NO: 61.

Certain embodiments provide a compound comprising a modified oligonucleotide targeting apo(a), wherein the nucleobase sequence of the modified oligonucleotide is at least 80%, at least 85%, at least 90%, at least 95%, or 100% complementary to any of SEQ ID NOs: 1-4. Certain embodiments provide a compound comprising a modified oligonucleotide targeting apo(a), wherein the nucleobase sequence of the modified oligonucleotide is at least 80%, at least 85%, at least 90%, at least 95%, or 100% complementary to any of the target segments shown in Tables 3-13 and 28-30.

Certain embodiments provide a compound comprising a modified oligonucleotide targeting apo(a) consisting of 12 to 30 linked nucleosides and comprising a nucleobase sequence comprising a portion of at least 8, at least 9, at least 10, at least 11, at least 12, at least 13, at least 14, at least 15, at least 16, at least 17, at least 18, at least 19, or 20 contiguous nucleobases complementary to an equal length portion of nucleobases 3901 to 3920 of SEQ ID NO: 1, wherein the nucleobase sequence of the modified oligonucleotide is at least 80% complementary to SEQ ID NO: 1.

Certain embodiments provide a compound comprising a modified oligonucleotide targeting apo(a) consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29 or 30 contiguous nucleobases complementary to an equal length portion of nucleobases 3900 to 3923 of SEQ ID NO: 1, wherein the nucleobase sequence of the modified oligonucleotide is at least 80% complementary to SEQ ID NO: 1.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 12-130, 133, 134. In certain embodiments, the modified oligonucleotide has a nucleobase sequence comprising at least 8 contiguous nucleobases of any one of the nucleobase sequences of SEQ ID NOs: 12-130, 133, 134.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 12-20, 22-33, 35-44, 47-50, 51, 53, 57-62, 65-66, 68, 70-79, 81, 85-86, 89-90, 92-94, 97, 105-110, 103-104, 133-134.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 12-19, 26-30, 32, 35, 38-44, 46-47, 50, 57-58, 61, 64-66, 68, 72-74, 76-77, 92-94, 103-110.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 111, 114-121, 123-129.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 14, 17, 18, 26-28, 39, 71, 106-107.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 14, 26-29, 39-40, 82.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 14, 16-18.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 26-27, 107.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 28-29, 39-40, 47.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 28, 93, 104, 134.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of the nucleobase sequence of SEQ ID NO: 58.

In certain embodiments, the modified oligonucleotide has a nucleobase sequence comprising at least 8 contiguous nucleobases of the nucleobase sequence of SEQ ID NO: 58.

Certain embodiments provide a compound comprising a modified oligonucleotide targeting apo(a), wherein the modified oligonucleotide is single-stranded.

Certain embodiments provide a compound comprising a modified oligonucleotide targeting apo(a), wherein at least one internucleoside linkage is a modified internucleoside linkage. In certain embodiments, each internucleoside linkage is a phosphorothioate internucleoside linkage.

Certain embodiments provide a compound comprising a modified oligonucleotide targeting apo(a), wherein at least one nucleoside comprises a modified nucleobase. In certain embodiments, the modified nucleobase is a 5-methylcytosine.

Certain embodiments provide a compound comprising a modified oligonucleotide targeting apo(a), wherein the modified oligonucleotide comprises at least one modified sugar. In certain embodiments, the modified sugar is a bicyclic sugar. In certain embodiments, the modified sugar comprises a 2'-O-methoxyethyl, a constrained ethyl, a 3'-fluoro-HNA or a 4'-$(CH_2)_n$—O-2' bridge, wherein n is 1 or 2.

Certain embodiments provide a compound comprising a modified oligonucleotide targeting apo(a), wherein the modified oligonucleotide consists of 12 to 30 linked nucleosides and comprises: (a) a gap segment consisting of linked deoxynucleosides; (b) a 5' wing segment consisting of linked nucleosides; (c) a 3' wing segment consisting of linked nucleosides; and wherein the gap segment is positioned between the 5' wing segment and the 3' wing segment and wherein each nucleoside of each wing segment comprises a modified sugar.

Certain embodiments provide a compound comprising a modified oligonucleotide targeting apo(a), wherein the modified oligonucleotide consists of 20 linked nucleosides and comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein each internucleoside linkage is a phosphorothioate linkage and wherein each cytosine residue is a 5-methylcytosine.

Certain embodiments provide a compound comprising a modified oligonucleotide targeting apo(a), wherein the modified oligonucleotide consists of 20 linked nucleosides and has a nucleobase sequence comprising at least 8 contiguous nucleobases of any of SEQ ID NOs: 12-130, 133, 134, wherein the modified oligonucleotide comprises: (a) a gap segment consisting often linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein each internucleoside linkage is a phosphorothioate linkage and wherein each cytosine residue is a 5-methylcytosine.

Certain embodiments provide a compound comprising a modified oligonucleotide targeting apo(a), wherein the modified oligonucleotide consists of 20 linked nucleosides and has a nucleobase sequence comprising at least 8 contiguous nucleobases of SEQ ID NO: 58, wherein the modified oligonucleotide comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein each internucleoside linkage is a phosphorothioate linkage and wherein each cytosine residue is a 5-methylcytosine.

Certain embodiments provide a modified oligonucleotide targeting apo(a), wherein the modified oligonucleotide consists of 20 linked nucleosides with the nucleobase sequence of SEQ ID NO: 58, wherein the modified oligonucleotide comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein each internucleoside linkage is a phosphorothioate linkage and wherein each cytosine residue is a 5-methylcytosine.

In certain embodiments, the compound is in a salt form. In further embodiments, the compound further comprises of a pharmaceutically acceptable carrier or diluent. In certain embodiments, the compound comprising a modified oligonucleotide targeting apo(a), or a salt thereof, and a pharmaceutically acceptable carrier or diluent.

Certain embodiments provide a composition comprising a compound as described herein, wherein the viscosity level of the compound is less than 40 centipoise (cP). In certain embodiments, the antisense compounds as described herein are efficacious by virtue of having a viscosity of less than 40 cP, less than 35 cP, less than 30 cP, less than 25 cP, less than 20 cP or less than 15 cP when measured by the parameters as described in Example 13.

Certain embodiments provide compositions and methods for use in therapy to treat an apo(a) related disease, disorder or condition. Certain embodiments provide compositions and methods for use in therapy to treat an Lp(a) related disease, disorder or condition. In certain embodiments, the composition is a compound comprising an apo(a) specific inhibitor. In certain embodiments, the apo(a) specific inhibitor is a nucleic acid. In certain embodiments, the nucleic acid is an antisense compound. In certain embodiments, the antisense compound is a modified oligonucleotide targeting apo(a). In certain embodiments, the modified oligonucleotide targeting apo(a), is used in treating, preventing, slowing progression, ameliorating a cardiovascular and/or metabolic disease, disorder or condition. In certain embodiments, the compositions and methods for therapy include administering an apo(a) specific inhibitor to an individual in need thereof.

Certain embodiments provide compositions and methods for reducing apo(a) levels. Certain embodiments provide compositions and methods for reducing Lp(a) levels. In certain embodiments, reducing apo(a) levels in a tissue, organ or subject improves the ratio of LDL to HDL or the ratio of TG to HDL.

Certain embodiments provide compositions and methods for preventing, treating, delaying, slowing the progression and/or ameliorating apo(a) related diseases, disorders, and conditions in a subject in need thereof. Certain embodiments provide compositions and methods for preventing, treating, delaying, slowing the progression and/or ameliorating Lp(a) related diseases, disorders, and conditions in a subject in need thereof. In certain embodiments, such diseases, disorders, and conditions include cardiovascular and/or metabolic diseases, disorders, and conditions. Certain such cardiovascular diseases, disorders or conditions include, but are not limited to, aneurysm (e.g., abdominal aortic aneurysm), angina, arrhythmia, atherosclerosis, cerebrovascular disease, coronary artery disease, coronary heart disease, dyslipidemia, hypercholesterolemia, hyperlipidemia, hypertension, hypertriglyceridemia, myocardial infarction, peripheral vascular disease (e.g., peripheral artery disease, peripheral artery occlusive disease), retinal vascular occlusion, or stroke. Certain such metabolic diseases, disorders or conditions include, but are not limited to, hyperglycemia, prediabetes, diabetes (type I and type II), obesity, insulin resistance, metabolic syndrome and diabetic dyslipidemia. Certain such inflammatory diseases, disorders or conditions include, but are not limited to, coronary artery disease (CAD), Alzheimer's Disease and thromboembolic diseases, disorder or conditions Certain thromboembolic diseases, disorders or conditions include, but are not limited to, stroke, thrombosis (e.g., venous thromboembolism), myocardial infarction and peripheral vascular disease.

Certain embodiments provide a method of reducing at least one symptom of a cardiovascular disease, disorder or condition. In certain embodiments, the symptoms include, but are not limited to, angina, chest pain, shortness of breath, palpitations, weakness, dizziness, nausea, sweating, tachycardia, bradycardia, arrhythmia, atrial fibrillation, swelling in the lower extremities, cyanosis, fatigue, fainting, numbness of the face, numbness of the limbs, claudication or cramping of muscles, bloating of the abdomen, and fever.

In certain embodiments, the modulation of apo(a) or Lp(a) expression occurs in a cell, tissue or organ. In certain embodiments, the modulations occur in a cell, tissue or organ in an animal. In certain embodiments, the modulation is a reduction in apo(a) mRNA level. In certain embodiments, the modulation is a reduction in apo(a) protein level.

In certain embodiments, both apo(a) mRNA and protein levels are reduced. In certain embodiments, the modulation is a reduction in Lp(a) level. Such reduction may occur in a time-dependent or in a dose-dependent manner.

In certain embodiments, the subject or animal is human.

In certain embodiments, the compound is parenterally administered. In further embodiments, the parenteral administration is subcutaneous.

In certain embodiments, the compound is co-administered with a second agent or therapy. In certain embodiments, the second agent is a glucose-lowering agent. In certain embodiments, the second agent is a LDL, TG or cholesterol lowering agent. In certain embodiments, the second agent is an anti-inflammatory agent. In certain embodiments, the second agent is an Alzheimer Disease drug. In certain embodiments, the second agent can be, but is not limited to, a non-steroidal anti-inflammatory drug (NSAID e.g., aspirin), niacin (e.g., Niaspan), nicotinic acid, an apoB inhibitor (e.g., Mipomersen), a CETP inhibitor (e.g., Anacetrapib), an apo(a) inhibitor, a thyroid hormone analog (e.g., Eprotirome), a HMG-CoA reductase inhibitor (e.g., a statin), a fibrate (e.g., Gemfibrozil) and an microsomal triglyceride transfer protein inhibitor (e.g., Lomitapide). The therapy can be, but is not limited to, Lp(a) apheresis. Agents or therapies can be co-administered or administered concomitantly. Agents or therapies can be sequentially or subsequently administered.

Certain embodiments provide use of a compound targeted to apo(a) for decreasing apo(a) levels in an animal. Certain embodiments provide use of a compound targeted to apo(a) for decreasing Lp(a) levels in an animal. Certain embodiments provide use of a compounds targeted to apo(a) for the treatment, prevention, or amelioration of a disease, disorder, or condition associated with apo(a). Certain embodiments provide use of a compounds targeted to apo(a) for the treatment, prevention, or amelioration of a disease, disorder, or condition associated with Lp(a).

Certain embodiments provide use of a compound targeted to apo(a) in the preparation of a medicament for decreasing apo(a) levels in an animal. Certain embodiments provide use of a compound targeted to apo(a) in the preparation of a medicament for decreasing Lp(a) levels in an animal. Certain embodiments provide use of a compound for the preparation of a medicament for the treatment, prevention, or amelioration of a disease, disorder, or condition associated with apo(a). Certain embodiments provide use of a compound for the preparation of a medicament for the treatment, prevention, or amelioration of a disease, disorder, or condition associated with Lp(a).

Certain embodiments provide a kit for treating, preventing, or ameliorating a disease, disorder or condition as described herein wherein the kit comprises: (i) an apo(a) specific inhibitor as described herein; and optionally (ii) a second agent or therapy as described herein.

A kit of the present invention can further include instructions for using the kit to treat, prevent, or ameliorate a disease, disorder or condition as described herein by combination therapy as described herein.

Antisense Compounds

Oligomeric compounds include, but are not limited to, oligonucleotides, oligonucleosides, oligonucleotide analogs, oligonucleotide mimetics, antisense compounds, antisense oligonucleotides, ribozymes, microRNAs and siRNAs. An oligomeric compound may be "antisense" to a target nucleic acid, meaning that it is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to an apo(a) nucleic acid is 12 to 30 subunits in length. In other words, such antisense compounds are from 12 to 30 linked subunits. In other embodiments, the antisense compound is 8 to 80, 10 to 80, 12 to 50, 15 to 30, 18 to 24, 19 to 22, 13 to 25, 14 to 25 or 15 to 25 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In certain such embodiments, the antisense compounds are 8 linked subunits in length. In some embodiments the antisense compound is an antisense oligonucleotide. In some embodiments, the linked subunits are nucleosides.

In certain embodiments, the antisense compound comprises a shortened or truncated modified oligonucleotide. The shortened or truncated modified oligonucleotide can have one or more nucleosides deleted from the 5' end (5' truncation), one or more nucleosides deleted from the 3' end (3' truncation) or one or more nucleosides deleted from the central portion. Alternatively, the deleted nucleosides can be dispersed throughout the modified oligonucleotide, for example, in an antisense compound having one nucleoside deleted from the 5' end and one nucleoside deleted from the 3' end.

When a single additional nucleoside is present in a lengthened oligonucleotide, the additional nucleoside can be located at the central portion, 5' or 3' end of the oligonucleotide. When two or more additional nucleosides are present, the added nucleosides can be adjacent to each other, for example, in an oligonucleotide having two nucleosides added to the central portion, to the 5' end (5' addition), or alternatively to the 3' end (3' addition), of the oligonucleotide. Alternatively, the added nucleosides can be dispersed throughout the antisense compound, for example, in an oligonucleotide having one nucleoside added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to an apo(a) nucleic acid have chemically modified subunits arranged in patterns, or motifs, to confer to the antisense compounds properties, such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of a RNA:DNA duplex.

Antisense compounds having a gapmer motif are considered chimeric antisense compounds. In a gapmer an internal region having a plurality of nucleotides that supports RNase H cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include those having a 4'-(CH2) n-O-2' bridge, where n=1 or n=2). Preferably, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region. As used herein, a gapmer described as "X-Y-Z" has a configuration such that the gap segment is positioned immediately adjacent to each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same; in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more nucleotides. Thus, gapmers include, but are not limited to, for example 5-10-5, 4-8-4, 4-12-3, 4-12-4, 3-14-3, 2-13-5, 2-12-2, 2-16-2, 1-18-1, 3-10-3, 2-10-2, 1-10-1, 2-8-2, 6-8-6, 5-8-5, 1-8-1, 2-6-2, 2-13-2, 1-8-2, 2-8-3, 3-10-2, 1-18-2 or 2-18-2.

In certain embodiments, the antisense compound as a "wingmer" motif, having a wing-gap or gap-wing configuration, i.e. an X-Y or Y-Z configuration as described above for the gapmer configuration. Thus, wingmer configurations include, but are not limited to, for example 5-10, 8-4, 4-12, 12-4, 3-14, 16-2, 18-1, 10-3, 2-10, 1-10, 8-2, 2-13 or 5-13.

In certain embodiments, antisense compounds targeted to an apo(a) nucleic acid possess a 5-10-5 gapmer motif.

In certain embodiments, an antisense compound targeted to an apo(a) nucleic acid has a gap-widened motif.

Target Nucleic Acids, Target Regions and Nucleotide Sequences

Nucleotide sequences that encode the apo(a) target sequence include, without limitation, the following: GENBANK Accession No. NM_005577.2, incorporated herein as SEQ ID NO: 1; GENBANK Accession No. NT_007422.12 truncated from nucleotides 3230000 to 3380000, incorporated herein as SEQ ID NO: 2; GENBANK Accession No. NT_025741.15 truncated from nucleotides 65120000 to 65258000, designated herein as SEQ ID NO: 3; and GENBANK Accession No. NM_005577.1, incorporated herein as SEQ ID NO: 4.

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage or a nucleobase. Antisense compounds described by Isis Number (Isis No.) indicate a combination of nucleobase sequence and motif.

In certain embodiments, a "target region" is a structurally defined region of the target nucleic acid. For example, a target region can encompass a 3' UTR, a 5' UTR, an exon, an intron, an exon/intron junction, a coding region, a translation initiation region, a translation termination region, or other defined nucleic acid region. The structurally defined regions for apo(a) can be obtained by accession number from sequence databases such as NCBI and such information is incorporated herein by reference. In certain embodiments, a target region can encompass the sequence from a 5' target site of one target segment within the target region to a 3' target site of another target segment within the same target region.

In certain embodiments, a "target segment" is a smaller, sub-portion of a target region within a nucleic acid. For example, a target segment can be the sequence of nucleotides of a target nucleic acid to which one or more antisense compounds are targeted. "5' target site" refers to the 5'-most nucleotide of a target segment. "3' target site" refers to the 3'-most nucleotide of a target segment.

A target region can contain one or more target segments. Multiple target segments within a target region can be overlapping. Alternatively, they can be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed, herein.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

Suitable target segments can be found within a 5' UTR, a coding region, a 3' UTR, an intron, an exon, or an exon/intron junction. Target segments containing a start codon or a stop codon are also suitable target segments. A suitable target segment can specifically exclude a certain structurally defined region, such as the start codon or stop codon.

The determination of suitable target segments can include a comparison of the sequence of a target nucleic acid to other sequences throughout the genome. For example, the BLAST algorithm can be used to identify regions of similarity amongst different nucleic acids. This comparison can prevent the selection of antisense compound sequences that can hybridize in a non-specific manner to sequences other than a selected target nucleic acid (i.e., non-target or off-target sequences).

There can be variation in activity (e.g., as defined by percent reduction of target nucleic acid levels) of the antisense compounds within an active target region. In certain embodiments, reductions in apo(a) mRNA levels can be indicative of inhibition of apo(a) expression. Reductions in levels of an apo(a) protein can be indicative of inhibition of target mRNA expression. Further, phenotypic changes can be indicative of inhibition of apo(a) expression. For example, an increase in HDL levels, decrease in LDL levels, decrease in cholesterol levels or decrease in triglyceride levels, are among phenotypic changes that can be assessed for inhibition of apo(a) expression. Other phenotypic indications, e.g., symptoms associated with a cardiovascular disease, may also be assessed; for example, angina; chest pain; shortness of breath; palpitations; weakness; dizziness; nausea; sweating; tachycardia; bradycardia; arrhythmia; atrial fibrillation; swelling in the lower extremities; cyanosis; fatigue; fainting; numbness of the face; numbness of the limbs; claudication or cramping of muscles; bloating of the abdomen; or fever.

Hybridization

In some embodiments, hybridization occurs between an antisense compound disclosed herein and an apo(a) nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art (Sambrooke and Russell, Molecular Cloning: A Laboratory Manual, $3^{rd}$ Ed., 2001). In certain embodiments, the antisense compounds provided herein are specifically hybridizable with an apo(a) nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an apo(a) nucleic acid).

Noncomplementary nucleobases between an antisense compound and an apo(a) nucleic acid can be tolerated provided that the antisense compound remains able to specifically hybridize to a target nucleic acid. Moreover, an antisense compound can hybridize over one or more segments of an apo(a) nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 75%, 80%, 85%, 86%, 87%, 88%, 89%, 90%, 91%, 92%, 93%, 94%, 95%, 96%, 97%, 98%, 99%, or 100% complementary to an apo(a) nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases can be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, an antisense compound may be fully complementary to an apo(a) nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase(s) can be at the 5' end or 3' end of the antisense compound. Alternatively, the non-complementary nucleobase(s) can be at an internal position of the antisense compound. When two or more non-complementary nucleobases are present, they can be contiguous (i.e. linked) or non-contiguous. In one embodiment, a non-complementary nucleobase is located in the wing segment of a gapmer antisense oligonucleotide.

In certain embodiments, antisense compounds that are, or are up to, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an apo(a) nucleic acid, or specified portion thereof.

In certain embodiments, antisense compounds that are, or are up to, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an apo(a) nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein can also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases can be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, 25, 26, 27, 28, 29 or 30 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, 25, 26, 27, 28, 29 or 30 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides can also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to an apo(a) nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH$_3$, 2'-OCH$_2$CH$_3$, 2'-OCH$_2$CH$_2$F and 2'-O(CH$_2$)$_2$OCH$_3$ substituent groups. The substituent at the 2' position can also be selected from allyl, amino, azido, thio, O-allyl, O—C$_1$-C$_{10}$ alkyl, OCF$_3$, OCH$_2$F, O(CH$_2$)$_2$SCH$_3$, O(CH$_2$)$_2$—O—N(R$_m$)(R$_n$), O—CH$_2$—C(=O)—N(R$_m$)(R$_n$), and O—CH$_2$—C(=O)—N(R)—(CH$_2$)$_2$—N(R$_m$)(R$_n$), where each R$_1$, R$_m$ and R$_n$ is, independently, H or substituted or unsubstituted C$_1$-C$_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-(CH$_2$)—O-2' (LNA); 4'-(CH$_2$)—S-2; 4'-(CH$_2$)$_2$—O-2' (ENA); 4'-CH(CH$_3$)—O-2' and 4'-CH(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N(OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya et al., J. Org. Chem., 2009, 74, 118-134); and 4'-CH$_2$—C(=CH$_2$)-2' (and analogs thereof see published International Application WO 2008/154401, published on Dec. 8, 2008).

Further reports related to bicyclic nucleosides can also be found in published literature (see for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 2007, 129(26) 8362-8379; Elayadi et al., Curr. Opinion Invest. Drugs, 2001, 2, 558-561; Braasch et al., Chem. Biol., 2001, 8, 1-7; and Orum et al., Curr. Opinion Mol. Ther., 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C(R$_a$)(R$_b$)]$_n$—, —C(R$_a$)=C(R$_b$)—, —C(R$_a$)=N—, —C(=O)—, —C(=NR$_a$)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

In certain embodiments, the bridge of a bicyclic sugar moiety is —[C(R$_a$)(R$_b$)]$_n$—, —[C(R$_a$)(R$_b$)]$_n$—O—, —C(R$_a$R$_b$)—N(R)—O— or —C(R$_a$R$_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or C$_1$-C$_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., Nucleic Acids Research, 2003, 21, 6365-6372).

In certain embodiments, bicyclic nucleosides include, but are not limited to, (A) α-L-methyleneoxy (4'-CH$_2$—O-2')

BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, and (F) methyl(methyleneoxy) (4'-CH(CH$_3$)—O-2') BNA, (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

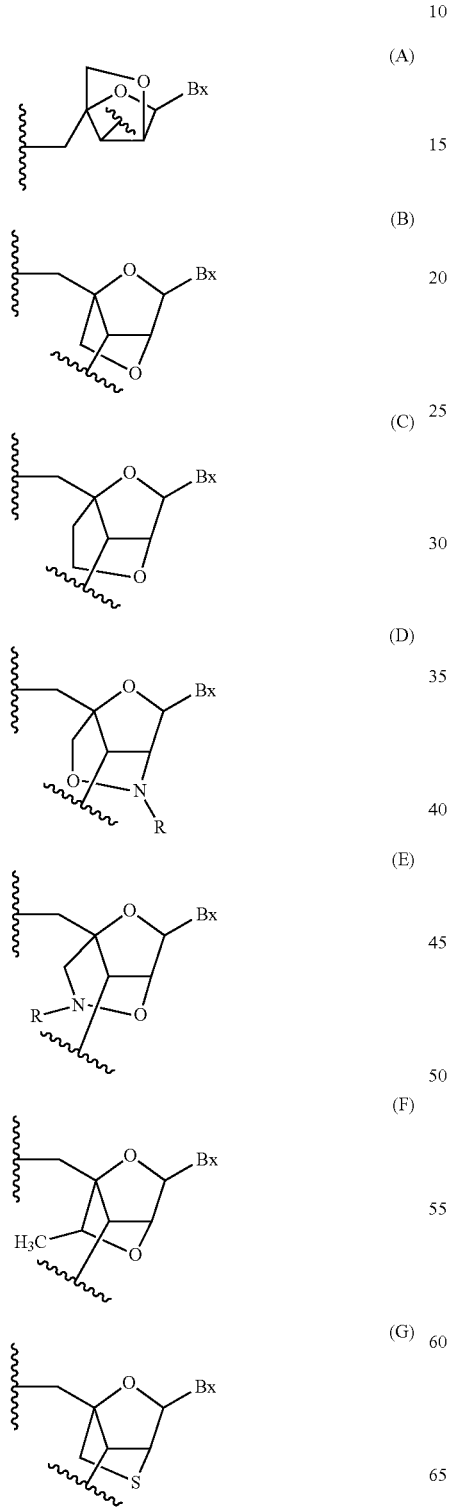

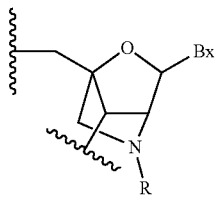

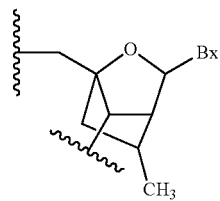

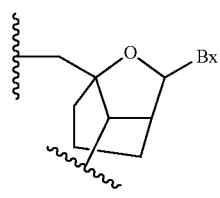

wherein Bx is the base moiety and R is independently H, a protecting group or C$_1$-C$_{12}$ alkyl.

In certain embodiments, bicyclic nucleosides are provided having Formula I:

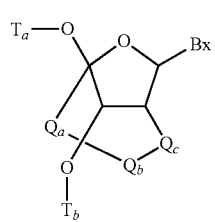

wherein:
Bx is a heterocyclic base moiety;
-Q$_a$-Q$_b$-Q$_c$- is —CH$_2$—N(R$_c$)—CH$_2$—, —C(=O)—N(R$_c$)—CH$_2$—, —CH$_2$—O—N(R$_c$)—, —CH$_2$—N(R$_c$)—O— or —N(R$_c$)—O—CH$_2$;
R$_c$ is C$_1$-C$_{12}$ alkyl or an amino protecting group; and
T$_a$ and T$_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

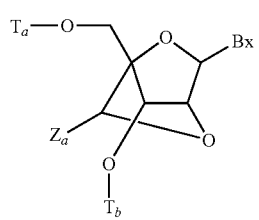

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_cC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

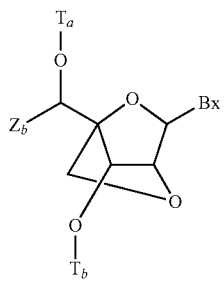

III wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides are provided having Formula IV:

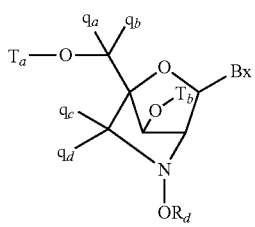

IV wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_a$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

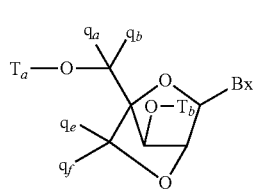

V wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)—$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-$CH_2$—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

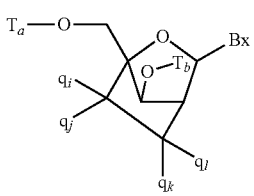

VI wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and
$q_j$ and $q_l$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-(CH$_2$)$_3$-2' bridge and the alkenyl analog bridge 4'-CH=CH—CH$_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocyclic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[(CH$_2$)$_n$O]$_m$CH$_3$, O(CH$_2$)$_n$NH$_2$, O(CH$_2$)$_n$CH$_3$, O(CH$_2$)$_n$F, O(CH$_2$)$_n$ONH$_2$, OCH$_2$C(=O)N(H)CH$_3$, and O(CH$_2$)$_n$ON[(CH$_2$)$_n$CH$_3$]$_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, SCH$_3$, OCN, Cl, Br, CN, F, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854), fluoro HNA (F-HNA) or those compounds having Formula VII:

VII

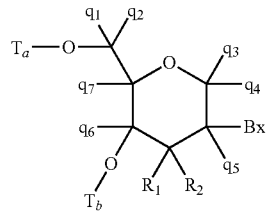

wherein independently for each of said at least one tetrahydropyran nucleoside analog of Formula VII:
Bx is a heterocyclic base moiety;
$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;
$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, OC(=X)$J_1$, OC(=X)$NJ_1J_2$, $NJ_3$C(=X)$NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is methoxyethoxy and $R_2$ is H. In certain embodiments, $R_1$ is H and $R_2$ is fluoro; $R_1$ is H and $R_2$ is methoxy, and $R_1$ is H and $R_2$ is methoxyethoxy.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O—$C_1$-$C_{10}$ alkyl, —OCF$_3$, O—(CH$_2$)$_2$—O—CH$_3$, 2'-O(CH$_2$)$_2$SCH$_3$, O—(CH$_2$)$_2$—

O—N($R_m$)($R_n$), or O—CH$_2$—C(=O)—N($R_m$)($R_n$), where each $R_m$ and $R_n$ is, independently, H or substituted or unsubstituted C$_1$-C$_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-OCH$_3$" or "2'-O-methyl" each refers to a nucleoside comprising a sugar comprising an —OCH$_3$ group at the 2' position of the sugar ring.

As used herein, "MOE" or "2'-MOE" or "2'-OCH$_2$CH$_2$OCH$_3$" or "2'-O-methoxyethyl" each refers to a nucleoside comprising a sugar comprising a —OCH$_2$CH$_2$OCH$_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854). Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH(CH$_3$)—O-2') bridging group. In certain embodiments, the (4'-CH(CH$_3$)—O-2') modified nucleosides are arranged throughout the wings of a gapmer motif. In certain embodiments, the modified sugar moiety is a cEt. In certain embodiments, the cEt modified nucleotides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to an apo(a) nucleic acid comprise one or more modified nucleobases. In certain embodiments, gap-widened antisense oligonucleotides targeted to an apo(a) nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to an apo(a) nucleic acid can be utilized in pharmaceutical compositions by combining the antisense compound with a suitable pharmaceutically acceptable diluent or carrier.

In certain embodiments, the "pharmaceutical carrier" or "excipient" is a pharmaceutically acceptable solvent, suspending agent or any other pharmacologically inert vehicle for delivering one or more nucleic acids to an animal. The excipient can be liquid or solid and can be selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipients, which do not deleteriously react with nucleic acids, suitable for parenteral or non-parenteral administration can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to an apo(a) nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or an oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds can be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602, published on Jan. 16, 2003.

Cell Culture and Antisense Compounds Treatment

The effects of antisense compounds on the level, activity or expression of apo(a) nucleic acids can be tested in vitro in a variety of cell types. Cell types used for such analyses are available from commercial vendors (e.g. American Type Culture Collection, Manassas, Va.; Zen-Bio, Inc., Research Triangle Park, N.C.; Clonetics Corporation, Walkersville, Md.) and are cultured according to the vendor's instructions using commercially available reagents (e.g., Invitrogen Life Technologies, Carlsbad, Calif.). Illustrative cell types include, but are not limited to, HepG2 cells, Hep3B cells, Huh7 (hepatocellular carcinoma) cells, primary hepatocytes, A549 cells, GM04281 fibroblasts and LLC-MK2 cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, Calif.). Antisense oligonucleotide is mixed with LIPOFECTAMINE 2000® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, Calif.). Antisense oligonucleotide is mixed with Cytofectin® in OPTI-MEM® 1 reduced serum medium (Invitrogen, Carlsbad, Calif.) to achieve the desired concentration of antisense oligonucleotide and a Cytofectin® concentration that typically ranges 2 to 12 ug/mL per 100 nM antisense oligonucleotide.

Another reagent used to introduce antisense oligonucleotides into cultured cells includes Oligofectamine™ (Invitrogen Life Technologies, Carlsbad, Calif.). Antisense oligonucleotide is mixed with Oligofectamine™ in Opti-MEM™-1 reduced serum medium (Invitrogen Life Technologies, Carlsbad, Calif.) to achieve the desired concentration of oligonucleotide with an Oligofectamine™ to oligonucleotide ratio of approximately 0.2 to 0.8 µL per 100 nM.

Another reagent used to introduce antisense oligonucleotides into cultured cells includes FuGENE 6 (Roche Diagnostics Corp., Indianapolis, Ind.). Antisense oligomeric compound was mixed with FuGENE 6 in 1 mL of serum-free RPMI to achieve the desired concentration of oligonucleotide with a FuGENE 6 to oligomeric compound ratio of 1 to 4 µL of FuGENE 6 per 100 nM.

Another technique used to introduce antisense oligonucleotides into cultured cells includes electroporation (Sambrooke and Russell in *Molecular Cloning. A Laboratory Manual*. Third Edition. Cold Spring Harbor Laboratory Press, Cold Spring Harbor, N.Y. 2001).

Cells are treated with antisense oligonucleotides by routine methods. Cells are typically harvested 16-24 hours after antisense oligonucleotide treatment, at which time RNA or protein levels of target nucleic acids are measured by methods known in the art and described herein (Sambrooke and Russell in *Molecular Cloning. A Laboratory Manual*. Third Edition. Cold Spring Harbor Laboratory Press, Cold Spring Harbor, N.Y. 2001). In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art (Sambrooke and Russell in *Molecular Cloning. A Laboratory Manual*. Third Edition. Cold Spring Harbor Laboratory Press, Cold Spring Harbor, N.Y. 2001). Antisense oligonucleotides are typically used at concentrations ranging from 1 nM to 300 nM when transfected with LIPOFECTAMINE2000® (Invitrogen, Carlsbad, Calif.), Lipofectin® (Invitrogen, Carlsbad, Calif.)

or Cytofectin™ (Genlantis, San Diego, Calif.). Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art (Sambrooke and Russell in *Molecular Cloning. A Laboratory Manual*. Third Edition. Cold Spring Harbor Laboratory Press, Cold Spring Harbor, N.Y. 2001). For example, RNA can be prepared using TRIZOL® (Invitrogen, Carlsbad, Calif.) according to the manufacturer's recommended protocols.

Analysis of Inhibition of Target Levels or Expression

Inhibition of levels or expression of an apo(a) nucleic acid can be assayed in a variety of ways known in the art (Sambrooke and Russell in *Molecular Cloning. A Laboratory Manual*. Third Edition. Cold Spring Harbor Laboratory Press, Cold Spring Harbor, N.Y., 2001). For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems (Foster City, Calif.) and used according to manufacturer's instructions.

Quantitative Real-Time PCR Analysis of Target RNA Levels

Quantitation of target RNA levels can be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT and real-time-PCR reactions are carried out by methods well known to those skilled in the art.

Gene (or RNA) target quantities obtained by real time PCR can be normalized using either the expression level of a gene whose expression is constant, such as cyclophilin A or GAPDH, or by quantifying total RNA using RIBOGREEN® (Invitrogen, Inc. Carlsbad, Calif.). Cyclophilin A or GAPDH expression can be quantified by real time PCR, by being run simultaneously with the target, multiplexing, or separately. Total RNA is quantified using RIBOGREEN® RNA quantification reagent (Invitrogen, Inc. Carlsbad, Calif.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems, Foster City, Calif.) is used to measure RIBOGREEN® fluorescence.

Probes and primers can be designed to hybridize to an apo(a) nucleic acid. Methods for designing real-time PCR probes and primers are well known in the art, and may include the use of software such as PRIMER EXPRESS® Software (Applied Biosystems, Foster City, Calif.).

Analysis of Protein Levels

Antisense inhibition of apo(a) nucleic acids can be assessed by measuring apo(a) protein levels. Protein levels of apo(a) can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS) (Sambrooke and Russell in *Molecular Cloning. A Laboratory Manual*. Third Edition. Cold Spring Harbor Laboratory Press, Cold Spring Harbor, N.Y. 2001). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of apo(a) are commercially available.

In Vivo Testing of Antisense Compounds

Antisense compounds, for example, antisense oligonucleotides, are tested in animals to assess their ability to inhibit expression of apo(a) and produce phenotypic changes. Testing can be performed in normal animals, or in experimental disease models. For administration to animals, antisense oligonucleotides are formulated in a pharmaceutically acceptable diluent, such as saline or phosphate-buffered saline. Administration includes parenteral routes of administration. Calculation of antisense oligonucleotide dosage and dosing frequency depends upon factors such as route of administration and animal body weight. Following a period of treatment with antisense oligonucleotides, RNA is isolated from tissue and changes in apo(a) nucleic acid expression are measured. Changes in apo(a) protein levels are also measured.

Certain Indications

In certain embodiments, provided herein are methods of treating an individual comprising administering one or more pharmaceutical compositions as described herein. In certain embodiments, the individual has an apo(a) related disease. In certain embodiments, the individual has an Lp(a) related disease. In certain embodiments, the individual has an inflammatory, cardiovascular and/or a metabolic disease, disorder or condition.

In certain embodiments, the cardiovascular diseases, disorders or conditions include, but are not limited to, aneurysm (e.g., abdominal aortic aneurysm), angina, arrhythmia, atherosclerosis, cerebrovascular disease, coronary artery disease, coronary heart disease, dyslipidemia, hypercholesterolemia, hyperlipidemia, hypertension, hypertriglyceridemia, myocardial infarction, peripheral vascular disease (e.g., peripheral artery disease), stroke and the like.

In certain embodiments, the compounds targeted to apo(a) described herein modulate physiological markers or phenotypes of the cardiovascular disease, disorder or condition. For example, administration of the compounds to animals can decrease LDL and cholesterol levels in those animals compared to untreated animals. In certain embodiments, the modulation of the physiological markers or phenotypes can be associated with inhibition of apo(a) by the compounds.

In certain embodiments, the physiological markers of the cardiovascular disease, disorder or condition can be quantifiable. For example, LDL or cholesterol levels can be measured and quantified by, for example, standard lipid tests. For such markers, in certain embodiments, the marker can be decreased by about 5, 10, 15, 20, 25, 30, 35, 40, 45, 50, 55, 60, 65, 70, 75, 80, 85, 90, 95 or 99%, or a range defined by any two of these values.

Also, provided herein are methods for preventing, treating or ameliorating a symptom associated with the cardiovascular disease, disorder or condition in a subject in need thereof. In certain embodiments, provided is a method for reducing the rate of onset of a symptom associated with the cardiovascular disease, disorder or condition. In certain embodiments, provided is a method for reducing the severity of a symptom associated with the cardiovascular disease, disorder or condition. In such embodiments, the methods comprise administering a therapeutically effective amount of a compound targeted to an apo(a) nucleic acid to an individual in need thereof.

The cardiovascular disease, disorder or condition can be characterized by numerous physical symptoms. Any symptom known to one of skill in the art to be associated with the cardiovascular disease, disorder or condition can be prevented, treated, ameliorated or otherwise modulated with the compounds and methods described herein. In certain embodiments, the symptom can be any of, but not limited to, angina, chest pain, shortness of breath, palpitations, weakness, dizziness, nausea, sweating, tachycardia, bradycardia, arrhythmia, atrial fibrillation, swelling in the lower extremities, cyanosis, fatigue, fainting, numbness of the face, numbness of the limbs, claudication or cramping of muscles, bloating of the abdomen or fever.

In certain embodiments, the metabolic diseases, disorders or conditions include, but are not limited to, hyperglycemia, prediabetes, diabetes (type I and type II), obesity, insulin resistance, metabolic syndrome and diabetic dyslipidemia.

In certain embodiments, compounds targeted to apo(a) as described herein modulate physiological markers or phenotypes of the metabolic disease, disorder or condition. For example, administration of the compounds to animals can decrease glucose and insulin resistance levels in those animals compared to untreated animals. In certain embodiments, the modulation of the physiological markers or phenotypes can be associated with inhibition of apo(a) by the compounds.

In certain embodiments, physiological markers of the metabolic disease, disorder or condition can be quantifiable. For example, glucose levels or insulin resistance can be measured and quantified by standard tests known in the art. For such markers, in certain embodiments, the marker can be decreased by about 5, 10, 15, 20, 25, 30, 35, 40, 45, 50, 55, 60, 65, 70, 75, 80, 85, 90, 95 or 99%, or a range defined by any two of these values. In another example, insulin sensitivity can be measured and quantified by standard tests known in the art. For such markers, in certain embodiments, the marker can be increase by about 5, 10, 15, 20, 25, 30, 35, 40, 45, 50, 55, 60, 65, 70, 75, 80, 85, 90, 95 or 99%, or a range defined by any two of these values.

Also, provided herein are methods for preventing, treating or ameliorating a symptom associated with the metabolic disease, disorder or condition in a subject in need thereof. In certain embodiments, provided is a method for reducing the rate of onset of a symptom associated with the metabolic disease, disorder or condition. In certain embodiments, provided is a method for reducing the severity of a symptom associated with the metabolic disease, disorder or condition. In such embodiments, the methods comprise administering a therapeutically effective amount of a compound targeted to an apo(a) nucleic acid to an individual in need thereof.

The metabolic disease, disorder or condition can be characterized by numerous physical symptoms. Any symptom known to one of skill in the art to be associated with the metabolic disease, disorder or condition can be prevented, treated, ameliorated or otherwise modulated with the compounds and methods described herein. In certain embodiments, the symptom can be any of, but not limited to, excessive urine production (polyuria), excessive thirst and increased fluid intake (polydipsia), blurred vision, unexplained weight loss and lethargy.

In certain embodiments, the inflammatory diseases, disorders or conditions include, but are not limited to, coronary artery disease (CAD), Alzheimer's Disease and thromboembolic diseases, disorder or conditions. Certain thromboembolic diseases, disorders or conditions include, but are not limited to, stroke, thrombosis, myocardial infarction and peripheral vascular disease.

In certain embodiments, the compounds targeted to apo(a) described herein modulate physiological markers or phenotypes of the inflammatory disease, disorder or condition. For example, administration of the compounds to animals can decrease inflammatory cytokine or other inflammatory markers levels in those animals compared to untreated animals. In certain embodiments, the modulation of the physiological markers or phenotypes can be associated with inhibition of apo(a) by the compounds.

In certain embodiments, the physiological markers of the inflammatory disease, disorder or condition can be quantifiable. For example, cytokine levels can be measured and quantified by standard tests known in the art. For such markers, in certain embodiments, the marker can be decreased by about 5, 10, 15, 20, 25, 30, 35, 40, 45, 50, 55, 60, 65, 70, 75, 80, 85, 90, 95 or 99%, or a range defined by any two of these values.

Also, provided herein are methods for preventing, treating or ameliorating a symptom associated with the inflammatory disease, disorder or condition in a subject in need thereof. In certain embodiments, provided is a method for reducing the rate of onset of a symptom associated with the inflammatory disease, disorder or condition. In certain embodiments, provided is a method for reducing the severity of a symptom associated with the inflammatory disease, disorder or condition. In such embodiments, the methods comprise administering a therapeutically effective amount of a compound targeted to an apo(a) nucleic acid to an individual in need thereof.

In certain embodiments, provided are methods of treating an individual with an apo(a) related disease, disorder or condition comprising administering a therapeutically effective amount of one or more pharmaceutical compositions as described herein. In certain embodiments, the individual has elevated apo(a) levels. In certain embodiments, provided are methods of treating an individual with an Lp(a) related disease, disorder or condition comprising administering a therapeutically effective amount of one or more pharmaceutical compositions as described herein. In certain embodiments, the individual has elevated Lp(a) levels. In certain embodiments, the individual has an inflammatory, cardiovascular and/or metabolic disease, disorder or condition. In certain embodiments, administration of a therapeutically effective amount of an antisense compound targeted to an apo(a) nucleic acid is accompanied by monitoring of apo(a) or Lp(a) levels. In certain embodiments, administration of a therapeutically effective amount of an antisense compound targeted to an apo(a) nucleic acid is accompanied by monitoring of markers of inflammatory, cardiovascular and/or metabolic disease, or other disease process associated with the expression of apo(a), to determine an individual's response to the antisense compound. An individual's response to administration of the antisense compound targeting apo(a) can be used by a physician to determine the amount and duration of therapeutic intervention with the compound.

In certain embodiments, administration of an antisense compound targeted to an apo(a) nucleic acid results in reduction of apo(a) expression by at least about 15, 20, 25, 30, 35, 40, 45, 50, 55, 60, 65, 70, 75, 80, 85, 90, 95 or 99%, or a range defined by any two of these values. In certain embodiments, apo(a) expression is reduced to ≤100 mg/dL, ≤90 mg/dL, ≤80 mg/dL, ≤70 mg/dL, ≤60 mg/dL, ≤50 mg/dL, ≤40 mg/dL, ≤30 mg/dL, ≤20 mg/dL or ≤10 mg/dL.

In certain embodiments, administration of an antisense compound targeted to an apo(a) nucleic acid results in reduction of Lp(a) expression by at least about 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to apo(a) are used for the preparation of a medicament for treating a patient suffering or susceptible to an inflammatory, cardiovascular and/or a metabolic disease, disorder or condition.

Dosing

In certain embodiments, pharmaceutical compositions are administered according to a dosing regimen (e.g., dose, dose frequency, and duration) wherein the dosing regimen can be selected to achieve a desired effect. The desired effect can be, for example, reduction of apo(a) or the prevention, reduction, amelioration or slowing the progression of a disease or condition associated with apo(a).

In certain embodiments, the variables of the dosing regimen are adjusted to result in a desired concentration of pharmaceutical composition in a subject. "Concentration of pharmaceutical composition" as used with regard to dose regimen can refer to the compound, oligonucleotide, or active ingredient of the pharmaceutical composition. For example, in certain embodiments, dose and dose frequency are adjusted to provide a tissue concentration or plasma concentration of a pharmaceutical composition at an amount sufficient to achieve a desired effect.

Dosing is dependent on severity and responsiveness of the disease state to be treated, with the course of treatment lasting from several days to several months, or until a cure is effected or a diminution of the disease state is achieved. Dosing is also dependent on drug potency and metabolism. In certain embodiments, dosage is from 0.01 μg to 100 mg per kg of body weight, or within a range of 0.001 mg-1000 mg dosing, and may be given once or more daily, weekly, monthly or yearly, or even once every 2 to 20 years. Following successful treatment, it can be desirable to have the patient undergo maintenance therapy to prevent the recurrence of the disease state, wherein the oligonucleotide is administered in maintenance doses, ranging from 0.01 μg to 100 mg per kg of body weight or ranging from 0.001 mg to 1000 mg dosing, once or more daily, weekly, monthly, yearly to once every 2 to 20 years.

Certain Combination Therapies

In certain embodiments, a first agent comprising the compound described herein is co-administered with one or more secondary agents or therapy. In certain embodiments, such second agents are designed to treat the same disease, disorder, or condition as the first agent described herein. In certain embodiments, such second agents are designed to treat a different disease, disorder, or condition as the first agent described herein. In certain embodiments, a first agent is designed to treat an undesired side effect of a second agent. In certain embodiments, second agents are co-administered with the first agent to treat an undesired effect of the first agent. In certain embodiments, such second agents are designed to treat an undesired side effect of one or more pharmaceutical compositions as described herein. In certain embodiments, second agents are co-administered with the first agent to produce a combinational effect. In certain embodiments, second agents are co-administered with the first agent to produce a synergistic effect. In certain embodiments, the co-administration of the first and second agents permits use of lower dosages than would be required to achieve a therapeutic or prophylactic effect if the agents were administered as independent therapy.

In certain embodiments, one or more compositions described herein and one or more other pharmaceutical agents are administered at the same time. In certain embodiments, one or more compositions of the invention and one or more other pharmaceutical agents are administered at different times. In certain embodiments, one or more compositions described herein and one or more other pharmaceutical agents are prepared together in a single formulation. In certain embodiments, one or more compositions described herein and one or more other pharmaceutical agents are prepared separately.

In certain embodiments, second agents include, but are not limited to, an apo(a) lowering agent, a Lp(a) lowering agent, an agent for treating Alzheimer's Disease, an agent to reduce thromboembolism formation, a cholesterol lowering agent, a non-HDL lipid lowering (e.g., LDL) agent, a HDL raising agent, fish oil, niacin, nicotinic acid, a fibrate, a statin, DCCR (salt of diazoxide), a glucose-lowering agent, an anti-inflammatory agent and/or an anti-diabetic agent. In certain embodiments, the first agent is administered in combination with the maximally tolerated dose of the second agent. In certain embodiments, the first agent is administered to a subject that fails to respond to a maximally tolerated dose of the second agent.

Examples of apo(a) lowering agents include an apo(a) antisense oligonucleotide different from the first agent, niacin, nicotinic acid, or an apoB antisense oligonucleotide (i.e. Mipomersen). An example of an apo(a) lowering therapy is Lp(a) apheresis.

Examples of glucose-lowering and/or anti-diabetic agents include, but are not limited to, a therapeutic lifestyle change, PPAR agonist, a dipeptidyl peptidase (IV) inhibitor, a GLP-1 analog, insulin or an insulin analog, an insulin secretagogue, a SGLT2 inhibitor, a human amylin analog, a biguanide, an alpha-glucosidase inhibitor, metformin, sulfonylurea, rosiglitazone, meglitinide, thiazolidinedione, alpha-glucosidase inhibitor and the like. The sulfonylurea can be acetohexamide, chlorpropamide, tolbutamide, tolazamide, glimepiride, a glipizide, a glyburide, or a gliclazide. The meglitinide can be nateglinide or repaglinide. The thiazolidinedione can be pioglitazone or rosiglitazone. The alpha-glucosidase can be acarbose or miglitol.

Examples of cholesterol or lipid lowering therapy include, but are not limited to, a therapeutic lifestyle change, statins, bile acids sequestrants, niacin, nicotinic acid, CETP inhibitors and peroxisome proliferation activated receptor agonists such as fibrates. The statins can be atorvastatin, fluvastatin, lovastatin, pravastatin, rosuvastatin and simvastatin and the like. The bile acid sequestrants can be colesevelam, cholestyramine, colestipol and the like. The fibrates can be gemfibrozil, fenofibrate, clofibrate and the like. The CETP inhibitor can be a CETP antisense oligonucleotide or Torcetrapib.

Certain Treatment Populations

Certain subjects with high Lp(a) levels are at a significant risk of various diseases (Lippi et al., Clinica Chimica Acta, 2011, 412:797-801; Solfrizz et al.). In many subjects with high Lp(a) levels, current treatments cannot reduce their Lp(a) levels to safe levels. Apo(a) plays an important role in the formation of Lp(a), hence reducing apo(a) can reduce Lp(a) and prevent, treat or ameliorate a disease associated with Lp(a).

In certain embodiments, treatment with the compounds and methods disclosed herein is indicated for a human animal with elevated apo(a) levels and/or Lp(a) levels. In certain embodiments, the human has elevated apo(a) levels ≥30 mg/dL, ≥40 mg/dL, ≥50 mg/dL, ≥60 mg/dL, ≥70 mg/dL, ≥80 mg/dL, ≥90 mg/dL or ≥100 mg/dL.

Certain Compounds

Selected gapmer antisense oligonucleotides from PCT application WO2005/000201 (incorporated by reference in its entirety herein) were assessed (Example 1) and the most potent compound, ISIS 144367, was used as a benchmark comparison for the newly designed antisense oligonucleotides described herein.

About 90 of the newly designed antisense oligonucleotides were found to be more potent than the benchmark, ISIS 144367, as assessed by single dose in vitro studies (Examples 2-3, 5). Of the about 90 antisense oligonucleotides, about 83 were selected for in vitro multi-dose response studies and 64 antisense oligonucleotides were found to be more potent than the benchmark (Examples 4, 6).

About 32 antisense oligonucleotides were further selected for in vivo studies in human apo(a) transgenic mice (Example 7). Multiple antisense oligonucleotides were identified that were more potent than the benchmark in vivo.

About 24 antisense oligonucleotides were further selected for viscosity testing in vitro (Example 13). Antisense oligonucleotides that were viscous were not carried forward in further studies.

About 14 antisense oligonucleotides were further selected for in vivo studies in rodent tolerability and pharmacokinetics (Examples 8-10). The studies indicated that ISIS 494372 was the best tolerated antisense oligonucleotide.

ISIS 494283, 494284, 494286, 494301, 494302 and 494372 were tested in cynomolgus monkeys (Examples 11-12). The studies indicated that ISIS 494372 was well tolerated and potent in monkeys.

EXAMPLES

Non-Limiting Disclosure and Incorporation by Reference

While certain compounds, compositions, and methods described herein have been described with specificity in accordance with certain embodiments, the following examples serve only to illustrate the compounds described herein and are not intended to limit the same. Each of the references recited in the present application is incorporated herein by reference in its entirety.

Example 1: Dose-Dependent Antisense Inhibition of Human Apolipoprotein (a) (Apo(a)) in Human Primary Hepatocytes Selected gapmer antisense oligonucleotides from a previous publication (WO2005/000201, the content of which is incorporated by reference in its entirety herein) were tested in a single dose assay in human primary hepatocytes. Cells were obtained from Tissue Transformation Technologies (BD Biosciences, Franklin Lakes, N.J.) and treated with 150 nM of antisense oligonucleotide. After a treatment period of approximately 16 hours, RNA was isolated from the cells and apo(a) mRNA levels were measured by quantitative real-time PCR. Human apo(a) primer probe set hAPO(a)3' (forward sequence ACAGCAATCAAACGAAGACACTG, designated herein as SEQ ID NO: 5; reverse sequence AGCTTATACACAAAAATACCAAAAATGC, designated herein as SEQ ID NO: 6; probe sequence TCCCAGCTAC-CAGCTATGCCAAACCTT, designated herein as SEQ ID NO: 7) was used to measure mRNA levels. Additionally, mRNA levels were also measured using human apo(a) primer probe set hAPO(a)12 kB (forward sequence CCACAGTGGCCCCGGT, designated herein as SEQ ID NO: 8; reverse sequence ACAGGGCTTTTCTCAG-GTGGT, designated herein as SEQ ID NO: 9; probe sequence CCAAGCACAGAGGCTCCTTCTGAACAAG, designated herein as SEQ ID NO: 10). Apo(a) mRNA levels were normalized to GAPDH mRNA expression. Results are presented in Table 1 as percent inhibition of apo(a), relative to untreated control cells.

TABLE 1

Antisense inhibition of human apo(a) in human primary hepatocytes

| ISIS No | % inhibition (hAPO(a)3' PPset) | % inhibition (hAPO(a)12 kB PPset) |
| --- | --- | --- |
| 144367 | 68 | 77 |
| 144368 | 42 | 59 |
| 144369 | 43 | 69 |
| 144370 | 80 | 75 |
| 144371 | 42 | 57 |
| 144372 | 87 | 54 |
| 144373 | 63 | 49 |
| 144374 | 45 | 80 |
| 144375 | 33 | 11 |
| 144376 | 62 | 82 |
| 144377 | 42 | 72 |
| 144378 | 0 | 72 |
| 144379 | 73 | 46 |
| 144380 | 75 | 78 |
| 144381 | 63 | 64 |
| 144382 | 0 | 58 |
| 144383 | 63 | 79 |
| 144384 | 38 | 0 |
| 144385 | 40 | 94 |
| 144386 | 47 | 61 |
| 144387 | 38 | 60 |
| 144388 | 0 | 57 |
| 144389 | 52 | 39 |
| 144390 | 12 | 0 |
| 144391 | 73 | 57 |
| 144392 | 43 | 50 |
| 144393 | 83 | 82 |
| 144394 | 40 | 76 |
| 144395 | 80 | 84 |
| 144396 | 53 | 72 |
| 144397 | 23 | 64 |
| 144398 | 7 | 33 |
| 144399 | 43 | 44 |
| 144400 | 70 | 75 |
| 144401 | 87 | 72 |

Several antisense oligonucleotides were selected for further testing in a dose response assay.

The selected antisense oligonucleotides were tested in human primary hepatocytes with 25 nM, 50 nM, 150 nM, or 300 nM concentrations of antisense oligonucleotide, as specified in Table 2 below. After a treatment period of approximately 16 hours, RNA was isolated from the cells and apo(a) mRNA levels were measured by quantitative real-time PCR. Human apo(a) primer probe set hAPO(a)3' was used to measure mRNA levels. Apo(a) mRNA levels were normalized to GAPDH mRNA expression. Results are presented as percent inhibition of apo(a), relative to untreated control cells.

TABLE 2

Dose-dependent antisense inhibition of human apo(a) in human primary hepatocytes, as measured with hAPO(a)3'

| ISIS No | 25 nM | 50 nM | 150 nM | 300 nM |
|---|---|---|---|---|
| 144367 | 52 | 78 | 76 | 74 |
| 144370 | 64 | 74 | 68 | 66 |
| 144385 | 0 | 15 | 43 | 5 |
| 144393 | 0 | 9 | 39 | 25 |
| 144395 | 17 | 9 | 8 | 32 |

ISIS 144367 demonstrated better efficacy and dose-dependency than the other antisense oligonucleotides. Hence, ISIS 144367 was considered the benchmark antisense oligonucleotide to compare the potency of newly designed antisense oligonucleotides disclosed herein.

Example 2: Antisense Inhibition of Human Apo(a) in Transgenic Mouse Primary Hepatocytes Antisense oligonucleotides were newly designed targeting an apo(a) nucleic acid and were tested for their effects on apo(a) mRNA in vitro. The antisense oligonucleotides were tested for potency in a series of parallel experiments that had similar culture conditions. Primary hepatocytes from human apo(a) transgenic mice (Frazer, K. A. et al., Nat. Genet. 1995. 9: 424-431) were used in this study. Hepatocytes at a density of 35,000 cells per well were transfected using electroporation with 1,000 nM antisense oligonucleotide. After a treatment period of approximately 24 hours, RNA was isolated from the cells and apo(a) mRNA levels were measured by quantitative real-time PCR. Human primer probe set hAPO(a)12 kB was used to measure mRNA levels. Apo(a) mRNA levels were adjusted according to total RNA content, as measured by RIBOGREEN®. The results for each experiment are presented in separate tables shown below. ISIS 144367 from was used as a benchmark for the new antisense oligonucleotides and also included in the studies. Results are presented as percent inhibition of apo(a), relative to untreated control cells. A total of 1,511 gapmers were tested under these culture conditions. Only those antisense oligonucleotides that were selected for further study are presented in the table below with each table representing a separate experiment.

The newly designed chimeric antisense oligonucleotides were designed as 5-10-5 MOE gapmers. The gapmers are 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines.

The apo(a) target sequence contains multiple Kringle repeat sequences, therefore, an antisense oligonucleotide may target one or more regions of apo(a) depending whether on the oligonucleotide targets a Kringle sequence or not. "Start site" indicates the 5'-most nucleoside to which the gapmer is targeted in the human sequence. "Stop site" indicates the 3'-most nucleoside to which the gapmer is targeted human sequence. An apo(a) antisense oligonucleotide may have more than one "Start site" or "Stop site" depending on whether or not it targets a Kringle repeat.

Most gapmers listed in the Tables are targeted with 100% complementarity to one or more regions of either the human apo(a) mRNA, designated herein as SEQ ID NO: 1 (GENBANK Accession No. NM_005577.2) or the human apo(a) genomic sequence, designated herein as SEQ ID NO: 2 (GENBANK Accession No. NT_007422.12 truncated from nucleotides 3230000 to 3380000), or both. 'n/a' indicates that the antisense oligonucleotide does not target that particular sequence with 100% complementarity.

TABLE 3

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 90 | 21210 | 21229 | 11 |
| 494157 | 238 | 257 | CCTGTGACAGTGGTGGAGTA | 95 | 21199 | 21218 | 12 |
|  | 580 | 599 |  |  | 26690 | 26709 |  |
|  | 922 | 941 |  |  | 32237 | 32256 |  |
|  | 1606 | 1625 |  |  | 43330 | 43349 |  |
|  | 1948 | 1967 |  |  | 48874 | 48893 |  |
|  | 2290 | 2309 |  |  | 54420 | 54439 |  |
|  | 3316 | 3335 |  |  | 72037 | 72056 |  |
| 494158 | 239 | 258 | TCCTGTGACAGTGGTGGAGT | 95 | 21200 | 21219 | 13 |
|  | 581 | 600 |  |  | 26691 | 26710 |  |
|  | 923 | 942 |  |  | 32238 | 32257 |  |
|  | 1607 | 1626 |  |  | 43331 | 43350 |  |
|  | 1949 | 1968 |  |  | 48875 | 48894 |  |
|  | 2291 | 2310 |  |  | 54421 | 54440 |  |
|  | 3317 | 3336 |  |  | 72038 | 72057 |  |
| 494159 | 241 | 260 | CTTCCTGTGACAGTGGTGGA | 97 | 21202 | 21221 | 14 |
|  | 583 | 602 |  |  | 26693 | 26712 |  |
|  | 925 | 944 |  |  | 32240 | 32259 |  |
|  | 1609 | 1628 |  |  | 43333 | 43352 |  |
|  | 1951 | 1970 |  |  | 48877 | 48896 |  |
|  | 2293 | 2312 |  |  | 54423 | 54442 |  |
|  | 3319 | 3338 |  |  | 72040 | 72059 |  |
|  | 4663 | 4682 |  |  | 94404 | 94423 |  |
|  | 5005 | 5024 |  |  | 115515 | 115534 |  |

TABLE 3-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 494160 | 242<br>4664<br>5006 | 261<br>4683<br>5025 | CCTTCCTGTGACAGTGGTGG | 97 | 21203<br>94405<br>115516 | 21222<br>94424<br>115535 | 15 |
| 494161 | 243<br>4665<br>5007 | 262<br>4684<br>5026 | TCCTTCCTGTGACAGTGGTG | 96 | 21204<br>94406<br>115517 | 21223<br>94425<br>115536 | 16 |
| 494162 | 244<br>3664<br>4666<br>5008 | 263<br>3683<br>4685<br>5027 | GTCCTTCCTGTGACAGTGGT | 95 | 21205<br>77585<br>94407<br>115518 | 21224<br>77604<br>94426<br>115537 | 17 |
| 494163 | 245<br>4667 | 264<br>4686 | GGTCCTTCCTGTGACAGTGG | 96 | 21206<br>94408 | 21225<br>94427 | 18 |
| 494164 | 246<br>4668 | 265<br>4687 | AGGTCCTTCCTGTGACAGTG | 93 | 21207<br>94409 | 21226<br>94428 | 19 |
| 494165 | 247<br>4669 | 266<br>4688 | CAGGTCCTTCCTGTGACAGT | 91 | 21208<br>94410 | 21227<br>94429 | 20 |
| 494166 | 248 | 267 | GCAGGTCCTTCCTGTGACAG | 89 | 21209 | 21228 | 21 |
| 494167 | 250 | 269 | TGGCAGGTCCTTCCTGTGAC | 92 | 21211 | 21230 | 22 |
| 494168 | 251 | 270 | TTGGCAGGTCCTTCCTGTGA | 89 | 21212 | 21231 | 23 |
| 494169 | 252 | 271 | CTTGGCAGGTCCTTCCTGTG | 92 | 21213 | 21232 | 24 |
| 494170 | 253 | 272 | GCTTGGCAGGTCCTTCCTGT | 88 | 21214 | 21233 | 25 |

TABLE 4

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 91<br>84 | 21210 | 21229 | 11 |
| 494283 | 584<br>926<br>1610<br>1952<br>2294<br>3320 | 603<br>945<br>1629<br>1971<br>2313<br>3339 | TCTTCCTGTGACAGTGGTGG | 93 | 26694<br>32241<br>43334<br>48878<br>54424<br>72041 | 26713<br>32260<br>43353<br>48897<br>54443<br>72060 | 26 |
| 494284 | 585<br>927<br>1611<br>1953<br>2295<br>3321 | 604<br>946<br>1630<br>1972<br>2314<br>3340 | TTCTTCCTGTGACAGTGGTG | 95 | 26695<br>32242<br>43335<br>48879<br>54425<br>72042 | 26714<br>32261<br>43354<br>48898<br>54444<br>72061 | 27 |
| 494285 | 586<br>928<br>1612<br>1954<br>2296<br>3322 | 605<br>947<br>1631<br>1973<br>2315<br>3341 | GTTCTTCCTGTGACAGTGGT | 95 | 26696<br>32243<br>43336<br>48880<br>54426<br>72043 | 26715<br>32262<br>43355<br>48899<br>54445<br>72062 | 28 |
| 494286 | 587<br>929<br>1613<br>1955<br>2297 | 606<br>948<br>1632<br>1974<br>2316 | GGTTCTTCCTGTGACAGTGG | 95 | 26697<br>32244<br>43337<br>48881<br>54427 | 26716<br>32263<br>43356<br>48900<br>54446 | 29 |

TABLE 4-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 494287 | 588 | 607 | AGGTTCTTCCTGTGACAGTG | 95 | 26698 | 26717 | 30 |
|  | 930 | 949 |  |  | 32245 | 32264 |  |
|  | 1614 | 1633 |  |  | 43338 | 43357 |  |
|  | 1956 | 1975 |  |  | 48882 | 48901 |  |
|  | 2298 | 2317 |  |  | 54428 | 54447 |  |
| 494288 | 589 | 608 | CAGGTTCTTCCTGTGACAGT | 91 | 26699 | 26718 | 31 |
|  | 931 | 950 |  |  | 32246 | 32265 |  |
|  | 1615 | 1634 |  |  | 43339 | 43358 |  |
|  | 1957 | 1976 |  |  | 48883 | 48902 |  |
|  | 2299 | 2318 |  |  | 54429 | 54448 |  |
|  | 2983 | 3002 |  |  | 66500 | 66519 |  |
| 494290 | 592 | 611 | TGGCAGGTTCTTCCTGTGAC | 90 | 26702 | 26721 | 32 |
|  | 934 | 953 |  |  | 32249 | 32268 |  |
|  | 1618 | 1637 |  |  | 43342 | 43361 |  |
|  | 1960 | 1979 |  |  | 48886 | 48905 |  |
|  | 2302 | 2321 |  |  | 54432 | 54451 |  |
|  | 2986 | 3005 |  |  | 66503 | 66522 |  |
| 494291 | 593 | 612 | TTGGCAGGTTCTTCCTGTGA | 89 | 26703 | 26722 | 33 |
|  | 935 | 954 |  |  | 32250 | 32269 |  |
|  | 1619 | 1638 |  |  | 43343 | 43362 |  |
|  | 1961 | 1980 |  |  | 48887 | 48906 |  |
|  | 2303 | 2322 |  |  | 54433 | 54452 |  |
|  | 2987 | 3006 |  |  | 66504 | 66523 |  |
| 494292 | 594 | 613 | CTTGGCAGGTTCTTCCTGTG | 94 | 26704 | 26723 | 35 |
|  | 936 | 955 |  |  | 32251 | 32270 |  |
|  | 1620 | 1639 |  |  | 43344 | 43363 |  |
|  | 1962 | 1981 |  |  | 48888 | 48907 |  |
|  | 2304 | 2323 |  |  | 54434 | 54453 |  |
|  | 2988 | 3007 |  |  | 66505 | 66524 |  |
| 494294 | 596 | 615 | AGCTTGGCAGGTTCTTCCTG | 90 | 26706 | 26725 | 36 |
|  | 938 | 957 |  |  | 32253 | 32272 |  |
|  | 1622 | 1641 |  |  | 43346 | 43365 |  |
|  | 1964 | 1983 |  |  | 48890 | 48909 |  |
|  | 2306 | 2325 |  |  | 54436 | 54455 |  |
|  | 2990 | 3009 |  |  | 66507 | 66526 |  |
| 494299 | 626 | 645 | ACTATGCGAGTGTGGTGTCA | 91 | 26736 | 26755 | 37 |
|  | 968 | 987 |  |  | 32283 | 32302 |  |
|  | 1310 | 1329 |  |  | 37830 | 37849 |  |
|  | 1652 | 1671 |  |  | 43376 | 43395 |  |
|  | 1994 | 2013 |  |  | 48920 | 48939 |  |
|  | 2336 | 2355 |  |  | 54466 | 54485 |  |
|  | 2678 | 2697 |  |  | 60021 | 60040 |  |
|  | 3020 | 3039 |  |  | 66537 | 66556 |  |
| 494300 | 627 | 646 | GACTATGCGAGTGTGGTGTC | 93 | 26737 | 26756 | 38 |
|  | 969 | 988 |  |  | 32284 | 32303 |  |
|  | 1311 | 1330 |  |  | 37831 | 37850 |  |
|  | 1653 | 1672 |  |  | 43377 | 43396 |  |
|  | 1995 | 2014 |  |  | 48921 | 48940 |  |
|  | 2337 | 2356 |  |  | 54467 | 54486 |  |
|  | 2679 | 2698 |  |  | 60022 | 60041 |  |
|  | 3021 | 3040 |  |  | 66538 | 66557 |  |
| 494301 | 628 | 647 | CGACTATGCGAGTGTGGTGT | 93 | 26738 | 26757 | 39 |
|  | 970 | 989 |  |  | 32285 | 32304 |  |
|  | 1312 | 1331 |  |  | 37832 | 37851 |  |
|  | 1654 | 1673 |  |  | 43378 | 43397 |  |
|  | 1996 | 2015 |  |  | 48922 | 48941 |  |
|  | 2338 | 2357 |  |  | 54468 | 54487 |  |
|  | 2680 | 2699 |  |  | 60023 | 60042 |  |
|  | 3022 | 3041 |  |  | 66539 | 66558 |  |
| 494302 | 629 | 648 | CCGACTATGCGAGTGTGGT | 94 | 26739 | 26758 | 40 |
|  | 971 | 990 | G |  | 32286 | 32305 |  |
|  | 1313 | 1332 |  |  | 37833 | 37852 |  |
|  | 1655 | 1674 |  |  | 43379 | 43398 |  |

TABLE 4-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| | 1997 | 2016 | | | 48923 | 48942 | |
| | 2339 | 2358 | | | 54469 | 54488 | |
| | 2681 | 2700 | | | 60024 | 60043 | |
| | 3023 | 3042 | | | 66540 | 66559 | |
| 494303 | 630 | 649 | TCCGACTATGCGAGTGTGGT | 93 | 26740 | 26759 | 41 |
| | 972 | 991 | | | 32287 | 32306 | |
| | 1314 | 1333 | | | 37834 | 37853 | |
| | 1656 | 1675 | | | 43380 | 43399 | |
| | 1998 | 2017 | | | 48924 | 48943 | |
| | 2340 | 2359 | | | 54470 | 54489 | |
| | 2682 | 2701 | | | 60025 | 60044 | |
| | 3024 | 3043 | | | 66541 | 66560 | |
| 494304 | 631 | 650 | GTCCGACTATGCGAGTGTG | 94 | 26741 | 26760 | 42 |
| | 973 | 992 G | | | 32288 | 32307 | |
| | 1315 | 1334 | | | 37835 | 37854 | |
| | 1657 | 1676 | | | 43381 | 43400 | |
| | 1999 | 2018 | | | 48925 | 48944 | |
| | 2341 | 2360 | | | 54471 | 54490 | |
| | 2683 | 2702 | | | 60026 | 60045 | |
| | 3025 | 3044 | | | 66542 | 66561 | |
| 494305 | 632 | 651 | GGTCCGACTATGCGAGTGT | 93 | 26742 | 26761 | 43 |
| | 974 | 993 G | | | 32289 | 32308 | |
| | 1316 | 1335 | | | 37836 | 37855 | |
| | 1658 | 1677 | | | 43382 | 43401 | |
| | 2000 | 2019 | | | 48926 | 48945 | |
| | 2342 | 2361 | | | 54472 | 54491 | |
| | 2684 | 2703 | | | 60027 | 60046 | |
| | 3026 | 3045 | | | 66543 | 66562 | |
| 494306 | 633 | 652 | GGGTCCGACTATGCGAGTG | 92 | 26743 | 26762 | 44 |
| | 975 | 994 T | | | 32290 | 32309 | |
| | 1317 | 1336 | | | 37837 | 37856 | |
| | 1659 | 1678 | | | 43383 | 43402 | |
| | 2001 | 2020 | | | 48927 | 48946 | |
| | 2343 | 2362 | | | 54473 | 54492 | |
| | 2685 | 2704 | | | 60028 | 60047 | |
| | 3027 | 3046 | | | 66544 | 66563 | |
| 494307 | 1190 | 1209 | CTGCTCAGTCGGTGCTTGTT | 91 | n/a | n/a | 45 |
| | 2558 | 2577 | | | | | |
| 494310 | 1193 | 1212 | CCTCTGCTCAGTCGGTGCTT | 90 | n/a | n/a | 46 |
| | 2561 | 2580 | | | | | |
| 494311 | 1194 | 1213 | GCCTCTGCTCAGTCGGTGCT | 88 | 37714 | 37733 | 47 |
| | 2562 | 2581 | | | 59905 | 59924 | |
| 494334 | 1267 | 1286 | CTTCCAGTGACAGTGGTGG | 90 | 37787 | 37806 | 48 |
| | 2635 | 2654 A | | | 59978 | 59997 | |
| 494336 | 1269 | 1288 | TTCTTCCAGTGACAGTGGTG | 90 | 37789 | 37808 | 49 |
| | 2637 | 2656 | | | 59980 | 59999 | |
| 494337 | 1270 | 1289 | GTTCTTCCAGTGACAGTGGT | 95 | 37790 | 37809 | 50 |
| | 2638 | 2657 | | | 59981 | 60000 | |
| 494338 | 1271 | 1290 | GGTTCTTCCAGTGACAGTGG | 91 | 37791 | 37810 | 133 |
| | 2639 | 2658 | | | 59982 | 60001 | |
| 494521 | 6393 | 6412 | GACCTTAAAAGCTTATACAC | 82 | 140049 | 140068 | 51 |
| 494525 | 6397 | 6416 | GTCAGACCTTAAAAGCTTAT | 84 | 140053 | 140072 | 52 |
| 494530 | 6402 | 6421 | TGTCAGTCAGACCTTAAAAG | 82 | 140058 | 140077 | 53 |

TABLE 4-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 494535 | 6407 | 6426 | GAATTTGTCAGTCAGACCTT | 85 | 140063 | 140082 | 54 |
| 494536 | 6408 | 6427 | AGAATTTGTCAGTCAGACCT | 83 | 140064 | 140083 | 55 |
| 494544 | 6417 | 6436 | CCTTAATACAGAATTTGTCA | 82 | 140073 | 140092 | 56 |

TABLE 5

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 84 | 21210 | 21229 | 11 |
| 494371 | 3900 | 3919 | GCTCCGTTGGTGCTTGTTCA | 93 | n/a | n/a | 57 |
| 494372 | 3901 | 3920 | TGCTCCGTTGGTGCTTGTTC | 93 | n/a | n/a | 58 |
| 494373 | 3902 | 3921 | TTGCTCCGTTGGTGCTTGTT | 83 | n/a | n/a | 59 |
| 494374 | 3903 | 3922 | TTTGCTCCGTTGGTGCTTGT | 89 | n/a | n/a | 60 |
| 494375 | 3904 | 3923 | CTTTGCTCCGTTGGTGCTTG | 85 | n/a | n/a | 61 |
| 494386 | 3977 | 3996 | TCCTGTAACAGTGGTGGAGA | 86 | 81985 | 82004 | 62 |
| 494387 | 3978 | 3997 | TTCCTGTAACAGTGGTGGAG | 82 | 81986 | 82005 | 63 |
| 494388 | 3979 | 3998 | CTTCCTGTAACAGTGGTGGA | 86 | 81987 | 82006 | 64 |
| 494389 | 3980 | 3999 | CCTTCCTGTAACAGTGGTGG | 92 | 81988 | 82007 | 65 |
| 494390 | 3981 | 4000 | TCCTTCCTGTAACAGTGGTG | 92 | 81989 | 82008 | 66 |
| 494391 | 3982 | 4001 | GTCCTTCCTGTAACAGTGGT | 84 | 81990 | 82009 | 67 |
| 494392 | 3983 | 4002 | TGTCCTTCCTGTAACAGTGG | 81 | 81991 | 82010 | 68 |

TABLE 6

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 86 | 21210 | 21229 | 11 |
| 498369 | 3203 | 3222 | TGGAGCCAGAATAACATTCG | 91 | 70667 | 70686 | 69 |
| 498379 | 3213 | 3232 | CCTCTAGGCTTGGAGCCAGA | 85 | 70677 | 70696 | 70 |
| 498408 | 3323 | 3342 | AGTTCTTCCTGTGACAGTGG | 86 | 72044 | 72063 | 71 |
| 498433 | 3367 | 3386 | GTCCGACTATGCTGGTGTGG | 87 | 72088 | 72107 | 72 |
| 498434 | 3368 | 3387 | GGTCCGACTATGCTGGTGTG | 86 | 72089 | 72108 | 73 |
| 498435 | 3369 | 3388 | GGGTCCGACTATGCTGGTGT | 83 | 72090 | 72109 | 74 |

TABLE 7

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 90 | 21210 | 21229 | 11 |
| 498229 | 2871 | 2890 | CCTCTAGGCTTGGAATCGGG | 90 | 65117 | 65136 | 75 |
| 498238 | 2883 | 2902 | GTTCAGAAGGAGCCTCTAGG | 93 | 65129 | 65148 | 76 |
| 498239 | 2884 | 2903 | TGTTCAGAAGGAGCCTCTAG | 94 | 65130 | 65149 | 77 |
| 498240 | 2887 4573 | 2906 4592 | GCTTGTTCAGAAGGAGCCTC | 98 | n/a | n/a | 78 |
| 498241 | 2888 4574 | 2907 4593 | TGCTTGTTCAGAAGGAGCCT | 94 | n/a | n/a | 79 |
| 498242 | 2889 4575 | 2908 4594 | GTGCTTGTTCAGAAGGAGCC | 96 | n/a | n/a | 80 |
| 498243 | 2890 4576 | 2909 4595 | GGTGCTTGTTCAGAAGGAGC | 97 | n/a | n/a | 81 |
| 498244 | 2891 4577 | 2910 4596 | TGGTGCTTGTTCAGAAGGAG | 92 | n/a | n/a | 82 |
| 498251 | 2898 | 2917 | GCTCAGTTGGTGCTTGTTCA | 90 | n/a | n/a | 83 |
| 498252 | 2899 | 2918 | TGCTCAGTTGGTGCTTGTTC | 90 | n/a | n/a | 84 |

TABLE 8

| ISIS NO | SEQ ID NO: 1 Start Site | SEQ ID NO: 1 Stop Site | Sequence | % inhiition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 91 | 21210 | 21229 | 11 |
| 498517 | 3548 | 3567 | GCTTGGATCTGGGACCACCG | 89 | 76233 | 76252 | 85 |

TABLE 9

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 94 | 21210 | 21229 | 11 |
| 498833 | 4900 | 4919 | GCCTCCATGCTTGGAACTGG | 94 | 114205 | 114224 | 86 |
| 498859 | 4926 | 4945 | GCTCAGTTGGTGCTGCTTCA | 92 | n/a | n/a | 87 |
| 498868 | 4978 | 4997 | CCTCGATAACTCTGGCCATT | 94 | 115488 | 115507 | 88 |
| 498875 | 5003 | 5022 | TCCTGTGACAGTGGTGGAGA | 94 | 115513 | 115532 | 89 |

TABLE 10

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 92 | 21210 | 21229 | 11 |
| 499020 | 6257 | 6276 | GTAGGTTGATGCTTCACTCT | 91 | 139913 | 139932 | 90 |
| 499041 | 6318 | 6337 | CGTTTGATTGCTGTCTATTA | 90 | 139974 | 139993 | 91 |

TABLE 11

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 91 | 21210 | 21229 | 11 |
| 498523 | 3554 | 3573 | CTCTGTGCTTGGATCTGGGA | 94 | 76239 | 76258 | 92 |
| 498524 | 3555 | 3574 | CCTCTGTGCTTGGATCTGGG | 96 | 76240 | 76259 | 93 |
| 498525 | 3556 | 3575 | GCCTCTGTGCTTGGATCTGG | 94 | 76241 | 76260 | 94 |
| 498529 | 3560 | 3579 | AGAAGCCTCTGTGCTTGGAT | 89 | 76245 | 76264 | 95 |
| 498535 | 3566 | 3585 | TTCAGAAGAAGCCTCTGTGC | 89 | 76251 | 76270 | 96 |
| 498550 | 3582 | 3601 | GCTCCGTTGGTGCTTCTTCA | 90 | n/a | n/a | 97 |
| 498553 | 3585 | 3604 | TTTGCTCCGTTGGTGCTTCT | 87 | n/a | n/a | 98 |
| 498555 | 3587<br>3905 | 3606<br>3924 | GCTTTGCTCCGTTGGTGCTT | 90 | n/a | n/a | 99 |
| 498556 | 3588<br>3906 | 3607<br>3925 | GGCTTTGCTCCGTTGGTGCT | 89 | 77509<br>81914 | 77528<br>81933 | 100 |
| 498557 | 3589<br>3907 | 3608<br>3926 | GGGCTTTGCTCCGTTGGTGC | 89 | 77510<br>81915 | 77529<br>81934 | 101 |
| 498579 | 3662 | 3681 | CCTTCCTGTGACAGTGGTAG | 87 | 77583 | 77602 | 102 |
| 498580 | 3663 | 3682 | TCCTTCCTGTGACAGTGGTA | 92 | 77584 | 77603 | 103 |
| 498581 | 3665<br>5009 | 3684<br>5028 | TGTCCTTCCTGTGACAGTGG | 94 | 77586<br>115519 | 77605<br>115538 | 104 |

TABLE 12

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 100 | 21210 | 21229 | 11 |
| 494230 | 477<br>819<br>1161<br>1503<br>1845<br>2187<br>2529 | 496<br>838<br>1180<br>1522<br>1864<br>2206<br>2548 | CCTCTAGGCTTGGAACCGGG | 95 | 25380<br>30927<br>36471<br>42020<br>47564<br>53110<br>58662 | 25399<br>30946<br>36490<br>42039<br>47583<br>53129<br>58681 | 105 |
| 494243 | 494<br>836<br>1178<br>1520<br>1862<br>2204<br>2546 | 513<br>855<br>1197<br>1539<br>1881<br>2223<br>2565 | TGCTTGTTCGGAAGGAGCCT | 93 | n/a | n/a | 106 |
| 494244 | 495<br>837<br>1179<br>1521<br>1863<br>2205<br>2547 | 514<br>856<br>1198<br>1540<br>1882<br>2224<br>2566 | GTGCTTGTTCGGAAGGAGCC | 95 | n/a | n/a | 107 |

TABLE 13

| ISIS NO | SEQ ID NO: 1 Start Site | SEQ ID NO: 1 Stop Site | Sequence | % inhibition | SEQ ID NO: 2 Start Site | SEQ ID NO. 2 Stop Site | SEQ ID NO |
|---|---|---|---|---|---|---|---|
| 144367 | 249 | 268 | GGCAGGTCCTTCCTGTGACA | 96 | 21210 | 21229 | 11 |
| 494466 | 4208 | 4227 | GCTTGGAACTGGGACCACCG | 95 | 85138 | 85157 | 108 |
| 494470 | 4212 | 4231 | CTGTGCTTGGAACTGGGACC | 94 | 85142 | 85161 | 109 |
| 494472 | 4214 | 4233 | CTCTGTGCTTGGAACTGGGA | 92 | 85144 | 85163 | 110 |

Example 3: Dose-Dependent Antisense Inhibition of Apo(a) in Transgenic Mouse Primary Hepatocytes Gapmers from the studies described above exhibiting significant in vitro inhibition of apo(a) mRNA were selected and tested at various doses in transgenic mouse primary hepatocytes in a series of parallel studies with similar culture conditions. Cells were plated at a density of 35,000 per well and transfected using electroporation with 0.0625 µM, 0.125 µM, 0.25 µM, 0.500 µM, or 1.000 µM concentrations of antisense oligonucleotide. After a treatment period of approximately 16 hours, RNA was isolated from the cells and apo(a) mRNA levels were measured by quantitative real-time PCR. Apo(a) primer probe set hAPO(a)12 kB was used to measured mRNA levels. Apo(a) mRNA levels were adjusted according to total RNA content, as measured by RIBOGREEN®. Results are presented as percent inhibition of apo(a), relative to untreated control cells.

The results of each of the studies are depicted in the Tables presented below with each table representing a separate experiment. The half maximal inhibitory concentration ($IC_{50}$) of each oligonucleotide is also presented in the Tables. Apo(a) mRNA levels were significantly reduced in a dose-dependent manner in antisense oligonucleotide treated cells. The potency of the newly designed oligos was compared with the benchmark oligonucleotide ISIS 144367.

TABLE 14

| ISIS No | 0.0625 µM | 0.125 µM | 0.250 µM | 0.500 µM | 1.000 µM | $IC_{50}$ (µM) |
|---|---|---|---|---|---|---|
| 144367 | 11 | 27 | 46 | 62 | 80 | 0.31 |
| 494157 | 11 | 47 | 53 | 76 | 87 | 0.23 |
| 494158 | 19 | 57 | 75 | 84 | 88 | 0.13 |
| 494159 | 41 | 65 | 77 | 84 | 92 | 0.07 |
| 494160 | 44 | 69 | 76 | 85 | 91 | 0.06 |
| 494161 | 40 | 64 | 74 | 85 | 91 | 0.08 |
| 494162 | 36 | 63 | 76 | 87 | 88 | 0.09 |
| 494163 | 20 | 59 | 75 | 85 | 92 | 0.13 |
| 494164 | 3 | 45 | 62 | 74 | 90 | 0.21 |
| 494165 | 25 | 39 | 57 | 71 | 75 | 0.19 |
| 494166 | 17 | 30 | 47 | 59 | 76 | 0.31 |
| 494167 | 30 | 43 | 55 | 72 | 80 | 0.18 |
| 494168 | 25 | 36 | 44 | 59 | 75 | 0.28 |
| 494169 | 19 | 39 | 51 | 61 | 81 | 0.25 |

TABLE 15

| ISIS No | 0.0625 µM | 0.125 µM | 0.250 µM | 0.500 µM | 1.000 µM | $IC_{50}$ (µM) |
|---|---|---|---|---|---|---|
| 144367 | 23 | 40 | 58 | 76 | 88 | 0.19 |
| 494170 | 38 | 34 | 60 | 76 | 84 | 0.13 |
| 494230 | 55 | 71 | 89 | 95 | 97 | 0.03 |
| 494243 | 47 | 73 | 87 | 92 | 97 | 0.05 |
| 494244 | 58 | 73 | 86 | 92 | 96 | 0.03 |
| 494283 | 54 | 70 | 84 | 93 | 94 | 0.05 |
| 494284 | 45 | 62 | 83 | 92 | 95 | 0.07 |
| 494285 | 56 | 70 | 84 | 92 | 95 | 0.04 |
| 494286 | 51 | 70 | 87 | 93 | 95 | 0.05 |
| 494287 | 32 | 60 | 67 | 87 | 91 | 0.11 |
| 494288 | 26 | 41 | 61 | 79 | 88 | 0.17 |
| 494290 | 30 | 43 | 64 | 81 | 87 | 0.15 |
| 494291 | 29 | 40 | 56 | 75 | 85 | 0.18 |

TABLE 16

| ISIS No | 0.0625 µM | 0.125 µM | 0.250 µM | 0.500 µM | 1.000 µM | $IC_{50}$ (µM) |
|---|---|---|---|---|---|---|
| 144367 | 10 | 38 | 62 | 68 | 84 | 0.23 |
| 494292 | 17 | 36 | 74 | 85 | 90 | 0.17 |
| 494294 | 10 | 34 | 53 | 80 | 91 | 0.22 |
| 494299 | 32 | 29 | 56 | 77 | 88 | 0.16 |
| 494300 | 34 | 46 | 76 | 86 | 90 | 0.12 |
| 494301 | 44 | 56 | 72 | 86 | 89 | 0.09 |
| 494302 | 42 | 59 | 78 | 88 | 89 | 0.08 |
| 494303 | 37 | 58 | 70 | 86 | 89 | 0.10 |
| 494304 | 46 | 71 | 78 | 89 | 90 | 0.05 |
| 494305 | 39 | 58 | 62 | 85 | 87 | 0.10 |
| 494306 | 31 | 52 | 65 | 79 | 88 | 0.13 |
| 494307 | 23 | 23 | 39 | 65 | 78 | 0.34 |
| 494310 | 14 | 29 | 62 | 70 | 88 | 0.25 |

TABLE 17

| ISIS No | 0.0625 µM | 0.125 µM | 0.250 µM | 0.500 µM | 1.000 µM | $IC_{50}$ (µM) |
|---|---|---|---|---|---|---|
| 144367 | 0 | 29 | 45 | 73 | 92 | 0.27 |
| 494311 | 28 | 53 | 65 | 85 | 95 | 0.13 |
| 494334 | 20 | 44 | 66 | 86 | 96 | 0.16 |
| 494336 | 15 | 38 | 54 | 84 | 97 | 0.20 |
| 494337 | 28 | 50 | 77 | 90 | 98 | 0.12 |
| 494338 | 21 | 40 | 68 | 91 | 98 | 0.15 |
| 494371 | 19 | 0 | 71 | 89 | 97 | 0.15 |
| 494372 | 33 | 44 | 77 | 91 | 97 | 0.12 |
| 494373 | 15 | 36 | 65 | 83 | 95 | 0.19 |
| 494374 | 3 | 17 | 51 | 83 | 90 | 0.24 |
| 494375 | 1 | 34 | 56 | 80 | 93 | 0.23 |
| 494386 | 13 | 26 | 46 | 73 | 91 | 0.25 |
| 494387 | 17 | 27 | 45 | 67 | 88 | 0.28 |

TABLE 18

| ISIS No | 0.0625 μM | 0.125 μM | 0.250 μM | 0.500 μM | 1.000 μM | IC$_{50}$ (μM) |
|---|---|---|---|---|---|---|
| 144367 | 35 | 42 | 62 | 70 | 91 | 0.15 |
| 494537 | 19 | 34 | 54 | 79 | 90 | 0.21 |
| 494544 | 10 | 38 | 73 | 86 | 94 | 0.17 |
| 498229 | 36 | 58 | 80 | 92 | 97 | 0.10 |
| 498238 | 41 | 57 | 75 | 91 | 97 | 0.09 |
| 498239 | 56 | 71 | 79 | 90 | 94 | 0.03 |
| 498240 | 91 | 94 | 98 | 99 | 100 | <0.06 |
| 498241 | 75 | 84 | 91 | 96 | 98 | <0.06 |
| 498242 | 11 | 27 | 42 | 47 | 63 | 0.49 |
| 498243 | 91 | 93 | 96 | 98 | 99 | <0.06 |
| 498244 | 4 | 0 | 0 | 13 | 43 | >1.00 |
| 498251 | 30 | 30 | 42 | 73 | 89 | 0.26 |
| 498252 | 37 | 33 | 58 | 80 | 92 | 0.20 |
| 498369 | 22 | 22 | 10 | 22 | 34 | >1.00 |

TABLE 19

| ISIS No | 0.0625 μM | 0.125 μM | 0.250 μM | 0.500 μM | 1.000 μM | IC$_{50}$ (μM) |
|---|---|---|---|---|---|---|
| 144367 | 15 | 32 | 54 | 75 | 90 | 0.22 |
| 498379 | 29 | 48 | 71 | 80 | 95 | 0.13 |
| 498408 | 38 | 57 | 77 | 88 | 96 | 0.09 |
| 498433 | 29 | 36 | 70 | 88 | 96 | 0.15 |
| 498434 | 49 | 43 | 50 | 78 | 90 | 0.19 |
| 498435 | 27 | 39 | 57 | 78 | 93 | 0.18 |
| 498517 | 64 | 72 | 82 | 93 | 98 | <0.06 |
| 498721 | 77 | 84 | 88 | 96 | 97 | <0.06 |
| 498833 | 73 | 78 | 91 | 95 | 99 | <0.06 |
| 498859 | 7 | 24 | 37 | 62 | 75 | 0.36 |
| 498868 | 7 | 14 | 39 | 63 | 81 | 0.36 |
| 498875 | 16 | 21 | 33 | 55 | 81 | 0.39 |
| 499020 | 7 | 24 | 23 | 55 | 78 | 0.36 |
| 499041 | 6 | 16 | 33 | 64 | 83 | 0.35 |

TABLE 20

| ISIS No | 0.0625 μM | 0.125 μM | 0.250 μM | 0.500 μM | 1.000 μM | IC$_{50}$ (μM) |
|---|---|---|---|---|---|---|
| 144367 | 14 | 47 | 64 | 79 | 91 | 0.14 |
| 498523 | 36 | 50 | 80 | 87 | 95 | 0.11 |
| 498524 | 43 | 79 | 87 | 93 | 97 | 0.01 |
| 498525 | 32 | 49 | 75 | 86 | 96 | 0.12 |
| 498529 | 21 | 49 | 57 | 78 | 90 | 0.17 |
| 498535 | 20 | 34 | 55 | 76 | 86 | 0.21 |
| 498550 | 12 | 50 | 69 | 84 | 96 | 0.11 |
| 498553 | 8 | 43 | 55 | 77 | 91 | 0.21 |
| 498555 | 13 | 35 | 68 | 86 | 94 | 0.19 |
| 498556 | 27 | 37 | 71 | 85 | 91 | 0.15 |
| 498557 | 18 | 42 | 75 | 89 | 95 | 0.16 |
| 498579 | 16 | 38 | 67 | 89 | 95 | 0.16 |
| 498580 | 36 | 57 | 81 | 91 | 96 | 0.10 |
| 498581 | 34 | 64 | 75 | 93 | 97 | 0.05 |

TABLE 21

| ISIS No | 0.0625 μM | 0.125 μM | 0.250 μM | 0.500 μM | 1.000 μM | IC$_{50}$ (μM) |
|---|---|---|---|---|---|---|
| 144367 | 0 | 9 | 26 | 49 | 77 | 0.47 |
| 494388 | 0 | 0 | 21 | 33 | 55 | 0.89 |
| 494389 | 0 | 15 | 22 | 50 | 79 | 0.46 |
| 494390 | 5 | 20 | 37 | 68 | 81 | 0.33 |
| 494391 | 7 | 20 | 32 | 54 | 68 | 0.46 |
| 494392 | 18 | 24 | 40 | 57 | 76 | 0.35 |
| 494466 | 33 | 45 | 58 | 69 | 82 | 0.16 |
| 494470 | 45 | 58 | 68 | 79 | 87 | 0.08 |
| 494472 | 37 | 50 | 60 | 69 | 83 | 0.13 |
| 494521 | 0 | 0 | 0 | 15 | 54 | 0.17 |

TABLE 21-continued

| ISIS No | 0.0625 μM | 0.125 μM | 0.250 μM | 0.500 μM | 1.000 μM | IC$_{50}$ (μM) |
|---|---|---|---|---|---|---|
| 494525 | 0 | 0 | 2 | 28 | 65 | 0.85 |
| 494530 | 0 | 6 | 27 | 51 | 80 | 0.46 |
| 494535 | 0 | 7 | 24 | 53 | 74 | 0.49 |
| 494536 | 0 | 2 | 15 | 42 | 67 | 0.63 |

TABLE 22

| ISIS No | 0.0625 μM | 0.125 μM | 0.250 μM | 0.500 μM | 1.000 μM | IC$_{50}$ (μM) |
|---|---|---|---|---|---|---|
| 144367 | 0 | 4 | 16 | 26 | 77 | 0.65 |
| 498379 | 12 | 18 | 27 | 32 | 63 | 0.81 |
| 498408 | 0 | 11 | 46 | 50 | 77 | 0.41 |
| 498433 | 22 | 30 | 46 | 60 | 83 | 0.27 |
| 498434 | 39 | 29 | 25 | 47 | 78 | 0.40 |
| 498435 | 21 | 28 | 26 | 43 | 73 | 0.50 |
| 498517 | 44 | 48 | 63 | 70 | 84 | 0.11 |
| 498721 | 54 | 54 | 66 | 75 | 89 | <0.06 |
| 498833 | 44 | 51 | 58 | 67 | 83 | 0.11 |
| 498859 | 0 | 29 | 14 | 35 | 66 | 0.69 |
| 498868 | 0 | 12 | 9 | 26 | 60 | 1.07 |
| 498875 | 0 | 30 | 31 | 53 | 78 | 0.40 |
| 499020 | 0 | 27 | 19 | 45 | 74 | 0.51 |
| 499041 | 0 | 12 | 10 | 37 | 65 | 0.77 |

As presented in the Tables above, ISIS 494157 (SEQ ID NO: 12), ISIS 494158 (SEQ ID NO:13), ISIS 494159 (SEQ ID NO:14), ISIS 494160 (SEQ ID NO: 15), ISIS 494161 (SEQ ID NO:16), ISIS 494162 (SEQ ID NO: 17), ISIS 494163 (SEQ ID NO: 18), ISIS 494164 (SEQ ID NO: 19), ISIS 494165 (SEQ ID NO: 20), ISIS 494167 (SEQ ID NO: 22), ISIS 494168 (SEQ ID NO: 23), ISIS 494169 (SEQ ID NO: 24), ISIS 494170 (SEQ ID NO: 25), ISIS 494230 (SEQ ID NO: 105), ISIS 494243 (SEQ ID NO: 106), ISIS 494244 (SEQ ID NO: 107), ISIS 494283 (SEQ ID NO: 26), ISIS 494284 (SEQ ID NO: 27), ISIS 494285 (SEQ ID NO: 28), ISIS 494286 (SEQ ID NO: 29), ISIS 494287 (SEQ ID NO: 30), ISIS 494288 (SEQ ID NO: 31), ISIS 494290 (SEQ ID NO: 32), ISIS 494291 (SEQ ID NO: 33), ISIS 494292 (SEQ ID NO: 35), ISIS 494294 (SEQ ID NO: 36), ISIS 494299 (SEQ ID NO: 37), ISIS 494300 (SEQ ID NO: 38), ISIS 494301 (SEQ ID NO: 39), ISIS 494302 (SEQ ID NO: 40), ISIS 494303 (SEQ ID NO: 41), ISIS 494304 (SEQ ID NO: 42), ISIS 494305 (SEQ ID NO:43), ISIS 494306 (SEQ ID NO: 44), ISIS 494311 (SEQ ID NO: 47), ISIS 494334 (SEQ ID NO: 48), ISIS 494336 (SEQ ID NO: 49), ISIS 494337 (SEQ ID NO: 50), ISIS 494338 (SEQ ID NO: 133), ISIS 494371 (SEQ ID NO: 57), ISIS 494372 (SEQ ID NO: 58), ISIS 494373 (SEQ ID NO: 59), ISIS 494374 (SEQ ID NO: 60), ISIS 494375 (SEQ ID NO: 61), ISIS 494386 (SEQ ID NO: 62), ISIS 494389 (SEQ ID NO: 65), ISIS 494390 (SEQ ID NO: 66), ISIS 494392 (SEQ ID NO: 68), ISIS 494466 (SEQ ID NO: 108), ISIS 494470 (SEQ ID NO: 109), ISIS 494472 (SEQ ID NO: 110), ISIS 494521 (SEQ ID NO: 51), ISIS 494530 (SEQ ID NO: 53), ISIS 498229 (SEQ ID NO: 75), ISIS 498238 (SEQ ID NO: 76), ISIS 498239 (SEQ ID NO: 77), ISIS 498240 (SEQ ID NO: 78), ISIS 498241 (SEQ ID NO: 79), ISIS 498243 (SEQ ID NO: 81), ISIS 498379 (SEQ ID NO: 70), ISIS 498408 (SEQ ID NO: 71), ISIS 498433 (SEQ ID NO: 72), ISIS 498434 (SEQ ID NO: 73), ISIS 498435 (SEQ ID NO: 74), ISIS 498517 (SEQ ID NO: 85), ISIS 498523 (SEQ ID NO: 92), ISIS 498524 (SEQ ID NO: 93), ISIS 498525 (SEQ ID NO: 94), ISIS 498550 (SEQ ID NO: 97), ISIS 498580 (SEQ ID NO: 103), ISIS 498581 (SEQ ID NO: 104), ISIS 498721 (ATGCCTCGATAACTC-CGTCC; SEQ ID NO: 134), ISIS 498833 (SEQ ID NO: 86), ISIS 498875 (SEQ ID NO: 89), and ISIS 499020 (SEQ ID NO: 90) were more potent than ISIS 144367 (SEQ ID NO: 11).

Example 4: Dose-Dependent Antisense Inhibition of Apo(a) in Transgenic Mouse Primary Hepatocytes Potent gapmers from the studies described above were further selected and tested at various doses in transgenic mouse primary hepatocytes in a series of studies with similar culture conditions. Cells were plated at a density of 35,000 per well and transfected using electroporation with 0.049 μM, 0.148 μM, 0.444 μM, 1.333 μM, or 4.000 μM concentrations of antisense oligonucleotide, as specified in Tables below. After a treatment period of approximately 16 hours, RNA was isolated from the cells and apo(a) mRNA levels were measured by quantitative real-time PCR. Apo(a) primer probe set hAPO(a)12 kB was used to measured mRNA levels. Apo(a) mRNA levels were adjusted according to total RNA content, as measured by RIBOGREEN®. Results are presented as percent inhibition of apo(a), relative to untreated control cells.

The results of each of the studies are depicted in the Tables presented below with each table representing a separate experiment. The half maximal inhibitory concentration (IC$_{50}$) of each oligonucleotide is also presented in the Tables. Apo(a) mRNA levels were significantly reduced in a dose-dependent manner in antisense oligonucleotide treated cells. The potency of the newly designed oligos was compared with the benchmark oligonucleotide, ISIS 144367. As presented in the Tables below, ISIS 494157 (SEQ ID NO: 12), ISIS 494158 (SEQ ID NO:13), ISIS 494159 (SEQ ID NO:14), ISIS 494160 (SEQ ID NO: 15), ISIS 494161 (SEQ ID NO:16), ISIS 494162 (SEQ ID NO: 17), ISIS 494163 (SEQ ID NO: 18), ISIS 494164 (SEQ ID NO: 19), ISIS 494230 (SEQ ID NO: 105), ISIS 494243 (SEQ ID NO: 106), ISIS 494244 (SEQ ID NO: 107), ISIS 494283 (SEQ ID NO: 26), ISIS 494284 (SEQ ID NO: 27), ISIS 494285 (SEQ ID NO: 28), ISIS 494286 (SEQ ID NO: 29), ISIS 494287 (SEQ ID NO: 30), ISIS 494290 (SEQ ID NO: 32), ISIS 494292 (SEQ ID NO: 35), ISIS 494300 (SEQ ID NO: 38), ISIS 494301 (SEQ ID NO: 39), ISIS 494302 (SEQ ID NO: 40), ISIS 494303 (SEQ ID NO: 41), ISIS 494304 (SEQ ID NO: 42), ISIS 494305 (SEQ ID NO: 43), ISIS 494306 (SEQ ID NO: 44), ISIS 494310 (SEQ ID NO: 46), ISIS 494311 (SEQ ID NO: 47), ISIS 494337 (SEQ ID NO: 50), ISIS 494371 (SEQ ID NO: 57), ISIS 494372 (SEQ ID NO: 58), ISIS 494375 (SEQ ID NO: 61), ISIS 494388 (SEQ ID NO: 64), ISIS 494389 (SEQ ID NO: 65), ISIS 494390 (SEQ ID NO: 66), ISIS 494392 (SEQ ID NO: 68), ISIS 494466 (SEQ ID NO: 108), ISIS 494470 (SEQ ID NO: 109), ISIS 494472 (SEQ ID NO: 110), ISIS 498238 (SEQ ID NO: 76), ISIS 498239 (SEQ ID NO: 77), ISIS 498433 (SEQ ID NO: 72), ISIS 498434 (SEQ ID NO: 73), ISIS 498435 (SEQ ID NO: 74), ISIS 498523 (SEQ ID NO: 92), ISIS 498524 (SEQ ID NO: 93), ISIS 498525 (SEQ ID NO: 94), ISIS 498580 (SEQ ID NO: 103), and ISIS 498581 (SEQ ID NO: 104) were more potent than ISIS 144367 (SEQ ID NO: 11).

TABLE 23

| ISIS No | 0.049 μM | 0.148 μM | 0.444 μM | 1.333 μM | 4.000 μM | IC$_{50}$ (μM) |
|---|---|---|---|---|---|---|
| 144367 | 0 | 26 | 67 | 89 | 92 | 0.32 |
| 494157 | 23 | 50 | 83 | 96 | 96 | 0.15 |
| 494158 | 26 | 62 | 85 | 96 | 96 | 0.11 |
| 494159 | 42 | 65 | 87 | 95 | 94 | 0.07 |
| 494160 | 51 | 70 | 88 | 94 | 94 | <0.05 |
| 494161 | 36 | 67 | 87 | 95 | 96 | 0.08 |
| 494162 | 40 | 69 | 89 | 94 | 95 | 0.07 |
| 494163 | 41 | 57 | 87 | 95 | 94 | 0.08 |
| 494164 | 15 | 43 | 75 | 93 | 96 | 0.20 |
| 494230 | 39 | 77 | 94 | 99 | 99 | 0.05 |
| 494243 | 39 | 76 | 92 | 98 | 99 | 0.06 |
| 494244 | 58 | 79 | 91 | 97 | 99 | 0.02 |
| 494283 | 18 | 45 | 80 | 93 | 91 | 0.18 |
| 494284 | 9 | 53 | 80 | 95 | 94 | 0.18 |

TABLE 24

| ISIS No | 0.049 μM | 0.148 μM | 0.444 μM | 1.333 μM | 4.000 μM | IC$_{50}$ (μM) |
|---|---|---|---|---|---|---|
| 144367 | 21 | 40 | 79 | 94 | 93 | 0.18 |
| 494285 | 53 | 68 | 90 | 97 | 97 | <0.05 |
| 494286 | 46 | 69 | 89 | 96 | 97 | 0.05 |
| 494287 | 31 | 38 | 79 | 94 | 95 | 0.15 |
| 494290 | 22 | 53 | 74 | 93 | 94 | 0.16 |
| 494292 | 37 | 51 | 81 | 93 | 95 | 0.11 |
| 494294 | 22 | 40 | 72 | 91 | 94 | 0.19 |
| 494299 | 15 | 43 | 75 | 93 | 95 | 0.20 |
| 494300 | 25 | 38 | 79 | 95 | 95 | 0.17 |
| 494301 | 23 | 48 | 82 | 92 | 95 | 0.15 |
| 494302 | 26 | 59 | 86 | 93 | 94 | 0.12 |
| 494303 | 10 | 58 | 84 | 92 | 91 | 0.16 |
| 494304 | 25 | 62 | 83 | 93 | 93 | 0.12 |

TABLE 25

| ISIS No | 0.049 μM | 0.148 μM | 0.444 μM | 1.333 μM | 4.000 μM | IC$_{50}$ (μM) |
|---|---|---|---|---|---|---|
| 144367 | 23 | 40 | 70 | 90 | 94 | 0.19 |
| 494305 | 20 | 48 | 82 | 93 | 95 | 0.16 |
| 494306 | 26 | 53 | 78 | 91 | 92 | 0.14 |
| 494310 | 36 | 50 | 79 | 88 | 92 | 0.12 |
| 494311 | 38 | 50 | 74 | 93 | 95 | 0.12 |
| 494334 | 20 | 42 | 73 | 90 | 94 | 0.19 |
| 494336 | 5 | 39 | 74 | 92 | 95 | 0.23 |
| 494337 | 23 | 51 | 87 | 96 | 96 | 0.14 |
| 494338 | 12 | 42 | 82 | 93 | 95 | 0.19 |
| 494371 | 28 | 49 | 82 | 94 | 94 | 0.14 |
| 494372 | 28 | 54 | 81 | 93 | 88 | 0.13 |
| 494373 | 21 | 28 | 67 | 86 | 92 | 0.25 |
| 494375 | 26 | 40 | 77 | 85 | 92 | 0.18 |

TABLE 26

| ISIS No | 0.049 μM | 0.148 μM | 0.444 μM | 1.333 μM | 4.000 μM | IC$_{50}$ (μM) |
|---|---|---|---|---|---|---|
| 144367 | 5 | 33 | 65 | 78 | 81 | 0.32 |
| 494388 | 30 | 32 | 60 | 82 | 86 | 0.25 |
| 494389 | 30 | 45 | 69 | 84 | 84 | 0.17 |
| 494390 | 32 | 47 | 67 | 83 | 87 | 0.16 |
| 494392 | 23 | 38 | 54 | 79 | 82 | 0.31 |
| 494466 | 48 | 67 | 86 | 91 | 95 | 0.04 |
| 494470 | 74 | 87 | 92 | 96 | 98 | <0.05 |
| 494472 | 69 | 84 | 92 | 96 | 97 | <0.05 |
| 494544 | 5 | 18 | 49 | 74 | 79 | 0.48 |
| 498238 | 25 | 51 | 76 | 92 | 96 | 0.15 |
| 498239 | 25 | 62 | 83 | 93 | 97 | 0.12 |
| 498379 | 5 | 21 | 53 | 71 | 81 | 0.55 |

TABLE 26-continued

| ISIS No | 0.049 µM | 0.148 µM | 0.444 µM | 1.333 µM | 4.000 µM | IC$_{50}$ (µM) |
|---|---|---|---|---|---|---|
| 498408 | 1 | 38 | 63 | 79 | 80 | 0.32 |
| 498433 | 23 | 43 | 70 | 77 | 79 | 0.21 |

TABLE 27

| ISIS No | 0.049 µM | 0.148 µM | 0.444 µM | 1.333 µM | 4.000 µM | IC$_{50}$ (µM) |
|---|---|---|---|---|---|---|
| 144367 | 0 | 40 | 76 | 90 | 93 | 0.26 |
| 498434 | 32 | 44 | 64 | 78 | 84 | 0.20 |
| 498435 | 24 | 42 | 64 | 77 | 79 | 0.23 |
| 498517 | 28 | 23 | 53 | 81 | 85 | 0.45 |
| 498523 | 50 | 64 | 81 | 90 | 93 | <0.05 |
| 498524 | 53 | 70 | 84 | 93 | 96 | <0.05 |
| 498525 | 38 | 55 | 80 | 92 | 96 | 0.09 |
| 498550 | 12 | 18 | 62 | 81 | 83 | 0.33 |
| 498557 | 13 | 33 | 67 | 79 | 83 | 0.33 |
| 498579 | 6 | 42 | 69 | 80 | 85 | 0.31 |
| 498580 | 6 | 46 | 76 | 82 | 83 | 0.23 |
| 498581 | 5 | 40 | 78 | 81 | 84 | 0.25 |
| 498721 | 40 | 31 | 58 | 78 | 83 | 0.35 |
| 498833 | 21 | 20 | 58 | 80 | 90 | 0.44 |

Example 5: Antisense Inhibition of Human Apo(a) in Transgenic Mouse Primary Hepatocytes Additional antisense oligonucleotides were newly designed targeting an apo(a) nucleic acid and were tested for their effects on apo(a) mRNA in vitro. The antisense oligonucleotides were tested in a series of experiments that had similar culture conditions. Primary hepatocytes from human apo(a) transgenic mice were used in this study. Hepatocytes at a density of 35,000 cells per well were transfected using electroporation with 1,000 nM antisense oligonucleotide. After a treatment period of approximately 24 hours, RNA was isolated from the cells and apo(a) mRNA levels were measured by quantitative real-time PCR. Human primer probe set hAPO(a)12 kB was used to measure mRNA levels. Apo(a) mRNA levels were adjusted according to total RNA content, as measured by RIBOGREEN®. The results for each experiment are presented in separate tables shown below. ISIS 144367 was also included in the studies for comparison. Results are presented as percent inhibition of apo(a), relative to untreated control cells. A total of 231 antisense oligonucleotides were tested under these culture conditions. Only those antisense oligonucleotides that were selected for further studies are presented below.

The newly designed chimeric antisense oligonucleotides were designed as 3-10-4 MOE gapmers. The gapmers are 17 nucleosides in length, wherein the central gap segment comprises of ten 2'-deoxynucleosides and is flanked by wing segments on the 5' direction and the 3' direction comprising three nucleosides and four nucleosides respectively. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines.

The apo(a) target sequence contains multiple Kringle repeat sequences, therefore, an antisense oligonucleotide may target one or more regions of apo(a) depending whether on the oligonucleotide targets a Kringle sequence or not. "Start site" indicates the 5'-most nucleoside to which the gapmer is targeted in the human sequence. "Stop site" indicates the 3'-most nucleoside to which the gapmer is targeted human sequence. An apo(a) antisense oligonucleotide may have more than one "Start site" or "Stop site" depending on whether or not it targets a Kringle repeat.

Most gapmers listed in the Tables are targeted with 100% complementarity to multiple regions of either the human apo(a) mRNA, designated herein as SEQ ID NO: 1 (GENBANK Accession No. NM_005577.2) or the human apo(a) genomic sequence, designated herein as SEQ ID NO: 2 (GENBANK Accession No. NT_007422.12 truncated from nucleotides 3230000 to 3380000), or both. 'n/a' indicates that the antisense oligonucleotide does not target that particular sequence with 100% complementarity.

TABLE 28

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 64 | 21210 | 21229 | 11 |
| 510542 | 241 | 257 | CCTGTGACAGTGGTGGA | 79 | 21202 | 21218 | 111 |
|  | 583 | 599 | CCTGTGACAGTGGTGGA |  | 26693 | 26709 |  |
|  | 925 | 941 | CCTGTGACAGTGGTGGA |  | 32240 | 32256 |  |
|  | 1609 | 1625 | CCTGTGACAGTGGTGGA |  | 43333 | 43349 |  |
|  | 1951 | 1967 | CCTGTGACAGTGGTGGA |  | 48877 | 48893 |  |
|  | 2293 | 2309 | CCTGTGACAGTGGTGGA |  | 54423 | 54439 |  |
|  | 3319 | 3335 | CCTGTGACAGTGGTGGA |  | 72040 | 72056 |  |
|  | 4663 | 4679 | CCTGTGACAGTGGTGGA |  | 94404 | 94420 |  |
|  | 5005 | 5021 | CCTGTGACAGTGGTGGA |  | 115515 | 115531 |  |
| 510543 | 242 | 258 | TCCTGTGACAGTGGTGG | 75 | 21203 | 21219 | 112 |
|  | 584 | 600 | TCCTGTGACAGTGGTGG |  | 26694 | 26710 |  |
|  | 926 | 942 | TCCTGTGACAGTGGTGG |  | 32241 | 32257 |  |
|  | 1610 | 1626 | TCCTGTGACAGTGGTGG |  | 43334 | 43350 |  |
|  | 1952 | 1968 | TCCTGTGACAGTGGTGG |  | 48878 | 48894 |  |
|  | 2294 | 2310 | TCCTGTGACAGTGGTGG |  | 54424 | 54440 |  |
|  | 3320 | 3336 | TCCTGTGACAGTGGTGG |  | 72041 | 72057 |  |
|  | 4664 | 4680 | TCCTGTGACAGTGGTGG |  | 94405 | 94421 |  |
|  | 5006 | 5022 | TCCTGTGACAGTGGTGG |  | 115516 | 115532 |  |

TABLE 28-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 510544 | 243 | 259 | TTCCTGTGACAGTGGTG | 73 | 21204 | 21220 | 113 |
|  | 585 | 601 | TTCCTGTGACAGTGGTG |  | 26695 | 26711 |  |
|  | 927 | 943 | TTCCTGTGACAGTGGTG |  | 32242 | 32258 |  |
|  | 1611 | 1627 | TTCCTGTGACAGTGGTG |  | 43335 | 43351 |  |
|  | 1953 | 1969 | TTCCTGTGACAGTGGTG |  | 48879 | 48895 |  |
|  | 2295 | 2311 | TTCCTGTGACAGTGGTG |  | 54425 | 54441 |  |
|  | 3321 | 3337 | TTCCTGTGACAGTGGTG |  | 72042 | 72058 |  |
|  | 4665 | 4681 | TTCCTGTGACAGTGGTG |  | 94406 | 94422 |  |
|  | 5007 | 5023 | TTCCTGTGACAGTGGTG |  | 115517 | 115533 |  |
| 510545 | 244 | 260 | CTTCCTGTGACAGTGGT | 65 | 21205 | 21221 | 114 |
|  | 586 | 602 | CTTCCTGTGACAGTGGT |  | 26696 | 26712 |  |
|  | 928 | 944 | CTTCCTGTGACAGTGGT |  | 32243 | 32259 |  |
|  | 1612 | 1628 | CTTCCTGTGACAGTGGT |  | 43336 | 43352 |  |
|  | 1954 | 1970 | CTTCCTGTGACAGTGGT |  | 48880 | 48896 |  |
|  | 2296 | 2312 | CTTCCTGTGACAGTGGT |  | 54426 | 54442 |  |
|  | 3322 | 3338 | CTTCCTGTGACAGTGGT |  | 72043 | 72059 |  |
|  | 3664 | 3680 | CTTCCTGTGACAGTGGT |  | 77585 | 77601 |  |
|  | 4666 | 4682 | CTTCCTGTGACAGTGGT |  | 94407 | 94423 |  |
|  | 5008 | 5024 | CTTCCTGTGACAGTGGT |  | 115518 | 115534 |  |
| 510546 | 245 | 261 | CCTTCCTGTGACAGTGG | 74 | 21206 | 21222 | 115 |
|  | 3665 | 3681 | CCTTCCTGTGACAGTGG |  | 77586 | 77602 |  |
|  | 4667 | 4683 | CCTTCCTGTGACAGTGG |  | 94408 | 94424 |  |
|  | 5009 | 5025 | CCTTCCTGTGACAGTGG |  | 115519 | 115535 |  |
| 510547 | 246 | 262 | TCCTTCCTGTGACAGTG | 77 | 21207 | 21223 | 116 |
|  | 3666 | 3682 | TCCTTCCTGTGACAGTG |  | 77587 | 77603 |  |
|  | 4668 | 4684 | TCCTTCCTGTGACAGTG |  | 94409 | 94425 |  |
|  | 5010 | 5026 | TCCTTCCTGTGACAGTG |  | 115520 | 115536 |  |
| 510548 | 247 | 263 | GTCCTTCCTGTGACAGT | 73 | 21208 | 21224 | 117 |
|  | 3667 | 3683 | GTCCTTCCTGTGACAGT |  | 77588 | 77604 |  |
|  | 4669 | 4685 | GTCCTTCCTGTGACAGT |  | 94410 | 94426 |  |
|  | 5011 | 5027 | GTCCTTCCTGTGACAGT |  | 115521 | 115537 |  |
| 510549 | 248 | 264 | GGTCCTTCCTGTGACAG | 67 | 21209 | 21225 | 118 |
|  | 4670 | 4686 | GGTCCTTCCTGTGACAG |  | 94411 | 94427 |  |
| 510595 | 632 | 648 | CCGACTATGCGAGTGTG | 76 | 26742 | 26758 | 119 |
|  | 974 | 990 | CCGACTATGCGAGTGTG |  | 32289 | 32305 |  |
|  | 1316 | 1332 | CCGACTATGCGAGTGTG |  | 37836 | 37852 |  |
|  | 1658 | 1674 | CCGACTATGCGAGTGTG |  | 43382 | 43398 |  |
|  | 2000 | 2016 | CCGACTATGCGAGTGTG |  | 48926 | 48942 |  |
|  | 2342 | 2358 | CCGACTATGCGAGTGTG |  | 54472 | 54488 |  |
|  | 2684 | 2700 | CCGACTATGCGAGTGTG |  | 60027 | 60043 |  |
|  | 3026 | 3042 | CCGACTATGCGAGTGTG |  | 66543 | 66559 |  |
| 510597 | 634 | 650 | GTCCGACTATGCGAGTG | 70 | 26744 | 26760 | 120 |
|  | 976 | 992 | GTCCGACTATGCGAGTG |  | 32291 | 32307 |  |
|  | 1318 | 1334 | GTCCGACTATGCGAGTG |  | 37838 | 37854 |  |
|  | 1660 | 1676 | GTCCGACTATGCGAGTG |  | 43384 | 43400 |  |
|  | 2002 | 2018 | GTCCGACTATGCGAGTG |  | 48928 | 48944 |  |
|  | 2344 | 2360 | GTCCGACTATGCGAGTG |  | 54474 | 54490 |  |
|  | 2686 | 2702 | GTCCGACTATGCGAGTG |  | 60029 | 60045 |  |
|  | 3028 | 3044 | GTCCGACTATGCGAGTG |  | 66545 | 66561 |  |
| 510598 | 635 | 651 | GGTCCGACTATGCGAGT | 70 | 26745 | 26761 | 121 |
|  | 977 | 993 | GGTCCGACTATGCGAGT |  | 32292 | 32308 |  |
|  | 1319 | 1335 | GGTCCGACTATGCGAGT |  | 37839 | 37855 |  |
|  | 1661 | 1677 | GGTCCGACTATGCGAGT |  | 43385 | 43401 |  |
|  | 2003 | 2019 | GGTCCGACTATGCGAGT |  | 48929 | 48945 |  |
|  | 2345 | 2361 | GGTCCGACTATGCGAGT |  | 54475 | 54491 |  |
|  | 2687 | 2703 | GGTCCGACTATGCGAGT |  | 60030 | 60046 |  |
|  | 3029 | 3045 | GGTCCGACTATGCGAGT |  | 66546 | 66562 |  |

TABLE 29

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 83 | 21210 | 21229 | 11 |
| 510783 | 6400 | 6416 | GTCAGACCTTAAAAGCT | 75 | 140056 | 140072 | 122 |
| 512944 | 3561 | 3577 | AAGCCTCTGTGCTTGGA | 81 | 76246 | 76262 | 123 |
| 512947 | 3560 | 3576 | AGCCTCTGTGCTTGGAT | 85 | 76245 | 76261 | 124 |
| 512958 | 3559 | 3575 | GCCTCTGTGCTTGGATC | 82 | 76244 | 76260 | 125 |
| 512959 | 3585 | 3601 | GCTCCGTTGGTGCTTCT | 77 | n/a | n/a | 126 |

TABLE 30

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 76 | 21210 | 21229 | 11 |
| 510701 | 4217 | 4233 | CTCTGTGCTTGGAACTG | 78 | 85147 | 85163 | 127 |
| 510702 | 219 | 235 | TGCCTCGATAACTCTGT | 79 | 21180 | 21196 | 128 |
|  | 561 | 577 |  |  | 26671 | 26687 |  |
|  | 903 | 919 |  |  | 32218 | 32234 |  |
|  | 1245 | 1261 |  |  | 37765 | 37781 |  |
|  | 1587 | 1603 |  |  | 43311 | 43327 |  |
|  | 1929 | 1945 |  |  | 48855 | 48871 |  |
|  | 2271 | 2287 |  |  | 54401 | 54417 |  |
|  | 2613 | 2629 |  |  | 59956 | 59972 |  |
|  | 4299 | 4315 |  |  | 86472 | 86488 |  |
| 510704 | 563 | 579 | TGTGCCTCGATAACTCT | 80 | 26673 | 26689 | 129 |
|  | 905 | 921 |  |  | 32220 | 32236 |  |
|  | 1247 | 1263 |  |  | 37767 | 37783 |  |
|  | 1589 | 1605 |  |  | 43313 | 43329 |  |
|  | 1931 | 1947 |  |  | 48857 | 48873 |  |
|  | 2273 | 2289 |  |  | 54403 | 54419 |  |
|  | 2615 | 2631 |  |  | 59958 | 59974 |  |
|  | 4301 | 4317 |  |  | 86474 | 86490 |  |
|  | 4985 | 5001 |  |  | 115495 | 115511 |  |
| 510757 | 4929 | 4945 | GCTCAGTTGGTGCTGCT | 74 | n/a | n/a | 130 |

Example 6: Dose-Dependent Antisense Inhibition of Apo(a) in Transgenic Mouse Primary Hepatocytes Potent gapmers from the studies described above were further selected and tested at various doses in transgenic mouse primary hepatocytes in a series of studies with similar culture conditions. Cells were plated at a density of 35,000 per well and transfected using electroporation with 0.156 µM, 0.313 µM, 0.625 µM, 1.250 µM, 2.500 µM, or 5.000 µM concentrations of antisense oligonucleotide, as specified in the Tables below. After a treatment period of approximately 16 hours, RNA was isolated from the cells and apo(a) mRNA levels were measured by quantitative real-time PCR. Apo(a) primer probe set hAPO(a)12 kB was used to measured mRNA levels. Apo(a) mRNA levels were adjusted according to total RNA content, as measured by RIBOGREEN®. Results are presented as percent inhibition of apo(a), relative to untreated control cells.

The results of each of the studies are depicted in the Tables presented below with each study represented in a separate table. The half maximal inhibitory concentration ($IC_{50}$) of each oligonucleotide is also presented in the Tables.

TABLE 31

| ISIS No | 0.156 µM | 0.312 µM | 0.625 µM | 1.250 µM | 2.500 µM | 5.000 µM | $IC_{50}$ (µM) |
|---|---|---|---|---|---|---|---|
| 144367 | 28 | 55 | 70 | 83 | 90 | 92 | 0.31 |
| 510542 | 33 | 58 | 75 | 87 | 89 | 90 | 0.27 |
| 510543 | 33 | 45 | 68 | 78 | 89 | 89 | 0.34 |
| 510544 | 33 | 50 | 65 | 78 | 88 | 90 | 0.33 |
| 510545 | 33 | 58 | 76 | 87 | 91 | 90 | 0.26 |
| 510546 | 39 | 62 | 76 | 87 | 89 | 91 | 0.22 |
| 510547 | 36 | 66 | 82 | 84 | 86 | 91 | 0.22 |
| 510548 | 50 | 70 | 82 | 91 | 88 | 90 | 0.13 |
| 510549 | 32 | 59 | 73 | 85 | 86 | 90 | 0.27 |
| 510595 | 26 | 57 | 78 | 88 | 90 | 90 | 0.29 |
| 510597 | 30 | 53 | 76 | 85 | 89 | 89 | 0.30 |

TABLE 32

| ISIS No | 0.156 µM | 0.312 µM | 0.625 µM | 1.250 µM | 2.500 µM | 5.000 µM | $IC_{50}$ (µM) |
|---|---|---|---|---|---|---|---|
| 144367 | 36 | 52 | 78 | 87 | 93 | 94 | 0.26 |
| 510598 | 48 | 58 | 81 | 88 | 93 | 92 | 0.18 |
| 510701 | 45 | 59 | 78 | 87 | 95 | 95 | 0.18 |

TABLE 32-continued

| ISIS No | 0.156 μM | 0.312 μM | 0.625 μM | 1.250 μM | 2.500 μM | 5.000 μM | IC$_{50}$ (μM) |
|---|---|---|---|---|---|---|---|
| 510702 | 49 | 63 | 75 | 90 | 94 | 95 | 0.15 |
| 510704 | 55 | 67 | 80 | 93 | 94 | 95 | <0.16 |
| 510757 | 34 | 48 | 68 | 79 | 90 | 93 | 0.33 |
| 510783 | 21 | 32 | 51 | 58 | 78 | 84 | 0.69 |
| 512944 | 57 | 72 | 81 | 91 | 96 | 97 | <0.16 |
| 512947 | 64 | 74 | 86 | 92 | 96 | 97 | <0.16 |
| 512958 | 48 | 69 | 83 | 91 | 96 | 97 | 0.13 |
| 512959 | 39 | 59 | 76 | 84 | 93 | 93 | 0.22 |

TABLE 33

| ISIS No | 0.156 μM | 0.312 μM | 0.625 μM | 1.250 μM | 2.500 μM | 5.000 μM | IC$_{50}$ (μM) |
|---|---|---|---|---|---|---|---|
| 144367 | 41 | 58 | 75 | 81 | 88 | 87 | 0.22 |
| 510542 | 38 | 54 | 69 | 74 | 85 | 83 | 0.27 |
| 510545 | 21 | 43 | 73 | 77 | 80 | 78 | 0.39 |
| 510546 | 37 | 58 | 73 | 81 | 83 | 81 | 0.24 |
| 510547 | 38 | 58 | 72 | 79 | 84 | 86 | 0.24 |
| 510548 | 40 | 63 | 77 | 79 | 81 | 84 | 0.21 |
| 510549 | 37 | 47 | 67 | 77 | 81 | 83 | 0.31 |
| 510595 | 34 | 66 | 73 | 81 | 80 | 75 | 0.23 |
| 510597 | 39 | 59 | 74 | 83 | 76 | 77 | 0.23 |

TABLE 34

| ISIS No | 0.156 μM | 0.312 μM | 0.625 μM | 1.250 μM | 2.500 μM | 5.000 μM | IC$_{50}$ (μM) |
|---|---|---|---|---|---|---|---|
| 144367 | 33 | 60 | 72 | 83 | 81 | 81 | 0.26 |
| 510598 | 47 | 62 | 75 | 75 | 76 | 76 | 0.18 |
| 510701 | 41 | 67 | 80 | 87 | 92 | 91 | 0.19 |
| 510702 | 51 | 64 | 77 | 80 | 80 | 83 | 0.13 |
| 510704 | 54 | 61 | 77 | 84 | 89 | 80 | 0.12 |
| 512944 | 71 | 74 | 81 | 88 | 92 | 94 | 0.02 |
| 512947 | 65 | 77 | 86 | 90 | 93 | 95 | 0.03 |
| 512958 | 63 | 73 | 84 | 92 | 93 | 96 | 0.06 |
| 512959 | 39 | 62 | 80 | 82 | 86 | 82 | 0.22 |

Apo(a) mRNA levels were significantly reduced in a dose-dependent manner in antisense oligonucleotide-treated cells. The potency of the newly designed oligonucleotides was compared with the benchmark oligonucleotide, ISIS 144367. As presented in the Tables above, ISIS 510542 (SEQ ID NO: 111), ISIS 510545 (SEQ ID NO: 114), ISIS 510546 (SEQ ID NO: 115), ISIS 510547 (SEQ ID NO: 116), ISIS 510548 (SEQ ID NO: 117), ISIS 510549 (SEQ ID NO: 118), ISIS 510595 (SEQ ID NO: 119), ISIS 510597 (SEQ ID NO: 120), ISIS 510598 (SEQ ID NO: 121), ISIS 510701 (SEQ ID NO: 127), ISIS 510702 (SEQ ID NO: 128), ISIS 510704 (SEQ ID NO: 129), ISIS 512944 (SEQ ID NO: 123), ISIS 512947 (SEQ ID NO: 124), ISIS 512958 (SEQ ID NO: 125), and ISIS 512959 (SEQ ID NO: 126) were more potent than ISIS 144367 (SEQ ID NO: 11).

Example 7: Effect of In Vivo Antisense Inhibition of Human Apo(a) in Human Apo(a) Transgenic Mice Transgenic mice with the human apo(a) gene (Frazer, K. A. et al., Nat. Genet. 1995. 9: 424-431) were utilized in the studies described below. ISIS antisense oligonucleotides that demonstrated statistically significant inhibition of apo(a) mRNA in vitro as described above were evaluated further in this model.

Study 1

Female human apo(a) transgenic mice were maintained on a 12-hour light/dark cycle and fed ad libitum normal lab chow. The mice were divided into treatment groups consisting of 4 mice each. The groups received intraperitoneal injections of ISIS 494159, ISIS 494160, ISIS 494161, ISIS 494162, ISIS 494163, ISIS 494230, ISIS 494243, ISIS 494244, ISIS 494283, ISIS 494284, ISIS 494285, ISIS 494286, ISIS 494301, ISIS 494302, ISIS 494304, ISIS 494466, ISIS 494470, ISIS 494472, ISIS 498239, ISIS 498408, ISIS 498517, ISIS 494158, ISIS 494311, ISIS 494337, ISIS 494372, ISIS 498238, ISIS 498523, ISIS 498525, ISIS 510548, ISIS 512944, ISIS 512947, or ISIS 512958 at a dose of 25 mg/kg twice a week for 2 weeks. One group of mice received intraperitoneal injections of PBS twice a week for 2 weeks. The PBS group served as the control group. Two days following the final dose, the mice were euthanized, organs harvested and analyses done.

Inhibition of Human Apo(a) mRNA

Total RNA was extracted from the livers of some of the treatment groups, and human apo(a) mRNA was quantitated by RT-PCR. The results are presented in Table 35, expressed as percent inhibition of apo(a) mRNA compared to the PBS control.

TABLE 35

Percent inhibition of human apo(a) mRNA in transgenic mice

| ISIS No | % inhibition |
|---|---|
| 144367 | 98 |
| 494159 | 100 |
| 494160 | 95 |
| 494161 | 98 |
| 494162 | 100 |
| 494163 | 100 |
| 494230 | 96 |
| 494243 | 99 |
| 494244 | 99 |
| 494283 | 100 |
| 494284 | 100 |
| 494285 | 100 |
| 494286 | 98 |
| 494301 | 99 |
| 494302 | 96 |
| 494304 | 94 |
| 494466 | 97 |
| 494470 | 93 |
| 494472 | 98 |
| 498239 | 72 |
| 498408 | 100 |
| 498517 | 98 |

The data demonstrates significant inhibition of apo(a) mRNA by several ISIS oligonucleotides. ISIS 494159 (SEQ ID NO: 14), ISIS 494162 (SEQ ID NO: 17), ISIS 494163 (SEQ ID NO: 18), ISIS 494243 (SEQ ID NO: 106), ISIS 494244 (SEQ ID NO: 107), ISIS 494283 (SEQ ID NO: 26), ISIS 494284 (SEQ ID NO: 27), ISIS 494285 (SEQ ID NO: 28), ISIS 494301 (SEQ ID NO: 39), and ISIS 498408 (SEQ ID NO: 71) were more potent than the benchmark ISIS 144367 (SEQ ID NO: 11).

Inhibition of Human Apo(a) Protein

Plasma human apo(a) protein was measured from all treatment groups using an Apo(a) ELISA kit (Mercodia 10-1106-01, Uppsala, Sweden). The results are presented in Table 36, expressed as percent inhibition of apo(a) mRNA compared to the PBS control.

TABLE 36

Percent inhibition of human apo(a) protein in transgenic mice

| ISIS No | % inhibition |
|---|---|
| 144367 | 86 |
| 494159 | 86 |
| 494160 | 0 |
| 494161 | 82 |
| 494162 | 84 |
| 494163 | 82 |
| 494230 | 60 |
| 494243 | 84 |
| 494244 | 87 |
| 494283 | 98 |
| 494284 | 98 |
| 494285 | 89 |
| 494286 | 89 |
| 494301 | 93 |
| 494302 | 88 |
| 494304 | 83 |
| 494466 | 76 |
| 494470 | 73 |
| 494472 | 72 |
| 498239 | 54 |
| 498408 | 84 |
| 498517 | 56 |
| 494158 | 71 |
| 494311 | 83 |
| 494337 | 80 |
| 494372 | 78 |
| 498238 | 58 |
| 498523 | 47 |
| 498525 | 58 |
| 510548 | 74 |
| 512944 | 18 |
| 512947 | 65 |
| 512958 | 72 |

The data demonstrates significant inhibition of apo(a) mRNA by several ISIS oligonucleotides. ISIS 494159 (SEQ ID NO: 14), ISIS 494244 (SEQ ID NO: 82), ISIS 494283 (SEQ ID NO: 26), ISIS 494284 (SEQ ID NO: 27), ISIS 494285 (SEQ ID NO: 28), ISIS 494286 (SEQ ID NO: 29), ISIS 494301 (SEQ ID NO: 39), and ISIS 494302 (SEQ ID NO: 40) were as potent as or more potent than the benchmark ISIS 144367 (SEQ ID NO: 11).

Study 2

ISIS 494159, ISIS 494161, ISIS 494162, ISIS 494163, and ISIS 494243 were further evaluated in this transgenic model. ISIS 144367 was included for comparison.

Treatment

Female human apo(a) transgenic mice were divided into treatment groups consisting of 4 mice each. The groups received intraperitoneal injections of ISIS 144367, ISIS 494159, ISIS 494161, ISIS 494162, ISIS 494163, or ISIS 494243 at doses of 1.5 mg/kg, 5 mg/kg, 15 mg/kg, or 50 mg/kg twice a week for 2 weeks. One group of mice received intraperitoneal injections of PBS twice a week for 2 weeks. The PBS group served as the control group. Two days following the final dose, the mice were euthanized, organs harvested and analyses done.

Inhibition of Human Apo(a) mRNA

Total RNA was extracted from the livers of the treatment groups, and human apo(a) mRNA was quantitated by RT-PCR. The results are presented in Table 37, expressed as percent inhibition of apo(a) mRNA compared to the PBS control.

TABLE 37

Dose-dependent inhibition of human apo(a) mRNA in transgenic mice

| ISIS No | Dose (mg/kg/wk) | % inhibition | $ED_{50}$ |
|---|---|---|---|
| 144367 | 100 | 71 | 31 |
|  | 30 | 42 |  |
|  | 10 | 0 |  |
|  | 3 | 5 |  |
| 494159 | 100 | 91 | 5 |
|  | 30 | 67 |  |
|  | 10 | 48 |  |
|  | 3 | 39 |  |
| 494161 | 100 | 82 | 6 |
|  | 30 | 49 |  |
|  | 10 | 61 |  |
|  | 3 | 30 |  |
| 494162 | 100 | 90 | 5 |
|  | 30 | 67 |  |
|  | 10 | 58 |  |
|  | 3 | 25 |  |
| 494163 | 100 | 83 | 5 |
|  | 30 | 66 |  |
|  | 10 | 58 |  |
|  | 3 | 21 |  |
| 494243 | 100 | 80 | 32 |
|  | 30 | 26 |  |
|  | 10 | 0 |  |
|  | 3 | 6 |  |

The data demonstrates significant inhibition of apo(a) mRNA by several ISIS oligonucleotides. ISIS 494159 (SEQ ID NO: 14), ISIS 494161 (SEQ ID NO: 16), 494162 (SEQ ID NO:17), and ISIS 94163 (SEQ ID NO: 18) were more efficacious than the benchmark ISIS 144367 (SEQ ID NO: 11).

Reduction of Human Apo(a) Protein Levels

Blood was collected from the treatment groups, and human apo(a) protein levels were quantitated by an Apo(a) ELISA kit (Mercodia 10-1106-01, Uppsala, Sweden). The results are presented in Table 38, expressed as percent reduction of apo(a) protein levels compared to the PBS control.

TABLE 38

Dose-dependent inhibition of human apo(a) protein in transgenic mice

| ISIS No | Dose (mg/kg/wk) | % inhibition | $ED_{50}$ |
|---|---|---|---|
| 144367 | 100 | 73 | 71 |
|  | 30 | 0 |  |
|  | 10 | 6 |  |
|  | 3 | 69 |  |
| 494159 | 100 | 88 | 2 |
|  | 30 | 88 |  |
|  | 10 | 85 |  |
|  | 3 | 36 |  |
| 494161 | 100 | 90 | 2 |
|  | 30 | 85 |  |
|  | 10 | 73 |  |
|  | 3 | 44 |  |
| 494162 | 100 | 89 | 3 |
|  | 30 | 78 |  |
|  | 10 | 76 |  |
|  | 3 | 24 |  |
| 494163 | 100 | 90 | 3 |
|  | 30 | 86 |  |
|  | 10 | 60 |  |
|  | 3 | 37 |  |

TABLE 38-continued

Dose-dependent inhibition of human apo(a) protein in transgenic mice

| ISIS No | Dose (mg/kg/wk) | % inhibition | ED$_{50}$ |
|---|---|---|---|
| 494243 | 100 | 61 | 174 |
|  | 30 | 0 |  |
|  | 10 | 0 |  |
|  | 3 | 0 |  |

The data demonstrates significant reduction of apo(a) plasma protein levels by several ISIS oligonucleotides. ISIS 494159 (SEQ ID NO: 14), ISIS 494161 (SEQ ID NO: 16), ISIS 494162 (SEQ ID NO: 17), and ISIS 494163 (SEQ ID NO: 18) were more efficacious than the benchmark ISIS 144367 (SEQ ID NO: 11).

Study 3

ISIS 494244, ISIS 494283, and ISIS 494284 were further evaluated in this model. ISIS 144367 was included for comparison.

Treatment

Female human apo(a) transgenic mice were divided into treatment groups consisting of 4 mice each. The groups received intraperitoneal injections of ISIS 144367, ISIS 494244, ISIS 494283, or ISIS 494284 at doses of 0.75 mg/kg, 2.5 mg/kg, 7.5 mg/kg, or 25 mg/kg twice a week for 2 weeks. One group of mice received intraperitoneal injections of PBS twice a week for 2 weeks. The PBS group served as the control group. Two days following the final dose, the mice were euthanized, organs harvested and analyses done.

Inhibition of Human Apo(a) mRNA

Total RNA was extracted from the livers of the treatment groups, and human apo(a) mRNA was quantitated by RT-PCR. The results are presented in Table 39, expressed as percent inhibition of apo(a) mRNA compared to the PBS control.

TABLE 39

Dose-dependent inhibition of human apo(a) mRNA in transgenic mice

| ISIS No | Dose (mg/kg/wk) | % inhibition | ED$_{50}$ |
|---|---|---|---|
| 144367 | 50 | 75 | 22 |
|  | 15 | 60 |  |
|  | 5 | 0 |  |
|  | 1.5 | 0 |  |
| 494244 | 50 | 73 | 18 |
|  | 15 | 41 |  |
|  | 5 | 34 |  |
|  | 1.5 | 0 |  |
| 494283 | 50 | 74 | 16 |
|  | 15 | 52 |  |
|  | 5 | 24 |  |
|  | 1.5 | 0 |  |
| 494284 | 50 | 73 | 16 |
|  | 15 | 58 |  |
|  | 5 | 17 |  |
|  | 1.5 | 2 |  |

The data demonstrates significant inhibition of apo(a) mRNA by several ISIS oligonucleotides. ISIS 494244 (SEQ ID NO: 107), ISIS 494283 (SEQ ID NO: 26), and ISIS 494284 (SEQ ID NO: 27) were more efficacious than the benchmark, ISIS 144367 (SEQ ID NO: 11).

Reduction of Human Apo(a) Protein Levels

Blood was collected from the treatment groups, and human apo(a) protein levels were quantitated by an Apo(a) ELISA kit (Mercodia 10-1106-01, Uppsala, Sweden). The results are presented in Table 40, expressed as percent reduction of apo(a) protein levels compared to the PBS control.

TABLE 40

Dose-dependent inhibition of human apo(a) plasma protein in transgenic mice

| ISIS No | Dose (mg/kg/wk) | % inhibition | ED$_{50}$ |
|---|---|---|---|
| 144367 | 50 | 64 | 16 |
|  | 15 | 14 |  |
|  | 5 | 0 |  |
|  | 1.5 | 0 |  |
| 494244 | 50 | 67 | 2 |
|  | 15 | 60 |  |
|  | 5 | 58 |  |
|  | 1.5 | 0 |  |
| 494283 | 50 | 64 | 4 |
|  | 15 | 65 |  |
|  | 5 | 64 |  |
|  | 1.5 | 69 |  |
| 494284 | 50 | 66 | 4 |
|  | 15 | 63 |  |
|  | 5 | 51 |  |
|  | 1.5 | 54 |  |

The data demonstrates significant reduction of apo(a) plasma protein levels by several ISIS oligonucleotides. ISIS 494244 (SEQ ID NO: 107), ISIS 494283 (SEQ ID NO: 26), and ISIS 494284 (SEQ ID NO: 27) were more efficacious than the benchmark, ISIS 144367 (SEQ ID NO: 11).

Study 4

ISIS 494285, ISIS 494286, ISIS 494301, ISIS 494302, and ISIS 494311 were further evaluated in this model.

Treatment

Male human apo(a) transgenic mice were divided into treatment groups consisting of 4 mice each. Each such group received intraperitoneal injections of ISIS 494285, ISIS 494286, ISIS 494301, ISIS 494302, or ISIS 494311 at doses of 5 mg/kg, 15 mg/kg, or 50 mg/kg once a week for 2 weeks. One group of 3 mice received intraperitoneal injections of PBS once a week for 2 weeks. The PBS group served as the control group. Two days following the final dose, the mice were euthanized, organs harvested and analyses done.

Inhibition of Human Apo(a) mRNA

Total RNA was extracted from the livers of the treatment groups, and human apo(a) mRNA was quantitated by RT-PCR. The results are presented in Table 41, expressed as percent inhibition of apo(a) mRNA compared to the PBS control. The data demonstrates significant inhibition of apo(a) mRNA by ISIS 494285 (SEQ ID NO: 28), ISIS 494286 (SEQ ID NO: 29), ISIS 494301 (SEQ ID NO: 39), ISIS 494302 (SEQ ID NO: 40) and ISIS 494311 (SEQ ID NO: 47).

TABLE 41

Dose-dependent inhibition of human Apo(a) mRNA in transgenic mice

| ISIS No | Dose (mg/kg/wk) | % inhibition | ED$_{50}$ |
|---|---|---|---|
| 494285 | 50 | 98 | 1 |
|  | 15 | 97 |  |
|  | 5 | 79 |  |
| 494286 | 50 | 97 | 1 |
|  | 15 | 91 |  |
|  | 5 | 80 |  |

TABLE 41-continued

Dose-dependent inhibition of human Apo(a) mRNA in transgenic mice

| ISIS No | Dose (mg/kg/wk) | % inhibition | $ED_{50}$ |
|---|---|---|---|
| 494301 | 50 | 98 | 3 |
|  | 15 | 96 |  |
|  | 5 | 59 |  |
| 494302 | 50 | 98 | 2 |
|  | 15 | 88 |  |
|  | 5 | 72 |  |
| 494311 | 50 | 99 | 1 |
|  | 15 | 96 |  |
|  | 5 | 87 |  |

Reduction of Human Apo(a) Protein Levels

Blood was collected from the treatment groups, and human apo(a) protein levels were quantitated by an Apo(a) ELISA kit (Mercodia 10-1106-01, Uppsala, Sweden). The results are presented in Table 42, expressed as percent reduction of apo(a) protein levels compared to the PBS control. The data demonstrates significant reduction of apo (a) plasma protein levels by ISIS 494285, ISIS 494286, ISIS 494301, ISIS 494302 and ISIS 494311.

TABLE 42

Dose-dependent inhibition of human apo(a) protein in transgenic mice

| ISIS No | Dose (mg/kg/wk) | % inhibition | $ED_{50}$ |
|---|---|---|---|
| 494285 | 50 | 88 | 2 |
|  | 15 | 88 |  |
|  | 5 | 72 |  |
| 494286 | 50 | 90 | 2 |
|  | 15 | 85 |  |
|  | 5 | 75 |  |
| 494301 | 50 | 89 | 5 |
|  | 15 | 86 |  |
|  | 5 | 38 |  |
| 494302 | 50 | 90 | 3 |
|  | 15 | 82 |  |
|  | 5 | 61 |  |
| 494311 | 50 | 90 | 3 |
|  | 15 | 82 |  |
|  | 5 | 69 |  |

Study 5

ISIS 494372, ISIS 498524, ISIS 498581, ISIS 498721, and ISIS 498833 were further evaluated in this model.

Treatment

Female human apo(a) transgenic mice were divided into treatment groups consisting of 4 mice each. The groups received intraperitoneal injections of ISIS 494372, ISIS 498524, ISIS 498581, ISIS 498721, or ISIS 498833 at doses of 5 mg/kg, 15 mg/kg, or 50 mg/kg once a week for 2 weeks. One group of 3 mice received intraperitoneal injections of PBS once a week for 2 weeks. The PBS group served as the control group. Two days following the final dose, the mice were euthanized, organs harvested and analyses done.

Inhibition of Human Apo(a) mRNA

Total RNA was extracted from the livers of the treatment groups, and human apo(a) mRNA was quantitated by RT-PCR. The results are presented in Table 43, expressed as percent inhibition of apo(a) mRNA compared to the PBS control. The data demonstrates significant inhibition of apo(a) mRNA by ISIS 494372 (SEQ ID NO: 28), ISIS 498524 (SEQ ID NO: 93), ISIS 498581 (SEQ ID NO: 104), and ISIS 498721 (ATGCCTCGATAACTCCGTCC; SEQ ID NO: 134).

TABLE 43

Dose-dependent inhibition of human Apo(a) mRNA in transgenic mice

| ISIS No | Dose (mg/kg/wk) | % inhibition | $ED_{50}$ |
|---|---|---|---|
| 494372 | 50 | 88 | 18 |
|  | 15 | 49 |  |
|  | 5 | 0 |  |
| 498524 | 50 | 83 | 8 |
|  | 15 | 74 |  |
|  | 5 | 34 |  |
| 498581 | 50 | 98 | 7 |
|  | 15 | 58 |  |
|  | 5 | 48 |  |
| 498721 | 50 | 97 | 14 |
|  | 15 | 68 |  |
|  | 5 | 0 |  |
| 498833 | 50 | 61 | 155 |
|  | 15 | 0 |  |
|  | 5 | 17 |  |

Reduction of Human Apo(a) Protein Levels

Blood was collected from the treatment groups, and human apo(a) protein levels were quantitated by an Apo(a) ELISA kit (Mercodia 10-1106-01, Uppsala, Sweden). The results are presented in Table 44, expressed as percent reduction of apo(a) protein levels compared to the PBS control. The data demonstrates significant reduction of apo (a) plasma protein levels by ISIS 494372 (SEQ ID NO: 28), ISIS 498581 (SEQ ID NO: 104), and ISIS 498721 (ATGCCTCGATAACTCCGTCC; SEQ ID NO: 134).

TABLE 44

Dose-dependent inhibition of human apo(a) protein in transgenic mice

| ISIS No | Dose (mg/kg/wk) | % inhibition | $ED_{50}$ |
|---|---|---|---|
| 494372 | 50 | 68 | 32 |
|  | 15 | 25 |  |
|  | 5 | 12 |  |
| 498524 | 50 | 38 | 118 |
|  | 15 | 0 |  |
|  | 5 | 0 |  |
| 498581 | 50 | 79 | 9 |
|  | 15 | 52 |  |
|  | 5 | 49 |  |
| 498721 | 50 | 81 | 10 |
|  | 15 | 63 |  |
|  | 5 | 29 |  |
| 498833 | 50 | 15 | 738 |
|  | 15 | 0 |  |
|  | 5 | 67 |  |

Example 8: Tolerability of Antisense Oligonucleotides Targeting Human Apo(a) in Rodent Models Gapmer antisense oligonucleotides targeting human apo (a) were selected from the studies described above for tolerability studies in CD1 mice and in Sprague Dawley rats. Rodents do not express endogenous apo(a), hence these studies tested the tolerability of each human antisense oligonucleotide in an animal rather than any phenotypic changes that may be caused by inhibiting apo(a) in the animal.

Tolerability in CD1 Mice: Study 1

CD1® mice (Charles River, Mass.) are a multipurpose mice model, frequently utilized for safety and efficacy testing. The mice were treated with ISIS antisense oligonucleotides selected from studies described above and evaluated for changes in the levels of various plasma chemistry markers.

Treatment

Groups of male CD1 mice were injected subcutaneously twice a week for 6 weeks with 50 mg/kg of ISIS 494159, ISIS 494161, ISIS 494162, ISIS 494244, ISIS 494283, ISIS 494284, ISIS 494285, ISIS 494286, ISIS 494301, ISIS 494302, ISIS 494311, ISIS 494337, ISIS 494372, and ISIS 510548. One group of six-week old male CD1 mice was injected subcutaneously twice a week for 6 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, bilirubin, albumin, creatinine, and BUN were measured using an automated clinical chemistry analyzer (Hitachi Olympus AU400e, Melville, N.Y.). The results are presented in Table 45. ISIS oligonucleotides that caused changes in the levels of any of the liver or kidney function markers outside the expected range for antisense oligonucleotides were excluded in further studies.

TABLE 45

Plasma chemistry markers of CD1 mice

|  | ALT (IU/L) | AST (IU/L) | Albumin (g/dL) | BUN (mg/dL) | Creatinine (mg/dL) | Bilirubin (mg/dL) |
|---|---|---|---|---|---|---|
| PBS | 38 | 71 | 2.9 | 25.2 | 0.16 | 0.15 |
| ISIS 494159 | 615 | 525 | 2.7 | 23.9 | 0.11 | 0.20 |
| ISIS 494161 | 961 | 670 | 2.6 | 23.7 | 0.15 | 0.14 |
| ISIS 494162 | 1373 | 1213 | 2.7 | 23.7 | 0.14 | 0.18 |
| ISIS 494283 | 237 | 242 | 2.5 | 26.2 | 0.14 | 0.13 |
| ISIS 494284 | 192 | 307 | 2.3 | 27.1 | 0.14 | 0.10 |
| ISIS 494285 | 582 | 436 | 2.3 | 25.4 | 0.16 | 0.11 |
| ISIS 494286 | 191 | 227 | 2.5 | 21.1 | 0.12 | 0.15 |
| ISIS 494301 | 119 | 130 | 2.7 | 26.4 | 0.15 | 0.12 |
| ISIS 494302 | 74 | 96 | 2.8 | 24.8 | 0.14 | 0.15 |
| ISIS 494311 | 817 | 799 | 2.7 | 28.7 | 0.12 | 0.17 |
| ISIS 494337 | 722 | 397 | 2.5 | 20.0 | 0.13 | 0.11 |
| ISIS 494372 | 73 | 164 | 2.6 | 28.5 | 0.16 | 0.11 |
| ISIS 510548 | 2819 | 2245 | 3.1 | 26.0 | 0.15 | 0.15 |

Organ Weights

Liver, spleen and kidney weights were measured at the end of the study, and are presented in Table 46. ISIS oligonucleotides that caused any changes in organ weights outside the expected range for antisense oligonucleotides were excluded from further studies.

TABLE 46

Organ weights of CD1 mice (g)

|  | Kidney | Liver | Spleen |
|---|---|---|---|
| PBS | 0.68 | 2.0 | 0.13 |
| ISIS 494159 | 0.68 | 3.0 | 0.21 |
| ISIS 494161 | 0.62 | 3.5 | 0.20 |
| ISIS 494162 | 0.60 | 3.3 | 0.20 |
| ISIS 494283 | 0.65 | 2.8 | 0.24 |
| ISIS 494284 | 0.69 | 2.7 | 0.29 |
| ISIS 494285 | 0.59 | 3.2 | 0.21 |
| ISIS 494286 | 0.64 | 2.8 | 0.25 |
| ISIS 494301 | 0.72 | 3.0 | 0.43 |
| ISIS 494302 | 0.63 | 2.3 | 0.23 |
| ISIS 494311 | 0.61 | 3.2 | 0.19 |
| ISIS 494337 | 0.56 | 2.3 | 0.17 |
| ISIS 494372 | 0.60 | 2.5 | 0.27 |
| ISIS 510548 | 0.55 | 3.7 | 0.20 |

TABLE 46-continued

Organ weights of CD1 mice (g)

Tolerability in Sprague Dawley Rats

Sprague-Dawley rats are a multipurpose model used for safety and efficacy evaluations. The rats were treated with ISIS antisense oligonucleotides selected from studies described above and evaluated for changes in the levels of various plasma chemistry markers.

Treatment

Groups of male Sprague Dawley rats were injected subcutaneously twice a week for 8 weeks with 30 mg/kg of ISIS 494159, ISIS 494161, ISIS 494162, ISIS 494244, ISIS 494283, ISIS 494284, ISIS 494285, ISIS 494286, ISIS 494301, ISIS 494302, ISIS 494311, ISIS 494337, ISIS 494372, and ISIS 510548. One group of six male Sprague Dawley rats was injected subcutaneously twice a week for 8 weeks with PBS. Rats were euthanized 48 hours after the last dose, and organs and plasma were harvested for further analysis.

Plasma Chemistry Markers

To evaluate the effect of ISIS oligonucleotides on liver and kidney function, plasma levels of transaminases, bilirubin, albumin, creatinine, and BUN were measured using an automated clinical chemistry analyzer (Hitachi Olympus AU400e, Melville, N.Y.). The results are presented in Table 47. ISIS oligonucleotides that caused changes in the levels of any of the liver or kidney function markers outside the expected range for antisense oligonucleotides were excluded in further studies.

TABLE 47

Plasma chemistry markers of Sprague Dawley rats

|  | ALT (IU/L) | AST (IU/L) | Bilirubin (mg/dL) | Albumin (g/dL) | BUN (mg/dL) | Creatinine (mg/dL) |
|---|---|---|---|---|---|---|
| PBS | 30 | 82 | 0.09 | 3.2 | 19 | 0.28 |
| ISIS 494159 | 182 | 208 | 0.14 | 3.4 | 22 | 0.35 |
| ISIS 494161 | 36 | 86 | 0.13 | 3.4 | 23 | 0.35 |
| ISIS 494162 | 102 | 158 | 0.17 | 2.6 | 28 | 0.32 |
| ISIS 494283 | 53 | 156 | 0.13 | 2.9 | 24 | 0.32 |
| ISIS 494284 | 34 | 113 | 0.08 | 2.0 | 28 | 0.32 |
| ISIS 494285 | 110 | 294 | 0.10 | 1.4 | 110 | 0.52 |
| ISIS 494286 | 40 | 83 | 0.07 | 1.6 | 48 | 0.44 |
| ISIS 494301 | 38 | 132 | 0.08 | 3.0 | 18 | 0.33 |
| ISIS 494302 | 47 | 105 | 0.09 | 3.2 | 19 | 0.34 |
| ISIS 494311 | 93 | 185 | 0.51 | 2.7 | 23 | 0.30 |
| ISIS 494372 | 54 | 119 | 0.12 | 3.0 | 19 | 0.33 |
| ISIS 510548 | 116 | 181 | 0.11 | 1.7 | 65 | 0.66 |

Kidney Function

To evaluate the effect of ISIS oligonucleotides on kidney function, urine levels of total protein and creatinine were measured using an automated clinical chemistry analyzer (Hitachi Olympus AU400e, Melville, N.Y.). Results are presented in Table 48, expressed in mg/dL.

TABLE 48

Kidney function markers (mg/dL) in Sprague-Dawley rats

|  | Creatinine | Total protein |
|---|---|---|
| PBS | 103 | 118 |
| ISIS 494159 | 70 | 279 |
| ISIS 494161 | 105 | 315 |
| ISIS 494162 | 58 | 925 |
| ISIS 494283 | 114 | 1091 |
| ISIS 494284 | 97 | 2519 |
| ISIS 494285 | 38 | 2170 |
| ISIS 494286 | 51 | 625 |
| ISIS 494301 | 62 | 280 |
| ISIS 494302 | 101 | 428 |
| ISIS 494311 | 48 | 1160 |
| ISIS 494372 | 46 | 154 |
| ISIS 510548 | 55 | 2119 |

Organ Weights

Liver, spleen and kidney weights were measured at the end of the study, and are presented in Table 49. ISIS oligonucleotides that caused any changes in organ weights outside the expected range for antisense oligonucleotides were excluded from further studies.

TABLE 49

Organ weights of Sprague Dawley rats (g)

|  | Kidney | liver | Spleen |
|---|---|---|---|
| PBS | 3.5 | 13.1 | 0.9 |
| ISIS 494159 | 3.1 | 11.7 | 1.6 |
| ISIS 494161 | 2.8 | 12.5 | 2 |
| ISIS 494162 | 3.1 | 14.2 | 1.6 |
| ISIS 494283 | 3.3 | 12.9 | 2.3 |
| ISIS 494284 | 4.1 | 15.8 | 2.7 |
| ISIS 494285 | 3.8 | 13.4 | 0.8 |
| ISIS 494286 | 4.2 | 16.7 | 2.5 |
| ISIS 494301 | 3.2 | 12.1 | 2.3 |
| ISIS 494302 | 3.4 | 13.3 | 2.4 |
| ISIS 494311 | 3.5 | 17.4 | 3.2 |
| ISIS 494372 | 3.6 | 12.9 | 3.2 |
| ISIS 510548 | 6.4 | 21.2 | 1.5 |

The finding from the rodent tolerability studies showed that in general, taking into consideration all the tolerability markers screened, ISIS 494372 was the best tolerated antisense compound in both the CD1 mouse model and the Sprague Dawley rat model.

Example 9: Pharmacokinetics of Antisense Oligonucleotide in CD1 Mice

CD1 mice were treated with ISIS oligonucleotides and the oligonucleotide concentrations in the liver and kidney were evaluated.

Treatment

Groups of four CD1 mice each were injected subcutaneously twice per week for 6 weeks with 50 mg/kg of ISIS 494283, ISIS 494284, ISIS 494286, ISIS 494301, ISIS 494302, or ISIS 494372. The mice were sacrificed 2 days following the final dose. Livers were harvested for analysis.

Measurement of Oligonucleotide Concentration

The concentration of the total oligonucleotide concentration was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTT-GCTCTTCTTCTTGCGTTTTTT, designated herein as SEQ ID NO: 131) was added prior to extraction. Tissue sample concentrations were calculated using calibration curves, with a lower limit of quantitation (LLOQ) of approximately 1.14 µg/g. Half-lives were then calculated using WinNonlin software (PHARSIGHT).

The results are presented in Table 50, expressed as µ/g liver or kidney tissue. The data indicates that ISIS 494372 was at an acceptable concentration in the liver and kidneys.

TABLE 50

Oligonucleotide concentration (µg/g tissue) of ISIS oligonucleotides in CD1 mice

| ISIS No | Liver | Kidney |
|---|---|---|
| 494283 | 581 | 549 |
| 494284 | 511 | 678 |
| 494286 | 368 | 445 |
| 494301 | 812 | 347 |
| 494302 | 617 | 263 |
| 494372 | 875 | 516 |

Example 10: Pharmacokinetics of Antisense Oligonucleotide in Sprague Dawley Rats Male Sprague Dawley rats were treated with ISIS oligonucleotides and the oligonucleotide concentrations in the liver and kidney were evaluated.

Treatment

Groups of four rats each were injected subcutaneously twice per week for 3 weeks with 10 mg/kg of ISIS 494283, ISIS 494284, ISIS 494286, ISIS 494301, ISIS 494302, or ISIS 494372. The rats were sacrificed 2 days following the final dose. Livers were harvested for analysis.

Measurement of Oligonucleotide Concentration

The concentration of the total oligonucleotide concentration was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTT-GCTCTTCTTCTTGCGTTTTTT, designated herein as SEQ ID NO: 131) was added prior to extraction. Tissue sample concentrations were calculated using calibration curves, with a lower limit of quantitation (LLOQ) of approximately 1.14 µg/g. Half-lives were then calculated using WinNonlin software (PHARSIGHT).

The results are presented in Table 51, expressed as µg/g liver or kidney tissue. The data indicates that ISIS 494372 was at an acceptable concentration in the liver and kidneys.

TABLE 51

Oligonucleotide concentration (µg/g tissue) of ISIS oligonucleotides in Sprague Dawley rats

| ISIS No | Liver | Kidney |
|---|---|---|
| 494283 | 220 | 434 |
| 494284 | 178 | 573 |
| 494286 | 234 | 448 |
| 494301 | 279 | 540 |
| 494302 | 205 | 387 |
| 494372 | 288 | 663 |

Example 11: Effect of ISIS Antisense Oligonucleotides Targeting Human Apo(a) in Cynomolgus Monkeys Cynomolgus monkeys were treated with ISIS antisense oligonucleotides selected from studies described above. At the time this study was undertaken, the cynomolgus monkey genomic sequence was not available in the National Center for Biotechnology Information (NCBI) database; therefore, cross-reactivity with the cynomolgus monkey gene sequence could not be confirmed. Instead, the sequences of the ISIS antisense oligonucleotides used in the cynomolgus monkeys was compared to a rhesus monkey sequence for homology. It is expected that ISIS oligonucleotides with homology to the rhesus monkey sequence are fully cross-reactive with the cynomolgus monkey sequence as well.

The human antisense oligonucleotides tested are also cross-reactive with the rhesus mRNA sequence (XM_001098061.1; designated herein as SEQ ID NO: 132). The greater the complementarity between the human oligonucleotide and the rhesus monkey sequence, the more likely the human oligonucleotide can cross-react with the rhesus monkey sequence. The start and stop sites of each oligonucleotide to SEQ ID NO: 132 is presented in Table 52. Each antisense oligonucleotide targets more than one region in SEQ ID NO:132 and has multiple start sites. "Start site" indicates the 5'-most nucleotide to which the gapmer is targeted in the rhesus monkey sequence. 'Mismatches' indicates the number of nucleotides mismatched between the human oligonucleotide sequence and the rhesus sequence.

Antisense oligonucleotide tolerability, as well as their pharmacokinetic profile in the liver and kidney, was evaluated.

TABLE 52

Antisense oligonucleotides complementary to SEQ ID NO: 132

| ISIS No | Start Site | Mismatches |
|---|---|---|
| 494283 | 278 | 2 |
|  | 620 | 2 |
|  | 923 | 2 |
|  | 1265 | 2 |
|  | 1607 | 1 |
|  | 1949 | 1 |
|  | 2267 | 1 |
|  | 2609 | 1 |
|  | 2951 | 1 |
|  | 3293 | 1 |
| 494284 | 279 | 1 |
|  | 621 | 1 |
|  | 924 | 1 |
|  | 1266 | 1 |
|  | 1608 | 1 |
|  | 1950 | 1 |
|  | 2268 | 1 |
|  | 2610 | 1 |
|  | 2952 | 1 |
|  | 3294 | 1 |
| 494286 | 281 | 1 |
|  | 623 | 1 |
|  | 926 | 1 |
|  | 1268 | 1 |
|  | 1610 | 2 |
|  | 1952 | 2 |
|  | 2270 | 2 |
|  | 2612 | 2 |
|  | 2954 | 2 |
|  | 3296 | 2 |
| 494301 | 322 | 2 |
|  | 664 | 2 |
|  | 967 | 2 |
|  | 1309 | 1 |
|  | 1651 | 2 |

TABLE 52-continued

Antisense oligonucleotides complementary to SEQ ID NO: 132

| ISIS No | Start Site | Mismatches |
|---|---|---|
| 494302 | 323 | 2 |
|  | 968 | 2 |
|  | 1310 | 1 |
|  | 1652 | 2 |
| 494372 | 1186 | 2 |
|  | 1870 | 1 |
|  | 2188 | 1 |

Treatment

Prior to the study, the monkeys were kept in quarantine for at least a 30-day period, during which the animals were observed daily for general health. The monkeys were 2-4 years old and weighed between 2 and 4 kg. Seven groups of four randomly assigned male cynomolgus monkeys each were injected subcutaneously with ISIS oligonucleotide or PBS using a stainless steel dosing needle and syringe of appropriate size into the one of four sites on the back of the monkeys. The injections were given in clock-wise rotation; one site per dosing. The monkeys were dosed four times a week for the first week (days 1, 3, 5, and 7) as loading doses, and subsequently once a week for weeks 2-12, with 40 mg/kg of ISIS 494283, ISIS 494284, ISIS 494286, ISIS 494301, ISIS 494302, or ISIS 494372. A control group of 8 cynomolgus monkeys was injected with PBS subcutaneously thrice four times a week for the first week (days 1, 3, 5, and 7), and subsequently once a week for weeks 2-12.

During the study period, the monkeys were observed at least once daily for signs of illness or distress. Any animal experiencing more than momentary or slight pain or distress due to the treatment, injury or illness was treated by the veterinary staff with approved analgesics or agents to relieve the pain after consultation with the Study Director. Any animal in poor health or in a possible moribund condition was identified for further monitoring and possible euthanasia. For instance, one animal in the treatment group of ISIS 494302 was found moribund on day 56 and was euthanized. Scheduled euthanasia of the animals was conducted on days 86 and 87 by exsanguination under deep anesthesia. The protocols described in the Example were approved by the Institutional Animal Care and Use Committee (IACUC).

Target Reduction

RNA Analysis

On day 86, RNA was extracted from liver tissue for real-time PCR analysis of apo(a) using human primer probe set ABI Hs00916691_m1 (Applied Biosystems, Carlsbad Calif.). Results are presented as percent inhibition of apo(a) mRNA, relative to PBS control. As shown in Table 53, treatment with ISIS antisense oligonucleotides resulted in significant reduction of apo(a) mRNA in comparison to the PBS control.

The mRNA levels of plasminogen, another kringle-containing protein, were also measured. Treatment with ISIS 494372 did not alter the mRNA levels of plasminogen.

TABLE 53

Percent Inhibition of apo(a) mRNA in the cynomolgus monkey liver relative to the PBS control

| ISIS No | % inhibition |
|---|---|
| 494283 | 91 |
| 494284 | 99 |

TABLE 53-continued

Percent Inhibition of apo(a) mRNA
in the cynomolgus monkey liver relative to the PBS control

| ISIS No | % inhibition |
|---|---|
| 494286 | 96 |
| 494301 | 88 |
| 494302 | 89 |
| 494372 | 93 |

Protein Analysis

On different days, one mL of blood was collected from the cephalic, saphenous, or femoral vein of all study monkeys. The blood samples were put into tubes containing K2-EDTA for plasma separation. The tubes were centrifuged at 3,000 rpm for 10 min at room temperature to obtain plasma. Apo(a) protein levels were analyzed by an Apo(a) ELISA kit (Mercodia 10-1106-01, Uppsala, Sweden). Results are presented as percentage change of levels from the baseline. As shown in Table 54, treatment with several ISIS antisense oligonucleotides resulted in significant reduction of apo(a) protein levels in comparison to the PBS control. Specifically, treatment with ISIS 494372 reduced cynomolgous plasma protein levels of apo(a).

The protein levels of apoB were also measured in the study groups. Antisense inhibition of apo(a) had no effect on apoB levels.

TABLE 54

Apo(a) plasma protein levels (% inhibition over
baseline values) in the cynomolgus monkey

| | Day 16 | Day 30 | Day 44 | Day 56 | Day 72 | Day 86 |
|---|---|---|---|---|---|---|
| PBS | 0 | 0 | 10 | 0 | 0 | 0 |
| ISIS 494283 | 78 | 79 | 81 | 66 | 66 | 70 |
| ISIS 494284 | 92 | 95 | 95 | 93 | 93 | 94 |
| ISIS 494286 | 92 | 95 | 96 | 94 | 94 | 94 |
| ISIS 494301 | 41 | 45 | 52 | 20 | 17 | 29 |
| ISIS 494302 | 17 | 0 | 2 | 0 | 0 | 20 |
| ISIS 494372 | 67 | 80 | 83 | 79 | 78 | 81 |

Tolerability Studies

Body and Organ Weight Measurements

To evaluate the effect of ISIS oligonucleotides on the overall health of the animals, body and organ weights were measured at day 86. Body weights were measured and are presented in Table 55. Organ weights were measured and the data is presented in Table 56. The results indicate that treatment with ISIS 494372 was well tolerated in terms of the body and organ weights of the monkeys.

TABLE 55

Body weights (g) in the cynomolgus monkey

| | Day 14 | Day 35 | Day 49 | Day 56 | Day 70 | Day 84 |
|---|---|---|---|---|---|---|
| PBS | 2637 | 2691 | 2748 | 2733 | 2739 | 2779 |
| ISIS 494283 | 2591 | 2670 | 2698 | 2656 | 2704 | 2701 |
| ISIS 494284 | 2559 | 2661 | 2676 | 2675 | 2662 | 2646 |
| ISIS 494286 | 2693 | 2770 | 2838 | 2800 | 2796 | 2816 |
| ISIS 494301 | 2587 | 2604 | 2627 | 2591 | 2596 | 2604 |
| ISIS 494302 | 2759 | 2760 | 2839 | 2825 | 3113 | 3122 |
| ISIS 494372 | 2719 | 2877 | 2985 | 2997 | 3037 | 3036 |

TABLE 56

Organ weights (% body weight) in the cynomolgus monkey

| | Spleen | Kidneys | Liver | Heart | Lungs |
|---|---|---|---|---|---|
| PBS | 0.14 | 0.38 | 2.2 | 0.33 | 0.51 |
| ISIS 494283 | 0.24 | 0.95 | 2.8 | 0.33 | 0.49 |
| ISIS 494284 | 0.19 | 0.60 | 2.6 | 0.36 | 0.55 |
| ISIS 494286 | 0.22 | 0.63 | 2.7 | 0.38 | 0.55 |
| ISIS 494301 | 0.38 | 0.81 | 3.0 | 0.36 | 0.61 |
| ISIS 494302 | 0.17 | 0.95 | 2.5 | 0.39 | 0.57 |
| ISIS 494372 | 0.18 | 1.16 | 2.6 | 0.36 | 0.56 |

Liver Function

To evaluate the effect of ISIS oligonucleotides on hepatic function, monkeys were fasted overnight prior to blood collection. Approximately 1.5 mL of blood was collected from each animal and put into tubes without anticoagulant for serum separation. The tubes were kept at room temperature for a minimum of 90 min and then centrifuged at 3,000 rpm for 10 min at room temperature to obtain serum. Levels of various liver function markers were measured using a Toshiba 200FR NEO chemistry analyzer (Toshiba Co., Japan). Plasma levels of ALT and AST were measured and the results are presented in Table 57, expressed in IU/L. Bilirubin, a liver function marker, was similarly measured and is presented in Table 57, expressed in mg/dL. The results indicate that treatment with ISIS 494372 was well tolerated in terms of the liver function in monkeys.

TABLE 57

Liver function markers in cynomolgus monkey plasma

| | ALT (IU/L) | AST (IU/L) | Bilirubin (mg/dL) |
|---|---|---|---|
| PBS | 33 | 43 | 0.20 |
| ISIS 494283 | 75 | 73 | 0.12 |
| ISIS 494284 | 115 | 79 | 0.17 |
| ISIS 494286 | 67 | 73 | 0.13 |
| ISIS 494301 | 129 | 90 | 0.15 |
| ISIS 494302 | 141 | 75 | 0.15 |
| ISIS 494372 | 46 | 75 | 0.17 |

C-Reactive Protein Level Analysis

To evaluate any inflammatory effect of ISIS oligonucleotides in cynomolgus monkeys, blood samples were taken for analysis. The monkeys were fasted overnight prior to blood collection. Approximately 1.5 mL of blood was collected from each animal and put into tubes without anticoagulant for serum separation. The tubes were kept at room temperature for a minimum of 90 min and then centrifuged at 3,000 rpm for 10 min at room temperature to obtain serum. C-reactive protein (CRP), which is synthesized in the liver and which serves as a marker of inflammation, was measured using a Toshiba 200FR NEO chemistry analyzer (Toshiba Co., Japan). The results indicate that treatment with ISIS 494372 did not cause any inflammation in monkeys.

TABLE 58

C-reactive protein levels (mg/L) in cynomolgus monkey plasma

| | CRP |
|---|---|
| PBS | 1.4 |
| ISIS 494283 | 14.7 |
| ISIS 494284 | 7.7 |
| ISIS 494286 | 4.4 |
| ISIS 494301 | 3.5 |

TABLE 58-continued

C-reactive protein levels (mg/L) in cynomolgus monkey plasma

|  | CRP |
| --- | --- |
| ISIS 494302 | 2.4 |
| ISIS 494372 | 10.2 |

Complement C3 Analysis

To evaluate any effect of ISIS oligonucleotides on the complement pathway in cynomolgus monkeys, blood samples were taken for analysis on day 84 (pre-dose) and day 85 (24 hours post-dose). Approximately 0.5 mL of blood was collected from each animal and put into tubes without anticoagulant for serum separation. The tubes were kept at room temperature for a minimum of 90 min and then centrifuged at 3,000 rpm for 10 min at room temperature to obtain serum. C3 was measured using a Toshiba 200FR NEO chemistry analyzer (Toshiba Co., Japan). The results indicate that treatment with ISIS 494372 did not cause any effect on the complement pathway in monkeys.

TABLE 59

Complement C3 levels (mg/dL) in cynomolgus monkey plasma

|  | Pre-dose | Post-dose |
| --- | --- | --- |
| PBS | 140 | 139 |
| ISIS 494283 | 127 | 101 |
| ISIS 494284 | 105 | 75 |
| ISIS 494286 | 84 | 38 |
| ISIS 494301 | 118 | 76 |
| ISIS 494302 | 98 | 58 |
| ISIS 494372 | 123 | 109 |

Hematology

To evaluate any effect of ISIS oligonucleotides in cynomolgus monkeys on hematologic parameters, blood samples of approximately 0.5 mL of blood was collected on day 87 from each of the available study animals in tubes containing $K_2$-EDTA. Samples were analyzed for red blood cell (RBC) count, white blood cells (WBC) count, as well as for platelet count, using an ADVIA120 hematology analyzer (Bayer, USA). The data is presented in Table 60.

The data indicate that treatment with ISIS 494372 was well tolerated in terms of the hematologic parameters of the monkeys.

TABLE 60

Blood cell counts in cynomolgus monkeys

|  | WBC ($\times 10^3/\mu L$) | RBC ($\times 10^6/\mu L$) | Platelet ($\times 10^3/\mu L$) |
| --- | --- | --- | --- |
| PBS | 15 | 6.3 | 329 |
| ISIS 494283 | 16 | 5.3 | 456 |
| ISIS 494284 | 13 | 6.3 | 330 |
| ISIS 494286 | 14 | 5.5 | 304 |
| ISIS 494301 | 15 | 6.0 | 392 |
| ISIS 494302 | 12 | 6.3 | 305 |
| ISIS 494372 | 11 | 6.1 | 447 |

Example 12: Characterization of the Pharmacological Activity of ISIS 494372 in Cynomolgus Monkeys The pharmacological activity of ISIS 494372 was characterized by measuring liver apo(a) mRNA and plasma apo(a) levels in monkeys administered the compound over 13 weeks and allowed to recover for another 13 weeks.

Treatment

Five groups of 14 randomly assigned male and female cynomolgus monkeys each were injected subcutaneously with ISIS oligonucleotide or PBS using a stainless steel dosing needle and syringe of appropriate size into the one of four sites on the back (scapular region) of the monkeys. The monkeys were dosed four times a week for the first week (days 1, 3, 5, and 7) as loading doses, and subsequently once a week for weeks 2-13 as maintenance doses, as shown in the table below. The loading dose during the first week is expressed as mg/kg/dose, while the maintenance doses on weeks 2-13 are expressed as mg/kg/week.

TABLE 61

Dosing groups in cynomolgus monkeys

| Group | Test Article | Dose | Number of animals for necropsy | | |
| --- | --- | --- | --- | --- | --- |
|  |  |  | Interim | Terminal | Recovery |
| 1 | PBS | — | 4 | 6 | 4 |
| 2 | ISIS | 4 | — | 6 | — |
| 3 | 494372 | 8 | — | 6 | — |
| 4 |  | 12 | 4 | 6 | 4 |
| 5 |  | 40 | 4 | 6 | 4 |

Liver samples from animals were taken at the interim, terminal and recovery phases of the study for the analyses of apo(a) mRNA. In addition, plasma samples were collected on different days to measure apo(a) protein levels. This non-clinical study was conducted in accordance with the United States Food and Drug Administration (FDA) Good Laboratory Practice (GLP) Regulations, 21 CFR Part 58.

RNA Analysis

Liver samples were collected from monkeys on days 30, 93, and 182, and frozen. Briefly, a piece (0.2 g) of frozen liver was homogenized in 2 mL of RLT solution (Qiagen). The resulting lysate was applied to Qiagen RNeasy mini columns. After purification and quantification, the tissues were subjected to RT-PCR analysis. The Perkin-Elmer ABI Prism 7700 Sequence Detection System, which uses real-time fluorescent RT-PCR detection, was used to quantify apo(a) mRNA. The assay is based on a target-specific probe labeled with fluorescent reporter and quencher dyes at opposite ends. The probe was hydrolyzed through the 5'-exonuclease activity of Taq DNA polymerase, leading to an increasing fluorescence emission of the reporter dye that can be detected during the reaction. A probe set (ABI Rhesus LPA probe set ID Rh02789275_m1, Applied Biosystems, Carlsbad Calif.) targeting position 1512 of the rhesus monkey apo(a) mRNA transcript GENBANK Accession No XM_001098061.2 (SEQ ID NO: XXX) sequence was used to measure cynomolgus monkey liver apo(a) mRNA expression levels. Apo(a) expression was normalized using RIBOGREEN®. Results are presented as percent inhibition of apo(a) mRNA, relative to PBS control.

As shown in Table 62, treatment with ISIS 494372 resulted in a dose-dependent reduction of apo(a) mRNA in comparison to the PBS control. At day 30, hepatic apo(a) mRNA expression was reduced in a dose-dependent manner by 74% and 99% in the 12 mg/kg/week and 40 mg/kg/week dosing cohorts, respectively. These reductions are statistically significant by one-way ANOVA (Dunnett's multiple comparison test, P<0.05).

Apo(a) mRNA levels were also measured during the recovery phase. Liver expression levels at day 88 after the last dose were still reduced 49% and 69% in the 12 mg/kg/week and 40 mg/kg/week dosing cohorts, respectively.

TABLE 62

Percent inhibition levels of liver apo(a) mRNA
in the dosing phase in cynomolgus monkeys treated with ISIS 494372

| Day | Dose (mg/kg/wk) | % inhibition |
|---|---|---|
| 30 | 12 | 73 |
|  | 40 | 99 |
| 93 | 4 | 44 |
|  | 8 | 43 |
|  | 12 | 53 |
|  | 40 | 93 |

Protein Analysis

Approximately 20 μl of plasma was analyzed using a commercially available apo(a) ELISA kit (Mercodia 10-1106-01, Uppsala, Sweden). The assay protocol was performed as described by the manufacturer. The results are presented in Tables 63 and 64 as percentage change from Day 1 pre-dose apo(a) plasma protein concentrations. Statistically significant differences from Day 1 baseline plasma apo(a) using the Dunnett's multicomparison test are marked with an asterisk.

Maximal reduction in plasma apo(a) protein was observed in all dosing cohorts by Day 93. In the recovery phase, apo(a) plasma protein levels in the 40 mg/kg/week dosing cohort were at 22% and 93% of the baseline after 4 and 13 weeks (Days 121 and 182) of recovery, respectively. The rate of recovery in the 12 mg/kg/week cohort was similar to that seen in the 40 mg/kg/week cohort.

TABLE 63

Apo(a) plasma protein levels as a percent of Day 1 levels
in the dosing phase in cynomolgus monkeys treated with ISIS 494372

| Day | Dose (mg/kg/wk) | % |
|---|---|---|
| 30 | 4 | 93 |
|  | 8 | 70 |
|  | 12 | 49 |
|  | 40 | 15* |
| 93 | 4 | 73 |
|  | 8 | 56 |
|  | 12 | 32* |
|  | 40 | 11* |

TABLE 64

Apo(a) plasma protein levels as a percent of Day 1 levels
in the recovery phase in cynomolgus monkeys treated with ISIS 494372

| Day | Dose (mg/kg/wk) | % |
|---|---|---|
| 121 | 12 | 38* |
|  | 40 | 22* |
| 182 | 12 | 84 |
|  | 40 | 93 |

Example 13: Measurement of Viscosity of ISIS Antisense Oligonucleotides Targeting Human Apo(a)

The viscosity of select antisense oligonucleotides from the studies described above was measured with the aim of screening out antisense oligonucleotides which have a viscosity more than 40 cP. Oligonucleotides having a viscosity greater than 40 cP would have less than optimal viscosity.

ISIS oligonucleotides (32-35 mg) were weighed into a glass vial, 120 μL of water was added and the antisense oligonucleotide was dissolved into solution by heating the vial at 50° C. Part (75 μL) of the pre-heated sample was pipetted to a micro-viscometer (Cambridge). The temperature of the micro-viscometer was set to 25° C. and the viscosity of the sample was measured. Another part (20 μL) of the pre-heated sample was pipetted into 10 mL of water for UV reading at 260 nM at 85° C. (Cary UV instrument). The results are presented in Table 65 and indicate that most of the antisense oligonucleotides solutions are optimal in their viscosity under the criterion stated above. Those that were not optimal are marked as 'viscous'. Specifically, ISIS 494372 was optimal in its viscosity under the criterion stated above.

TABLE 65

Viscosity and concentration
of ISIS antisense oligonucleotides targeting human Apo(a)

| ISIS No | Motif | Viscosity (cP) | Concentration (mg/mL) |
|---|---|---|---|
| 494158 | 5-10-5 MOE | 9.0 | 350 |
| 494159 | 5-10-5 MOE | 11.7 | 325 |
| 494161 | 5-10-5 MOE | 12.0 | 350 |
| 494162 | 5-10-5 MOE | 25.8 | 350 |
| 494163 | 5-10-5 MOE | Viscous | 275 |
| 494243 | 5-10-5 MOE | 28.4 | 325 |
| 494244 | 5-10-5 MOE | 19.2 | 300 |
| 494283 | 3-10-4 MOE | 13.4 | 300 |
| 494284 | 5-10-5 MOE | 13.4 | 350 |
| 494285 | 5-10-5 MOE | 23.1 | 350 |
| 494286 | 5-10-5 MOE | 16.5 | 275 |
| 494301 | 5-10-5 MOE | 17.1 | 325 |
| 494302 | 5-10-5 MOE | 24.3 | 350 |
| 494304 | 5-10-5 MOE | 49.3 | 275 |
| 494311 | 5-10-5 MOE | 10.8 | 325 |
| 494337 | 5-10-5 MOE | 29.5 | 325 |
| 494372 | 5-10-5 MOE | 12.5 | 350 |
| 494466 | 5-10-5 MOE | Viscous | 275 |
| 494470 | 5-10-5 MOE | 16.7 | 350 |
| 494472 | 5-10-5 MOE | 23.6 | 350 |
| 498408 | 5-10-5 MOE | 31.5 | 300 |
| 510548 | 5-10-5 MOE | 9.0 | 350 |
| 512947 | 3-10-4 MOE | 6.8 | 350 |
| 512958 | 5-10-5 MOE | 26.0 | 350 |

The invention claimed is:

1. A compound comprising a modified oligonucleotide consisting of 17 to 20 linked nucleosides and having a nucleobase sequence comprising at least 17, at least 18, at least 19, or 20 contiguous nucleobases of any of the nucleobase sequences of SEQ ID NO: 26, 27, 29, 39 or 40.

2. The compound of claim 1, wherein the modified oligonucleotide is single-stranded.

3. The compound of claim 1, wherein at least one internucleoside linkage is a modified internucleoside linkage.

4. The compound of claim 3, wherein each internucleoside linkage is a phosphorothioate internucleoside linkage.

5. The compound of claim 1, wherein the modified oligonucleotide comprises at least one modified sugar.

6. The compound of claim 5, wherein at least one modified sugar is a bicyclic sugar.

7. The compound of claim 5, wherein at least one modified sugar comprises a 2'-O-methoxyethyl, a constrained ethyl, a 3'-fluoro-HNA or a 4'-$(CH_2)_n$—O-2' bridge, wherein n is 1 or 2.

8. The compound of claim 1, wherein at least one nucleoside comprises a modified nucleobase.

9. The compound of claim 8, wherein the modified nucleobase is a 5-methylcytosine.

10. The compound of claim 1, wherein the modified oligonucleotide comprises:
    a gap segment consisting of linked deoxynucleosides;
    a 5' wing segment consisting of linked nucleosides;
    a 3' wing segment consisting of linked nucleosides;
    wherein the gap segment is positioned between the 5' wing segment and the 3' wing segment and wherein each nucleoside of each wing segment comprises a modified sugar.

11. The compound of claim 10, wherein the modified oligonucleotide consists of 20 linked nucleosides and comprises:
    a gap segment consisting of ten linked deoxynucleosides;
    a 5' wing segment consisting of five linked nucleosides;
    a 3' wing segment consisting of five linked nucleosides;
    wherein the gap segment is positioned between the 5' wing segment and the 3' wing segment, wherein each nucleoside of each wing segment comprises a 2'-O-methoxyethyl sugar, wherein at least one internucleoside linkage is a phosphorothioate linkage and wherein each cytosine residue is a 5-methylcytosine.

12. The compound of claim 10, wherein the modified oligonucleotide consists of 20 linked nucleosides.

13. A modified oligonucleotide consisting of 20 linked nucleosides and having a nucleobase sequence of SEQ ID NO: 26, 27, 29, 39 or 40, wherein the modified oligonucleotide comprises:
    a gap segment consisting of ten linked deoxynucleosides;
    a 5' wing segment consisting of five linked nucleosides;
    a 3' wing segment consisting of five linked nucleosides;
    wherein the gap segment is positioned between the 5' wing segment and the 3' wing segment, wherein each nucleoside of each wing segment comprises a 2'-O-methoxyethyl sugar, wherein at least one internucleoside linkage is a phosphorothioate linkage and wherein each cytosine residue is a 5-methylcytosine.

14. A composition comprising a compound according to claim 1, and a pharmaceutically acceptable carrier or diluent.

15. A method of treating, preventing, or slowing progression of a disease, disorder or condition in a subject comprising administering to the subject the compound of claim 1.

16. The method of claim 15, wherein the disease is an apo(a) associated, Lp(a) associated, inflammatory, cardiovascular or metabolic disease, disorder or condition.

17. The compound of claim 1, wherein the modified oligonucleotide consists of 20 linked nucleosides.

18. The compound of claim 1, wherein the modified oligonucleotide comprises a nucleobase sequence comprising a portion of at least 18, at least 19, or at least 20 contiguous nucleobases complementary to an equal length portion of SEQ ID NO: 1.

19. The compound of claim 1, wherein the nucleobase sequence of the modified oligonucleotide at least 90%, at least 95%, or 100% complementary to SEQ ID NO: 1.

20. The method of claim 15, wherein the subject is a human.

* * * * *